US012578335B2

(12) United States Patent
Findlay et al.

(10) Patent No.: US 12,578,335 B2
(45) **Date of Patent: *Mar. 17, 2026**

(54) BIOPROBES FOR LYSYL OXIDASES AND USES THEREOF

(71) Applicant: Syntara Limited, Frenchs Forest (AU)

(72) Inventors: Alison Dorothy Findlay, Frenchs Forest (AU); Craig Ivan Turner, Frenchs Forest (AU); Mandar Deodhar, Frenchs Forest (AU); Jonathan Stuart Foot, Frenchs Forest (AU); Wolfgang Jarolimek, Frenchs Forest (AU); Heidi Schilter Sambade, Forestville (AU); Wenbin Zhou, Frenchs Forest (AU); Lara Anne Perryman, Frenchs Forest (AU)

(73) Assignee: Syntara Limited, Frenchs Forest (AU)

( * ) Notice: Subject to any disclaimer, the term of this patent is extended or adjusted under 35 U.S.C. 154(b) by 620 days.

This patent is subject to a terminal disclaimer.

(21) Appl. No.: 17/797,502

(22) PCT Filed: Feb. 5, 2021

(86) PCT No.: PCT/AU2021/050092

§ 371 (c)(1),
(2) Date: Aug. 4, 2022

(87) PCT Pub. No.: WO2021/155439

PCT Pub. Date: Aug. 12, 2021

(65) Prior Publication Data

US 2023/0349907 A1 Nov. 2, 2023

(30) Foreign Application Priority Data

Feb. 5, 2020 (AU) ................................ 2020900314

(51) Int. Cl.

| | |
|---|---|
| ***G01N 33/573*** | (2006.01) |
| ***C07D 495/04*** | (2006.01) |
| ***C07D 519/00*** | (2006.01) |
| ***C07K 16/40*** | (2006.01) |

(52) U.S. Cl.

CPC ......... *G01N 33/573* (2013.01); *C07D 495/04* (2013.01); *C07D 519/00* (2013.01); *C07K 16/40* (2013.01); *G01N 2333/90638* (2013.01)

(58) Field of Classification Search

CPC ............................ C07D 495/04; G01N 33/573
See application file for complete search history.

(56) References Cited

U.S. PATENT DOCUMENTS

| | | | |
|---|---|---|---|
| 4,454,158 A | 6/1984 | Bey | |
| 4,699,928 A | 10/1987 | McDonald | |
| 4,943,593 A | 7/1990 | Palfreyman et al. | |
| 4,965,288 A | 10/1990 | Palfreyman et al. | |
| 5,021,456 A | 6/1991 | Palfeyman et al. | |
| 5,059,714 A | 10/1991 | Palfreyman et al. | |
| 5,182,297 A | 1/1993 | Palfreyman et al. | |
| 5,252,608 A * | 10/1993 | Palfreyman .......... | A61K 31/135 514/432 |
| 12,178,791 B2 * | 12/2024 | Findlay ................ | C07D 209/10 |
| 2008/0293936 A1 | 11/2008 | Burchardt | |
| 2009/0053334 A1 | 2/2009 | Asaka et al. | |
| 2011/0044907 A1 | 2/2011 | Marshall et al. | |
| 2014/0120102 A1 * | 5/2014 | Bornstein ................. | A61P 1/16 424/139.1 |
| 2016/0123969 A1 * | 5/2016 | Rissin .................. | G01N 33/551 506/22 |
| 2017/0089892 A1 * | 3/2017 | Aghvanyan .......... | C12Q 1/6832 |
| 2021/0353571 A1 * | 11/2021 | Findlay .............. | A61K 31/4409 |
| 2023/0321075 A1 * | 10/2023 | Hofmann ................ | A61P 35/00 514/311 |
| 2025/0082593 A1 * | 3/2025 | Findlay .................. | A61K 31/47 |

FOREIGN PATENT DOCUMENTS

| | | | | |
|---|---|---|---|---|
| WO | 2003097612 A1 | 11/2003 | | |
| WO | 2006053555 A2 | 5/2006 | | |
| WO | 2007120528 A2 | 10/2007 | | |
| WO | WO-2009066152 A2 * | 5/2009 | ........... | C07C 217/46 |
| WO | 2016144702 A1 | 9/2016 | | |
| WO | 2016144703 A1 | 9/2016 | | |
| WO | 2017003862 A1 | 1/2017 | | |
| WO | 2017015221 A1 | 1/2017 | | |
| WO | 2017136870 A1 | 8/2017 | | |
| WO | 2017136871 A1 | 8/2017 | | |
| WO | 2017141049 A1 | 8/2017 | | |
| WO | 2018048930 A1 | 3/2018 | | |
| WO | WO-2018048928 A1 * | 3/2018 | ......... | A61K 49/0032 |
| WO | 2018167132 A1 | 9/2018 | | |

(Continued)

OTHER PUBLICATIONS

D. Wilson et al., 21 Journal of Laboratory Automation, 533-547 (2015) (Year: 2015).*

D. Rissin et al., 28 Nature Biotechnology, 595-600 (2010) (Year: 2010).*

L. Chang et al., J. Immunol Methods, 1-28 (2012) (Year: 2012).*

Aslam, T., et al., Optical Molecular Imaging of Lysyl Oxidase Activity—Detection of Active Fibrogenesis in Human Lung Tissue, Chem. Sci, 2015, vol. 6, pp. 4946-4953, London, UK.

Chanoki, M., et al., Increased Expression of Lysyl Oxidase in Skin with Scleroderma, British Journal of Dermatology, 1995; 133: pp. 710-715, UK.

Counts, D.F., et al., Collagen Lysyl Oxidase Activity in the Lung Increases During Bleomycin-Induced Lung Fibrosis, The Journal of Pharmacology and Experimental Therapeutics, 1981, 219, pp. 675-678, USA.

(Continued)

*Primary Examiner* — Alexander R Pagano

(74) *Attorney, Agent, or Firm* — Troutman Pepper Locke LLP

(57) ABSTRACT

The present invention relates to novel bioprobes which are capable of binding to certain amine oxidase enzymes. These bioprobes are useful in methods of detecting and determining the concentration of certain amine oxidase enzymes in a sample as well as in methods for the quantitative assessment of inhibition of certain amine oxidases.

22 Claims, 12 Drawing Sheets

(56) References Cited

FOREIGN PATENT DOCUMENTS

| | | | | | |
|---|---|---|---|---|---|
| WO | 2019073251 | A1 | | 4/2019 | |
| WO | WO-2020024017 | A1 | * | 2/2020 | ........... A61K 31/145 |
| WO | 2020099886 | A1 | | 5/2020 | |

OTHER PUBLICATIONS

Didonato, A., et al., Lysyl Oxidase Expression and Collagen Cross-Linking During Chronic Adriamycin Nephropathy, Nephron, Jun. 1997; 76: pp. 192-200, Genova, Italy.

Findlay, et al., Identification and Optimization of Mechanism-Based Fluoroallylamine Inhibitors of Lysyl Oxidase-like ⅔, J. Med. Chem. Vol. 62, No. 21, 2019, pp. 9874-9889.

Halberg, N. et al., Hypoxia-Inducible Factor 1α Induces Fibrosis and Insulin Resistance in White Adipose Tissue, Molecular and Cellular Biology, Aug. 2009, pp. 4467-4483, vol. 29, No. 16, USA.

Herranz, N., et al., Lysyl Oxidase-like 2 Deaminates Lysine 4 in Histone H3, Molecular Cell, May 11, 2012, pp. 369-376, vol. 46, Elsevier Inc., Amsterdam, Netherlands.

Holt, A. and Palcic, M., A Peroxidase-Coupled Continuous Absorbance Plate-Reader Assay for Flavin Monoamine Oxidases, Copper-Containing Amine Oxidases and Related Enzymes, Nature Protocols, vol. 1, No. 5, 2006, pp. 2498-2505, UK.

International Search Report and Written Opinion issued in PCT/AU2021/050092 dated Mar. 23, 2021, International Filing Date Feb. 5, 2021.

Kagan, H. M., et al., Changes in Aortic Lysyl Oxidase Activity in Diet-Induced Atherosclerosis in the Rabbit, Arteriosclerosis, Jul./Aug. 1981, vol. 1, No. 4, pp. 287-291.

Kagan, H. M., Lysyl Oxidase, Mechanism, Regulation and Relationship to Liver Fibrosis, Pathology Research and Practice, 1994, 190, pp. 910-919, Elsevier Publishing, Netherlands.

Kagan, H.M., and Li, W., Lysyl Oxidase: Properties, Specificity, and Biological Roles Inside and Outside of the Cell, Journal of Cellular Biochemistry, 2003, vol. 88. pp. 660-672.

Lopez, B., et al, Role of Lysyl Oxidase in Myocardial Fibrosis: From Basic Science to Clinical Aspects, American Journal of Physiology Heart and Circulatory Physiology, Jul. 2010, vol. 299, pp. H1-H9, APS Publications, MD, USA.

Moon, H., et al., MCF-7 Cells Expressing Nuclear Associated Lysyl Oxidase-Like 2 (LOXL2) Exhibit an Epithelial-to-Mesenchymal Transition (EMT) Phenotype and Are Highly Invasive in Vitro, The Journal of Biological Chemistry, 2013, vol. 288, No. 42, pp. 30000-30008, USA.

Rissin, D.M., et al., Single-Molecule Enzyme-Linked Immunosorbent Assay Detects Serum Proteins at Subfemotomolar Concentrations, Nature Biotechnology, Jun. 2010, vol. 28(6), pp. 595-599, Nature Portfolio, London, UK.

Siddikiuzzaman, G.V.M. and Guruvayoorappan, C., Lysyl Oxidase: A Potential Target for Cancer Therapy, Inflammapharmocology, Jun. 2011, vol. 19, pp. 117-129, Spring Nature, Switzerland.

Siegel, R.C., et al, Biochemical and Immunochemical Study of Lysyl Oxidase in Experimental Hepatic Fibrosis in The Rat, Proceedings of the National Academy of Sciences of the USA, Jun. 1978; vol. 75 No. 6: pp. 2945-2949, USA.

Stewart, G.D., et al., Analysis of Hypoxia-Associated Gene Expression in Prostate Cancer: Lysyl Oxidase and Glucose Transporter-1 Expression Correlate with Gleason Score, Oncology Reports, 2008, vol. 20, pp. 1561-1567.

Tang S.S., et al., Reaction of Aortic Lysyl Oxidase with Beta Aminoproprionitrile, The Journal of Biological Chemistry, Apr. 10, 1983; vol. 258, No. 7, pp. 4331-4338, USA.

Woznick, A. R., et al., Lysyl Oxidase Expression in Bronchogenic Carcinoma, The American Journal of Surgery, 2005, vol. 189: pp. 297-301, USA.

* cited by examiner

| | |
|---|---|
| Bottom | = 0 |
| Top | 100.8 |
| LogIC50 | -7.985 |
| HillSlope | 0.8704 |
| IC50 | 1.036e-008 |

BIOPROBES FOR LYSYL OXIDASES AND USES THEREOF

CROSS-REFERENCE TO RELATED APPLICATIONS

This application is a U.S. National Phase of International Patent Application No. PCT/AU2021/050092, filed on Feb. 5, 2021, which claims priority to AU application No. 2020900314, filed Feb. 5, 2020. The entire contents of these applications are incorporated herein by reference in their entireties.

TECHNICAL FIELD

The present invention relates to novel bioprobes which are capable of binding to certain amine oxidase enzymes. These bioprobes are useful in methods of detecting and determining the concentration of certain amine oxidase enzymes in a sample as well as in methods for the quantitative assessment of inhibition of certain amine oxidases.

BACKGROUND

A family of five closely relating enzymes has been linked to fibrotic disease and to metastatic cancer. The enzymes are related to lysyl oxidase (LOX), the first family member to be described and four closely related enzymes, LOX-like1 (LOXL1), LOXL2, LOXL3, and LOXL4 (Kagan H. M. and Li W., Lysyl oxidase: properties, specificity, and biological roles inside and outside of the cell. *J Cell Biochem* 2003; 88: 660-672). Lysyl oxidase isoenzymes are copper-dependent amine oxidases which initiate the covalent cross-linking of collagen and elastin. A major function of lysyl oxidase isoenzymes is to facilitate the cross-linking of collagen and elastin by the oxidative deamination of lysine and hydroxylysine amino acid side chains to aldehydes which spontaneously react with neighbouring residues. The resulting cross-linked strands contribute to extracellular matrix (ECM) stability. Lysyl oxidase activity is essential to maintain the tensile and elastic features of connective tissues of skeletal, pulmonary, and cardiovascular systems, among others. The biosynthesis of LOX is well understood; the protein is synthesized as a pre-proLOX that undergoes a series of post-translational modifications to yield a 50 kDa pro-enzyme which is secreted into the extracellular environment. For LOX and LOXL1 proteolysis by bone morphogenetic protein-1 (BMP-1) and other procollagen C-proteinases releases the mature and active form. LOXL2, LOXL3 and LOXL4 contain scavenger receptor cysteine-rich protein domains and are directly secreted as active forms.

Lysyl oxidase isoenzymes belong to a larger group of amine oxidases which include flavin-dependent and copper-dependent oxidases which are described by the nature of the catalytic co-factor. Flavin-dependent enzymes include monoamine oxidase-A (MAO-A), MAO-B, polyamine oxidase and lysine demethylase (LSD1), and the copper-dependent enzymes include semicarbazide sensitive amine oxidase (vascular adhesion protein-1, SSAO/VAP-1), retinal amine oxidase, diamine oxidase and the lysyl oxidase isoenzymes. The copper-dependent amine oxidases have a second co-factor which varies slightly from enzyme to enzyme. In SSAO/VAP-1 it is an oxidized tyrosine residue (TPQ, oxidized to a quinone), whereas in the lysyl oxidase isoenzymes the TPQ has been further processed by addition of a neighboring lysine residue (to form LTQ); see Kagan, H. M. and Li, W., Lysyl oxidase: Properties, specificity, and biological roles inside and outside of the cell. *J Cell Biochem* 2003; 88: 660-672.

Since lysyl oxidase isoenzymes exhibit different in vivo expression patterns it is likely that specific isoenzymes will have specific biological roles. Catalytically active forms of LOX have been identified in the cytosolic and nuclear compartments which suggest the existence of undefined roles of LOX in cellular homeostasis. Significant research is currently underway to define these roles. LOX itself, for example, plays a major role in epithelial-to-mesenchymal transition (EMT), cell migration, adhesion, transformation and gene regulation. Different patterns of LOX expression/activity have been associated with distinct pathological processes including fibrotic diseases, Alzheimer's disease and other neurodegenerative processes, as well as tumour progression and metastasis. See, for example, Woznick, A. R., et al. Lysyl oxidase expression in bronchogenic carcinoma. *Am J Surg* 2005; 189: 297-301. Catalytically active forms of LOXL2 can be also found in the nucleus (J Biol Chem. 2013; 288: 30000-30008) and can deaminate lysine 4 in histone H3 (*Mol Cell* 2012 46: 369-376).

Directed replacement of dead or damaged cells with connective tissue after injury represents a survival mechanism that is conserved throughout evolution and appears to be most pronounced in humans serving a valuable role following traumatic injury, infection or diseases. Progressive scarring can occur following more chronic and/or repeated injuries that causes impaired function to parts or all of the affected organ. A variety of causes, such as chronic infections, chronic exposure to alcohol and other toxins, autoimmune and allergic reactions or radio- and chemotherapy can all lead to fibrosis. This pathological process, therefore, can occur in almost any organ or tissue of the body and, typically, results from situations persisting for several weeks or months in which inflammation, tissue destruction and repair occur simultaneously. In this setting, fibrosis most frequently affects the lungs, liver, skin and kidneys.

Liver fibrosis occurs as a complication of haemochromatosis, Wilson's disease, alcoholism, schistosomiasis, viral hepatitis, bile duct obstruction, exposure to toxins and metabolic disorders. Liver fibrosis is characterized by the accumulation of extracellular matrix that can be distinguished qualitatively from that in normal liver. This fibrosis can progress to cirrhosis, liver failure, cancer and eventually death. This is reviewed in Kagan, H. M. Lysyl oxidase: Mechanism, regulation and relationship to liver fibrosis. *Pathology—Research and Practice* 1994; 190: 910-919.

Fibrotic tissues can accumulate in the heart and blood vessels as a result of hypertension, hypertensive heart disease, atherosclerosis and myocardial infarction where the accumulation of extracellular matrix or fibrotic deposition results in stiffening of the vasculature and stiffening of the cardiac tissue itself. See Lopez, B., et al. Role of lysyl oxidase in myocardial fibrosis: from basic science to clinical aspects. *Am J Physiol Heart Circ Physiol* 2010; 299: H1-H9.

A strong association between fibrosis and increased lysyl oxidase activity has been demonstrated. For example, in experimental hepatic fibrosis in rat (Siegel, R. C., Chen, K. H. and Acquiar, J. M, Biochemical and immunochemical study of lysyl oxidase in experimental hepatic fibrosis in the rat. *Proc. Natl. Acad. Sci. USA* 1978; 75: 2945-2949), in models of lung fibrosis (Counts, D. F., et al., Collagen lysyl oxidase activity in the lung decreases during bleomycin-induced lung fibrosis. *J Pharmacol Exp Ther* 1981; 219: 675-678) in arterial fibrosis (Kagan, H. M., Raghavan, J. and Hollander, W., Changes in aortic lysyl oxidase activity in diet-induced atherosclerosis in the rabbit. *Arteriosclerosis* 1981; 1: 287-291.), in dermal fibrosis (Chanoki, M., et al., Increased expression of lysyl oxidase in skin with scleroderma. *Br J Dermatol* 1995; 133: 710-715) and in adriamycin-induced kidney fibrosis in rat (Di Donato, A., et al., Lysyl oxidase expression and collagen cross-linking during chronic adriamycin nephropathy. *Nephron* 1997; 76: 192-200). Of these experimental models of human disease, the most striking increases in enzyme activity are seen in the rat model of $CCl_4$-induced liver fibrosis. In these studies, the low level of enzyme activity in the healthy liver increased 15- to 30-fold in fibrotic livers. The rationale for the consistent and strong inhibition of fibrosis by lysyl oxidase isoenzyme blockers is that the lack of cross-linking activity renders the collagen susceptible to matrix metalloproteinases and, ultimately, degradation. Hence, any type of fibrosis should be reversed by treatment with lysyl oxidase isoenzyme inhibitors. In humans, there is also a significant association between lysyl oxidase activity measured in the plasma and liver fibrosis progression. Lysyl oxidase activity level is normally negligible in the serum of healthy subjects, but significantly increased in chronic active hepatitis and even more in cirrhosis, therefore lysyl oxidase might serve as a marker of internal fibrosis.

BAPN (β-aminopropionitrile) is a widely used, nonselective lysyl oxidase inhibitor. Since the 1960s BAPN has been used in animal studies (mainly rat, mouse and hamster) and has been efficacious in reducing collagen content in various models (eg. $CCl_4$, bleomycin, quartz) and tissues (eg. liver, lung and dermis). See Kagan, H. M. and Li, W., Lysyl oxidase: Properties, specificity and biological roles inside and outside of the cell. *J Cell Biochem* 2003; 88: 660-672.

Lysyl oxidase isoenzymes are highly regulated by Hypoxia-Induced Factor 1α (HIF-1α) and TGF-β, the two most prominent growth factors that cause fibrosis (Halberg et al., Hypoxia-inducible factor 1α induces fibrosis and insulin resistance in white adipose tissue. *Cell Biol* 2009; 29: 4467-4483). Collagen cross linking occurs in every type of fibrosis, hence a lysyl oxidase isoenzyme inhibitor could be used in idiopathic pulmonary fibrosis, scleroderma, kidney or liver fibrosis. Lysyl oxidase isoenzymes are not only involved in the cross-linking of elastin and collagen during wound healing and fibrosis but also regulate cell movement and signal transduction. Its intracellular and intranuclear function is associated with gene regulation and can lead to tumorgenesis and tumor progression (Siddikiuzzaman, Grace, V. M and Guruvayoorappan, C., Lysyl oxidase: a potential target for cancer therapy. *Inflammapharmacol* 2011; 19: 117-129). Both down and upregulation of lysyl oxidase isoenzymes in tumour tissues and cancer cell lines have been described, suggesting a dual role for lysyl oxidase isoenzymes and LOX pro-peptide as a metastasis promoter gene as well as a tumour suppressor gene.

To date, an increase in lysyl oxidase isoenzymes mRNA and/or protein has been observed in breast, CNS cancer cell lines, head and neck squamous cell, prostatic, clear cell renal cell and lung carcinomas, and in melanoma and osteosarcoma cell lines. Statistically significant clinical correlations between lysyl oxidase isoenzymes expression and tumor progression have been observed in breast, head and neck squamous cell, prostatic and clear cell renal cell carcinomas. The role of lysyl oxidase isoenzymes in tumor progression has been most extensively studied in breast cancer using in vitro models of migration/invasion and in in vivo tumorgenesis and metastasis mouse models. Increased lysyl oxidase isoenzymes expression was found in hypoxic patients, and was associated with negative estrogen receptor status (ER−), decreased overall survival in ER-patients and node-negative patients who did not receive adjuvant systemic treatment, as well as shorter metastasis-free survival in ER− patients and node negative patients. Lysyl oxidase isoenzymes mRNA was demonstrated to be up-regulated in invasive and metastatic cell lines (MDA-MB-231 and Hs578T), as well as in more aggressive breast cancer cell lines and distant metastatic tissues compared with primary cancer tissues.

In head and neck squamous cell carcinomas, increased lysyl oxidase isoenzyme expression was found in association with CA-IX, a marker of hypoxia, and was associated with decreased cancer specific survival, decreased overall survival and lower metastasis-free survival. In oral squamous cell carcinoma, lysyl oxidase isoenzyme mRNA expression was upregulated compared to normal mucosa.

Gene expression profiling of gliomas identified over-expressed lysyl oxidase isoenzyme as part of a molecular signature indicative of invasion, and associated with higher-grade tumors that are strongly correlated with poor patient survival. Lysyl oxidase isoenzyme protein expression was increased in glioblastoma and astrocytoma tissues, and in invasive U343 and U251 cultured astrocytoma cells.

In tissues, lysyl oxidase isoenzyme mRNA was upregulated in prostate cancer compared to benign prostatic hypertrophy, correlated with Gleason score, and associated with both high grade and short time to recurrence (Stewart, G. D., et al., Analysis of hypoxia-associated gene expression in prostate cancer: lysyl oxidase and glucose transporter-1 expression correlate with Gleason score. *Oncol Rep* 2008; 20: 1561-1567).

Up-regulation of lysyl oxidase isoenzyme mRNA expression was detected in renal cell carcinoma (RCC) cell lines and tissues. Clear cell RCC also demonstrated lysyl oxidase isoenzyme up-regulation. Indeed, LOX over expression appeared preferentially in clear cell RCC compared to mixed clear and granular, granular, oxyphil, tubulopapillary and chromophobe RCC/ontocytomas. In clear cell RCC, smoking was associated with allelic imbalances at chromosome 5q23.1, where the LOX gene is localized, and may involve duplication of the gene.

SiHa cervical cancer cells demonstrated increased invasion in vitro under hypoxic/anoxic conditions; this was repressed by inhibition of extracellular catalytically active lysyl oxidase activity by treatment with BAPN as well as LOX antisense oligos, LOX antibody, LOX shRNA or an extracellular copper chelator.

The scientific and patent literature describes small molecule inhibitors of lysyl oxidase isoenzymes and antibodies of LOX and LOXL2 with therapeutic effects in animal models of fibrosis and cancer metastasis. Some known MAO inhibitors also are reported to inhibit lysyl oxidase isoenzyme (e.g., the MAO-B inhibitor Mofegiline illustrated below). This inhibitor is a member of the haloallylamine family of MAO inhibitors; the halogen in Mofegiline is fluorine. Fluoroallylamine inhibitors are described in U.S. Pat. No. 4,454,158. There are issued patents claiming fluoroallylamines and chloroallylamines, for example MDL72274 (illustrated below) as inhibitors of lysyl oxidase (U.S. Pat. Nos. 4,943,593; 4,965,288; 5,021,456; 5,059,714; 5,182,297; 5,252,608). Many of the compounds claimed in these patents are also reported to be potent MAO-B and SSAO/VAP-1 inhibitors.

Mofegiline

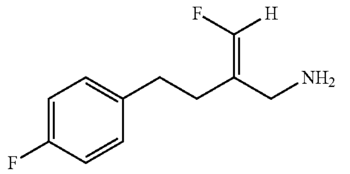

MDL72274

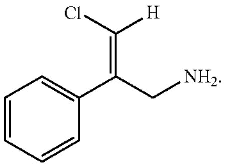

Additional fluoroallylamine inhibitors are described U.S. Pat. No. 4,699,928. Other examples structurally related to Mofegiline can be found in WO 2007/120528.

WO 2009/066152 discloses a family of 3-substituted 3-haloallylamines that are inhibitors of SSAO/VAP-1 useful as treatment for a variety of indications, including inflammatory disease.

WO 2017/136871 and WO 2017/136870 disclose haloallylamine indole and azaindole derivative inhibitors of lysyl oxidases and uses thereof.

WO 2018/048930, WO 2017/015221, WO 2017/003862, WO 2016/144702 and WO 2016/144703 disclose selective LOXL2 inhibitors.

WO 2020/024017 discloses haloallylamine sulfone derivative inhibitors of lysyl oxidases and uses thereof.

WO 2017/141049, WO 2019/073251 and WO 2020/099886 disclose families of methylamine and bridged homopiperazine derivatives respectively as lysyl oxidase inhibitors and their use in the treatment of cancer and diseases associated with fibrosis. WO 2003/097612, WO 2006/053555, and US 2008/0293936 disclose another class of lysyl oxidase inhibitors.

Antibodies to LOX and LOXL2 have been disclosed in US 2009/0053224 with methods to diagnostic and therapeutic applications. Anti-LOX and anti-LOXL2 antibodies can be used to identify and treat conditions such as a fibrotic condition, angiogenesis, or to prevent a transition from an epithelial cell state to a mesenchymal cell state: US 2011/0044907.

A family of chemical probes and uses for the detection of LOXL2, has been disclosed in WO 2018/048928. A novel antibody and its use in the detection of LOXL2 has been disclosed in WO2018/167132. An optical fluorescent probe for LOX activity in tissue is described in *Chem Sci.* 2015; 6: 4946-4953.

Whilst a number of small-molecule inhibitors for proteins of the LOX and LOXL family have been disclosed; some with potential therapeutic benefit, it is of particular interest to be able to quantify the extent of binding of such small-molecule inhibitors to specific members of the lysyl oxidase family of proteins in biological samples. Such information would be invaluable in understanding, for example, the relationship between the extent of inhibition of the protein of interest, and pharmacodynamics and/or pharmacokinetics. In order to properly interrogate small-molecule inhibitor-LOX/LOXL interactions for the purpose of generating useful quantitative analytical information, suitable techniques need to be developed. Thus, there is a clear need for highly selective and sensitive assays that can detect and measure LOX and LOXL proteins in a sample when present at low levels. For practical purposes, relating in part to routine application, such assays need to function using small quantities of biological sample.

The present invention provides for such assays that are capable of reliably, selectively and sensitively detecting LOX and LOXL in small quantities of biological matrices. Other aims and purposes of the current invention will become apparent in the detailed description.

SUMMARY

The present invention is directed to a selective LOX or LOXL assay capable of reliably and sensitively detecting LOX or LOXL in small quantities of biological sample, i.e. fluid sample of a patient or livestock. The inventive assays use bioprobe compounds of Formula W-L-Z, wherein W represents an affinity tag; L represents a linker; and Z represents a moiety that binds to an enzymatic pocket of the protein selected from a lysyl oxidase (LOX) protein and a lysyl oxidase-like (LOXL) protein. The invention further provides for the use of these bioprobe compounds in methods to determine the protein concentration of the LOX or LOXL protein in a sample and for methods for determining the extent of enzyme inhibition of a LOX or LOXL protein by a LOX or LOXL inhibitor.

A first aspect of the invention provides for a method for determining a measure of the concentration of a protein selected from a lysyl oxidase (LOX) protein and a lysyl oxidase-like (LOXL) protein in a sample containing or suspected of containing the protein, comprising: contacting the sample with (i) a capture antibody specific for the protein; (ii) a bioprobe of Formula W-L-Z, wherein W represents an affinity tag; L represents a linker; and Z represents a moiety that binds to the protein; wherein Z binds to an enzymatic pocket of the protein; and (iii) optionally a detection antibody specific for the protein.

A second aspect of the invention provides for a method for determining the extent of enzyme inhibition of a protein selected from a lysyl oxidase (LOX) protein and a lysyl oxidase-like (LOXL) protein by a LOX or LOXL inhibitor, the method comprising:

contacting a sample containing or suspected of containing the protein with (i) a capture antibody specific for the protein; a bioprobe of Formula W-L-Z, wherein W represents an affinity tag; L represents a linker; and Z represents a moiety that binds to the protein; wherein Z binds to the same enzymatic pocket of the protein as the LOX or LOXL inhibitor; and optionally a detection antibody specific for the protein.

A third aspect of the invention provides for a method for determining a measure of the concentration of a protein selected from a lysyl oxidase (LOX) protein and a lysyl oxidase-like (LOXL) protein in a sample containing or suspected of containing the protein, comprising (a) obtaining a sample containing or suspected of containing the protein from a subject;

(b) contacting the sample with:

(i) a capture antibody specific for the protein under conditions sufficient to form a protein/capture antibody complex; and (ii) a bioprobe of Formula W-L-Z, wherein W represents an affinity tag; L represents a linker; and Z represents a moiety that binds to the protein; wherein Z binds to an enzymatic pocket of the protein; and (c) performing an immunoassay to measure the total concentration of the protein in the sample.

A fourth aspect of the invention provides a method for determining the extent of enzyme inhibition of a protein selected from a lysyl oxidase (LOX) protein and a lysyl oxidase-like (LOXL) protein by a LOX or LOXL inhibitor, the method comprising:

(a) obtaining a sample containing or suspected of containing the protein from a subject;

(b) contacting the sample with a first amount of the LOX or LOXL inhibitor;

(c) contacting the sample with:

(i) a capture antibody specific for the protein under conditions sufficient to form a protein/capture antibody complex; and (ii) a bioprobe of Formula W-L-Z, wherein W represents an affinity tag; L represents a linker; and Z represents a moiety that binds to the protein; wherein Z binds to the same enzymatic pocket of the protein as the LOX or LOXL inhibitor;

(d) performing an immunoassay to measure the concentration of the protein with the enzymatic pocket occupied by the bioprobe.

A fifth aspect of the invention provides for a kit for determining a measure of the concentration of a protein selected from a lysyl oxidase (LOX) protein and a lysyl oxidase-like (LOXL) protein in a sample, the kit comprising a capture antibody specific for the protein, and a bioprobe of Formula W-L-Z, wherein W represents an affinity tag; L represents a linker; and Z represents a moiety that binds to the protein; wherein Z binds to an enzymatic pocket of the protein.

A sixth aspect of the invention provides for a kit for determining the extent of enzyme inhibtion of a protein selected from a lysyl oxidase (LOX) protein or lysyl oxidase-like (LOXL) protein by a LOX or LOXL inhibitor, the kit comprising:

a capture antibody specific for the protein, a bioprobe of Formula W-L-Z, wherein W represents an affinity tag; L represents a linker; and Z represents a moiety that binds to the protein; wherein Z binds to an enzymatic pocket of the protein, and a detection antibody specific for the protein.

A seventh aspect of the invention provides for a bioprobe of formula W-L-Z, wherein W represents an affinity tag; L represents a linker; and Z represents a moiety that binds to a protein selected from a lysyl oxidase (LOX) protein or lysyl oxidase-like (LOXL) protein, wherein Z is a moiety of Formula I:

Formula I

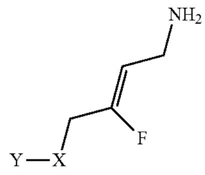

wherein:

X is absent, $CH_2$, O, S, S(O) or $SO_2$;

Y is aryl or heteroaryl; wherein each Y is optionally substituted by one or more $R^1$ and wherein Y contains an attachment point for L;

each $R^1$ is independently selected from the group consisting of halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^2R^3$, —C(O)$OR^4$, —C(O)$NR^2R^3$, —$NR^2$C(O)$R^5$, —S($O_2$)$NR^2R^3$, —$NR^2$S($O_2$)$R^5$, —S(O)$R^5$, —S($O_2$)$R^5$, aryl, —$CH_2$-aryl, —CH($OR^4$)-aryl, heteroaryl and —$CH_2$-heteroaryl; wherein each $C_{1-6}$alkyl is a straight or branched chain alkyl; and wherein each $C_{1-6}$alkyl, $C_{3-7}$cycloalkyl, aryl and heteroaryl is optionally substituted by one or more substituents selected from the group consisting of halogen, —OH, —$C_{1-3}$ alkyl, —O—$C_{1-3}$alkyl, —S($O_2$)$NR^2R^3$, —$CF_3$, —$CH_2CF_3$, and —O—$CF_3$;

$R^2$ and $R^3$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$; or $R^2$ and $R^3$ when attached to the same nitrogen atom are combined to form a 5- to 7-membered ring having from 0 to 2 additional heteroatoms as ring members;

$R^4$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$ alkyl, —$CF_3$, —$CH_2CF_3$, and —O—$CF_3$; and $R^5$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically states to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein the term "bioprobe", or biological probe, refers to a self-contained integrated molecular construct comprising a biological recognition moiety (or protein binding moiety), which is in direct spatial contact with a detection moiety and can be used to provide specific quantifiable analytical information regarding the presence or concentration of biological molecules of interest. The bioprobes of the present invention have a slow or no off-rate during the time course of the immunoassays described herein. In other words, the bioprobe remains bound to the enzymatic pocket of the LOX or LOXL enzyme during the time course of the immunoassay. The bioprobe may be an activity based probe.

As used herein, the term "moiety" refers to a specific segment or functional group of a molecule. Chemical moieties are often recognized as chemical entities embedded in or appended to a molecule.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies which specifically bind the biological molecule.

As used herein the term "capture antibody" refers to an antibody that is used as the capture antibody in the assays herein. The capture antibody as used herein binds to the LOX or LOXL protein that is being detected and/or measured in the sample.

As used herein, the term "specific for" refers to binding specificity. Accordingly, a molecule "specific for" another different molecule is one with binding specificity for that different molecule. For example, if molecule A is "specific for" molecule B, molecule A has the capacity to discriminate between molecule B and any other number of potential alternative binding partners. Accordingly, when exposed to a plurality of different but equally accessible molecules as potential binding partners, molecule A may selectively bind to molecule B and other alternative potential binding partners may remain substantially unbound by the reagent. In general, molecule A will preferentially bind to molecule B at least 10-fold, preferably 50-fold, more preferably 100-fold, and most preferably greater than 100-fold more frequently than other potential binding partners. Molecule A may be capable of binding to molecules that are not molecule B at a weak, yet detectable level. This is commonly known as background binding and is readily discernible from molecule B-specific binding, for example, by use of an appropriate control.

As used herein the term "immunoassay" may be referred to interchangeably as an immune-based assay or immunobased assay. In general, an immunoassay detects the presence and/or concentration (level) of a molecule (e.g., LOX or LOXL protein), in a sample using an agent that binds to the molecule, such as an antibody. Examples of immunoassays include Western blots, enzyme linked immunosorbent assays (ELISAs), lateral flow assay, radioimmunoassays, electrochemiluminescence-based detection assays, magnetic immunoassays, and related techniques. In some embodiments, the immunoassay is an ELISA assay. In some embodiments, the immunoassay is a sandwich ELISA assay. In some embodiments, the immunoassay is a digital ELISA.

As used herein, the term "alkyl" includes within its meaning monovalent ("alkyl") and divalent ("alkylene") straight chain or branched chain saturated hydrocarbon radicals having from 1 to 6 carbon atoms, e.g., 1, 2, 3, 4, 5 or 6 carbon atoms. The straight chain or branched alkyl group is attached at any available point to produce a stable compound. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" or "alkyloxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "cycloalkyl" as used herein includes within its meaning monovalent ("cycloalkyl") and divalent ("cycloalkylene") saturated, monocyclic, bicyclic, polycyclic or fused analogs. In the context of the present disclosure the cycloalkyl group may have from 3 to 10 carbon atoms. In the context of the present disclosure the cycloalkyl group may also have from 3 to 7 carbon atoms. A fused analog of a cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, adamantyl and the like.

The term "aryl" or variants such as "arylene" as used herein refers to monovalent ("aryl") and divalent ("arylene") single, polynuclear, conjugated and fused analogs of aromatic hydrocarbons having from 6 to 10 carbon atoms. A fused analog of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,3-benzodioxolyl, 1,4-benzodioxanyl, and the like. A "substituted aryl" is an aryl that is independently substituted, with one or more, preferably 1, 2 or 3 substituents, attached at any available atom to produce a stable compound.

The term "alkylaryl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of alkylaryl groups include benzyl.

The term "heteroaryl" and variants such as "heteroaromatic group" or "heteroarylene" as used herein, includes within its meaning monovalent ("heteroaryl") and divalent ("heteroarylene"), single, polynuclear, conjugated and fused heteroaromatic radicals having from 5 to 10 atoms, wherein 1 to 4 ring atoms, or 1 to 2 ring atoms are heteroatoms independently selected from O, N, NH and S. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. The heteroaromatic group may be $C_{5-8}$ heteroaromatic. A fused analog of heteroaryl means a heteroaryl group fused to a monocyclic cycloalkyl or monocyclic heterocyclyl group in which the point of attachment is on the aromatic portion. Examples of heteroaryl groups and fused analogs thereof include pyrazolyl, pyridyl, oxazolyl, oxadiazolyl, thiadiazolyl, tetrazolyl, triazinyl, thienyl, benzoxazolyl, benzothiazolyl, benzimidazolyl, benzofuranyl, benzothiophenyl, furo(2,3-b)pyridyl, quinolyl, indolyl, isoquinolyl, pyrimidinyl, pyridazinyl, pyrazinyl, 2,2'-bipyridyl, phenanthrolinyl, quinolinyl, isoquinolinyl, imidazolinyl, thiazolinyl, pyrrolyl, furanyl, thiophenyl, oxazolyl, isoxazolyl, isothiazolyl, triazolyl, and the like. "Nitrogen containing heteroaryl" refers to heteroaryl wherein any heteroatoms are N. A "substituted heteroaryl" is a heteroaryl that is independently substituted, with one or more, preferably 1, 2 or 3 substituents, attached at any available atom to produce a stable compound.

The term "heterocyclyl" and variants such as "heterocycloalkyl" as used herein, includes within its meaning monovalent ("heterocyclyl") and divalent ("heterocyclylene"), saturated, monocyclic, bicyclic, polycyclic or fused hydrocarbon radicals having from 3 to 10 ring atoms, wherein from 1 to 5, or from 1 to 3, ring atoms are heteroatoms independently selected from O, N, NH, or S, in which the point of attachment may be carbon or nitrogen. A fused analog of heterocyclyl means a monocyclic heterocycle fused to an aryl or heteroaryl group in which the point of attachment is on the non-aromatic portion. The heterocyclyl group may be $C_{3-8}$ heterocyclyl. The heterocycloalkyl group may be $C_{3-6}$ heterocyclyl. The heterocyclyl group may be $C_{3-5}$ heterocyclyl. Examples of heterocyclyl groups and fused analogs thereof include aziridinyl, pyrrolidinyl, thiazolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, quinuclidinyl, azetidinyl, morpholinyl, tetrahydrothiophenyl, tetrahydrofuranyl, tetrahydropyranyl, and the like. The term also includes partially unsaturated monocyclic rings that may be regarded as not aromatic, such as 2- or 4-pyridones attached through the nitrogen or N-substituted uracils.

The term "halogen" or variants such as "halide" or "halo" as used herein refers to fluorine, chlorine, bromine and iodine.

The term "heteroatom" or variants such as "hetero-" or "heterogroup" as used herein refers to O, N, NH and S.

In general, "substituted" refers to an organic group as defined herein (e.g., an alkyl group) in which one or more bonds to a hydrogen atom contained therein are replaced by a bond to non-hydrogen atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, hydroxyl, hydroxyalkyl, alkoxy, thioalkoxy, alkenyloxy, haloalkoxy, haloalkenyloxy, $NO_2$, NH(alkyl), $N(alkyl)_2$, alkylamino, dialkylamino, alkenylamine, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, phosphorus-containing groups such as phosphono and phosphinyl, aryl, heteroaryl, alkylaryl, aralkyl, alkylheteroaryl, cyano, $CO_2H$, $CO_2$alkyl, $C(O)NH_2$, —C(O)NH(alkyl), and —$C(O)N(alkyl)_2$. Preferred substituents include halogen, $C_1$-$C_6$alkyl, $C_2$-$C_6$alkenyl, $C_1$-$C_6$haloalkyl, $C_1$-$C_6$alkoxy, hydroxy($C_{1-6}$)alkyl, $C_3$-$C_6$cycloalkyl, C(O)H, C(O)OH, NHC(O)H, NHC(O)$C_1$-$C_4$alkyl, C(O)$C_1$-$C_4$alkyl, $NH_2$, NH$C_1$-$C_4$alkyl, N($C_1$-$C_4$alkyl)$_2$, $NO_2$, OH and CN. Particularly preferred substituents include $C_{1-3}$alkyl, $C_{1-3}$alkoxy, halogen, OH, hydroxy($C_{1-3}$)alkyl (e.g. $CH_2OH$), C(O)$C_1$-$C_4$alkyl (e.g. $C(O)CH_3$), and $C_{1-3}$haloalkyl (e.g. $CF_3$, $CH_2CF_3$). Further preferred optional substituents include halogen, —OH, —$C_{1-3}$alkyl, —O—$C_{1-3}$alkyl, —$CF_3$, —$CH_2CF_3$, and —O—$CF_3$.

The present invention includes within its scope all stereoisomeric and isomeric forms of the compounds disclosed herein, including all diastereomeric isomers, racemates, enantiomers and mixtures thereof. It is also understood that the compounds described by Formula I may be present as E and Z isomers, also known as cis and trans isomers. Thus, the present disclosure should be understood to include, for example, E, Z, cis, trans, (R), (S), (L), (D), (+), and/or (−) forms of the compounds, as appropriate in each case. Where a structure has no specific stereoisomerism indicated, it should be understood that any and all possible isomers are encompassed. Compounds of the present invention embrace all conformational isomers. Compounds of the present invention may also exist in one or more tautomeric forms, including both single tautomers and mixtures of tautomers. Also included in the scope of the present invention are all polymorphs and crystal forms of the compounds disclosed herein.

The present invention includes within its scope isotopes of different atoms. Any atom not specifically designated as a particular isotope is meant to represent any stable isotope of that atom. Thus, the present disclosure should be understood to include the deuterium isotope of hydrogen.

All references cited in this application are specifically incorporated by cross-reference in their entirety. Reference to any such documents should not be construed as an admission that the document forms part of the common general knowledge or is prior art.

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

As used herein, the term "subject" includes humans and individuals of any mammalian species of social, economic or research importance including, but not limited to, members of the genus ovine, bovine, equine, porcine, feline, canine, primates, and rodents. In one embodiment, the mammal is a human.

BRIEF DESCRIPTION OF THE FIGURES

FIG. 2A) 3.12 μg/mL of Antibody A (AF2639) was used as the capture antibody; recombinant human LOXL2 (rhLOXL2) was used as the antigen and 5 μg/mL Antibody B (Fitzgerald 70R-12876) was used as the detection antibody. Concentration of rhLOXL2 ranges from 0-1250 ng/mL. FIG. 2B) 1.56 μg/mL of Antibody B was used as the capture antibody, rhLOXL2 was used as the antigen and 5 μg/mL Antibody A was used as the detection antibody. Concentration of rhLOXL2 ranges from 0-1250 ng/mL.

FIG. 3A) Antibody A (AF2639) was used as the capture antibody, rhLOXL2 was used as the antigen and 80 nM of bioprobe Compound 1-1 was used as the detection. FIG. 3B) Antibody B (Fitzgerald 70R-12876) was used as the capture, rhLOXL2 was used as the antigen and 80 nM of the bioprobe Compound 1-1 was used as the detection.

FIG. 10A shows that Antibody D (used at 0.5 μg/mL) is specific to human recombinant LOX (rhLOX, 20 ng/lane) over other LOXL family members and can detect the native mature LOX (Human and bovine); Lane 1: Ladder; Lane 2: rhLOX; Lane 3: rhLOXL1; Lane 4: hrLOXL2; Lane 5: hrLOXL3; Lane 6: hrLOXL4; Lane 7: NHLF conditioned media; Lane 8: NHLF stimulated with TGFB (10 ng/mL) conditioned media; Lane 9: Bovine aorta lysate; Lane 10: Normal Mouse lung lysate; Lane 11: Fibrotic Mouse lung lysate. FIG. 10B shows that Antibody D (used at 0.5 μg/mL) is specific to native LOX as the NHLF LOX knockdown conditioned media and cell lysate is a lower detection than the control siRNA; Lane 1: Ladder; Lane 2: Bovine aorta lysate; Lane 3: NHLF Conditioned Media; Lane 4: NHLF stimulated with TGFB (10 ng/mL) conditioned media; Lane 5: Control SiRNA: NHLF stimulated with TGFB (10 ng/mL) conditioned media; Lane 6: LOX SiRNA: NHLF stimulated with TGFB (10 ng/mL) conditioned media; Lane 7: NHLF cell lysate; Lane 8: NHLF stimulated with TGFB (10 ng/mL) cell lysate; Lane 9: Control SiRNA: NHLF stimulated with TGFB (10 ng/mL) cell lysate; Lane 10: LOX SiRNA: NHLF stimulated with TGFB (10 ng/mL) cell lysate; Lane 11: Bovine aorta lysate. FIG. 10C demonstrates that Antibody E (used at 0.5 μg/mL) is specific to native LOX as the NHLF LOX knockdown conditioned media and cell lysate is a lower detection than the control siRNA; Lane 1: Ladder; Lane 2: rhLOX; Lane 3: rhLOXL1; Lane 4: hrLOXL2; Lane 5: hrLOXL3; Lane 6: hrLOXL4; Lane 7: Human skin lysate; Lane 8: Mouse skin lysate; Lane 9: Rat skin lysate; Lane 10: Control SiRNA: NHLF stimulated with TGFB (10 ng/mL) conditioned media; Lane 11: LOX SiRNA: NHLF stimulated with TGFB (10 ng/mL) conditioned media; Lane 12: Bovine aorta lysate; Lane 13: Mouse fibroblast cells stimulated with TGFB (10 ng/mL) conditioned media; Lane 14: Mouse fibroblast cells conditioned media.

DETAILED DESCRIPTION

Figure 1A:
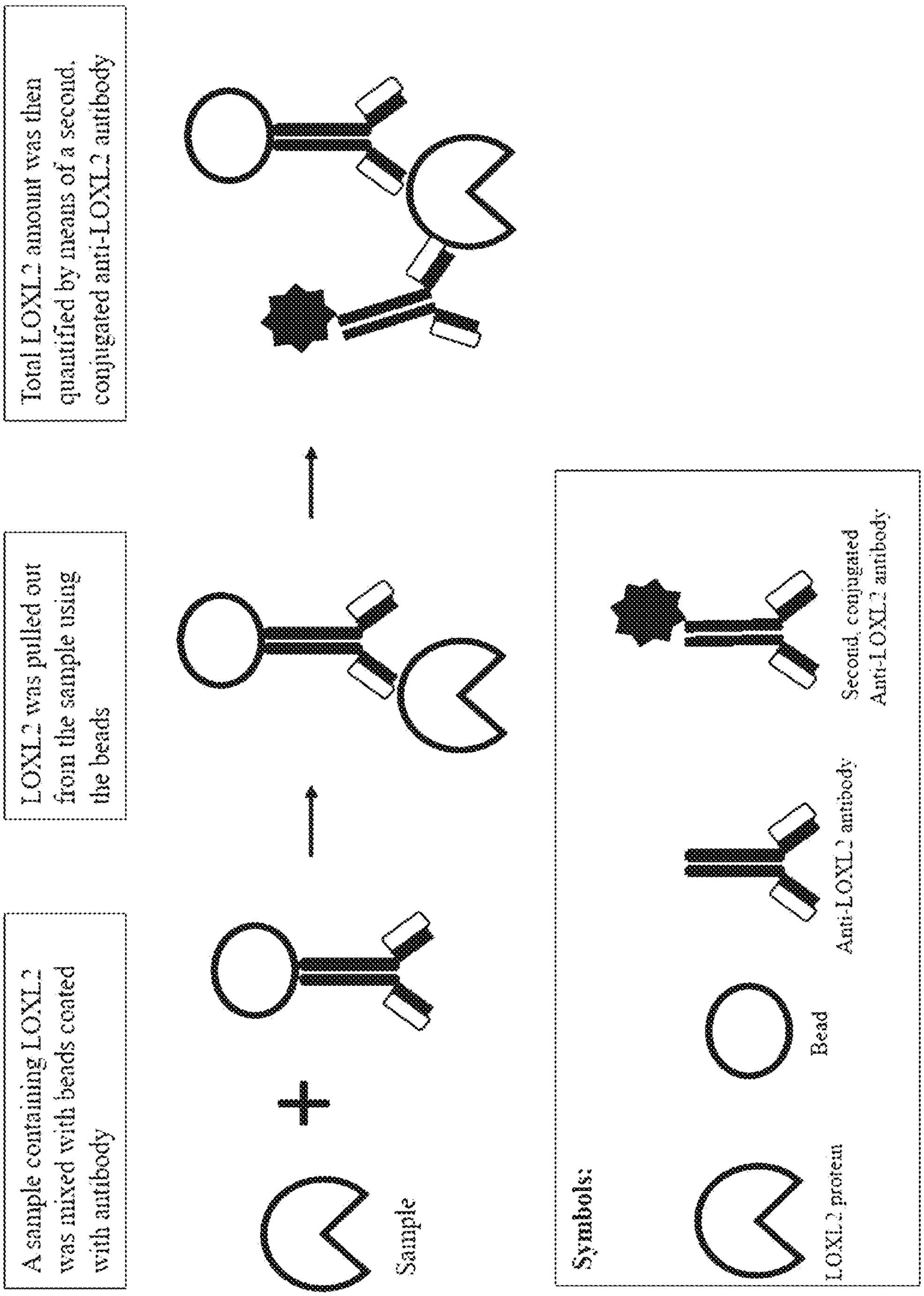
FIG. 1A illustrates schematically the general strategy for the use of a bead/antibody complex to capture, isolate and detect LOXL2 enzyme from biological samples.

The present invention relates to bioprobe compounds of Formula W-L-Z, wherein W represents an affinity tag; L represents a linker; and Z represents a moiety that binds to an enzymatic pocket of a protein selected from a lysyl oxidase (LOX) protein and a lysyl oxidase-like (LOXL) protein. The four lysyl oxidase-like proteins (LOXL1, LOXL2, LOXL3 and LOXL4) are referred to collectively as LOXL proteins for the purposes of the present disclosure. The invention further relates to the use of these bioprobe compounds in methods to sensitively determine the protein concentration of the LOX or LOXL protein in a sample and for methods for determining the extent of enzyme inhibition of a LOX or LOXL protein by a LOX or LOXL inhibitor.

Methods of the Invention

The methods of the present invention allow for the sensitive detection of LOX or LOXL proteins in a sample. The Applicant has developed an assay to sensitively determine the measure of concentration of a LOX or LOXL protein in a sample. In cetain embodiments of the methods of the present invention the method for detecting the LOX or LOXL protein in a sample is an enzyme-linked immunosorbent assay (ELISA).

The invention provides a method for detecting in a sample the presence or absence of a LOX or LOXL protein.

The Applicant has identified, for use in the methods of the present invention, a capture antibody specific for the LOX or LOXL protein, a detection antibody specific for the LOX or LOXL protein and a bioprobe of Formula W-L-Z, wherein W represents an affinity tag; L represents a linker; and Z represents a moiety that binds to the protein; wherein Z binds to an enzymatic pocket of the protein. In one embodiment, the Applicant has identified the capture antibody and the detection antibody for use in an immunoassay to detect a protein selected from a LOX or LOXL protein.

In one embodiment of the methods of the present invention the LOX or LOXL protein in a sample is detected through performing an immunoassay on a sample that has been contacted with a capture antibody and a detection antibody under conditions suitable to form a protein/antibody complex, with the LOX or LOXL protein simultaneously binding with the detection antidody.

In an alternative embodiment of the methods of the present invention the LOX or LOXL protein in a sample is detected through performing an immunoassay on a sample that has been contacted with a capture antibody and a bioprobe compound of Formula W-L-Z under conditions suitable to form a protein/antibody complex, with the bioprobe compound simultaneously binding to the enzymatic pocket of the LOX or LOXL protein. In this alternative embodiment the bioprobe, labelled with an affinity tag, is used in place of the detection antibody.

In one aspect, the invention provides for a method for determining a measure of the concentration of a protein selected from a lysyl oxidase (LOX) protein and a lysyl oxidase-like (LOXL) protein in a sample containing or suspected of containing the protein, comprising:

contacting the sample with (i) a capture antibody specific for the protein; (ii) a bioprobe of Formula W-L-Z, wherein W represents an affinity tag; L represents a linker; and Z represents a moiety that binds to the protein; wherein Z binds to an enzymatic pocket of the protein; and (iii) optionally a detection antibody specific for the protein In one embodiment of the methods of the present invention the capture antibody and the detection antibody are selected so as to provide the strongest signal to noise ratio over a large protein concentration range. A strong signal to noise ratio is indicative of a highly sensitive assay.

In one embodiment of the methods of the present invention the capture antibody, the detection antibody and the bioprobe are selected so that the binding of each of the capture antibody, the detection antibody and the bioprobe to the LOX or LOXL protein do not interfere with each other. In one embodiment of the methods of the present invention the binding of the bioprobe to the enzymatic pocket of the LOX or LOXL protein does not interfere with the immunoassay to measure the concentration of the protein, that is, the capture antibody, the detection antibody and the bioprobe can all simultaneously bind to the LOX or LOXL protein. In another embodiment of the methods of the present invention the binding of the capture antibody to the protein does not interfere with the binding of the bioprobe with the enzymatic pocket of the protein.

In one embodiment of the invention the LOX or LOXL protein is selected from the group consisting of LOX, LOXL1, LOXL2, LOXL3 and LOXL4 protein. In another embodiment of the invention the LOX or LOXL protein is LOX or LOXL2. In another embodiment of the invention, the LOX or LOXL protein is LOXL2. In another embodiment of the invention, the LOX or LOXL protein is LOX.

A person skilled in the art will appreciate that through the selection of capture antibodies and detection antibodies specific for a particular protein selected from the group consisting of LOX, LOXL1, LOXL2, LOXL3 and LOXL4 an assay can be developed for each of the LOX and LOXL family members.

One embodiment of the present invention provides for a method for detecting and determining the protein concentration of LOXL2 in a sample, comprising contacting a sample with a capture antibody specific for LOXL2 and a detection antibody specific for LOXL2, and preforming an immunoassay to detect the LOXL2 in the sample. In one embodiment, the concentration of the LOXL2 in the sample is determined. In one embodiment, the capture antibody specific for LOXL2 is AF2639. In one embodiment, the detection antibody specific for LOXL2 is Fitzgerald 70R-12876.

One embodiment of the present invention provides for a method for detecting and determining the protein concentration of LOX in a sample, comprising contacting a sample with a capture antibody specific for LOX and a detection antibody specific for LOX, and preforming an immunoassay to detect the LOX in the sample. In one embodiment, the concentration of the LOX in the sample is determined. In one embodiment, the capture antibody specific for LOX is L4794. In one embodiment, the detection antibody specific for LOX is ab219369.

An antibody "specific for" a target molecule is an antibody with the capacity to discriminate between a target molecule and any other number of potential alternative binding partners. Accordingly, when exposed to a plurality of different but equally accessible molecules as potential binding partners, an antibody specific for a target molecule will selectively bind to the target molecule and other alternative potential binding partners will remain substantially unbound by the antibody. In general, an antibody specific for a target molecule will preferentially bind to the target molecule at least 10-fold, preferably 50-fold, more preferably 100-fold, and most preferably greater than 100-fold more frequently than other potential binding partners that are not target molecules. An antibody specific for a target molecule may be capable of binding to other non-target molecules at a weak, yet detectable level. This is commonly known as background binding and is readily discernible from target molecule-specific binding, for example, by use of an appropriate control.

The antibody may be derived from any source. In one embodiment, the antibody is commercially available.

The high affinity of the capture antibody for the LOX or LOXL protein allows for a sensitive assay.

The capture antibody can be immobilized using conventional techniques, on the surface of a support. Suitable solid supports include synthetic polymer supports such as polypropylene, polystyrene, substituted polystyrene, polylacrylamides, polyamides, polyvinylchloride, glass beads, magnetic beads, agarose, or nitrocellulose. In one embodiment, the capture antibody is attached to a bead. In another embodiment, the capture antibody is attached to a paramagnetic bead.

The detection antibody may be conjugated to biotin or streptavidin. In one embodiment, the detection antibody is conjugated to biotin. In one embodiment, the biotinylated antibody is allowed to react with a streptavidin-horseradish peroxidase complex. The detection antibody can then be detected by fluorescence.

The sample may be a biological sample and may be derived from a healthy individual, or an individual suffering from a particular disease or condition. The biological sample may be collected from an individual and used directly in the methods of the invention. Alternatively, the biological sample may be processed prior to use in the methods of the invention. For example, the biological sample may be purified, concentrated, separated into various components, or otherwise modified prior to use.

The biological sample may be from any tissue or fluid from an individual. Non-limiting examples of biological samples include tissue samples (for example, connective tissue, muscle tissue, nervous tissue, or epithelial tissue), whole blood or a component thereof (e.g. plasma, serum), urine, saliva, lymph, bile fluid, sputum, tears, cerebrospinal fluid, bronchioalveolar lavage fluid, synovial fluid, semen, ascitic tumour fluid, breast milk and pus. In one embodiment, the tissue sample is a tissue sample obtained from a biosopy. The tissue sample may be derived from a healthly individual or from an individual suffering or suspected to be suffering from a particular disease or condition.

In one embodiment, the sample is a bodily fluid. In one embodiment, the bodily fluid is blood or a blood component.

In general, the sample is diluted to an appropriate level using a suitable buffer. The degree of sample dilution and selection of an appropriate buffer will depend on factors such as the nature of the sample under analysis and the type of support and capture antibody utilised in the assay. These factors can be addressed by those of ordinary skill in the art without inventive effort.

In the methods of the present invention the sample containing or suspected of containing the LOX or LOXL protein is contacted with the capture antibody specific for the protein under conditions suitable to form a protein/capture antibody complex. The sample is generally incubated under conditions suitable to maximise sensitivity of the assay and to minimize dissociation. The incubation may be performed at a generally constant temperature, ranging from about 0° C. to about 40° C., and preferably ranging from about 25° C. to about 37° C. The pH of the incubation mixture will generally be in the range of about 4 to about 10, preferably in the range of about 6 to about 9, and more preferably in the range of about 7 to about 8. In one embodiment, the incubation mixture is at pH 7.4. Various buffers may be employed to achieve and maintain the target pH during the incubation, non-limiting examples of which include Tris-phosphate, Tris-HCl borate, phosphate, acetate and carbonate. The incubation time is generally associated with the temperature, and will typically be less than about 12 hours to avoid non-specific binding. Preferably, the incubation time is from about 0.5 hours to about 3 hours, and more preferably from about 0.5 hours to about 1.5 hours at room temperature.

The protein/capture antibody complex can be isolated from other unrelated proteins in the sample. In one embodiment, the capture antibody is attached to a bead. The beads can be separated from the matrix, for example by means of magnetic separation, flow cytometry, centrifugation, density or gravity.

In one embodiment of the methods of the present invention, the capture antibody is combined with the sample containing or suspected of containing the LOX or LOXL protein and the detection antibody, and the target LOX or LOXL protein is simultaneously captured by the capture antibody and binds with the detection antibody.

In one embodiment of the methods of the present invention the protein/capture antibody complex bound to the detection antibody labelled with biotin is washed and then mixed with a streptavidin-β-galactosidase (SβG) complex. The SβG binds to the biotinylated detector antibodies, resulting in enzyme labelling of the captured target LOX or LOXL protein. In one embodiment, the enzyme labelled captured target is contacted with a substrate for the enzyme, wherein the enzyme converts the substrate to a molecule that releases a detectable signal. In one embodiment, the substrate for the enzyme is resorufin β-D-galactopyranoside (RGP). If the target LOX or LOXL protein has been captured and labelled, β-galactosidase hydrolyzes the RGP substrate into a fluorescent product that provides a signal for measurement.

Detection and quantitative measurements may be conducted based on the signal derived from the detection reagent(s) compared to background signal derived from control samples. A standard curve may be generated to assist in determining the concentration of the target LOX or LOXL protein molecules in a given sample.

In an alternative embodiment of the methods of the present invention, the capture antibody is combined with the sample containing or suspected of containing the LOX or LOXL protein and a bioprobe of formula W-L-Z, wherein W represents an affinity tag; L represents a linker; and Z represents a moiety that binds to the protein; wherein Z binds to an enzymatic pocket of the protein. The capture antibody, sample and bioprobe are combined under conditions such that the LOX or LOXL protein in the sample is captured by the capture antibody and the bioprobe simultaneously binds to the enzymatic pocket of the LOX or LOXL protein. In a preferred embodiment, the bioprobe is labelled with at least one biotin and the protein/capture antibody complex, with the bioprobe bound to the protein, is washed and then mixed with a streptavidin-β-galactosidase (SβG) complex. The SβG binds to the biotinylated bioprobe, resulting in enzyme labelling of the captured target LOX or LOXL protein. In one embodiment, the enzyme labelled captured target is contacted with a substrate for the enzyme, wherein the enzyme converts the substrate to a molecule that releases a detectable signal. In one embodiment, the substrate for the enzyme is resorufin β-D-galactopyranoside (RGP). If the target LOX or LOXL protein has been captured and labelled, β-galactosidase hydrolyzes the RGP substrate into a fluorescent product that provides a signal for measurement.

In an alternative embodiment of the methods of the present invention the sample containing or suspected of containing the LOX or LOXL protein is combined with a bioprobe of formula W-L-Z, wherein W represents an affinity tag; L represents a linker; and Z represents a moiety that binds to the protein; wherein Z binds to an enzymatic pocket of the protein. The sample and bioprobe are combined under conditions such that the bioprobe binds to the enzymatic pocket of the LOX or LOXL protein. In some embodiments, where the bioprobe is labelled with one or more biotin moieties, the bioprobe and LOX or LOXL protein complex is captured by the addition of streptavidin-coated beads. Subsequent addition of a detection antibody allows for the determination of the concentration of the LOX or LOXL protein bound to bioprobe. It will be understood by a person skilled in the art that further variations of this embodiment are possible. For example, the biotin labelled bioprobe could first be added to the streptavidin-coated beads before addition of the sample containing or suspected of containing the LOX or LOXL protein.

In one aspect, the present invention provides for a method for determining a measure of the concentration of a protein selected from a lysyl oxidase (LOX) protein and a lysyl oxidase-like (LOXL) protein in a sample containing or suspected of containing the protein, comprising:

(a) obtaining a sample containing or suspected of containing the protein from a subject;

(b) contacting the sample with:

(i) a capture antibody specific for the protein under conditions sufficient to form a protein/capture antibody complex; and (ii) a bioprobe of Formula W-L-Z, wherein W represents an affinity tag; L represents a linker; and Z represents a moiety that binds to the protein; wherein Z binds to an enzymatic pocket of the protein; and (c) performing an immunoassay to measure the total concentration of the protein in the sample.

In one embodiment, the capture antibody and the bioprobe are added to the sample at the same time so that the LOX or LOXL proteins are captured by the capture antibody and simulataneously bind to the bioprobe.

In another embodiment, the sample is first contacted with a capture antibody specific for the protein under conditions sufficient to form a protein/capture antibody complex and then the bioprobe is subsequently added to the sample.

In a further embodiment, the bioprobe is first added to the sample, followed by the capture antibody specific for the protein.

The methods of the present invention allow for the determination of the amount of enzymatically active LOX or LOXL protein within a sample. In one embodiment, the biological sample is incubated with the capture antibody and the protein/capture antibody complex is then isolated from other unrelated proteins in the sample. Addition of a detection antibody and performing the immunoassay as described above allows for the concentration of the LOX or LOXL protein in the sample to be calculated. Both enzymatically active and inactive protein can be measured with the capture antibody and detection antibody immunoassay. In the alternative method, the bioprobe is used in place of the detection antibody. The bioprobe specifically binds to the enzymatically active site of the LOX or LOXL protein. If the LOX or LOXL protein is not enzymatically active, the bioprobe will not bind to the protein. In this way, only the concentration of the enzymatically active LOX or LOXL protein is measured with the capture antibody and bioprobe immunoassay.

The methods of the present invention can be used in an enzyme inhibition assay. In the enzyme inhibition assay a LOX or LOXL inhibitor is contacted with the sample containing the LOX or LOXL protein. The LOX or LOXL inhibitor binds to the same enzymatic pocket of the enzyme as the bioprobe. Accordingly, if a bioprobe is added to a sample that has been "pre-dosed" with a LOX or LOXL inhibitor, the bioprobe will only bind to the LOX or LOXL protein that has not already been bound to a LOX or LOXL inhibitor. In one embodiment, the LOX or LOXL inhibitor is administered to a patient before a sample is taken from the patient. In another embodiment, the LOX or LOXL inhibitor is contacted with a sample containing or suspected of containing the LOX or LOXL protein ex vivo. An immunoassay can be performed by exposing the sample that has been contacted with the LOX or LOXL inhibitor to the capture antibody and the detection antibody in order to determine the concentration of the LOX or LOXL protein in the sample. A second immunoassay can be performed by exposing the sample that has been contacted with the LOX or LOXL inhibitor to the capture antibody and the bioprobe. The results of these assays will allow for determination of the extent of enzyme inhibition of the LOX or LOXL protein by the LOX or LOXL inhibitor. In order to preform these two immunoassays, the sample that has been exposed to the LOX or LOXL inhibitor can be split into Sample A and Sample B. In one embodiment, Sample A can be used to determine the overall concentration of the LOX or LOXL protein in the sample. In one embodiment, Sample B can be used to determine the fraction of the LOX or LOXL protein occupied by the LOX or LOXL inhibitor. Together these results will provide the extent of enzyme inhibition of the LOX or LOXL protein by the LOX or LOXL inhibitor. It will be understood that the sample can be split at any stage to allow for the two immunoassays to be performed.

In one embodiment, the detection antibody is labelled with a different label to the bioprobe so that sample does not need to be split, with the LOX or LOXL protein concentration and the fraction of the LOX or LOXL protein occupied by the LOX or LOXL inhibitor being determined from a single immunoassay, for example, through the detection of the fluorescence at different wavelengths from two distinct fluorescent labels. In another embodiment both the detector antibody and the bioprobe are labelled with biotin, so that the sample is split to determine either the LOX or LOXL protein concentration (with the detection antibody) or the fraction of the LOX or LOXL protein occupied by the LOX or LOXL inhibitor (with the biotinylated bioprobe).

One aspect of the present invention provides for a method for determining the extent of enzyme inhibition of a protein selected from a lysyl oxidase (LOX) protein and a lysyl oxidase-like (LOXL) protein by a LOX or LOXL inhibitor, the method comprising:

(a) obtaining a sample containing or suspected of containing the protein from a subject;

(b) contacting the sample with a first amount of the LOX or LOXL inhibitor;

(c) contacting the sample with:

(i) a capture antibody specific for the protein with the sample under conditions sufficient to form a protein/capture antibody complex; and (ii) a bioprobe of Formula W-L-Z, wherein W represents an affinity tag; L represents a linker; and Z represents a moiety that binds to the protein; wherein Z binds to the same enzymatic pocket of the protein as the LOX or LOXL inhibitor; and (d) performing an immunoassay to measure the concentration of the protein with the enzymatic pocket occupied by the bioprobe.

In one embodiment of step (c) the capture antibody and the bioprobe are added to the sample at the same time so that the LOX or LOXL proteins are captured by the capture antibody and simulataneously bind to the bioprobe. In another embodiment of step (c) the sample is first contacted with a capture antibody specific for the protein under conditions sufficient to form a protein/capture antibody complex and then the bioprobe is subsequently added to the sample. In a further embodiment of step (c) the bioprobe is first added to the sample, followed by the capture antibody.

In order to determine the extent of enzyme inhibition of a LOX or LOXL protein by a LOX or LOXL inhibitor, it is necessary to know the total concentration of the protein in the sample. It will be understood that this can be determined by performing a second immunoassay as described above to determine the protein concentration. For example, a sample could be taken before being contacted with the LOX or LOXL inhibitor and be contacted with a capture antibody specific for the protein and a bioprobe of formula W-L-Z as defined above. Alternatively, the protein concentration of the sample could be determined through an immunoassay where the sample is contacted with a capture antibody and a detection antibody, each specific for the LOX or LOXL protein. In other words, the total protein concentration of the sample can be determined In one embodiment of the method to determine the extent of enzyme inhibition, the method further comprises determining the measure of the concentration of the protein in the sample from step (a) by the methods described above.

In another embodiment of the method to determine the extent of enzyme inhibition, the method further comprises determining the concentration of the protein in the sample from step (a) or step (b) by:

(e) contacting the sample with a capture antibody specific for the protein under conditions sufficient to form a protein/capture antibody complex; and (f) addition of a detection antibody specific for the protein to the sample, then performing a second immunoassay to measure the total concentration of the protein in the sample.

In one embodiment of the methods of the present invention, the binding of the LOX or LOXL inhibitor to the enzymatic pocket of the protein does not interfere with the immunoassay to measure the concentration of the protein. In another embodiment of the methods of the present invention the binding of the bioprobe to the enzymatic pocket of the protein does not interfere with the immunoassay to measure the concentration of the protein. In a further embodiment the binding of the capture antibody to the protein does not interfere with the binding of the LOX or LOXL inhibitor with the enzymatic pocket of the protein. In another embodiment, the binding of the capture antibody to the protein does not interfere with the binding of the LOX or LOXL inhibitor with the enzymatic pocket of the protein.

In one embodiment of the present invention the LOX or LOXL inhibitor is administered to the subject before the sample is obtained, so that steps (a) and (b) are replaced with the following steps:

(a1) administering a first amount of the LOX or LOXL inhibitor to the subject; and (b1) obtaining a sample containing or suspected of containing the protein from the subject after a predetermined period of time.

In another embodiment, the method further comprises measuring the concentration of the protein in a sample obtained from the subject prior to administration of the LOX or LOXL inhibitor.

The methods of the present invention can be utilised to determine patients who are likely to benefit from treatment with a LOX or LOXL inhibitor. By determining the measure of the concentration of the LOX or LOXL protein, and then comparing the measured total concentration to a standard level it is possible to identify those patients likely to benefit from treatment with a LOX or LOXL inhibitor.

In one embodiment, the method of the present invention is a selective, sensitive patient classification assay that can differentiate disease patients from non-disease patients and/or stratify patients according to the severity of their disease.

The methods of the present invention can also be utilised to assist in the diagnosis of patients having a condition associated with a LOX or LOXL protein. In one embodiment of the methods of the present invention the measured total concentration of the protein in the sample is compared to a standard level, wherein a difference in the concentration of the protein in the sample to a standard level is indicative of the subject having a condition associated with the protein. In one embodiment, the condition associated with the LOX or LOXL protein is selected from the group consisting of a liver disorder, a kidney disorder, fibrosis, cancer and angiogenesis.

In another embodiment, the methods of the present invention provide a highly selective and sensitive measure of the extent of inhibition of LOX and LOXL protein and can measure inhibited LOX and LOXL as a surrogate end-point for the assessment of therapeutic efficacy.

In one embodiment of the present invention, multiple samples are taken and contacted with differing amounts of a LOX or LOXL inhibitor, allowing for dose titration studies and the calculation of the $IC_{50}$ for a particular LOX or LOXL inhibitor. In another embodiment, multiple samples are taken at different points in time from the one subject who had been administered a LOX or LOXL inhibitor, allowing for the efficacy of the LOX or LOXL inhibitor over time to be assessed. In some embodiments, the methods allow for the monitoring of a patient's response to treatment with a LOX or LOXL inhibitor.

The methods of the present invention allow for the determination of the appropriate dosage of a LOX or LOXL inhibitor and for the determination of an appropriate dosage regimen for a LOX or LOXL inhibitor.

In some embodiments, the methods of the present invention are useful for the evaluation of the pharmacodynamics and pharmacokinetics of a LOX or LOXL inhibitor.

In one embodiment of the methods of the present invention, the immunoassay is an ELISA. In a further embodiment of the methods of the present invention, the immunoassay is a digital ELISA. In one embodiment, the digital ELISA assay methods are based on single molecule array (Simoa) technology (Rissin Dm, Kan C W, Campbell T G et al. Single-molecule enzyme-linked immunosorbent assay detects serum proteins at subfemtomolar concentrations *Nat. Biotech.* 2010; 28:595-99). The detection assays described herein can be performed using a suitable detecting system or device, such as Simoa™ and Simoa HD-1 Analyzer™ provided by Quanterix.

Due to the sensitivity of the assay, it is possible to perform the immunoassay on a small sample. This allows for multiple samples to be taken from a subject over the course of the measurement without impacting adversely on the subject. The sensitivity of the assay means that it is possible to measure very low levels of LOX or LOXL protein in a sample. In one embodiment, the volume of sample used in the assay is less than 1 mL. In another embodiment, the volume of the sample used in the assay is less than 500 μL. In a further embodiment, the volume of the sample used in the assay is less than 100 μL.

Kits

In a further aspect, the present invention provides for a kit for determining a measure of the concentration of a protein selected from a lysyl oxidase (LOX) protein and a lysyl oxidase-like (LOXL) protein in a sample, the kit comprising a capture antibody specific for the protein, and a bioprobe of Formula W-L-Z, wherein W represents an affinity tag; L represents a linker; and Z represents a moiety that binds to the protein; wherein Z binds to an enzymatic pocket of the protein.

In another aspect, the present invention provides for a kit for determining the extent of enzyme inhibition of a protein selected from a lysyl oxidase (LOX) protein and a lysyl oxidase-like (LOXL) protein by a LOX or LOXL inhibitor, the kit comprising:

a capture antibody specific for the protein, a bioprobe of Formula W-L-Z, wherein W represents an affinity tag; L represents a linker; and Z represents a moiety that binds to the protein; wherein Z binds to an enzymatic pocket of the protein, and a detection antibody specific for the protein.

In one embodiment of the methods and kits of the present invention the LOX or LOXL protein is selected from the group consisting of LOX, LOXL1, LOXL2, LOXL3 and LOXL4 protein. In a further embodiment of the methods and kits of the present invention the LOX or LOXL protein is LOXL2. In another embodiment of the methods and kits of the present invention the LOX or LOXL protein is LOX.

In one embodiment of the methods and kits of the present invention the capture antibody specific for the LOXL2 protein is AF2639. In one embodiment of the method and kits of the present invention the detection antibody specific for LOXL2 is Fitzgerald 70R-12876.

In one embodiment, the present invention provides for a kit for determining the concentration of a LOXL2 protein in a sample, the kit comprising:

the capure antibody AF2639 specific for the LOXL2 protein, a bioprobe of Formula W-L-Z, wherein W represents an affinity tag; L represents a linker; and Z represents a moiety that binds to the protein; wherein Z binds to an enzymatic pocket of the LOXL2 protein.

In another embodiment, the present invention provides for a kit for determining the extent of enzyme inhibition of a LOXL2 protein by a LOXL2 inhibitor, the kit comprising:

the capure antibody AF2639 specific for the LOXL2 protein, a bioprobe of Formula W-L-Z, wherein W represents an affinity tag; L represents a linker; and Z represents a moiety that binds to the protein; wherein Z binds to an enzymatic pocket of the LOXL2 protein, and the detection antibody Fitzgerald 70R-12876 specific for the LOXL2 protein.

In one embodiment of the methods and kits of the present invention the capture antibody specific for the LOX protein is L4794. In one embodiment of the method and kits of the present invention the detection antibody specific for LOX is ab219369.

In one embodiment, the present invention provides for a kit for determining the concentration of a LOX protein in a sample, the kit comprising:

the capure antibody L4794 specific for the LOX protein, a bioprobe of Formula W-L-Z, wherein W represents an affinity tag; L represents a linker; and Z represents a moiety that binds to the protein; wherein Z binds to an enzymatic pocket of the LOX protein.

In another embodiment, the present invention provides for a kit for determining the extent of enzyme inhibition of a LOX protein by a LOX inhibitor, the kit comprising:

the capure antibody L4794 specific for the LOX protein, a bioprobe of Formula W-L-Z, wherein W represents an affinity tag; L represents a linker; and Z represents a moiety that binds to the protein; wherein Z binds to an enzymatic pocket of the LOX protein, and the detection antibody ab219369 specific for the LOX protein.

The kits of the present invention may be used to perform an ELISA. In another embodiment the kits of the present invention may be used to perform a digital ELISA.

Bioprobes

One aspect of the invention provides for a bioprobe of formula W-L-Z, wherein W represents an affinity tag; L represents a linker; and Z represents a moiety that binds to a protein selected from a LOX protein or a LOXL protein.

There are a number of publications describing compounds of the formula Z, including WO 2017/136871 and WO 2017/136870.

In one embodiment of the bioprobe of the present invention W is an affinity tag. In some embodiments W is an affinity tag that is capable of specific binding to a known protein to produce a tightly bound complex. In some embodiments of the invention W is an affinity tag that is capable of specific binding to avidin or streptavidin. In another embodiment of the invention W is biotin or a biotin analogue. In a further embodiment of the invention W is biotin.

In one embodiment of the methods, kits or bioprobes of the present invention Z is a moiety of Formula I:

Formula I

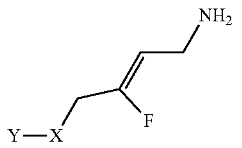

wherein:

X is absent, $CH_2$, O, S, S(O) or $SO_2$;

Y is aryl or heteroaryl; wherein each Y is optionally substituted by one or more $R^1$ and wherein Y contains an attachment point for L;

each $R^1$ is independently selected from the group consisting of halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^2R^3$, —C(O)$OR^4$, —C(O)$NR^2R^3$, —$NR^2$C(O)$R^5$, —$S(O_2)NR^2R^3$, —$NR^2S(O_2)R^5$, —S(O)$R^5$, —$S(O_2)R^5$, aryl, —$CH_2$-aryl, —CH($OR^4$)-aryl, heteroaryl and —$CH_2$-heteroaryl; wherein each $C_{1-6}$alkyl is a straight or branched chain alkyl; and wherein each $C_{1-6}$alkyl, $C_{3-7}$cycloalkyl, aryl and heteroaryl is optionally substituted by one or more substituents selected from the group consisting of halogen, —OH, —$C_{1-3}$ alkyl, —O—$C_{1-3}$alkyl, —$S(O_2)NR^2R^3$, —$CF_3$, —$CH_2CF_3$, and —O—$CF_3$;

$R^2$ and $R^3$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$; or $R^2$ and $R^3$ when attached to the same nitrogen atom are combined to form a 5- to 7-membered ring having from 0 to 2 additional heteroatoms as ring members;

$R^4$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$ alkyl, —$CF_3$, —$CH_2CF_3$, and —O—$CF_3$; and $R^5$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of the bioprobes of the present invention, X is absent, $CH_2$, O, S, S(O), or $SO_2$. In another embodiment X is absent or $SO_2$. In a further embodiment, X is absent. In a still further embodiment, X is $SO_2$.

In one embodiment of the bioprobes of the present invention, Y is aryl or heteroaryl; wherein each Y is optionally substituted by one or more $R^1$. In another embodiment, Y is phenyl, indole or triazole; wherein each Y is optionally substituted by one or more $R^1$. In a further embodiment, Y is phenyl optionally substituted by one or more $R^1$. In another embodiment, Y is indole optionally substituted by one or more RU.

In one embodiment of the bioprobes of the present invention, each $R^1$ is independently selected from the group consisting of halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^2R^3$, —C(O)$OR^4$, —C(O)$NR^2R^3$, —$NR^2$C(O)$R^5$, —S($O_2$)$NR^2R^3$, —$NR^2$S($O_2$)$R^5$, —S(O)$R^5$, —S($O_2$)$R^5$, aryl, —$CH_2$-aryl, —CH($OR^4$)-aryl, heteroaryl and —$CH_2$-heteroaryl; wherein each $C_{1-6}$alkyl is a straight or branched chain alkyl; and wherein each $C_{1-6}$alkyl, $C_{3-7}$cycloalkyl, aryl and heteroaryl is optionally substituted by one or more substituents selected from the group consisting of halogen, —OH, —$C_{1-3}$alkyl, —O—$C_{1-3}$alkyl, —S($O_2$)$NR^2R^3$, —$CF_3$, —$CH_2CF_3$, and —O—$CF_3$. In another embodiment each $R^1$ is independently selected from the group consisting of halogen, hydroxyl, $C_{1-6}$alkyl, —O—$C_{1-6}$alkyl, —C(O)$NR^2R^3$, —$NR^2$C(O)$R^5$, —S($O_2$)$NR^2R^3$, —$NR^2$S($O_2$)$R^5$, aryl, —$CH_2$-aryl and —CH($OR^4$)-aryl; wherein each $C_{1-6}$alkyl is a straight or branched chain alkyl; and wherein each $C_{1-6}$alkyl and aryl is optionally substituted by one or more substituents selected from the group consisting of halogen, —OH, —$C_{1-3}$alkyl, —O—$C_{1-3}$alkyl, —S($O_2$)$NR^2R^3$, —$CF_3$, —$CH_2CF_3$, and —O—$CF_3$. In a further embodiment of the bioprobes of the present invention, each $R^1$ is independently selected from the group consisting of $C_{1-6}$alkyl, —O—$C_{1-6}$alkyl, —C(O)$NR^2R^3$, aryl, —$CH_2$-aryl and —CH($OR^4$)-aryl; wherein each $C_{1-6}$alkyl is a straight or branched chain alkyl; and wherein each aryl is optionally substituted by one or more —S($O_2$)$NR^2R^3$.

In one embodiment of the bioprobes of the present invention, $R^2$ and $R^3$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$ alkyl, —$CF_3$, —$CH_2CF_3$, and —O—$CF_3$. In another embodiment, $R^2$ and $R^3$ are independently selected from the group consisting of hydrogen and $C_{1-6}$alkyl; wherein each $C_{1-6}$alkyl is a straight or branched chain alkyl. In a further embodiment, $R^2$ and $R^3$ are independently selected from the group consisting of hydrogen and $C_{1-6}$alkyl. In another embodiment, $R^2$ and $R^3$ are independently selected from the group consisting of hydrogen and methyl.

In one embodiment of the bioprobes of the present invention, $R^2$ and $R^3$ when attached to the same nitrogen atom are combined to form a 5- to 7-membered ring having from 0 to 2 additional heteroatoms as ring members. In another embodiment, $R^2$ and $R^3$ when attached to the same nitrogen atom are combined to form a 5- to 7-membered ring having from 0 to 1 additional heteroatoms as ring members. In a further embodiment, $R^2$ and $R^3$ when attached to the same nitrogen atom are combined to form a 5- to 7-membered ring having 1 additional heteroatoms as ring members. In another embodiment, $R^2$ and $R^3$ when attached to the same nitrogen atom are combined to form a 5- to 7-membered ring having 0 additional heteroatoms as ring members.

In one embodiment of the bioprobes of the present invention, $R^4$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$. In another embodiment, $R^4$ is selected from the group consisting of hydrogen and $C_{1-6}$alkyl.

In one embodiment of the bioprobes of the present invention, $R^5$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$. In another embodiment, $R^5$ is selected from the group consisting of $C_{1-6}$ alkyl and $C_{3-7}$ cycloalkyl. In a further embodiment, $R^5$ is $C_{1-6}$ alkyl.

In one embodiment of the methods, kits or bioprobes of the present invention Z is a moiety of Formula I, wherein X is absent or $SO_2$;

Y is phenyl or indole; wherein each Y is optionally substituted by one or more $R^1$ and wherein Y contains an attachment point for L;

each $R^1$ is independently selected from the group consisting $C_{1-6}$alkyl, —O—$C_{1-6}$alkyl, —C(O)$NR^2R^3$, aryl, —$CH_2$-aryl and heteroaryl; wherein each $C_{1-6}$alkyl is a straight or branched chain alkyl; and wherein each aryl is optionally substituted by one or more —S($O_2$)$NR^2R^3$; and $R^2$ and $R^3$ are independently selected from the group consisting of hydrogen and $C_{1-6}$alkyl.

In one embodiment, the present invention also relates to methods, kits or bioprobes wherein Z is a moiety of Formula Ia:

Formula Ia

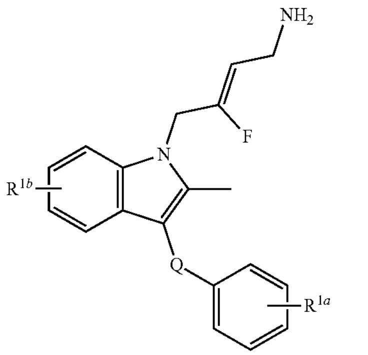

wherein:

Q is $CH_2$ or absent;

$R^{1a}$ is S($O_2$)$NR^2R^3$;

$R^{1b}$ is selected from the group consisting $C_{1-6}$alkyl, —C(O)$NR^2R^3$ and heteroaryl or represents an attachment point for L; and $R^2$ and $R^3$ are independently selected from the group consisting of hydrogen and $C_{1-6}$alkyl.

In another embodiment, the present invention also relates to methods, kits or bioprobes wherein Z is a moiety of Formula Ib:

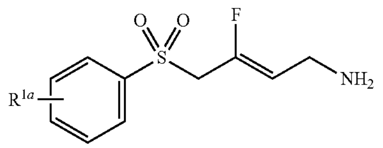

wherein:

$R^{1a}$ is selected from the group consisting of hydrogen, $C_{1-6}$alkyl, —O—$C_{1-6}$alkyl and —C(O)$NR^2R^3$ or represents an attachment point for L; and $R^2$ and $R^3$ are independently selected from the group consisting of hydrogen and $C_{1-6}$alkyl In one embodiment of the methods, kits or bioprobes of the present invention the linker L comprises one or more components selected from a connecting linker ($L_c$), a spacer linker ($L_S$) and a branching linker ($L_B$), and combinations thereof.

In one embodiment of the methods, kits or bioprobes of the present invention the bioprobe is of the formula selected from the group consisting of:

$W—L_C—Z$ $W—L_C—L_S—Z$ $W—L_C—L_S—L_C—Z$ $W—L_C—L_S—L_C—L_S—L_C—Z$ $W—L_C—L_S—L_C—L_S—L_C—L_S—Z$

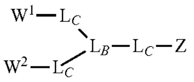

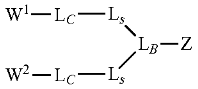

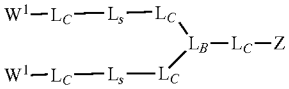
and

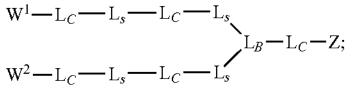

wherein $W^1$ and $W^2$ are the same or different and are an affinity tag; and

Z is as defined above.

In one embodiment of the methods, kits or bioprobes of the present invention each connecting linker ($L_c$) is independently selected from the group consisting of —O—, —$CH_2O$—, —$NR^6$—, —$CH_2NR^6$—, —C(O)$NR^2$—, —$NR^2$C(O)—, —$CH_2NR^2$C(O)—, —C(O)O—, —OC(O)—, —$CH_2$OC(O)—,

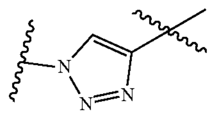

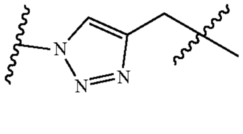
, and

-continued

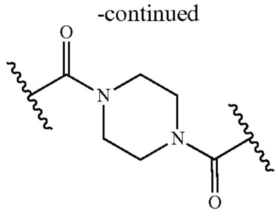
;

wherein $R^2$ is as defined above; and $R^6$ is hydrogen or $C_{1-6}$alkyl.

In one embodiment of the methods, kits or bioprobes of the present invention each spacer linker ($L_S$) is independently selected from the group consisting of —$(CH_2)_n$—, —$(CH_2CH_2O)_mCH_2CH_2$—, $(CH_2)$O—, and

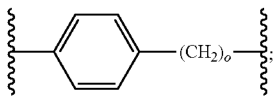

wherein n is 1, 2, 3, 4, 5 or 6;

m is 1, 2, 3 or 4; and o is 0, 1 or 2.

In one embodiment of the methods, kits or bioprobes of the present invention each branching linker ($L_B$) is independently selected from the group consisting of

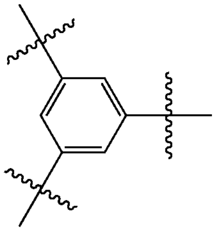
,

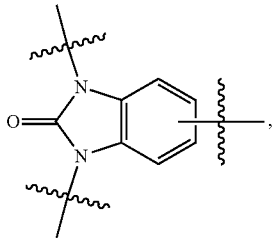
, and

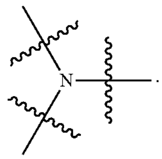
.

In one embodiment of the bioprobes of the present invention, the bioprobe includes a single affinity tag W. In another embodiment of the present invention, the bioprobe includes two affinity tags $W^1$ and $W^2$. The affinity tags $W^1$ and $W^2$ may be the same or different. In one embodiment of the bioprobes of the present invention, the bioprobe includes a single biotin. In another embodiment of the bioprobes of the present invention, the bioprobe includes two biotin groups. The sensitivity of the assay may be improved through the presence of two rather than one biotin, giving rise to a greater signal to noise ratio.

In the context of the present disclosure, any one or more aspect(s) or embodiment(s) may be combined with any other aspect(s) or embodiment(s).
Exemplary bioprobes according to the present invention include the compounds set forth in Table 1:
TABLE 1
| Compound | Structure | m/z [M + H]$^+$ |
|---|---|---|
| 1-1 | 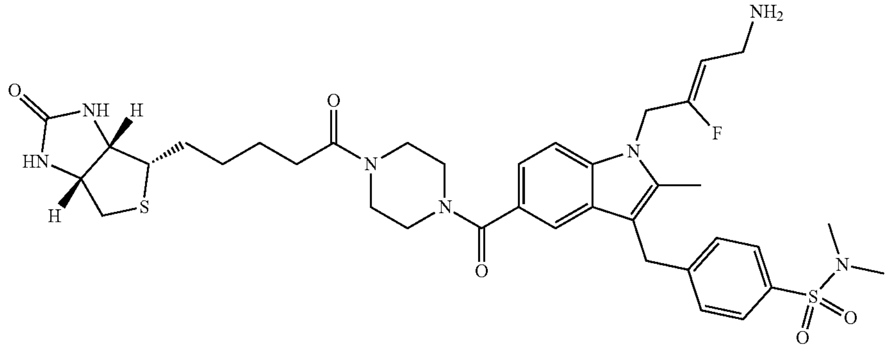 [SMILES: Cc1c(Cc2ccc(S(=O)(=O)N(C)C)cc2)c2cc(C(=O)N3CCN(C(=O)CCCC[C@@H]4SC[C@@H]5NC(=O)N[C@@H]54)CC3)ccc2n1C/C(F)=C/CN] | 754.4 |
| 1-2 | 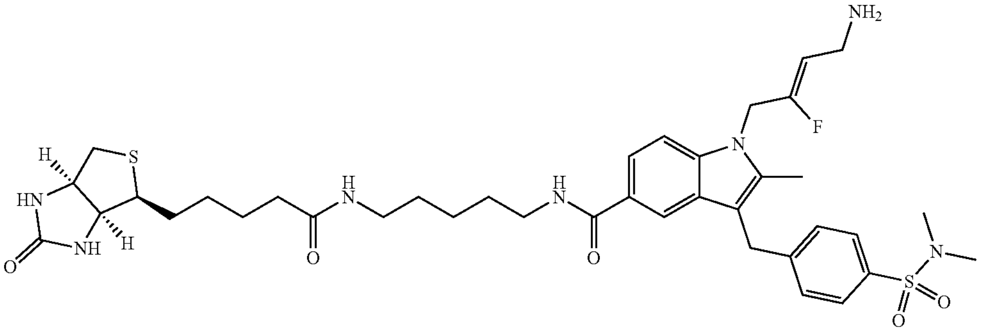 [SMILES: Cc1c(Cc2ccc(S(=O)(=O)N(C)C)cc2)c2cc(C(=O)NCCCCCNC(=O)CCCC[C@@H]3SC[C@@H]4NC(=O)N[C@@H]43)ccc2n1C/C(F)=C/CN] | 756.4 |
| 1-3 | 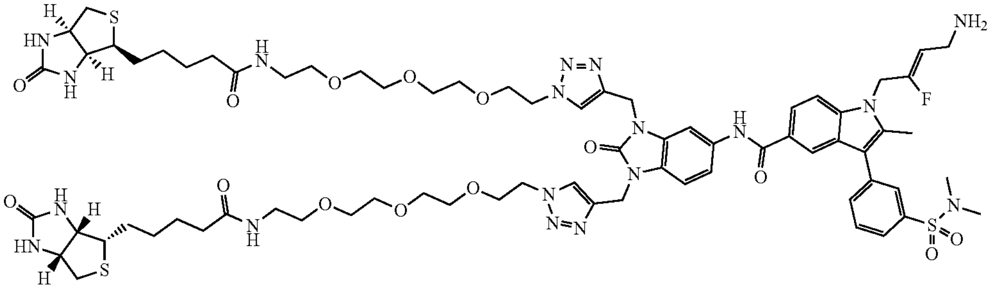 [SMILES: Cc1c(-c2cccc(S(=O)(=O)N(C)C)c2)c2cc(C(=O)Nc3ccc4c(c3)n(Cc3cn(CCOCCOCCOCCNC(=O)CCCC[C@@H]5SC[C@@H]6NC(=O)N[C@@H]65)nn3)c(=O)n4Cc3cn(CCOCCOCCOCCNC(=O)CCCC[C@@H]4SC[C@@H]5NC(=O)N[C@@H]54)nn3)ccc2n1C/C(F)=C/CN] | 1542.4 |
| 1-4 | 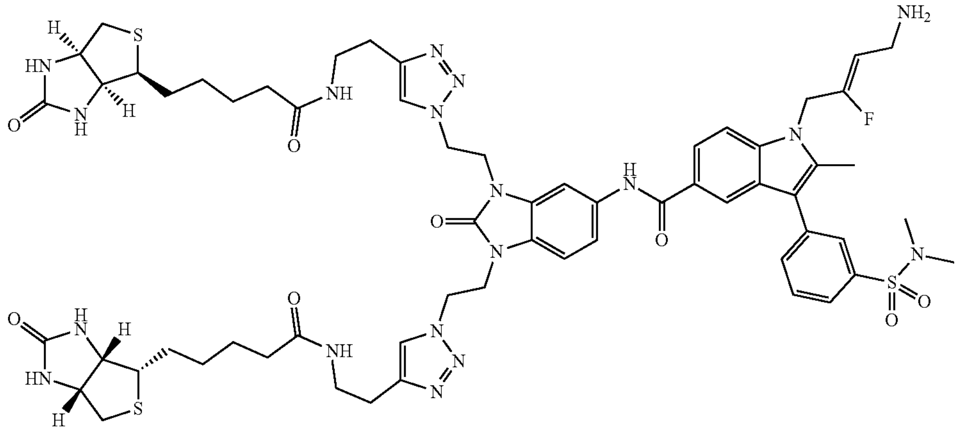 [SMILES: Cc1c(-c2cccc(S(=O)(=O)N(C)C)c2)c2cc(C(=O)Nc3ccc4c(c3)n(CCn3cc(CCNC(=O)CCCC[C@@H]5SC[C@@H]6NC(=O)N[C@@H]65)nn3)c(=O)n4CCn3cc(CCNC(=O)CCCC[C@@H]4SC[C@@H]5NC(=O)N[C@@H]54)nn3)ccc2n1C/C(F)=C/CN] | 1306.6 |

TABLE 1-continued
| Compound | Structure | m/z [M + H]+ |
|---|---|---|
| 1-5 | 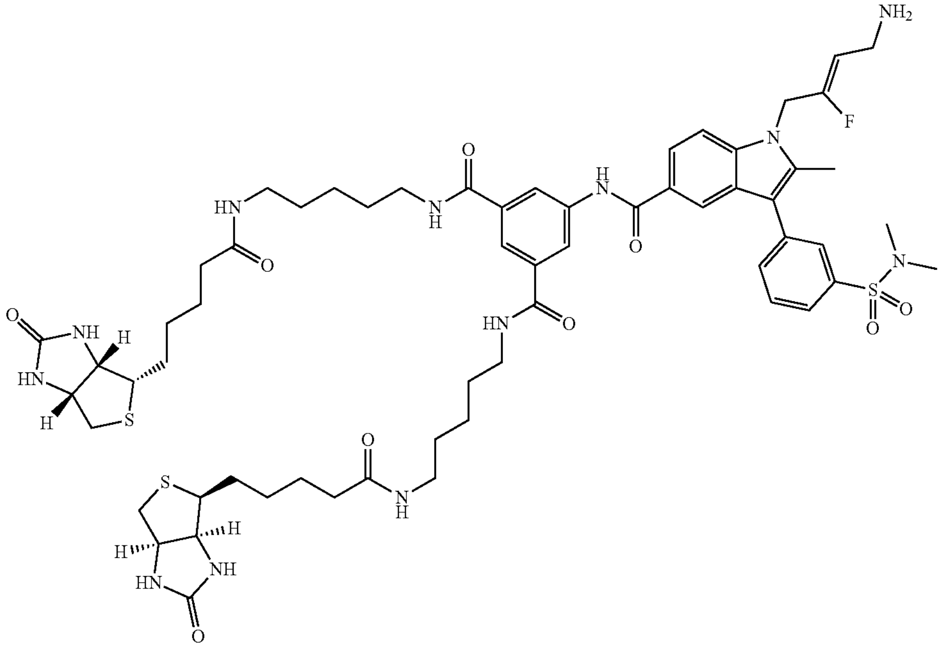 [SMILES: Cc1c(-c2cccc(S(=O)(=O)N(C)C)c2)c2cc(C(=O)Nc3cc(C(=O)NCCCCCNC(=O)CCCC[C@@H]4SC[C@@H]5NC(=O)N[C@@H]54)cc(C(=O)NCCCCCNC(=O)CCCC[C@@H]4SC[C@@H]5NC(=O)N[C@@H]54)c3)ccc2n1C/C(F)=C/CN] | 1231.1 |
| 1-6 | 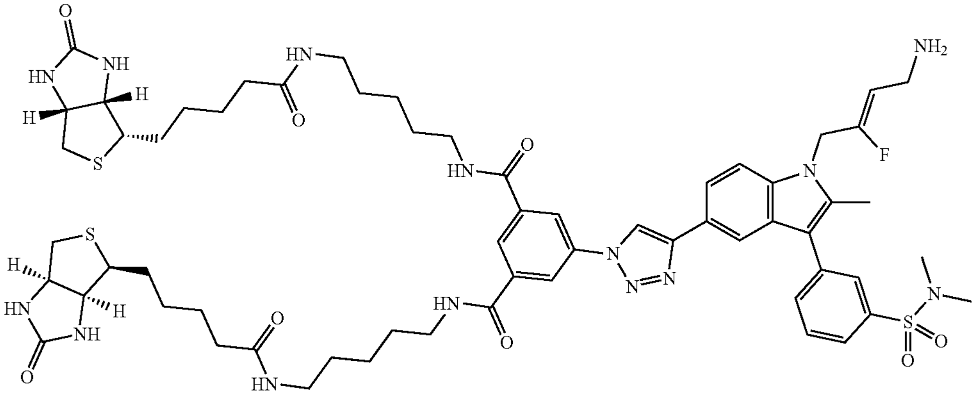 [SMILES: Cc1c(-c2cccc(S(=O)(=O)N(C)C)c2)c2cc(-c3cn(-c4cc(C(=O)NCCCCCNC(=O)CCCC[C@@H]5SC[C@@H]6NC(=O)N[C@@H]65)cc(C(=O)NCCCCCNC(=O)CCCC[C@@H]5SC[C@@H]6NC(=O)N[C@@H]65)c4)nn3)ccc2n1C/C(F)=C/CN] | 1254.4 |
| 1-7 | 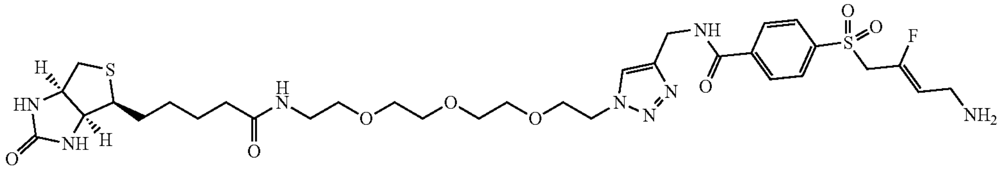 [SMILES: NC/C=C(\F)CS(=O)(=O)c1ccc(C(=O)NCc2cn(CCOCCOCCOCCNC(=O)CCCC[C@@H]3SC[C@@H]4NC(=O)N[C@@H]43)nn2)cc1] | 755.3 |
| 1-8 | 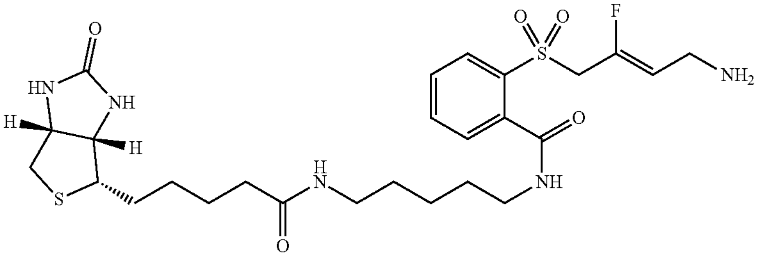 [SMILES: NC/C=C(\F)CS(=O)(=O)c1ccccc1C(=O)NCCCCCNC(=O)CCCC[C@@H]1SC[C@@H]2NC(=O)N[C@@H]21] | 584.3 |

TABLE 1-continued
| Compound | Structure | m/z [M + H]+ |
|---|---|---|
| 1-9 | 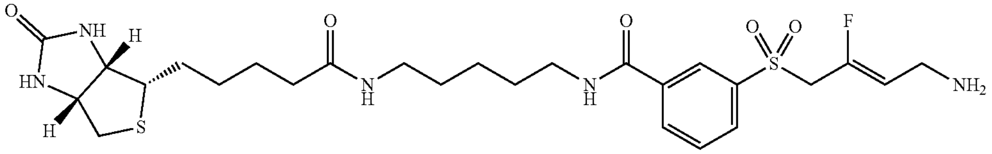 [SMILES: NC/C=C(\F)CS(=O)(=O)c1cccc(C(=O)NCCCCCNC(=O)CCCC[C@@H]2SC[C@@H]3NC(=O)N[C@@H]32)c1] | 584.3 |
| 1-10 | 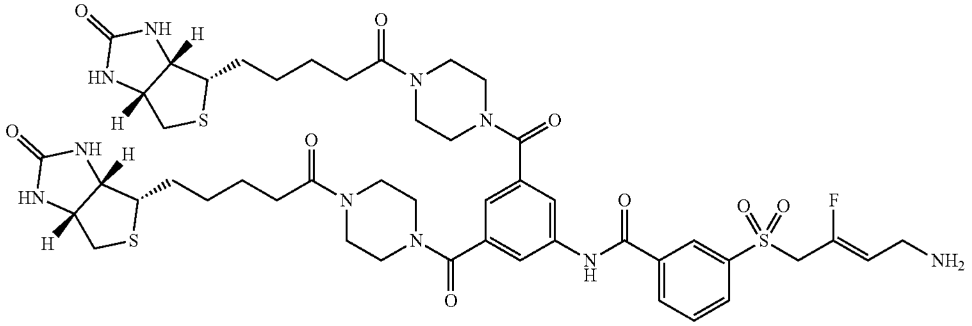 [SMILES: NC/C=C(\F)CS(=O)(=O)c1cccc(C(=O)Nc2cc(C(=O)N3CCN(C(=O)CCCC[C@@H]4SC[C@@H]5NC(=O)N[C@@H]54)CC3)cc(C(=O)N3CCN(C(=O)CCCC[C@@H]4SC[C@@H]5NC(=O)N[C@@H]54)CC3)c2)c1] | 1025.4 |
| 1-11 | 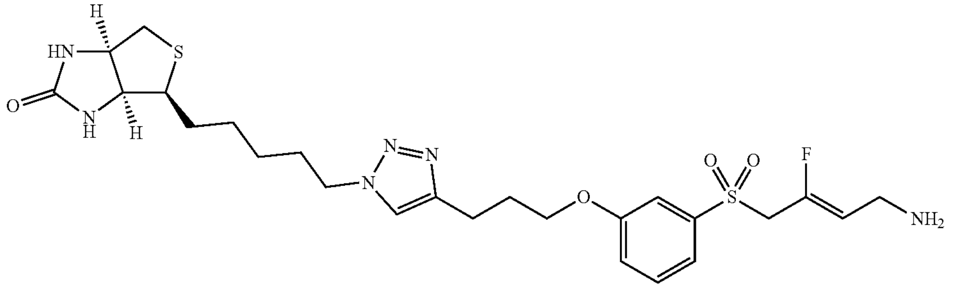 [SMILES: NC/C=C(\F)CS(=O)(=O)c1cccc(OCCCc2cn(CCCCC[C@@H]3SC[C@@H]4NC(=O)N[C@@H]43)nn2)c1] | 567.2 |
| 1-12 | 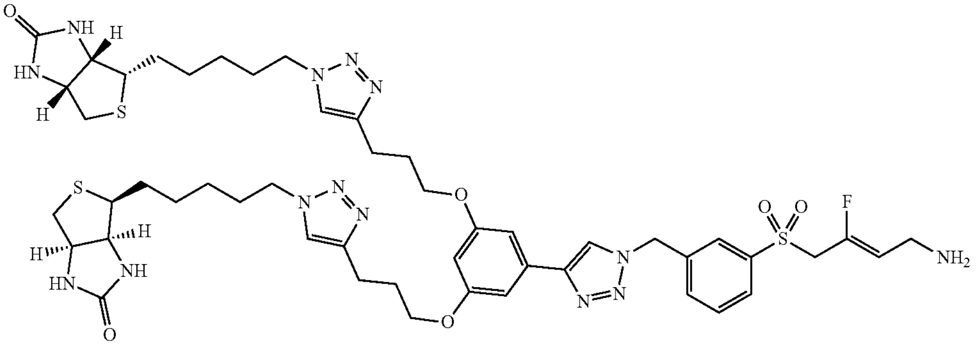 [SMILES: NC/C=C(\F)CS(=O)(=O)c1cccc(Cn2cc(-c3cc(OCCCc4cn(CCCCC[C@@H]5SC[C@@H]6NC(=O)N[C@@H]65)nn4)cc(OCCCc4cn(CCCCC[C@@H]5SC[C@@H]6NC(=O)N[C@@H]65)nn4)c3)nn2)c1] | 1061.5 |
| 1-13 | 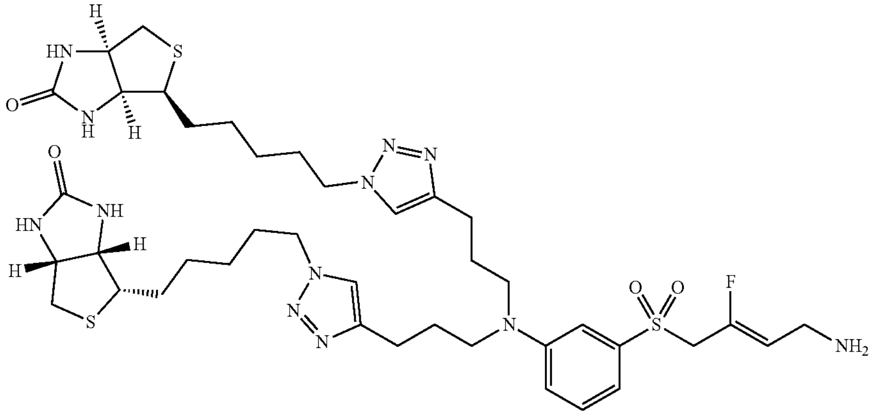 [SMILES: NC/C=C(\F)CS(=O)(=O)c1cccc(N(CCCc2cn(CCCCC[C@@H]3SC[C@@H]4NC(=O)N[C@@H]43)nn2)CCCc2cn(CCCCC[C@@H]3SC[C@@H]4NC(=O)N[C@@H]43)nn2)c1] | 887.4 |

TABLE 1-continued

| Compound | Structure | m/z [M + H]+ |
|---|---|---|
| 1-14 | 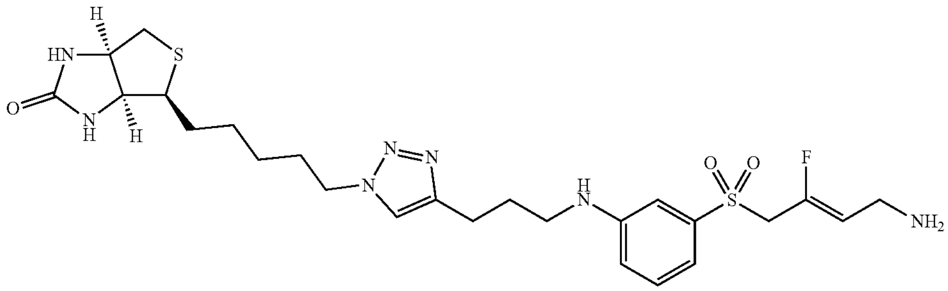 [SMILES: NC/C=C(\F)CS(=O)(=O)c1cccc(NCCCc2cn(CCCCC[C@@H]3SC[C@@H]4NC(=O)N[C@@H]43)nn2)c1] | 566.3 |
| 1-15 | 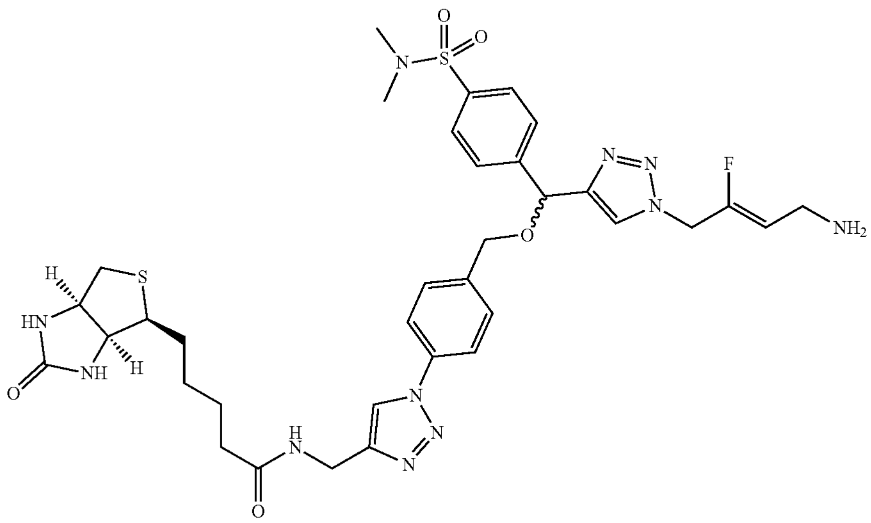 [SMILES: CN(C)S(=O)(=O)c1ccc(C(OCc2ccc(-n3cc(CNC(=O)CCCC[C@@H]4SC[C@@H]5NC(=O)N[C@@H]54)nn3)cc2)c2cn(C/C(F)=C/CN)nn2)cc1] | 782.4 |
| 1-16 | 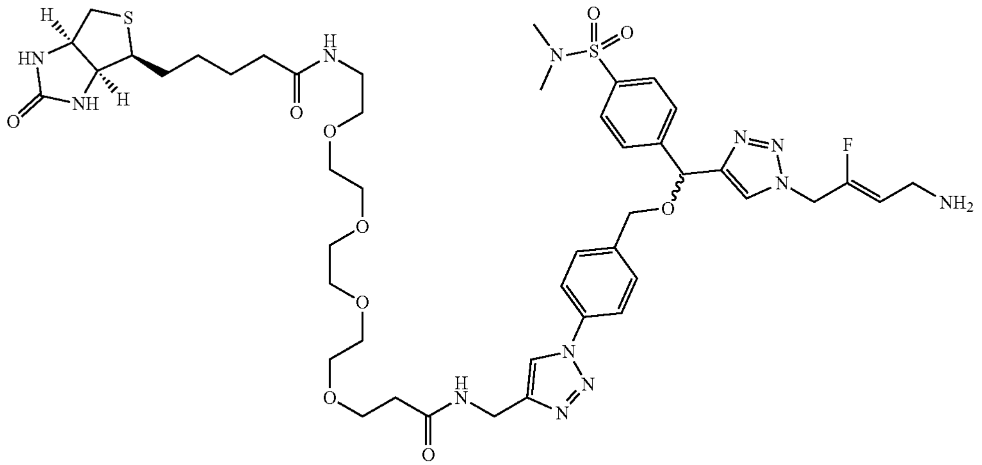 [SMILES: CN(C)S(=O)(=O)c1ccc(C(OCc2ccc(-n3cc(CNC(=O)CCOCCOCCOCCOCCNC(=O)CCCC[C@@H]4SC[C@@H]5NC(=O)N[C@@H]54)nn3)cc2)c2cn(C/C(F)=C/CN)nn2)cc1] | 1029.4 |

Preparation Bioprobes of Formula W-L-Z

Bioprobes of Formula W-L-Z described herein are synthesized using standard synthetic techniques using methods known in the art. The methods described are provided for illustrative purposes only and do not limit the scope of the claims provided herein.

Unless otherwise indicated, conventional methods of mass spectroscopy, NMR, HPLC and protein chemistry, biochemistry techniques are employed.

Compounds are prepared using standard organic techniques described, but not limited to, Advanced Organic Chemistry, 6th Edition by March, John Wiley and Sons Inc. Standard procedures for the use of protecting groups for the temporary protection of functional groups such as alcohols, amines and carboxylic acids are described in for example Protecting Groups in Organic Synthesis, 4th Edition, John Wiley and Sons Inc.

Alternative reaction conditions for the chemical transformations described herein may be employed such as variation in solvent, reaction temperature, reaction time as well as different chemical reagents. Unless stated otherwise, starting materials for chemical synthesis and biological applications are available from commercial sources.
Scheme 1
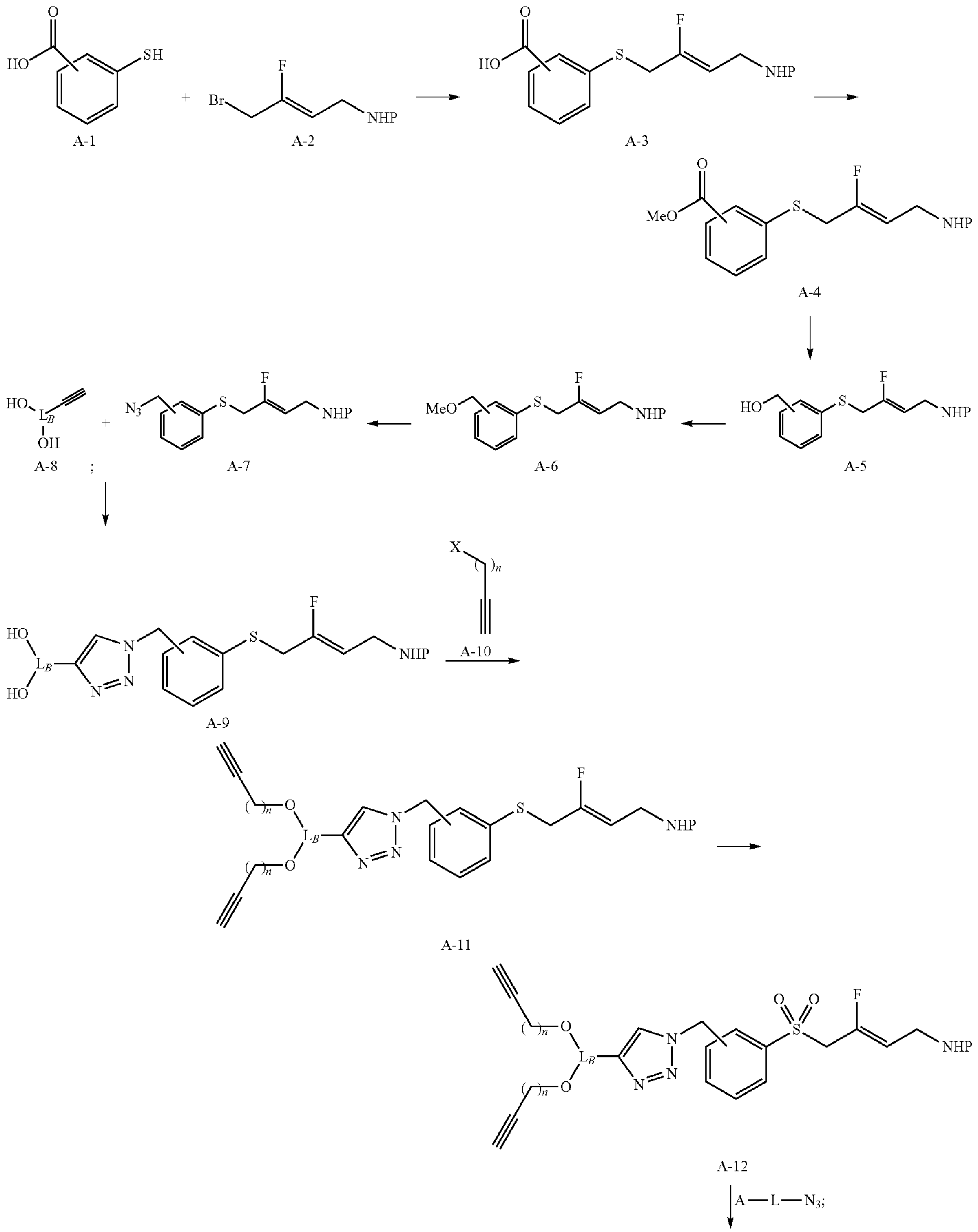

-continued

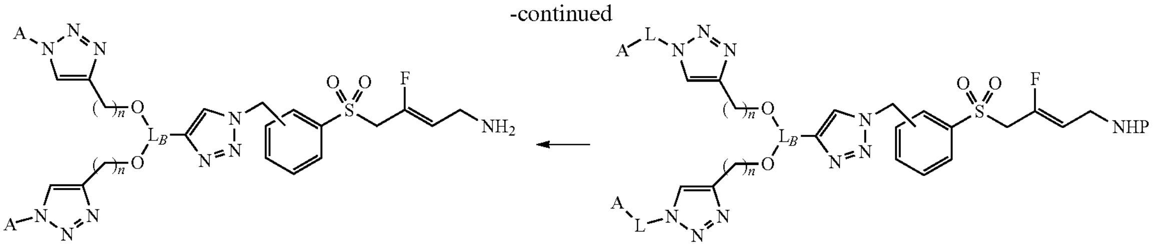

A-14 A-13

P is a functional group used to protect a nitrogen functionality. Examples of P are carbonates such as the tert-butyloxycarbonyl (BOC), the 9-fluorenylmethyloxycarbonyl (FMOC), and the benzyloxycarbonyl (CBZ) groups. In some embodiments, thiobenzoic acid A-1 is treated with allyl bromide A-2 (the synthesis of A-2 is described in patents WO 2017/136870 and WO 2017/136871) in the presence of a suitable base using a suitable polar solvent. In some embodiments, the base is $K_2CO_3$ or alternatively $Cs_2CO_3$. In some embodiments, the solvent is DMF or alternatively acetone. In some embodiments benzoic acid derivatives A-3 are converted to the corresponding methyl ester derivatives A-4 with a suitable alkylating reagent such as diazomethyl(trimethyl)silane in an appropriate solvent such as $CH_2Cl_2$/MeOH. In some embodiments, ester derivatives A-4 are converted, using a suitable reducing agent, to the corresponding benzyl alcohol derivatives A-5. In some embodiments, the reducing agent is diisobutylaluminum hydride in an appropriate solvent such as $CH_2Cl_2$. In some embodiments, the reducing agent is sodium borohydride in an appropriate solvent such as MeOH. In some embodiments, the alcohol moiety of A-5 is converted to the corresponding mesylate A-6 by treatment with methanesulfonyl chloride in the presence of a suitable organic base using an appropriate solvent. In some embodiments, the suitable base is triethylamine, and the appropriate solvent is acetone. In other embodiments, mesylate derivatives A-6 are converted to azide-derivatives A-7 using an azide transfer reagent such as sodium azide in a suitable polar solvent such as acetone. In other embodiments, alcohol derivatives A-5 are converted to azide derivatives A-7 without isolation of the intermediate mesylate derivatives A-6. In some embodiments, treatment of azide derivative A-7 with an appropriately substituted alkyne A-8 in the presence of a suitable catalyst such as $CuSO_4$, and in the presence of sodium ascorbate, in a suitable solvent such as THF-DMF yields triazole derivatives A-9. In other embodiments, diol derivative A-8 is treated with at least two equivalents of alkyne alkylating agent A-10 in the presence of a suitable base using suitable polar solvent to provide A-11. In some embodiments, X=Br. In other embodiments, the base is $K_2CO_3$ and the solvent is DMF. In some embodiments, thioether derivatives A-11 are converted. using a suitable oxidizing agent, to the corresponding sulfone derivatives A-12. In some embodiments, the oxidizing agent is 3-chloroperbenzoic acid (mCPBA) in the presence of an inorganic base such as $NaHCO_3$, in a suitable solvent such as $CH_2Cl_2$. In other embodiments, the oxidizing agent is Oxone™ in an appropriate solvent such as THF-MeOH—$H_2O$. In some embodiments, treatment of alkyne derivatives A-12 with at least two equivalents of an appropriately substituted azide A-L-$N_3$ in the presence of a suitable catalyst such as $CuSO_4$, and in the presence of sodium ascorbate, in a suitable solvent such as THF-DMF-$H_2O$ yields triazole derivatives A-13. In some embodiments, standard amine deprotection conditions affords A-14.

Scheme 2

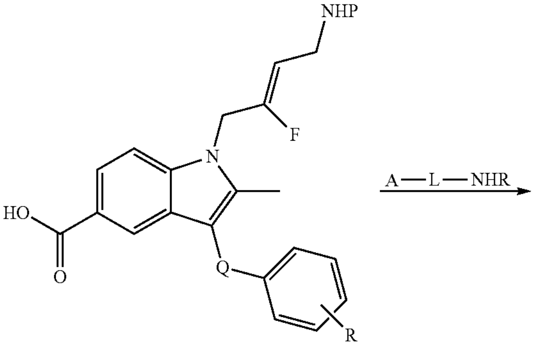

B-1

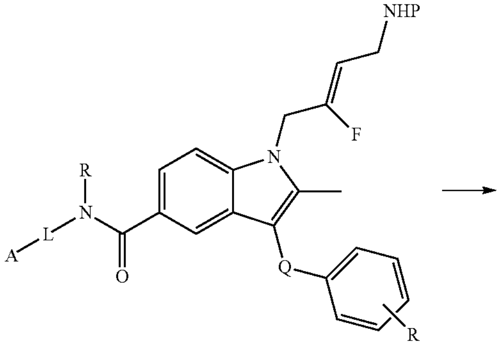

B-2

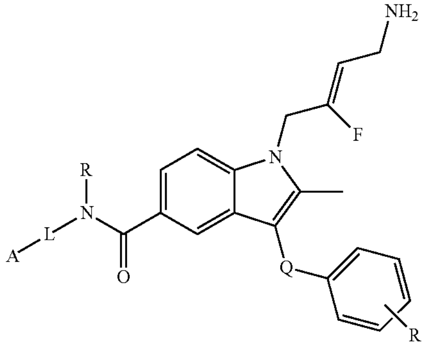

B-3

In some embodiments, standard peptide coupling conditions between carboxylic acid derivatives B-1 (prepared according to the general procedures described in patents WO 2017/136870 and WO 2017/136871) and an appropriately substituted amine A-L-NHR affords amides B-2. In some embodiments, standard amine deprotection conditions affords B-3.

Scheme 3

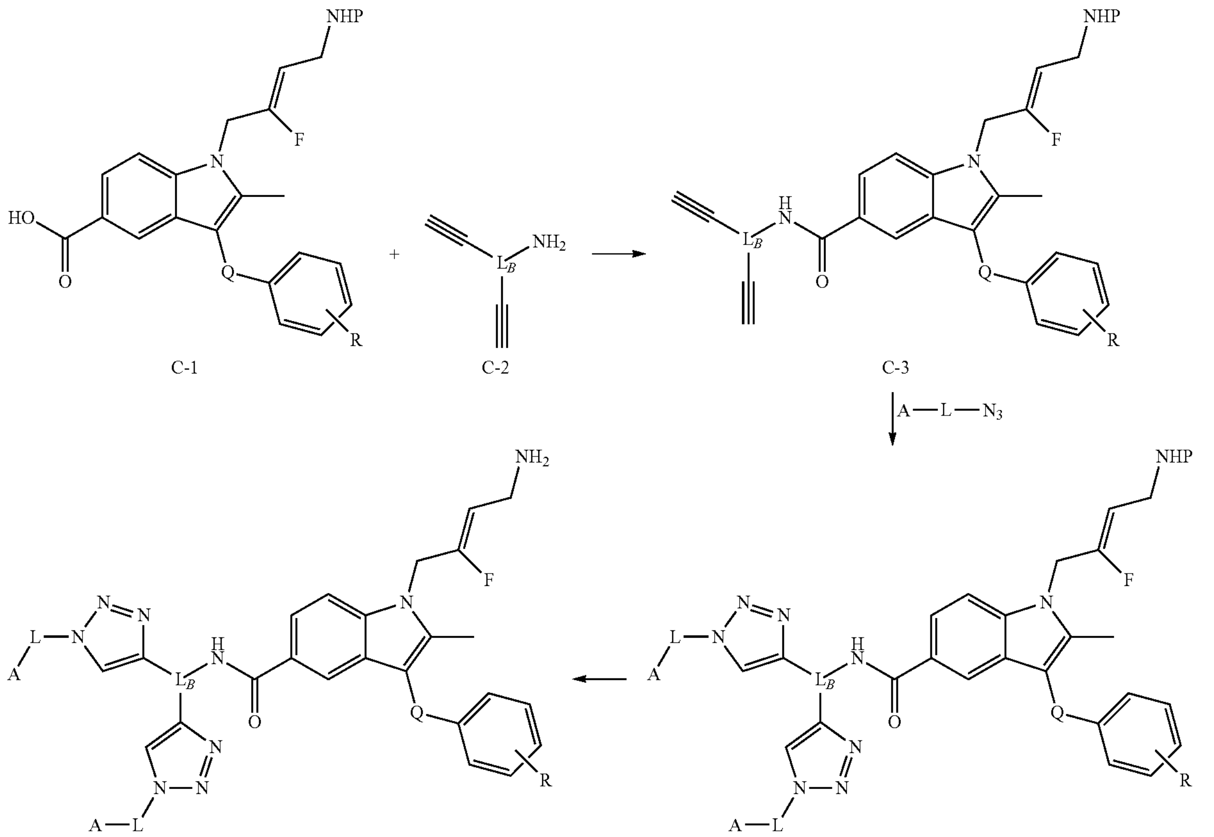

C-1 C-2 C-3 C-4 C-5

In some embodiments, standard peptide coupling conditions between carboxylic acid derivatives C-1 (prepared according to the general procedures described in patents WO 2017/136870 and WO 2017/136871) and an appropriately substituted amine C-2 affords bis-alkyne derivatives C-3. In some embodiments, treatment of alkyne derivatives C-3 with at least two equivalents of an appropriately substituted azide A-L-$N_3$ in the presence of a suitable catalyst such as $CuSO_4$, and in the presence of sodium ascorbate, in a suitable solvent such as THF-DMF-$H_2O$ yields triazole derivatives C-4. In some embodiments, standard amine deprotection conditions affords C-5.

Scheme 4

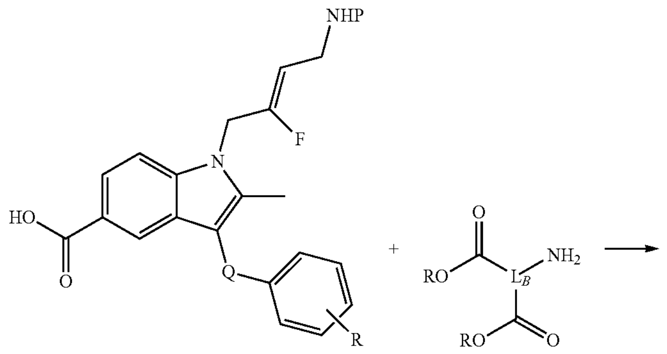

D-1 D-2

-continued

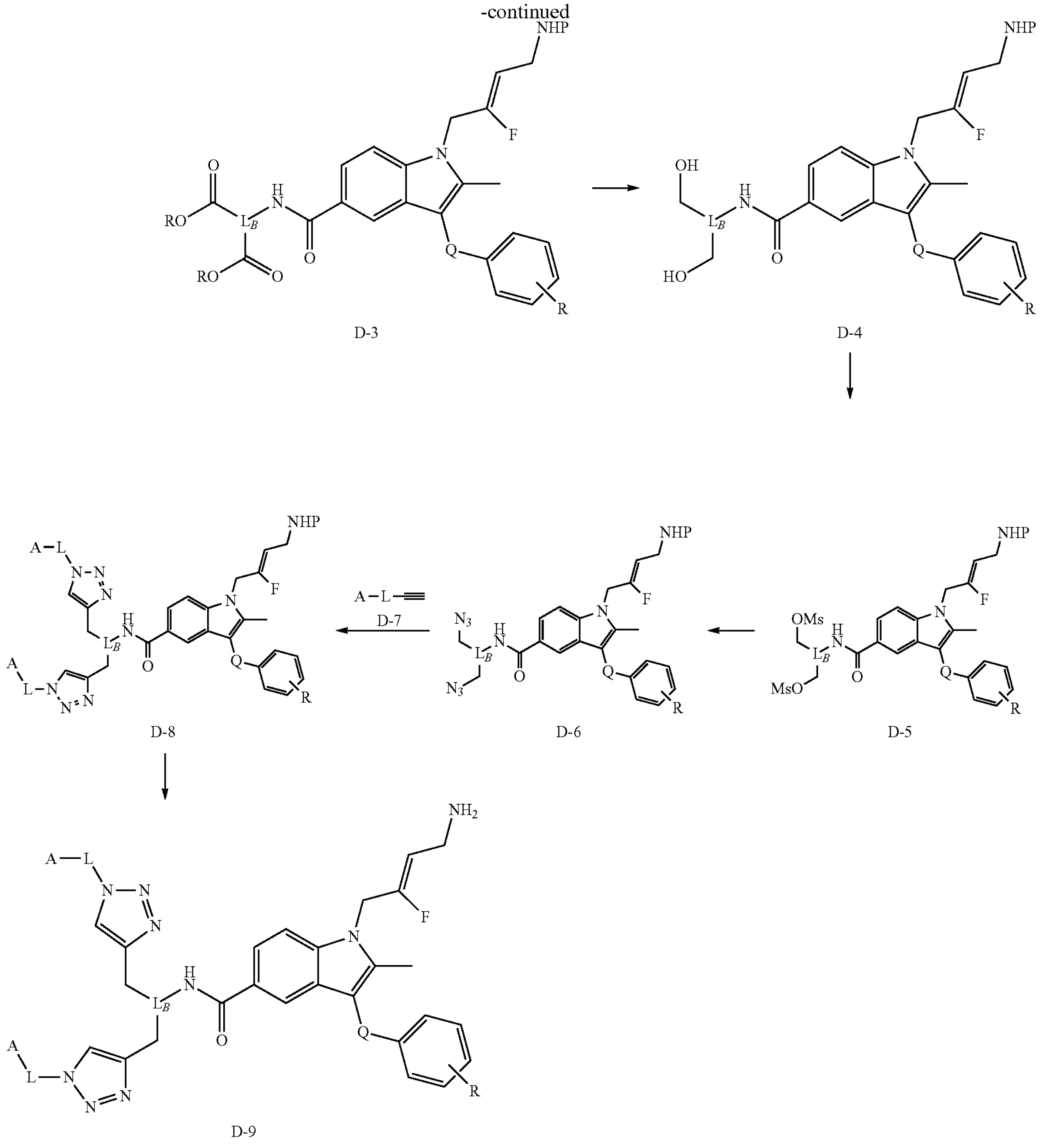

D-3, D-4, D-5, D-6, D-8, D-9

In some embodiments, standard peptide coupling conditions between carboxylic acid derivatives D-1 (prepared according to the general procedures described in patents WO 2017/136870 and WO 2017/136871) and an appropriately substituted amine D-2 affords bis-ester derivatives D-3. In some embodiments, bis-ester derivatives D-3 are converted, using a suitable reducing agent, to the corresponding diol derivatives D-4. In some embodiments, the reducing agent is sodium borohydride in an appropriate solvent such as MeOH. In some embodiments, the reducing agent is diisobutylaluminum hydride in an appropriate solvent such as $CH_2Cl_2$. In some embodiments, the alcohol moieties of D-4 are converted to the corresponding mesylate D-5 by treatment with at least two equivalents of methanesulfonyl chloride in the presence of a suitable organic base using an appropriate solvent. In some embodiments, the suitable base is triethylamine, and the appropriate solvent is acetone. In other embodiments, mesylate derivatives D-5 are converted to azide-derivatives D-6 using at least two equivalents of an azide transfer reagent such as sodium azide in a suitable polar solvent such as acetone. In other embodiments, diol derivatives D-4 are converted to azide derivatives D-6 without isolation of the intermediate mesylate derivative D-5. In some embodiments treatment of diazide derivative D-6 with at least two equivalents of an appropriately substituted alkyne D-7 in the presence of a suitable catalyst such as $CuSO_4$, and in the presence of sodium ascorbate, in a suitable solvent such as THF-DMF-$H_2O$ yields triazole derivatives D-8. In some embodiments, standard amine deprotection conditions affords D-9.

Scheme 5
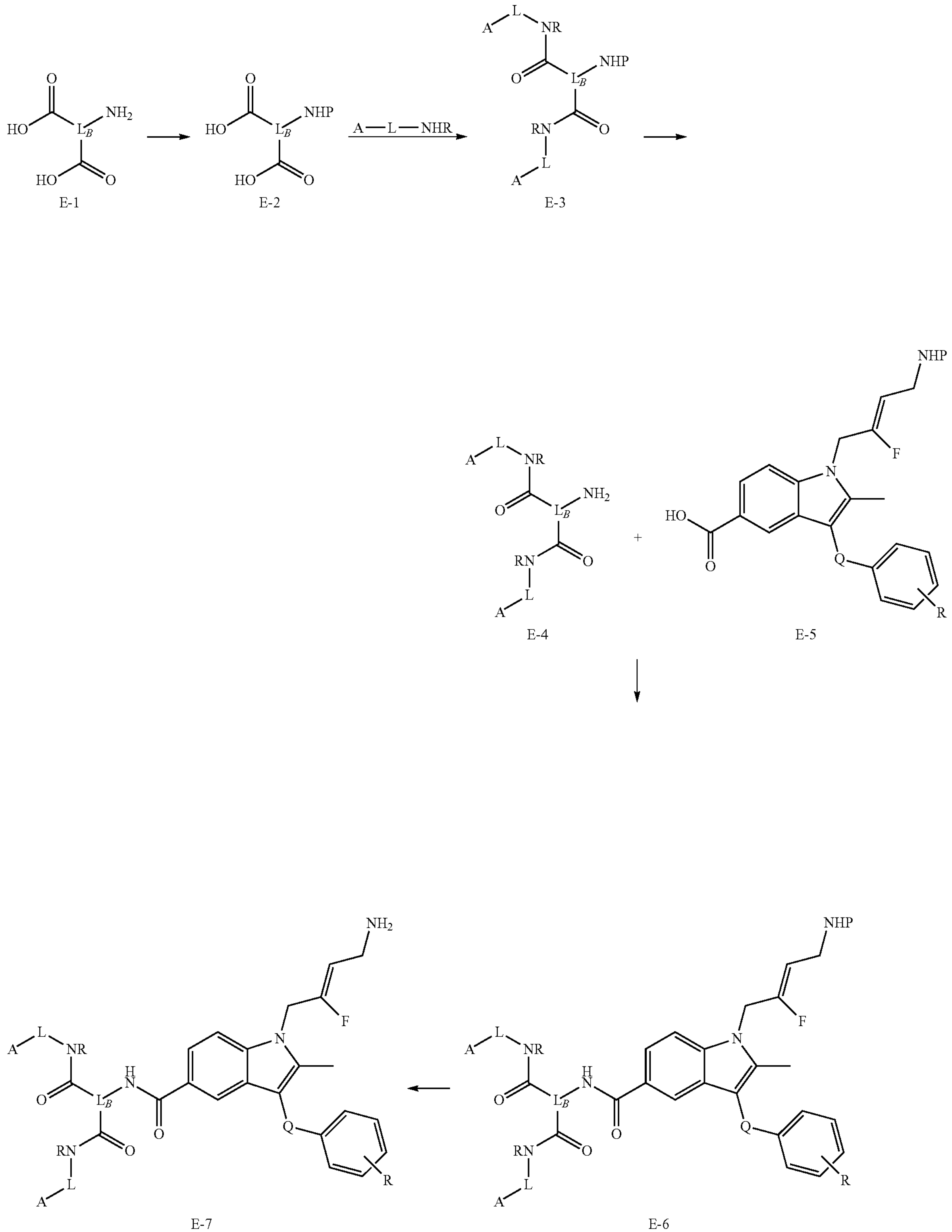
E-1 E-2 E-3
E-4 E-5
E-7 E-6

In some embodiments, the amino moiety of E-1 is protected with an appropriate protecting group to provide E-2. In some embodiments, treatment of amine derivative E-1 with di-tert-butyl dicarbonate ($Boc_2O$) in the presence of a suitable base such as NaOH and a suitable solvent such as 1,4-dioxane-$H_2O$ affords E-2 (P=Boc). In some embodiments, standard peptide coupling conditions between bis-carboxylic acid derivatives E-2 and an appropriately substituted amine A-L-NHR affords bis-ester derivatives E-3. In some embodiments, standard —NHBoc deprotection conditions affords E-4. In other embodiments, standard peptide coupling conditions between carboxylic acid derivatives E-5 (prepared according to the general procedures described in patents WO 2017/136870 and WO 2017/136871) and an appropriately substituted amine E-4 provides amide derivatives E-6. In some embodiments, treatment of E-6 under standard amine deprotection conditions affords E-7.

Scheme 6

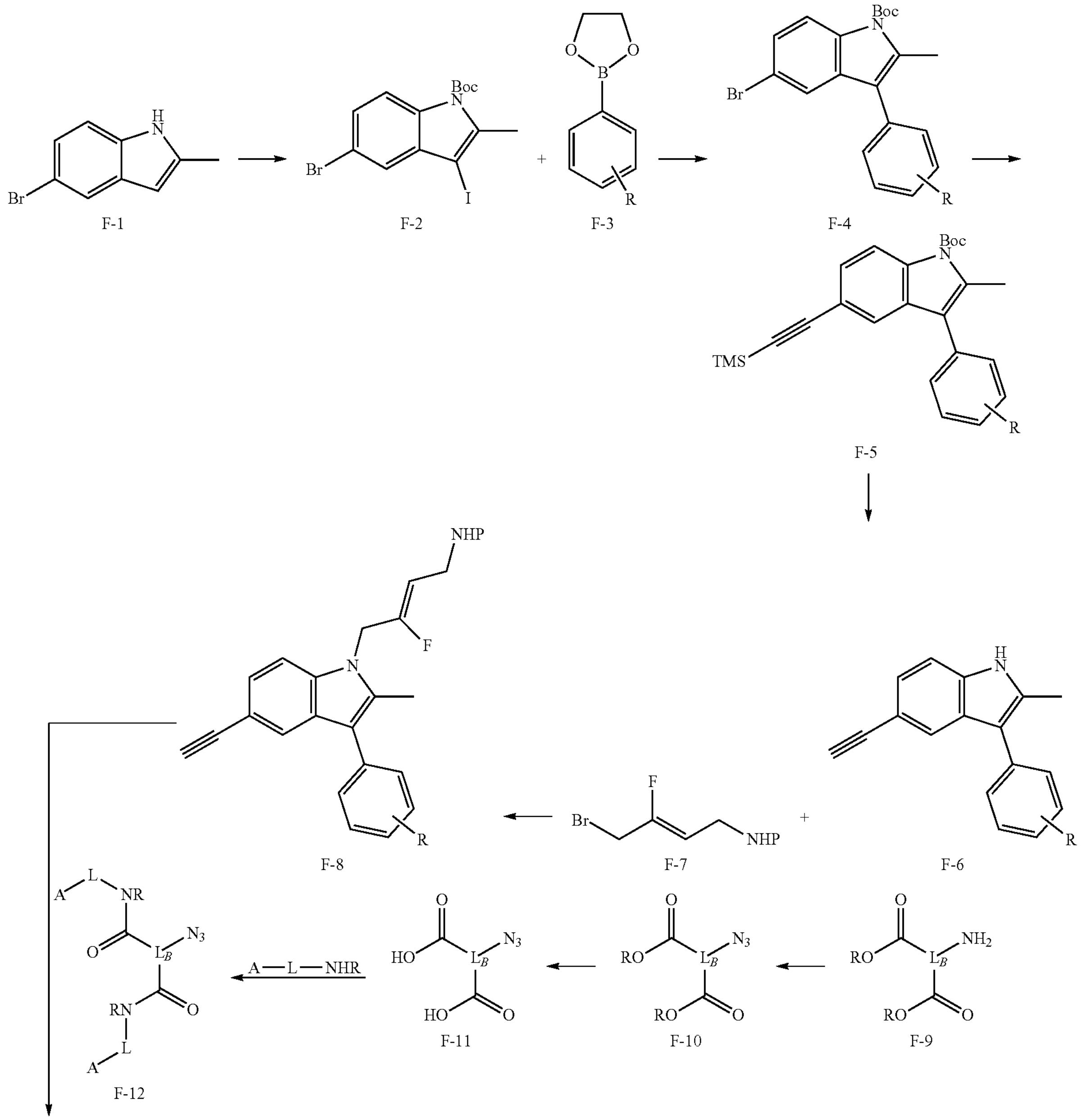

-continued

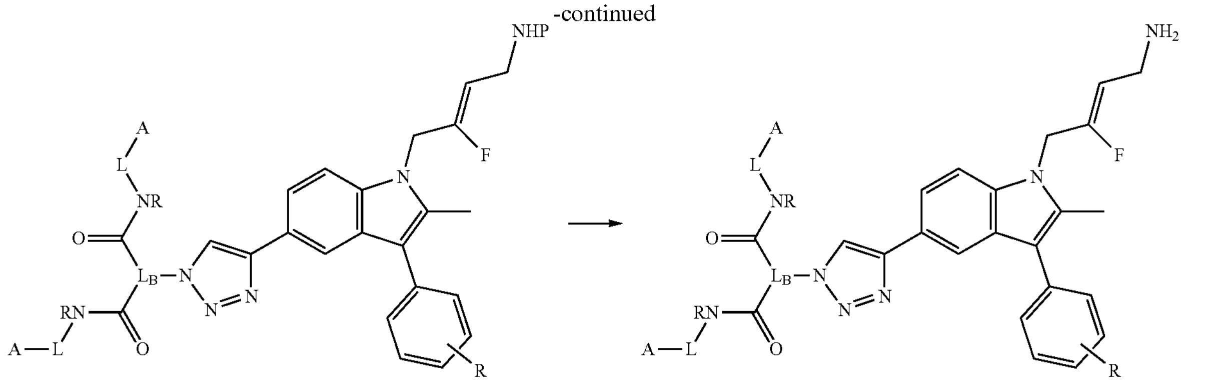

F-13 F-14

In some embodiments, 5-bromoindole F-1 was converted to the corresponding N-Boc protected 3-iodo-derivative F-2 by reaction with N-iodosuccinimide (NIS) in a suitable solvent such as DMF, followed by treatment with $Boc_2O$. In some embodiments, standard Suzuki coupling conditions between 3-iodoindole F-2 and boronic ester F-3 provided 3-arylated derivatives F-4. In other embodiments, standard Sonogashira coupling conditions between F-4 and trimethysilylacetylene afforded 5-acetylated-3-aryl indole derivatives F-5. In some embodiments, desilylation and —NBoc deprotection of derivatives F-5 is accomplished by treatment with aqueous KOH in a suitable solvent such as THF-MeOH to afford terminal acetylenic derivatives F-6. In some embodiments, treatment of derivatives F-6 with allylic bromide F-7 (prepared according to the general procedures described in patents WO 2017/136870 and WO 2017/136871) in the presence of an appropriate inorganic base using a suitable polar solvent provides derivatives F-8. In some embodiments, the appropriate base is $Cs_2CO_3$. In other embodiments, the suitable polar solvent is DMF. In some embodiments, the amino moiety of F-9 is diazotized under standard conditions to provide the corresponding azide derivatives F10. In some embodiments, the azido-diester derivatives F-10 are converted to the corresponding azido-diacids F-11 by treatment with a suitable inorganic base in an appropriate solvent. In some embodiments, the suitable base is KOH, and the appropriate solvent is THF-$H_2O$. In some embodiments, standard peptide coupling conditions between dicarboxylic acid derivatives F-11 and an appropriately substituted amine A-L-NHR affords bis-amide azido derivatives F-12. In some embodiments, treatment of alkyne derivatives F-8 with an appropriately substituted azide F-12 in the presence of a suitable catalyst such as $CuSO_4$, and in the presence of sodium ascorbate, in a suitable solvent such as THF-DMF-$H_2O$ yields triazole derivatives F-13. In some embodiments, standard amine deprotection conditions affords F-14.

Scheme 7

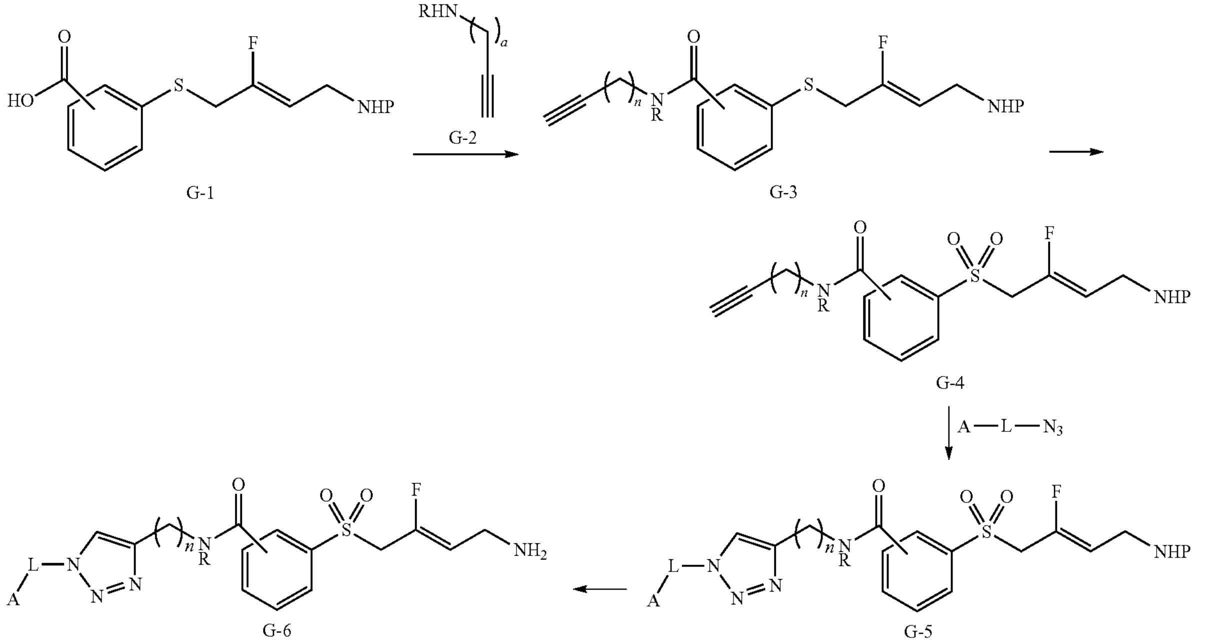

G-1 G-2 G-3 G-4 G-5 G-6

In some embodiments, standard peptide coupling conditions between carboxylic acid derivatives G-1 (prepared according to the general procedures outlined in Scheme 1) and an appropriately substituted amine G-2 affords alkynyl amide derivatives G-3. In some embodiments, thioether derivatives G-3 are converted, using a suitable oxidizing agent, to the corresponding sulfone derivatives G-4. In some embodiments, the oxidizing agent is mCPBA in the presence of an inorganic base such as $NaHCO_3$, using a suitable solvent such as $CH_2Cl_2$. In other embodiments, the oxidizing agent is Oxone™ in an appropriate solvent such as THF-MeOH—$H_2O$. In some embodiments, treatment of alkyne derivatives G-4 with an appropriately substituted azide A-L-$N_3$ in the presence of a suitable catalyst such as $CuSO_4$, and in the presence of sodium ascorbate, in a suitable solvent such as THF-DMF-$H_2O$ yields triazole derivatives G-5. In some embodiments, standard amine deprotection conditions affords G-6.

Scheme 8

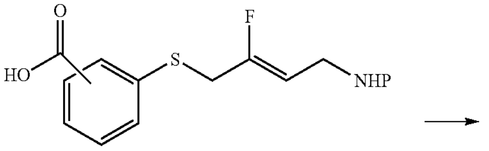

H-1

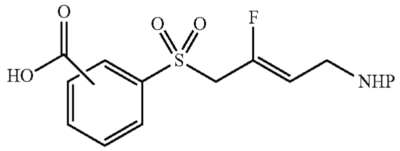

H-2

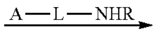

-continued

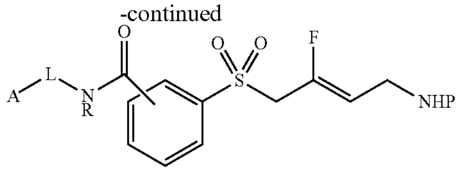

H-3

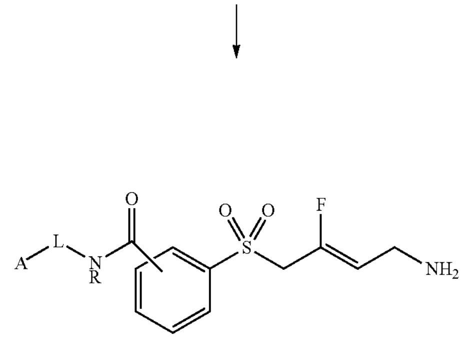

H-4

In some embodiments, thioether-acid derivatives H-1 are converted, using a suitable oxidizing agent, to the corresponding sulfone derivatives H-2. In some embodiments, the oxidizing agent is mCPBA in the presence of an inorganic base such as $NaHCO_3$, using a suitable solvent such as $CH_2Cl_2$. In other embodiments, the oxidizing agent is Oxone™ in an appropriate solvent such as THF-MeOH—$H_2O$. In some embodiments, standard peptide coupling conditions between carboxylic acid derivatives H-2 and an appropriately substituted amine A-L-NHR affords amide derivatives H-3. In some embodiments, standard amine deprotection conditions affords H-4.

Scheme 9

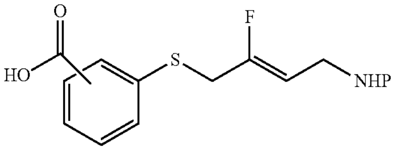

I-1

+

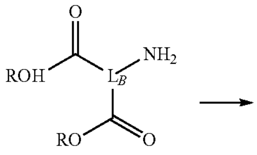

I-2

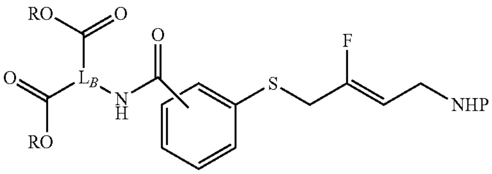

I-3

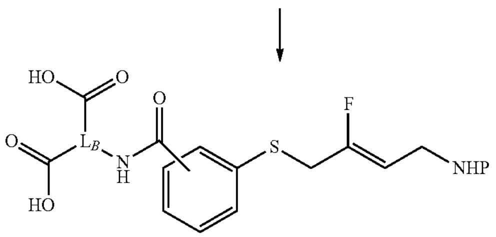

I-4

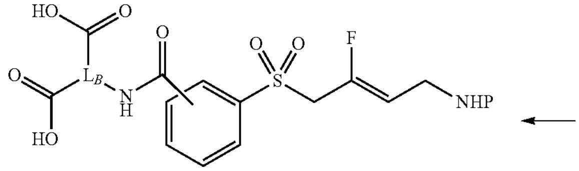

I-5

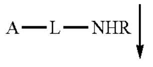

-continued

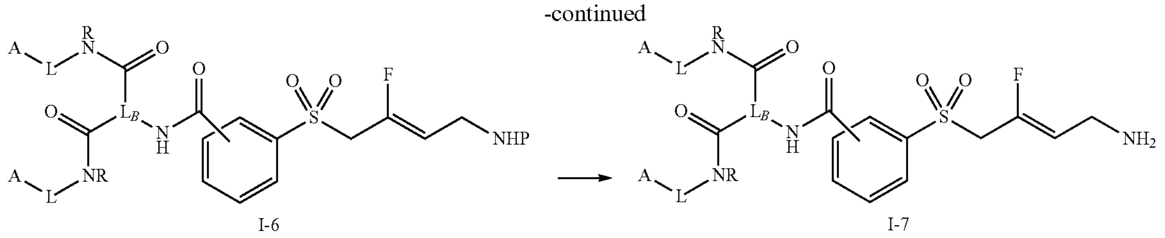

In some embodiments, standard peptide coupling conditions between carboxylic acid derivatives I-1 (prepared according to the general procedures outlined in Scheme 1) and an appropriately substituted diester-amine I-2 affords diester-amide derivatives I-3. In some embodiments, diester derivatives I-3 are converted to the corresponding diacids I-4 by treatment with a suitable inorganic base in an appropriate solvent. In some embodiments, the suitable base is NaOH, and the appropriate solvent is MeOH-THF-$H_2O$. In some embodiments, thioether derivatives I-4 are converted, using a suitable oxidizing agent, to the corresponding sulfone derivatives I-5. In other embodiments, the oxidizing agent is Oxone™ in an appropriate solvent such as THF-MeOH—$H_2O$. In some embodiments, the oxidizing agent is mCPBA in the presence of an inorganic base such as $NaHCO_3$, using a suitable solvent such as $CH_2Cl_2$. In some embodiments, standard peptide coupling conditions between dicarboxylic acid derivatives I-5 and an appropriately substituted amine A-L-NHR affords amide derivatives I-6. In some embodiments, standard amine deprotection conditions affords I-7.

Scheme 10
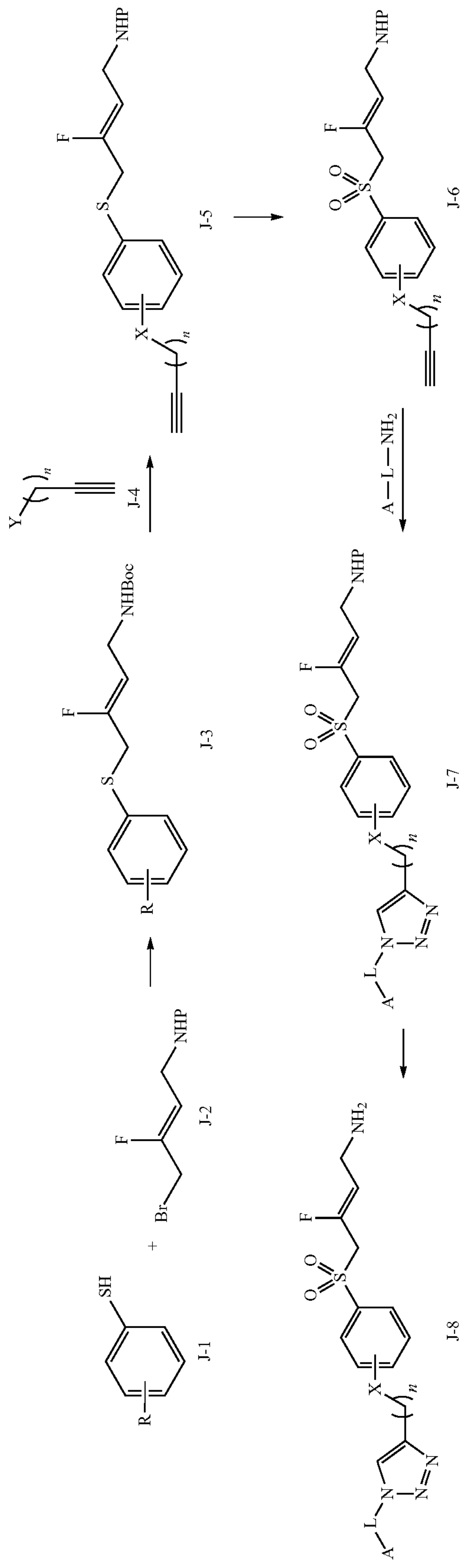
J-1 J-2 J-3 J-4 J-5 J-6 J-7 J-8

In some embodiments, treatment of thiophenol derivatives J-1 with allylic bromide J-2 (prepared according to the general procedures described in patents WO 2017/136870 and WO 2017/136871) in the presence of an appropriate inorganic base using a suitable polar solvent provides derivatives J-3. In some embodiments, the appropriate base is $K_2CO_3$. In other embodiments, the suitable polar solvent is DMF or alternatively acetone. In some embodiments, R=OH. In other embodiments, R=$NH_2$. In other embodiments, derivatives J-3 are treated with an alkyne alkylating agent J-4 in the presence of a suitable inorganic base using suitable polar solvent to provide derivatives J-5. In other embodiments, the base is $K_2CO_3$ and the solvent is DMF. In some embodiments, X=O. In other embodiments, X=NH. In some embodiments, thioether derivatives J-5 are converted, using a suitable oxidizing agent, to the corresponding sulfone derivatives J-6. In some embodiments, the oxidizing agent is mCPBA in the presence of an inorganic base such as $NaHCO_3$, using a suitable solvent such as $CH_2Cl_2$. In other embodiments, the oxidizing agent is Oxone™ in an appropriate solvent such as THF-MeOH—$H_2O$. In some embodiments, treatment of alkyne derivatives J-6 with an appropriately substituted azide A-L-$N_3$ in the presence of a suitable catalyst such as $CuSO_4$, and in the presence of sodium ascorbate, in a suitable solvent such as THF-DMF-$H_2O$ yields triazole derivatives J-7. In some embodiments, standard amine deprotection conditions affords J-8.

Scheme 11

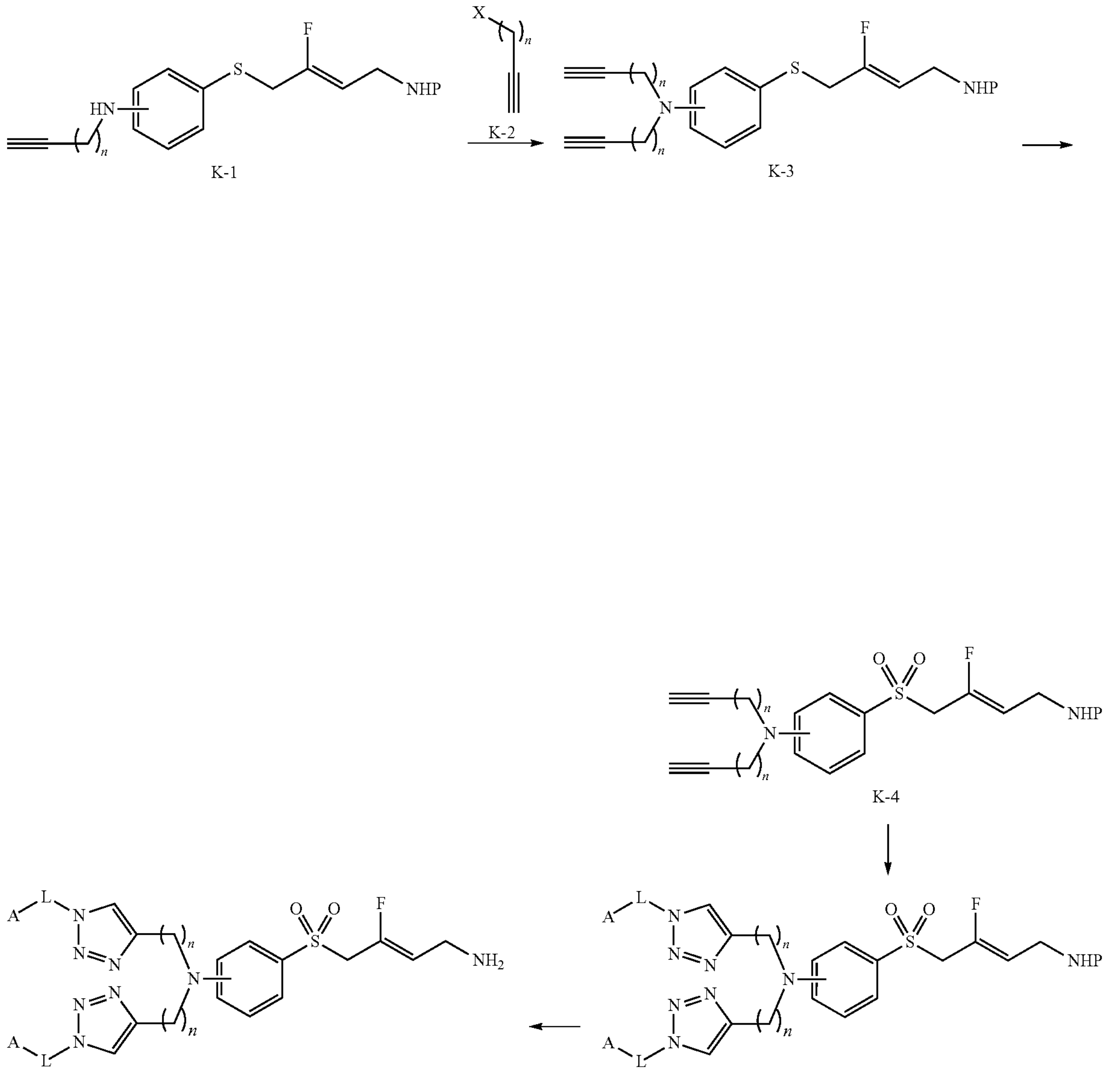

K-1 K-3 K-4 K-5 K-6

In some embodiments, derivatives K-1 (prepared according to the general procedures outlined in Scheme 10) are treated with an alkyne alkylating agent K-2 in the presence of a suitable inorganic base using suitable polar solvent to provide derivatives K-3. In other embodiments, the base is $K_2CO_3$ and the solvent is DMF. In some embodiments, thioether derivatives K-3 are converted, using a suitable oxidizing agent, to the corresponding sulfone derivatives K-4. In some embodiments, the oxidizing agent is mCPBA in the presence of an inorganic base such as $NaHCO_3$, using a suitable solvent such as $CH_2Cl_2$. In other embodiments, the oxidizing agent is Oxone™ in an appropriate solvent such as THF-MeOH—$H_2O$. In some embodiments, treatment of alkyne derivatives K-4 with at least two equivalents of an appropriately substituted azide A-L-$N_3$ in the presence of a suitable catalyst such as $CuSO_4$, and in the presence of sodium ascorbate, in a suitable solvent such as THF-DMF-$H_2O$ yields triazole derivatives K-5. In some embodiments, standard amine deprotection conditions affords K-6.

Scheme 12

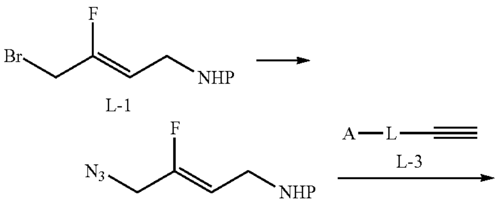

L-1

L-2

L-3

-continued

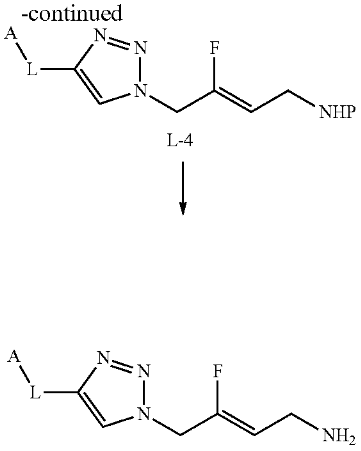

L-4

L-5

In some embodiments, the alcohol moiety of L-1 (prepared according to the general procedures described in patents WO 2017/136870 and WO 2017/136871) is converted to an azide L-2 using an azide transfer reagent such as sodium azide in a suitable polar solvent. In some embodiments, the polar solvent is DMF. In some embodiments treatment of azide derivative L-2 with an appropriately substituted alkyne L-3 in the presence of a suitable catalyst such as $CuSO_4$, and in the presence of sodium ascorbate, in a suitable solvent such as THF-DMF-$H_2O$ yields triazole derivatives L-4. In some embodiments, standard amine deprotection conditions affords L-5.

Scheme 13
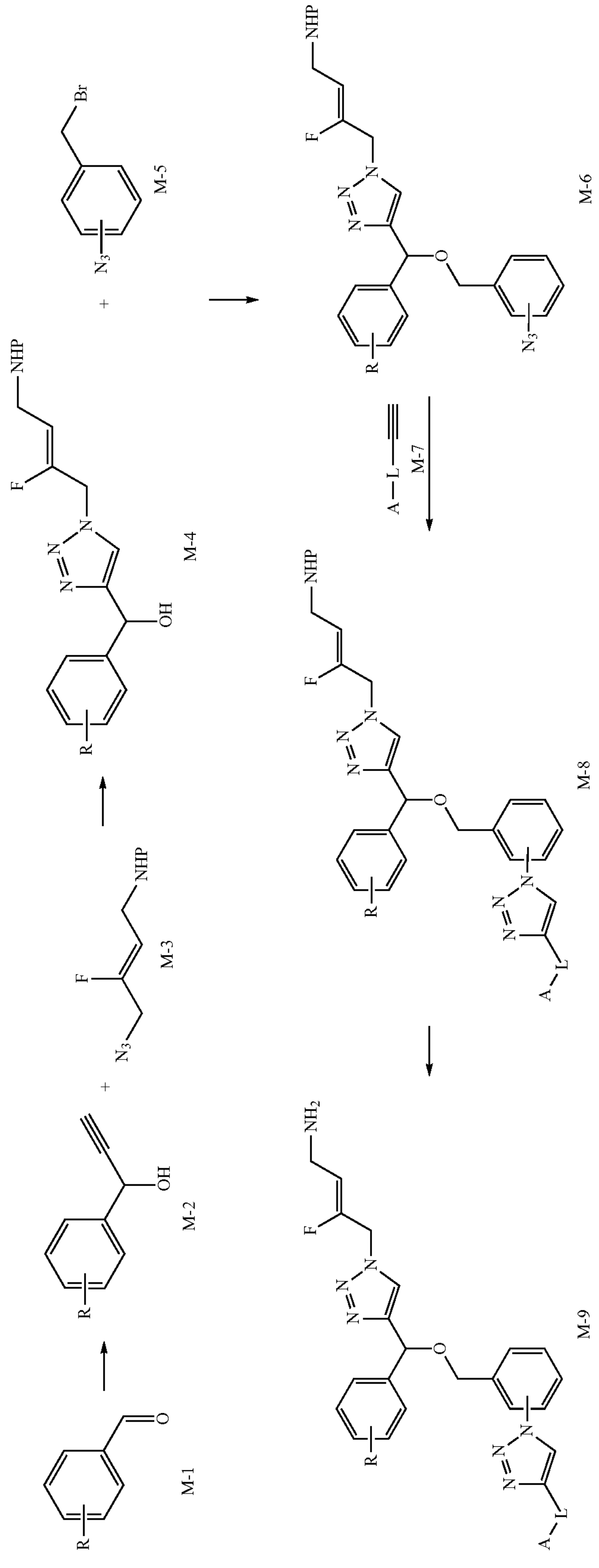

In some embodiments, aldehyde derivatives M-1 are treated with ethynylmagnesium bromide in a suitable solvent such as THF to afford ethynylalcohol derivatives M-2. In some embodiments, treatment of alkyne derivatives M-2 with azide M-3 (prepared according to the general procedures detailed in Scheme 12) in the presence of a suitable catalyst such as $CuSO_4$, and in the presence of sodium ascorbate, in a suitable solvent such as THF-DMF-$H_2O$ yields triazole derivatives M-4. In some embodiments, treatment of alcohol derivatives M-4 with arylbromide derivatives M-5 in the presence of a suitable base using an appropriate solvent provides M-6. In other embodiments, the suitable base is NaH, and the appropriate solvent is DMF. In some embodiments, treatment of azide derivatives M-6 with an appropriately substituted azide M-7 in the presence of a suitable catalyst such as $CuSO_4$, and in the presence of sodium ascorbate, in a suitable solvent such as THF-DMF-$H_2O$ yields triazole derivatives M-8. In some embodiments, standard amine deprotection conditions affords M-9.

The invention will now be described in greater detail, by way of illustration only, with reference to the following non-limiting examples. The examples are intended to serve to illustrate the invention and should not be construed as limiting the generality of the disclosure of the description throughout this specification.

Examples

The following examples are provided for illustrative purposes only and not to limit the scope of the claims provided herein.

Experimental: General Methods

All commercially available solvents and reagents were used as received. Where appropriate, reactions were carried out under an argon atmosphere. Reactions were monitored by either analytical thin-layer chromatography (TLC) or by analytical liquid chromatography-mass spectrometry (LCMS) recorded on either a Shimadzu LCMS 2020 instrument or an Agilent LC/MSD 1200 instrument using reverse-phase conditions. Purification of intermediates and final compounds was conducted, where necessary, using column chromatography or preparative HPLC. Normal-phase column chromatography was conducted under medium pressure either on silica gel or on prepacked silica gel cartridges using a flash chromatography system (CombiFlash Rf200, Teledyne Isco systems, USA). Reverse-phase column chromatography was conducted under low pressure on prepacked C18 cartridges using a flash chromatography system (Reveleris® X2). Eluents were monitored by UV light (X=254/280 nm). $^1$H-NMR and $^{19}$F-NMR spectra were recorded using either a Bruker 300 MHz NMR spectrometer, a Bruker Avance III plus 400 MHz NMR spectrometer or a Varian III plus 300 MHz spectrometer. Chemical shifts (6) are reported as parts per million (ppm) relative to tetramethylsilane (TMS; internal standard). The following abbreviations are used for multiplicities: s=singlet; br s=broad singlet; d=doublet; t=triplet; q=quartet; m=multiplet; and br m=broad multiplet. Low resolution mass spectra (MS) were obtained as electrospray-atmospheric pressure ionization (ES-API) mass spectra, which were recorded on either a Shimadzu LCMS 2020 instrument or an Agilent LC/MSD 1200 instrument using reverse-phase conditions. All animal experiments performed were conducted in compliance with institutional guidelines and approval from local ethics committees.

Synthesis of Int-A

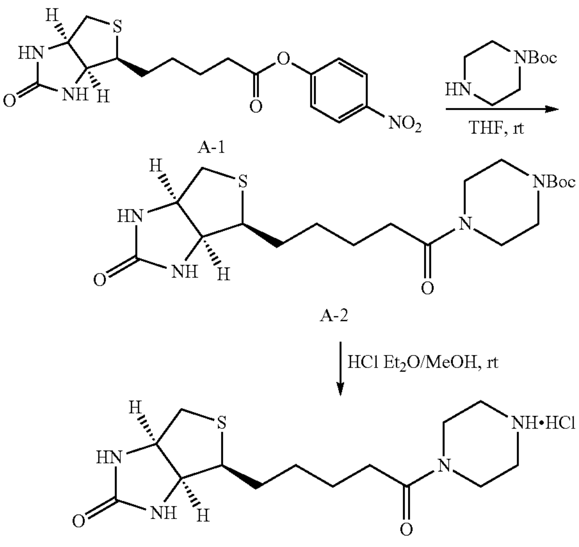

A-1
A-2
Int-A

Procedure 1: tert-butyl 4-(5-((3aS,4S,6aR)-2-oxo-hexahydro-1H-thieno[3,4-d]imidazol-4-yl)pentanoyl)piperazine-1-carboxylate (A-2)

To a stirring solution of A-1 (100 mg, 0.27 mmol) in THF (3 mL) under $N_2$ at room temperature (rt) was added tert-butyl piperazine-1-carboxylate (61.2 mg, 0.33 mmol). The resulting mixture was left to stir at rt overnight. The reaction mixture was concentrated in vacuo. The crude material was purified over silica gel, eluting with ethyl acetate followed by 10% methanol in $CH_2Cl_2$ to afford compound A-2 (112 mg, 99%) as a white solid. $^1$H NMR (300 MHz, $CDCl_3$) δ ppm: 6.15 (s, 1H), 5.51 (s, 1H), 4.56-4.46 (m, 1H), 4.32 (ddd, J=7.9, 4.6, 1.5 Hz, 1H), 3.58 (dd, J=6.7, 4.0 Hz, 2H), 3.44 (q, J=7.7, 6.1 Hz, 7H), 3.17 (td, J=7.1, 4.5 Hz, 1H), 2.91 (dd, J=12.8, 4.9 Hz, 1H), 2.75 (d, J=12.8 Hz, 1H), 2.37 (t, J=7.5 Hz, 2H), 2.05 (d, J=2.4 Hz, 1H), 1.71 (ddq, J=21.3, 14.2, 7.2 Hz, 4H), 1.48 (s, 9H).

Procedure 2: (3aS,4S,6aR)-4-(5-oxo-5-(piperazin-1-yl)pentyl)tetrahydro-1H-thieno[3,4-d]imidazol-2(3H)-one hydrochloride (Int-A)

To a stirring solution of A-2 (112 mg, 0.27 mmol) in MeOH (2 mL) at rt was added HCl (2.0 M in diethyl ether; 2.00 mL, 4.00 mmol). The resulting mixture was left to stir at rt for 4 hours (h). The reaction mixture was concentrated in vacuo to give a tan colored oily residue. Diethyl ether was added resulting in the precipitation of a fine powder. The suspension was transferred to a vial and the vial was spun down in a centrifuge (4000 rpm for 5 min.). The resulting "cake" was washed with diethyl ether and spun down once more. After removing the filtrate, the solid "cake" was dried under high vacuum to give Int-A (98.0 mg, 100%) as a tan colored solid. $^1$H NMR (300 MHz, Methanol-$d_4$) δ ppm: 4.67 (dd, J=8.0, 4.7 Hz, 1H), 4.48 (dd, J=8.0, 4.4 Hz, 1H), 3.92-3.79 (m, 4H), 3.42-3.17 (m, 5H), 3.01 (dd, J=13.0, 4.8 Hz, 1H), 2.80 (d, J=12.9 Hz, 1H), 2.50 (t, J=7.3 Hz, 2H), 1.65 (dddd, J=55.6, 27.6, 14.5, 6.9 Hz, 6H).

Synthesis of Int-B

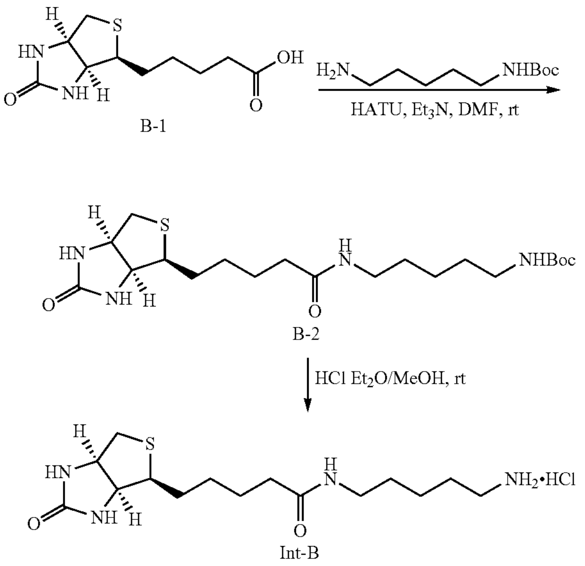

B-1

B-2

Int-B

Procedure 1: tert-butyl (5-(5-((3aS,4S,6aR)-2-oxo-hexahydro-1H-thieno[3,4-d]imidazol-4-yl)pentanamido)pentyl)carbamate (B-2)

To a stirring solution of biotin (B-1) (2.00 g, 8.19 mmol), tert-butyl (5-aminopentyl)carbamate (1.99 g, 9.82 mmol) and triethylamine (4.00 mL, 28.7 mmol) in DMF (20 mL) at rt under $N_2$ was added HATU (3.74 g, 9.82 mmol). The resulting yellow mixture was left to stir overnight. The reaction mixture was partitioned between water (200 mL) and ethyl acetate (40 ml). The aqueous layer was extracted with ethyl acetate (2×40 mL). To the aqueous layer was added NaCl solid until saturation was reached. The aqueous layer was then extracted with further ethyl acetate (40 mL) followed by $CH_2Cl_2$ (2×40 mL). The combined organics were dried over $Na_2SO_4$ and then concentrated in vacuo. The crude material was purified over silica gel (40 g), eluting with 5-20% methanol in $CH_2Cl_2$ to afford B-2 (3.50 g, 100%) as a colorless gel. $^1H$ NMR (300 MHz, $CDCl_3$) δ ppm: 6.38 (t, J=5.7 Hz, 1H), 6.18 (s, 1H), 5.62 (s, 1H), 4.80 (s, 1H), 4.55 (dd, J=7.9, 4.8 Hz, 1H), 4.35 (dd, J=8.3, 4.6 Hz, 1H), 3.18 (ddd, J=27.2, 12.9, 6.6 Hz, 5H), 2.99-2.87 (m, 1H), 2.76 (d, J=12.8 Hz, 1H), 2.27-2.17 (m, 2H), 1.83-1.59 (m, 4H), 1.59-1.25 (m, 17H).

Procedure 2: N-(5-aminopentyl)-5-((3aS,4S,6aR)-2-oxohexahydro-1H-thieno[3,4-d]imidazol-4-yl)pentanamide hydrochloride (Int-B)

Int-B was prepared from compound B-2 according to the protocol described for the synthesis of Int-A, procedure 2 (800 mg, 94%) as a white solid. LCMS: for $C_{15}H_{28}N_4O_2S$ calculated 328.2, found 329.2 $[M+H]^+$. $^1H$ NMR (300 MHz, Methanol-$d_4$) δ ppm: 4.76 (dd, J=8.1, 4.5 Hz, 1H), 4.56 (dd, J=8.0, 4.2 Hz, 1H), 3.42-3.28 (m, 4H), 3.05 (dd, J=13.1, 4.8 Hz, 1H), 3.01-2.91 (m, 1H), 2.85 (d, J=13.0 Hz, 1H), 2.42 (t, J=7.4 Hz, 2H), 1.91-1.38 (m, 12H).

Synthesis of Int-C

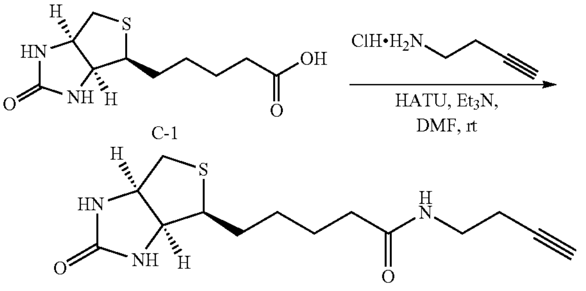

C-1

Int-C

Procedure 1 N-(but-3-yn-1-yl)-5-((3aS,4S,6aR)-2-oxohexahydro-1H-thieno[3,4-d]imidazol-4-yl)pentanamide (Int-C)

To a stirring solution of but-3-yn-1-amine hydrochloride (1.04 g, 9.82 mmol), biotin (C-1) (2.00 g, 8.19 mmol) and triethylamine (5.13 mL, 36.8 mmol) in DMF (15 mL) at rt under $N_2$ was added HATU (3.74 g, 9.82 mmol). The resulting yellow mixture was left to stir overnight. Diethyl ether (90 mL) was added to the mixture and the resulting suspension was stirred for 5 min. The organic layer was decanted. This was repeated once more to remove DMF. Residual diethyl ether was then removed to give a yellow, tacky solid. To the solid was added water (45 mL), and after brief sonication the mixture was transferred to a vial. The vial was then spun down in a centrifuge (4000 rpm, 5 min.). The supernatant was removed, further water was added, and the vial spun down. This process was repeated two more times to ensure complete removal of any residual HATU. The resulting white paste was lyophilized to afford Int-C (1.20 g, 50%) as a white solid. $^1H$ NMR (300 MHz, DMSO-$d_6$) δ ppm: 7.98 (t, J=5.8 Hz, 1H), 6.43 (s, 1H), 6.37 (s, 1H), 4.31 (dd, J=7.7, 5.0 Hz, 1H), 4.17-4.10 (m, 1H), 3.21-3.05 (m, 3H), 2.88-2.78 (m, 2H), 2.58 (d, J=12.4 Hz, 1H), 2.27 (td, J=7.1, 2.7 Hz, 2H), 2.06 (t, J=7.4 Hz, 2H), 1.71-1.13 (m, 6H).

Synthesis of Int-D

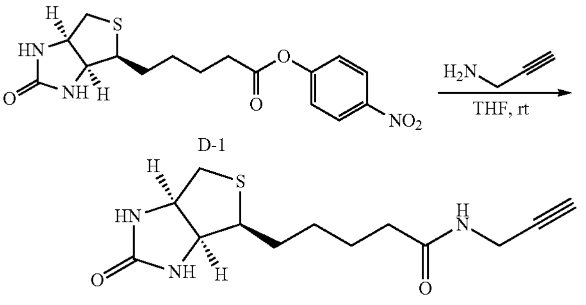

D-1

Int-D

Procedure 1: 5-((3aS,4S,6aR)-2-oxohexahydro-1H-thieno[3,4-d]imidazol-4-yl)-N-(prop-2-yn-1-yl)pentanamide (Int-D)

Int-D (32 mg, 83%) was prepared from compound D-1 according to the protocol described for the synthesis of Int-A (procedure 1). $^1H$ NMR (300 MHz, Methanol-$d_4$) δ ppm: 4.50 (ddd, J=7.9, 5.0, 1.0 Hz, 1H), 4.32 (dd, J=7.9, 4.5 Hz, 1H), 3.96 (d, J=2.6 Hz, 2H), 3.22 (ddd, J=8.7, 5.9, 4.4 Hz, 1H), 2.95 (dd, J=12.8, 5.0 Hz, 1H), 2.72 (d, J=12.7 Hz, 1H), 2.58 (t, J=2.6 Hz, 1H), 2.23 (t, J=7.5 Hz, 2H), 1.84-1.38 (m, 6H).

Synthesis of Int-E

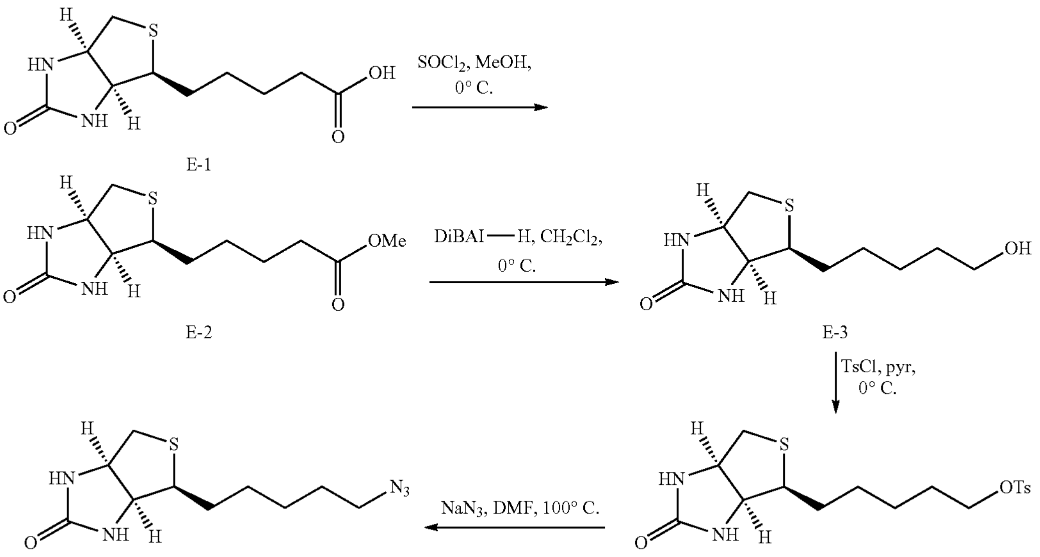

E-1 E-2 E-3 E-4 Int-E

Procedure 1: methyl 5-((3aS,4S,6aR)-2-oxohexahydro-1H-thieno[3,4-d]imidazol-4-yl)pentanoate 1: (E-2)

To a reaction vessel charged with methanol (10 mL) at 0° C. was added thionyl chloride (1.00 mL, 13.7 mmol) dropwise. Biotin (E-1) (1.00 g, 4.09 mmol) was then added in one lot. The resulting mixture was allowed to warm to rt, and left to stir overnight. The reaction mixture was then concentrated in vacuo. Water (20 mL) was added and stirring was continued for 10 min. The resulting solid was then filtered and dried under high vacuum to afford compound E-2 (1.00 g, 95%) as a white solid. $^1$H NMR (300 MHz, DMSO-$d_6$) δ ppm: 6.45 (s, 1H), 4.31 (ddd, J=7.8, 5.1, 1.0 Hz, 1H), 4.13 (dd, J=7.8, 4.4 Hz, 1H), 3.67 (s, 1H), 3.59 (s, 3H), 3.10 (ddd, J=8.5, 6.1, 4.4 Hz, 1H), 2.83 (dd, J=12.4, 5.0 Hz, 1H), 2.58 (d, J=12.4 Hz, 1H), 2.31 (t, J=7.4 Hz, 2H), 1.70-1.23 (m, 6H).

Procedure 2: (3aS,4S,6aR)-4-(5-hydroxypentyl)tetrahydro-1H-thieno[3,4-d]imidazol-2(3H)-one (E-3)

To a stirring solution of compound E-2 (800 mg, 3.10 mmol) in $CH_2Cl_2$ (20 mL) at 0° C. was added diisobutylaluminum hydride (1.0 M in $CH_2Cl_2$; 10.8 mL, 10.8 mmol) dropwise. The resulting reaction mixture was stirred at this temperature for 2 h. After warming to rt, stirring was continued for a further 1 h. Methanol/water (10 ml; 1:1) was added and the mixture was stirred vigorously for 10 min. After concentrating to dryness in vacuo, the residue was taken up in ethanol (10 mL) and then sonicated. The ethanolic mixture was filtered through Celite™, and the filtrate was concentrated in vacuo to afford compound E-3 (503 mg, 71%) as a white solid. $^1$H NMR (300 MHz, Methanol-d4) δ ppm: 4.51 (ddd, J=7.9, 5.0, 1.0 Hz, 1H), 4.32 (dd, J=7.9, 4.4 Hz, 1H), 3.57 (t, J=6.4 Hz, 2H), 3.23 (ddd, J=8.9, 5.7, 4.4 Hz, 1H), 2.95 (dd, J=12.8, 5.0 Hz, 1H), 2.72 (d, J=12.7 Hz, 1H), 1.83-1.34 (m, 8H).

Procedure 3: 5-((3aS,4S,6aR)-2-oxohexahydro-1H-thieno[3,4-d]imidazol-4-yl)pentyl 4-methylbenzenesulfonate (E-4)

To a stirring solution of compound E-3 (248 mg, 1.08 mmol) in pyridine (4.0 mL) at 0° C. was added 4-methylbenzenesulfonyl chloride (TsCl) (534 mg, 2.80 mmol). The resulting mixture was stirred at 0° C. for 1 h. The reaction mixture was partitioned between $CH_2Cl_2$ (40 mL) and water (40 mL). The organic layer was washed with HCl (1 M, 20 mL), water (20 mL) and sat. aq. NaCl (20 mL). After drying over $Na_2SO_4$ the solvent was removed in vacuo to afford compound E-4 (331 mg, 80%) as a white solid. $^1$H NMR (300 MHz, Methanol-$d_4$) δ ppm: 7.85-7.78 (m, 2H), 7.47 (d, J=8.0 Hz, 2H), 4.50 (ddd, J=8.0, 5.0, 1.0 Hz, 1H), 4.29 (dd, J=7.9, 4.4 Hz, 1H), 4.05 (t, J=6.2 Hz, 2H), 3.16 (ddd, J=9.0, 5.7, 4.4 Hz, 1H), 2.94 (dd, J=12.7, 4.9 Hz, 1H), 2.72 (d, J=12.8 Hz, 1H), 2.48 (s, 3H), 1.77-1.24 (m, 8H).

Procedure 5: (3aS,4S,6aR)-4-(5-azidopentyl)tetrahydro-1H-thieno[3,4-d]imidazol-2(3H)-one (Int-E)

To a stirring solution of compound E-4 (400 mg, 1.04 mmol) in DMF (3 mL) was added sodium azide (203 mg, 3.12 mmol). The resulting mixture was heated at 100° C. for 1 h. The reaction mixture was partitioned between $CH_2Cl_2$ (20 mL) and water (10 mL). The organic layer was washed with further water (2×10 mL), sat. aq. NaCl, and dried over $Na_2SO_4$. The solvent was removed in vacuo to afford the title compound Int-E (258 mg, 84%) as a white solid. LCMS: for $C_{10}H_{17}N_5OS$ calculated 255.1, found 256.2 $[M+H]^+$. $^1$H NMR (300 MHz, $CDCl_3$) δ ppm: 5.42 (s, 1H), 5.17 (s, 1H), 4.54 (ddt, J=7.8, 5.0, 1.3 Hz, 1H), 4.34 (ddd, J=7.9, 4.6, 1.6 Hz, 1H), 3.30 (t, J=6.8 Hz, 2H), 3.19 (ddd, J=8.4, 6.4, 4.6 Hz, 1H), 2.96 (dd, J=11.4, 6.2 Hz, 1H), 2.76 (dd, J=12.8, 1.1 Hz, 1H), 1.79-1.37 (m, 8H).

Int-F and Int-G

Int-F

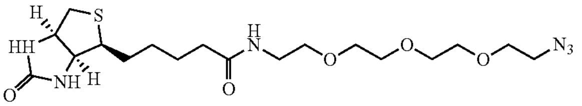

Int-G

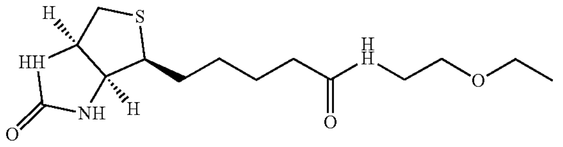

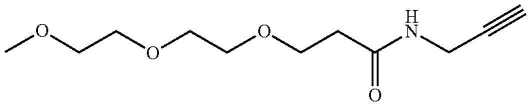

Int-F and Int-G were obtained from commercial sources (Carbosynth).

Int-H and Int-I

Int-H

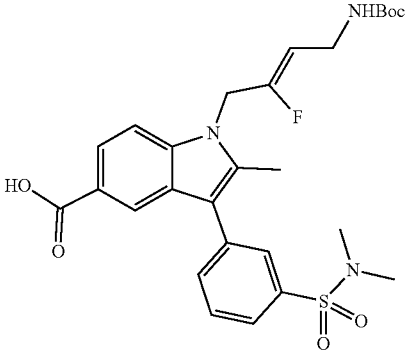

-continued

Int-I

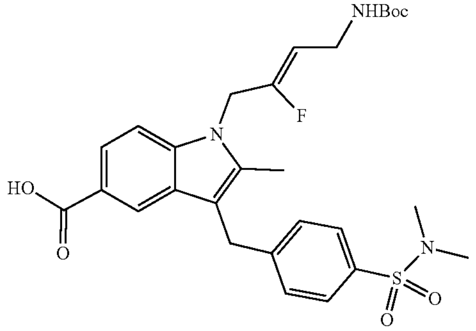

The synthesis of Int-H and Int-I has been described in detail in patents WO 2017/136870 A1 and WO 2017/136871 respectively.

Synthesis of Int-L

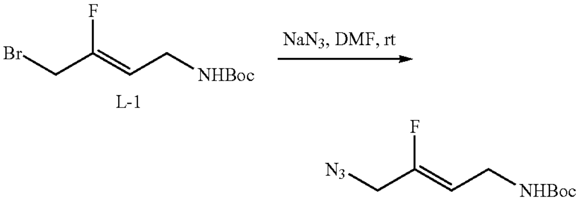

L-1

Int-L

Procedure 1: tert-butyl (Z)-(4-azido-3-fluorobut-2-en-1-yl)carbamate (Int-L)

To a stirring mixture of L-1 (the synthesis has been described in patent WO 2017/136870 A1) (5.00 g, 18.6 mmol) in acetone (100 mL) was added sodium azide (6.06 g, 93.2 mmol) in one lot. The resulting mixture was stirred at rt overnight. The reaction mixture was then filtered. The filtrate was concentrated in vacuo, re-dissolved in ethyl acetate (120 mL), and then washed with water and sat. aq. NaCl. After drying over $Na_2SO_4$, solvent was removed in vacuo to afford Int-L (4.30 g, 100%). $^1$H NMR (300 MHz, $CDCl_3$) δ ppm: 5.07 (dt, J=35.1, 7.0 Hz, 1H), 4.67 (br. s, 1H), 3.93-3.76 (m, 4H), 1.47 (s, 9H).

Synthesis of Int-M

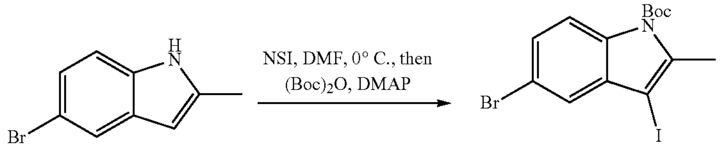

M-1

M-2

+

-continued

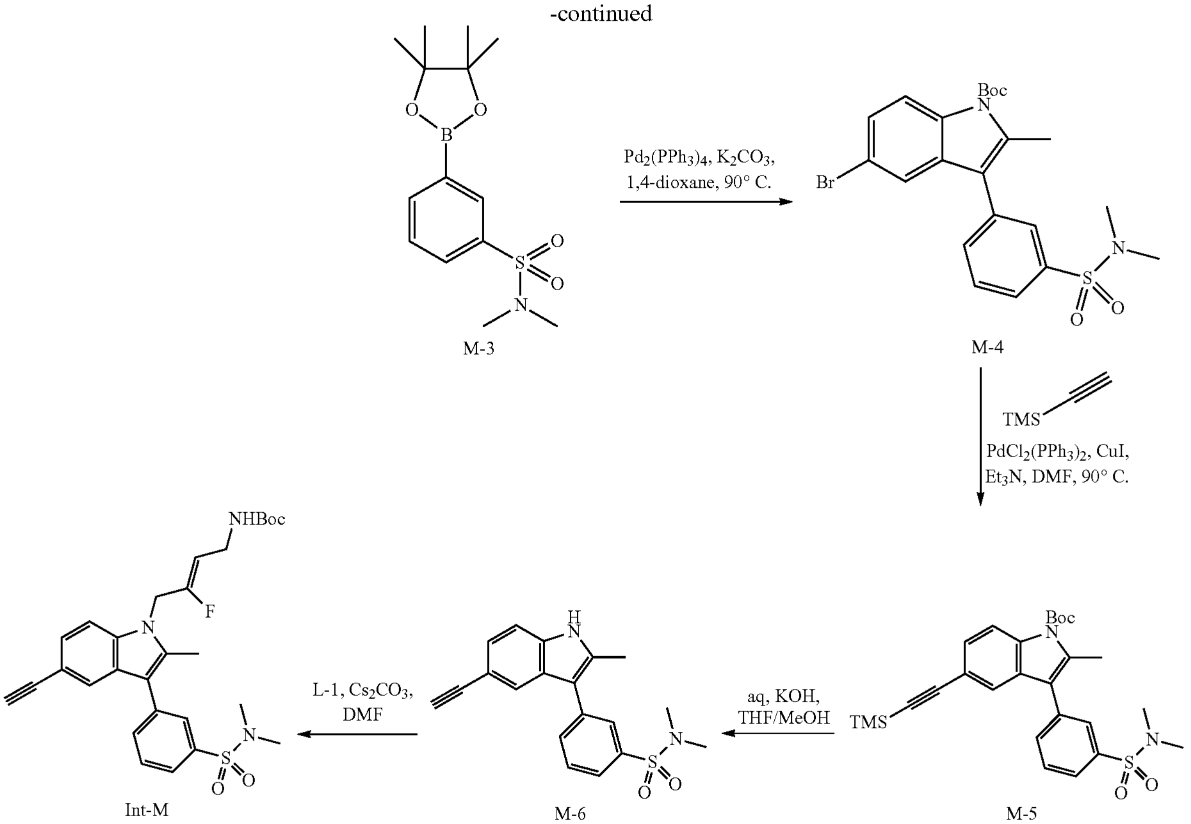

M-3
M-4
Int-M
M-6
M-5

Procedure 1: tert-butyl 5-bromo-3-iodo-2-methyl-1H-indole-1-carboxylate (M-2)

To a stirring solution of compound M-1 (3.00 g, 14.3 mmol) in DMF (30 mL) at 0° C. was added N-iodosuccinimide (NIS) (3.53 g, 15.7 mmol) in one portion. Then the resulting mixture was stirred at rt for 45 min. The reaction mixture was warmed to rt and di-tert-butyl dicarbonate (4.68 g, 21.4 mmol) in DMF (10 mL) was added followed by 4-(dimethylamino)pyridine (DMAP) (1.92 g, 15.7 mmol). Stirring was continued at rt overnight. The reaction mixture was poured into water (400 mL) with stirring, and the resultant brown solid was isolated by filtration. The solid was dried under high vacuum to afford compound M-2 (5.80 g, 93%) as a brown solid. $^1$H NMR (300 MHz, $CDCl_3$) δ ppm: 7.96 (d, J=8.9 Hz, 1H), 7.52 (d, J=2.0 Hz, 1H), 7.39 (dd, J=8.8, 2.0 Hz, 1H), 2.72 (s, 3H), 1.70 (s, 9H).

Procedure 2: tert-butyl 5-bromo-3-(3-(N,N-dimethylsulfamoyl)phenyl)-2-methyl-1H-indole-1-carboxylate (M-4)

A stirring solution of compound M-2 (2.20 g, 5.04 mmol), aqueous potassium carbonate (2.0 M, 12.6 mL, 25.2 mmol) and compound M-3 (the synthesis has been described in patent WO 2017/136870 A1) (1.73 g, 5.55 mmol) in dioxane (36 mL) was degassed by passing though it a stream of $N_2$ gas for 10 mins. Tetrakis(triphenylphosphine)palladium (0) (583 mg, 0.50 mmol) was then added under nitrogen, and the reaction mixture heated at 90° C. for 6 h. The reaction mixture was cooled to rt and diluted with $CH_2Cl_2$ (60 mL). The mixture was then filtered through Celite™ and the filtrate was evaporated to dryness. The crude residue was purified over silica gel (40 g), eluting with 20-90% ethyl acetate in hexanes to afford compound M-4 (690 mg, 28%) as a white solid. $^1$H NMR (300 MHz, $CDCl_3$) S ppm: 8.08 (d, J=8.9 Hz, 1H), 7.82 (dq, J=4.4, 2.0 Hz, 2H), 7.73-7.66 (m, 2H), 7.51 (d, J=2.0 Hz, 1H), 7.41 (dd, J=8.8, 2.0 Hz, 1H), 2.81 (s, 6H), 2.61 (s, 3H), 1.73 (s, 9H).

Procedure 3: tert-butyl 3-(3-(N,N-dimethylsulfamoyl)phenyl)-2-methyl-5-((trimethylsilyl)ethynyl)-1H-indole-1-carboxylate (M-5)

A stirring solution of compound M-4 (690 mg, 1.40 mmol), triethylamine (2.40 mL, 17.2 mmol) and copper (I) iodide (26.6 mg, 0.14 mmol) in DMF (2.4 mL) was degassed by passing through it a stream of argon gas for 5 min. Ethynyl(trimethyl)silane (593 uL, 4.20 mmol), and dichlorobis(triphenylphosphine)palladium (II) (98.2 mg, 0.14 mmol) were then added and the resulting mixture was stirred at 90° C. overnight. The reaction was concentrated under vacuum to remove triethylamine. Water (20 mL) was added and the product was extracted with ethyl acetate (3×20 mL). The combined organic extract was washed with sat. aq. NaCl (2×20 mL). The organic layer was dried and then concentrated in vacuo. The crude material was purified over silica gel, eluting with 20-80% $CH_2Cl_2$ in hexanes to afford compound M-5 (550 mg, 77%) as a pale yellow solid. 1H NMR (300 MHz, $CDCl_3$) δ ppm: 8.13 (dd, J=8.7, 0.7 Hz, 1H), 7.87-7.78 (m, 2H), 7.72-7.66 (m, 2H), 7.53 (dd, J=1.7, 0.6 Hz, 1H), 7.43 (dd, J=8.7, 1.6 Hz, 1H), 2.81 (s, 6H), 2.61 (s, 3H), 1.58 (s, 9H), 0.25 (s, 9H).

Procedure 4: 3-(5-ethynyl-2-methyl-1H-indol-3-yl)-N,N-dimethylbenzenesulfonamide (M-6)

To a stirring solution of M-5 (250 mg, 0.49 mmol) in THF (2.0 mL) at rt was added methanol (2.0 mL) followed by aqueous KOH (10% w/w, 20 mL, 38.8 mmol). The resulting mixture heated at reflux for 8 h. After cooling to rt, the reaction mixture was concentrated in vacuo. Water (5 mL) was added and the pH was adjusted to 2 by addition of 2 M aq. HCl. The product was then extracted with ethyl acetate (3×10 mL). The combined organic layer was dried over $Na_2SO_4$ and concentrated in vacuo to afford compound M-6 (168 mg, 100%) as a white solid. $^1$H NMR (300 MHz, Methanol-$d_4$) δ ppm: 7.88-7.80 (m, 2H), 7.78-7.66 (m, 3H), 7.33 (dd, J=8.4, 0.7 Hz, 1H), 7.23 (dd, J=8.4, 1.5 Hz, 1H), 3.27 (s, 1H), 2.78 (s, 6H), 2.54 (s, 3H).

Procedure 5: tert-butyl (Z)-(4-(3-(3-(N,N-dimethylsulfamoyl)phenyl)-5-ethynyl-2-methyl-1H-indol-1-yl)-3-fluorobut-2-en-1-yl)carbamate (Int-M)

To a stirring suspension of M-6 (168 mg, 0.50 mmol) and cesium carbonate (243 mg, 0.74 mmol) in DMF (1.5 mL) was added compound L-1 (126 mg, 0.47 mmol). The resulting mixture was stirred overnight at rt. The reaction mixture was diluted with water (15 mL) and the product was extracted with ethyl acetate (3×15 mL). The combined organics were washed with water, dried over $Na_2SO_4$ and then concentrated in vacuo. The crude material was purified over silica gel (12 g), eluting with 10-60% ethyl acetate in hexanes to afford Int-M (180 mg, 69%) as a colorless, tacky solid. $^1$H NMR (300 MHz, $CDCl_3$) δ ppm: 7.85 (t, J=1.7 Hz, 1H), 7.78-7.71 (m, 3H), 7.69-7.63 (m, 1H), 7.38 (dd, J=8.5, 1.5 Hz, 1H), 7.31-7.26 (m, 1H), 4.91-4.69 (m, 3H), 4.63 (br. s, 1H), 3.81 (s, 2H), 3.01 (s, 1H), 2.79 (s, 6H), 2.49 (s, 3H), 1.42 (s, 9H).

Example 1

Preparation of 4-((1-((Z)-4-amino-2-fluorobut-2-en-1-yl)-2-methyl-5-(4-(5-((3aS,4S,6aR)-2-oxohexahydro-1H-thieno[3,4-d]imidazol-4-yl)pentanoyl)piperazine-1-carbonyl)-1H-indol-3-yl)methyl)-N,N-dimethylbenzenesulfonamide hydrochloride (Compound 1-1)

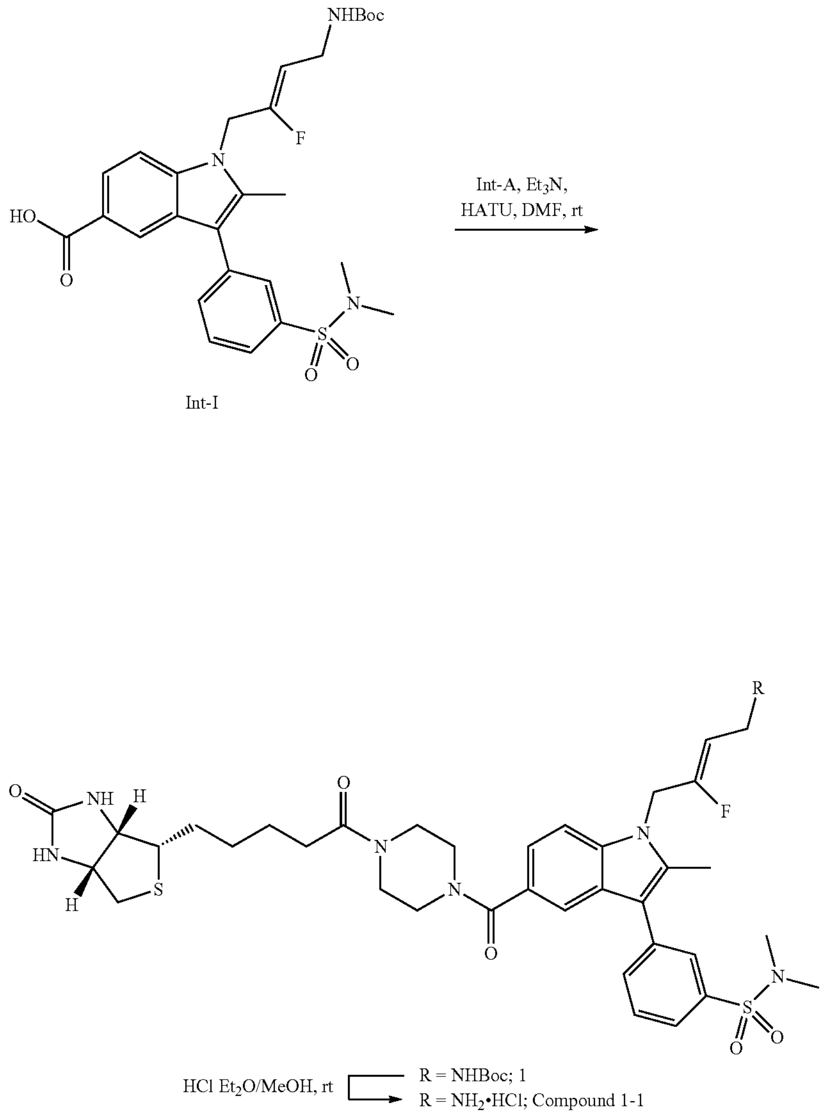

Procedure 1: tert-butyl ((Z)-4-(3-(4-(N,N-dimethylsulfamoyl)benzyl)-2-methyl-5-(4-(5-((3aS,4S,6aR)-2-oxohexahydro-1H-thieno[3,4-d]imidazol-4-yl)pentanoyl)piperazine-1-carbonyl)-1H-indol-1-yl)-3-fluorobut-2-en-1-yl)carbamate (1)

To a stirring solution of Int-A (84.2 mg, 0.24 mmol), Int-I (90.0 mg, 0.16 mmol) and triethylamine (0.11 mL, 0.80 mmol) in DMF (1.5 mL) at rt under $N_2$ was added HATU (73.4 mg, 0.19 mmol). The resulting yellow mixture was left to stir at rt for 3 h. The reaction mixture was partitioned between water (20 mL) and ethyl acetate (20 ml) and the organic layer was washed with aqueous HCl (2 M, 20 mL), sat. aq. $NH_4Cl$ (2×20 mL), dried over $Na_2SO_4$ and then concentrated in vacuo. The crude material was purified over silica gel, eluting with ethyl acetate to afford compound (1) (112 mg, 82%) as a pale yellow, foam solid. $^1H$ NMR (300 MHz, $CDCl_3$) δ ppm: $^1H$ NMR (300 MHz, $CDCl_3$) δ ppm: 7.73-7.57 (m, 2H), 7.49-7.18 (m, 5H), 6.03 (s, 1H), 5.44 (s, 1H), 5.30 (s, 1H), 4.78 (d, J=9.5 Hz, 4H), 4.48 (dd, J=7.8, 4.9 Hz, 1H), 4.37-4.25 (m, 1H), 4.16 (s, 2H), 3.89-3.25 (m, 8H), 3.16 (td, J=7.3, 4.5 Hz, 1H), 2.89 (dd, J=12.7, 4.8 Hz, 1H), 2.74 (s, 8H), 2.39 (d, J=8.1 Hz, 5H), 1.83-1.57 (m, 4H), 1.42 (s, 11H).

Procedure 2: 4-((1-((Z)-4-amino-2-fluorobut-2-en-1-yl)-2-methyl-5-(4-(5-((3aS,4S,6aR)-2-oxohexahydro-1H-thieno[3,4-d]imidazol-4-yl)pentanoyl)piperazine-1-carbonyl)-1H-indol-3-yl)methyl)-N,N-dimethylbenzenesulfonamide hydrochloride (Compound 1-1)

To a stirring solution of compound (1) (112 mg, 0.13 mmol) in methanol (2.0 mL) at rt was added HCl (2.0 M in diethyl ether; 2.00 mL, 4.00 mmol). The resulting mixture was left to stir for 5 h. The reaction mixture was concentrated in vacuo to give a pale brown residue. The residue was dried under high vacuum to give the title compound 1-1 (95.0 mg, 92%) as a pale brown solid. LCMS: for $C_{37}H_{48}FN_7O_5S_2$ calculated 753.3, found 754.4 $[M+H]^+$. 1H NMR (300 MHz, DMSO-$d_6$) δ 7.97 (s, 3H), 7.68-7.61 (m, 2H), 7.54 (d, J=8.5 Hz, 1H), 7.51-7.43 (m, 3H), 7.17 (dd, J=8.5, 1.6 Hz, 1H), 6.42 (br. s, 2H), 5.12 (d, J=12.1 Hz, 2H), 4.99 (dt, J=35.7, 7.4 Hz, 1H), 4.31 (dd, J=7.8, 4.8 Hz, 1H), 4.20 (s, 2H), 4.14 (dd, J=7.8, 4.5 Hz, 1H), 3.57-3.32 (m, 8H), 3.11 (q, J=6.3, 5.0 Hz, 1H), 2.83 (dd, J=12.4, 5.0 Hz, 1H), 2.62-2.55 (m, 7H), 2.46 (s, 3H), 2.31 (q, J=7.3 Hz, 2H), 1.72-1.28 (m, 6H).

Example 2

Preparation of 1-((Z)-4-amino-2-fluorobut-2-en-1-yl)-3-(3-(N,N-dimethylsulfamoyl)phenyl)-2-methyl-N-(5-(5-((3aS,4S,6aR)-2-oxohexahydro-1H-thieno[3,4-d]imidazol-4-yl)pentanamido)pentyl)-1H-indole-5-carboxamide (Compound 1-2)

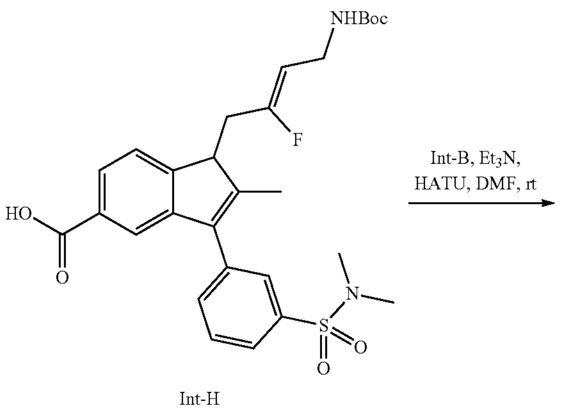

Int-H

-continued

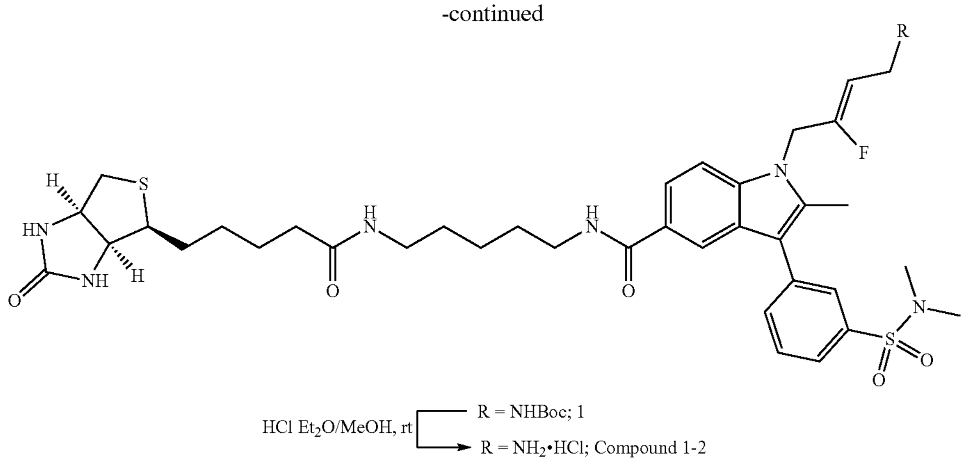

The title compound 1-2 was prepared using the protocols outlined in Example 1, procedure 1 (using Int-H and Int-B as the coupling partners) followed by Example 1, procedure 2 as an off-white solid (108 mg, 90%). LCMS: for $C_{37}H_{50}FN_7O_5S_2$ calculated 755.3, found 756.4 $[M+H]^+$. $^1H$ NMR (300 MHz, Methanol-$d_4$) δ ppm: 8.11 (d, J=1.6 Hz, 1H), 7.91-7.83 (m, 2H), 7.83-7.79 (m, 2H), 7.76 (dd, J=8.6, 1.7 Hz, 1H), 7.59 (d, J=8.7 Hz, 1H), 5.19 (d, J=9.2 Hz, 2H), 4.91 (dt, J=33.9, 7.3 Hz, 1H), 4.59-4.49 (m, 1H), 4.32 (dd, J=7.9, 4.5 Hz, 1H), 3.64 (d, J=7.5 Hz, 2H), 3.40 (t, J=6.9 Hz, 2H), 3.21 (t, J=6.7 Hz, 3H), 2.94 (dd, J=12.8, 4.9 Hz, 1H), 2.79 (s, 6H), 2.73 (d, J=12.8 Hz, 1H), 2.59 (s, 3H), 2.20 (t, J=7.3 Hz, 2H), 1.84-1.52 (m, 8H), 1.50-1.35 (m, 4H).

Example 3

Preparation of N,N'-((((((((((5-(1-((Z)-4-amino-2-fluorobut-2-en-1-yl)-3-(3-(N,N-dimethylsulfamoyl)phenyl)-2-methyl-1H-indole-5-carboxamido)-2-oxo-1H-benzo[d]imidazole-1,3(2H)-diyl)bis(methylene))bis(1H-1,2,3-triazole-4,1-diyl))bis(ethane-2,1-diyl))bis(oxy))bis(ethane-2,1-diyl))bis(oxy))bis(ethane-2,1-diyl))bis(oxy))bis(ethane-2,1-diyl))bis(5-((3aS,4S,6aR)-2-oxohexahydro-1H-thieno[3,4-d]imidazol-4-yl)pentanamide) hydrochloride (Compound 1-3)

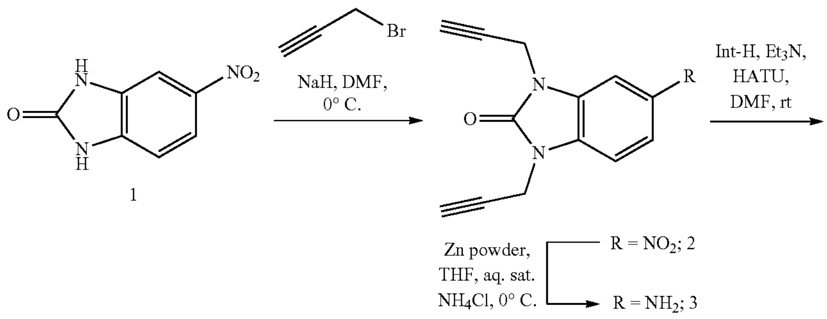

-continued

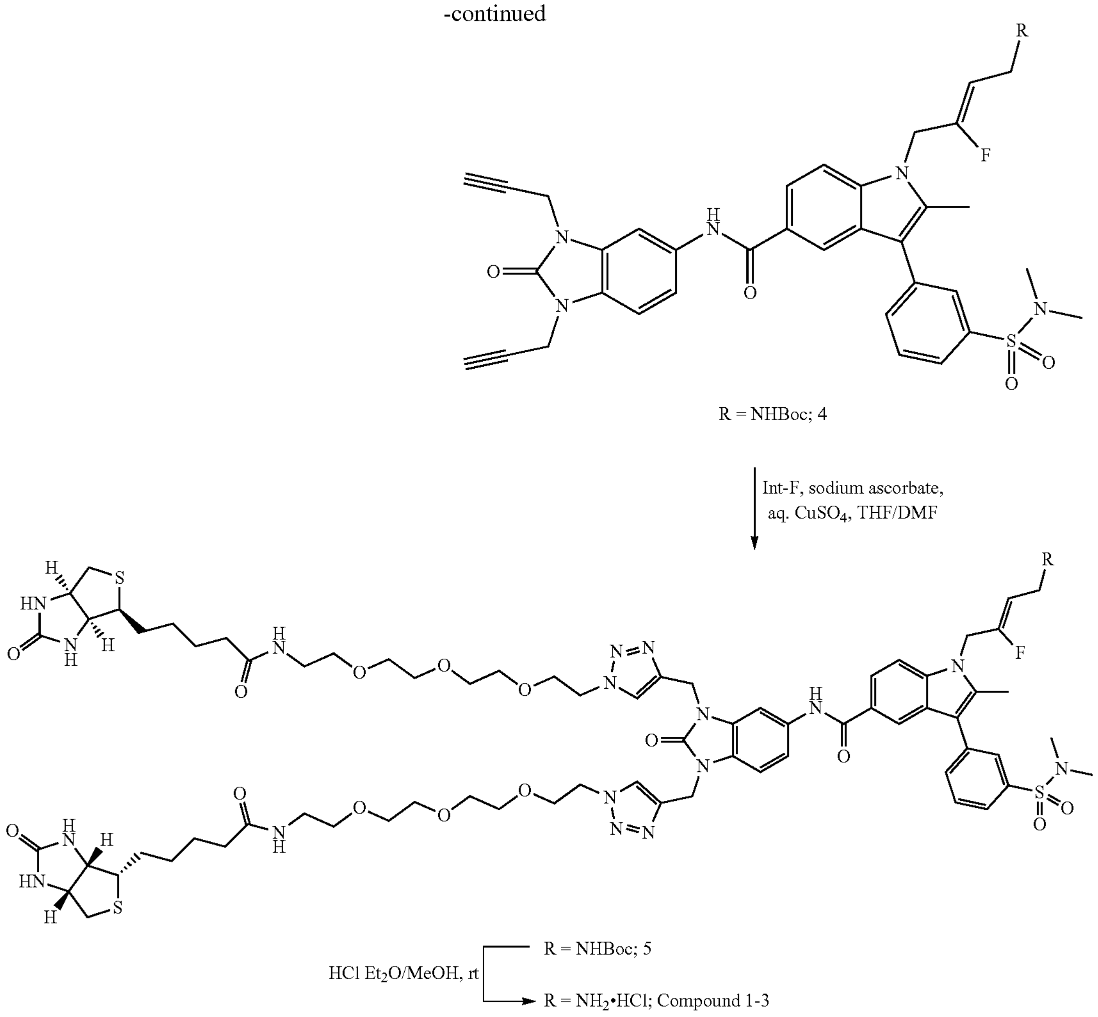

Procedure 1: 5-nitro-1,3-di(prop-2-yn-1-yl)-1,3-dihydro-2H-benzo[d]imidazol-2-one (2)

To a stirring solution of compound (1) (500 mg, 2.79 mmol) in DMF (10 mL) at 0° C. under Ar was added sodium hydride (60 wt. % in paraffin oil; 200 mg, 8.34 mmol) in one lot. The resulting mixture was left to stir at 0° C. for 15 min. Propargyl bromide (80 wt. % solution in toluene; 1.87 mL, 16.7 mmol) was then added dropwise. After complete addition, stirring was continued at 0° C. for a further 1 h. The reaction mixture was partitioned between water (30 mL) and ethyl acetate (30 mL). The organic layer was washed with further water (2×30 mL) and sat. aq. NaCl (30 mL). After drying over $Na_2SO_4$, the organics were removed in vacuo to afford compound (2) (701 mg, 98%). $^1H$ NMR (300 MHz, $CDCl_3$) δ ppm: 8.18 (dd, J=8.6, 2.2 Hz, 1H), 8.13 (d, J=2.1 Hz, 1H), 7.31 (d, J=8.7 Hz, 1H), 4.78-4.74 (m, 4H), 2.42-2.39 (m, 2H).

Procedure 2: 5-amino-1,3-di(prop-2-yn-1-yl)-1,3-dihydro-2H-benzo[d]imidazol-2-one (3)

To a vigorously stirring solution of compound (2) in THF (10 mL) and sat. aq. $NH_4Cl$ (10 mL) at 0° C. was added zinc powder (3.38 g, 51.7 mmol). The resulting mixture was left to stir at 0° C. for 2 h. The reaction mixture was filtered to remove the zinc. The filtrate was then extracted with ethyl acetate (40 mL). The aqueous layer was extracted with further ethyl acetate (2×30 mL). The combined organics were dried over $Na_2SO_4$ and concentrated in vacuo. The crude compound (3) (465 mg) was progressed immediately to the next step and purification was performed subsequently.

Procedure 3: tert-butyl (Z)-(4-(3-(3-(N,N-dimethylsulfamoyl)phenyl)-2-methyl-5-((2-oxo-1,3-di(prop-2-yn-1-yl)-2,3-dihydro-1H-benzo[d]imidazol-5-yl)carbamoyl)-1H-indol-1-yl)-3-fluorobut-2-en-1-yl)carbamate (4)

Compound (4) was prepared from crude compound (3) using the protocols outlined in Example 1, procedure 1 (employing Int-H as the coupling partner). $^1H$ NMR (300 MHz, $CDCl_3$) δ ppm: 8.27 (s, 1H), 8.19 (d, J=1.6 Hz, 1H), 7.87 (q, J=1.9 Hz, 2H), 7.81-7.70 (m, 3H), 7.64 (t, J=7.6 Hz, 1H), 7.39 (d, J=8.6 Hz, 1H), 7.25 (dd, J=8.4, 2.0 Hz, 1H), 7.14 (d, J=8.4 Hz, 1H), 4.95-4.70 (m, 4H), 4.68-4.62 (m, 4H), 3.82 (s, 2H), 2.79 (s, 6H), 2.52 (s, 3H), 2.31 (td, J=2.5, 0.9 Hz, 2H), 1.42 (s, 9H).

Procedure 4: tert-butyl ((Z)-4-(3-(3-(N,N-dimethylsulfamoyl)phenyl)-2-methyl-5-((2-oxo-3-((1-(13-oxo-17-((3aR,4R,6aS)-2-oxohexahydro-1H-thieno[3,4-d]imidazol-4-yl)-3,6,9-trioxa-12-azaheptadecyl)-1H-1,2,3-triazol-4-yl)methyl)-1-((1-(13-oxo-17-((3aS,4S,6aR)-2-oxohexahydro-1H-thieno[3,4-d]imidazol-4-yl)-3,6,9-trioxa-12-azaheptadecyl)-1H-1,2,3-triazol-4-yl)methyl)-2,3-dihydro-1H-benzo[d]imidazol-5-yl)carbamoyl)-1H-indol-1-yl)-3-fluorobut-2-en-1-yl)carbamate (5)

To a stirring solution of compound (4) (50.0 mg, 0.07 mmol) and Int-F (59.0 mg, 0.13 mmol) in THF/DMF (1:1; 1.0 mL) at rt was added sequentially water (0.5 mL), sodium ascorbate (1.0 M in water; 30.0 μL, 30.0 μmol) and $CuSO_4$ solution (1.0 M in water; 30.0 μL, 30.0 μmol). The resulting mixture was left to stir at rt overnight. The reaction mixture was purified directly using reverse-phase chromatography (C18; 40 g), eluting with 20-50% acetonitrile in water to afford compound (5) (52.0 mg, 48%). $^1$H NMR (300 MHz, Methanol-$d_4$) δ 8.22 (d, J=1.7 Hz, 1H), 8.13 (t, J=6.0 Hz, 2H), 7.93-7.77 (m, 5H), 7.68-7.60 (m, 2H), 7.37 (dd, J=8.5, 1.9 Hz, 1H), 7.21 (d, J=8.5 Hz, 1H), 5.26 (s, 4H), 5.09 (d, J=11.9 Hz, 2H), 4.96 (dt, J=33.9, 7.2 Hz, 1H), 4.59 (t, J=4.8 Hz, 4H), 4.52-4.45 (m, 2H), 4.34-4.24 (m, 2H), 3.88 (q, J=4.4 Hz, 4H), 3.73 (d, J=6.9 Hz, 2H), 3.63-3.39 (m, 22H), 3.35-3.26 (m, 2H), 3.20-3.11 (d, J=4.3 Hz, 2H), 2.89 (dd, J=12.8, 4.8 Hz, 2H), 2.78 (d, J=1.6 Hz, 6H), 2.69 (d, J=12.8 Hz, 2H), 2.59 (d, J=5.9 Hz, 3H), 2.17 (q, J=6.9 Hz, 4H), 1.76-1.26 (m, 21H).

Procedure 5: N,N'-(((((((((((5-(1-((Z)-4-amino-2-fluorobut-2-en-1-yl)-3-(3-(N,N-dimethylsulfamoyl)phenyl)-2-methyl-1H-indole-5-carboxamido)-2-oxo-1H-benzo[d]imidazole-1,3(2H)-diyl)bis(methylene))bis(1H-1,2,3-triazole-4,1-diyl))bis(ethane-2,1-diyl))bis(oxy))bis(ethane-2,1-diyl))bis(oxy))bis(ethane-2,1-diyl))bis(oxy))bis(ethane-2,1-diyl))bis(5-((3aS,4S,6aR)-2-oxohexahydro-1H-thieno[3,4-d]imidazol-4-yl)pentanamide) hydrochloride (Compound 1-3)

Title compound 1-3 was prepared from compound (5) according to the protocol outlined in Example 1, procedure 2 as a white solid (50.0 mg, 100%). LCMS: for $C_{71}H_{97}FN_{18}O_{14}S_3$ calculated 1540.7, found 1542.4 $[M+H]^+$. $^1$H NMR (300 MHz, Methanol-$d_4$) δ ppm: 8.42 (d, J=9.0 Hz, 2H), 8.26-8.20 (m, 1H), 7.95-7.85 (m, 3H), 7.85-7.76 (m, 2H), 7.75-7.64 (m, 2H), 7.39 (d, J=8.1 Hz, 1H), 7.23 (d, J=8.3 Hz, 1H), 5.44-5.29 (m, 4H), 5.22 (d, J=10.4 Hz, 2H), 5.17-5.04 (m, 1H), 4.69 (d, J=5.2 Hz, 6H), 4.49 (s, 2H), 3.93 (s, 4H), 3.72-3.35 (m, 22H), 3.27 (s, 2H), 3.05-2.93 (m, 2H), 2.78 (s, 8H), 2.61 (s, 3H), 2.29 (q, J=6.9 Hz, 4H), 1.86-1.34 (m, 12H).

Example 4

Preparation of N,N'-((((5-(1-((Z)-4-amino-2-fluorobut-2-en-1-yl)-3-(3-(N,N-dimethylsulfamoyl)phenyl)-2-methyl-1H-indole-5-carboxamido)-2-oxo-1H-benzo[d]imidazole-1,3(2H)-diyl)bis(ethane-2,1-diyl))bis(1H-1,2,3-triazole-1,4-diyl))bis(ethane-2,1-diyl))bis(5-((3aS,4S,6aR)-2-oxohexahydro-1H-thieno[3,4-d]imidazol-4-yl)pentanamide) hydrochloride (Compound 1-4)

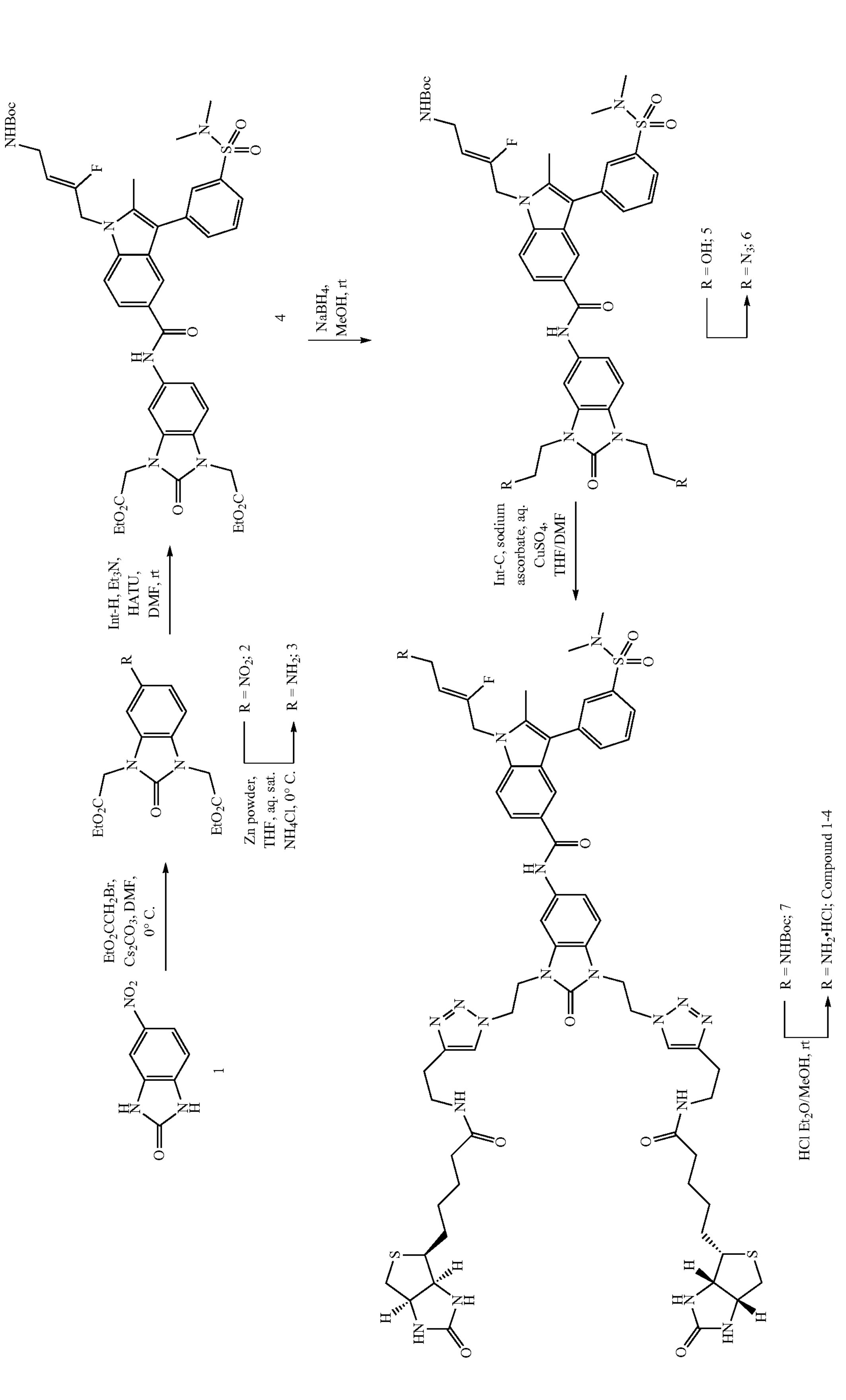
1
$EtO_2CCH_2Br$, $Cs_2CO_3$, DMF, 0° C.
Zn powder, THF, aq. sat. $NH_4Cl$, 0° C.
R = $NO_2$; 2
R = $NH_2$; 3
Int-H, $Et_3N$, HATU, DMF, rt
4
$NaBH_4$, MeOH, rt
R = OH; 5
R = $N_3$; 6
Int-C, sodium ascorbate, aq. $CuSO_4$, THF/DMF
HCl $Et_2O$/MeOH, rt
R = NHBoc; 7
R = $NH_2$•HCl; Compound 1-4

Procedure 1: diethyl 2,2'-(5-nitro-2-oxo-1H-benzo[d]imidazole-1,3(2H)-diyl)diacetate (2)

To a stirring suspension of cesium carbonate (13.6 g, 41.7 mmol) and compound (1) (3.00 g, 16.7 mmol) in DMF (15 mL), in an ice bath, was added ethyl bromoacetate (4.09 mL, 36.8 mmol). The resulting mixture was left to stir for 45 min. The reaction mixture was poured into water (200 mL) and stirred for 1 h, affording a fine solid. The solid was isolated by filtration and dried in an oven at 60° C. overnight to afford compound (2) (5.02 g, 85%) as a tan coloured solid. $^1$H NMR (300 MHz, $CDCl_3$) δ ppm: 8.15 (dd, J=8.7, 2.1 Hz, 1H), 7.86 (d, J=2.2 Hz, 1H), 7.01 (d, J=8.7 Hz, 1H), 4.72 (d, J=1.4 Hz, 4H), 4.29 (qd, J=7.2, 5.3 Hz, 4H), 1.33 (q, J=7.1 Hz, 6H).

Procedure 2: diethyl 2,2'-(5-amino-2-oxo-1H-benzo[d]imidazole-1,3(2H)-diyl)diacetate (3)

Compound (3) was prepared from compound (2) according to the protocol outlined in Example 3, procedure 2 (520 mg, 57%) as a white powder. LCMS: for $C_{15}H_{19}N_3O_5$ calculated 321.1, found 322.2 $[M+H]^+$. $^1$H NMR (300 MHz, $CDCl_3$) δ ppm: 6.71 (d, J=8.3 Hz, 1H), 6.46 (dd, J=8.3, 2.1 Hz, 1H), 6.32 (d, J=2.0 Hz, 1H), 4.60 (d, J=1.4 Hz, 4H), 4.24 (qd, J=7.1, 3.4 Hz, 4H), 1.29 (td, J=7.1, 4.3 Hz, 6H).

Procedure 3: diethyl 2,2'-(5-(1-(4-((tert-butoxycarbonyl)amino)-2-fluorobut-2-en-1-yl)-3-(3-(N,N-dimethylsulfamoyl)phenyl)-2-methyl-1H-indole-5-carboxamido)-2-oxo-1H-benzo[d]imidazole-1,3(2H)-diyl)(Z)-diacetate (4)

Compound (4) was prepared according to the protocol outlined in Example 1, procedure 1 using compound (3) and Int-H (217 mg, 70%) as a white solid. LCMS: for $C_{42}H_{49}FN_6O_{10}S$ calculated 848.3, found 849.3 $[M+H]^+$. 1H NMR (300 MHz, $CDCl_3$) δ ppm: 8.16 (d, J=1.8 Hz, 1H), 7.95-7.88 (m, 2H), 7.82-7.66 (m, 4H), 7.43 (d, J=8.6 Hz, 1H), 7.10 (dd, J=8.4, 2.0 Hz, 1H), 6.89 (d, J=8.4 Hz, 1H), 4.89 (d, J=10.2 Hz, 2H), 4.74 (dt, J=32.8, 6.8 Hz, 1H), 4.68 (s, 2H), 4.64 (s, 2H), 4.25 (qd, J=7.1, 1.4 Hz, 4H), 3.84 (s, 2H), 2.81 (s, 6H), 2.54 (s, 3H), 1.44 (s, 9H), 1.34-1.25 (m, 6H).

Procedure 4: tert-butyl (Z)-(4-(5-((1,3-bis(2-hydroxyethyl)-2-oxo-2,3-dihydro-1H-benzo[d]imidazol-5-yl)carbamoyl)-3-(3-(N,N-dimethylsulfamoyl)phenyl)-2-methyl-1H-indol-1-yl)-3-fluorobut-2-en-1-yl)carbamate (5)

To a stirring solution of compound (4) (210 mg, 0.25 mmol) in MeOH/THF (1:2, 12 mL) was added sodium borohydride (47.0 mg, 1.24 mmol) in one portion. The resulting reaction mixture was stirred at rt for 2 h. The reaction mixture was partitioned between ethyl acetate (20 mL) and water (10 mL). The organic layer was washed with sat. aq. NaCl, dried over $Na_2SO_4$ and concentrated in vacuo to afford compound (5) (157 mg, 83%) as a white foam. LCMS: for $C_{38}H_{45}FN_6O_8S$ calculated 764.3, found 765.3 $[M+H]^+$. $^1$H NMR (300 MHz, Methanol-$d_4$) δ 8.23 (d, J=1.7 Hz, 1H), 7.93-7.82 (m, 3H), 7.82-7.76 (m, 2H), 7.68 (d, J=1.9 Hz, 1H), 7.62 (d, J=8.6 Hz, 1H), 7.33 (dd, J=8.5, 2.0 Hz, 1H), 7.21 (d, J=8.5 Hz, 1H), 5.09 (d, J=11.5 Hz, 2H), 4.92 (dt, J=33.4, 7.1 Hz, 1H), 4.04 (td, J=5.6, 1.9 Hz, 4H), 3.87 (q, J=5.2 Hz, 4H), 3.74 (d, J=6.9 Hz, 2H), 2.78 (s, 6H), 2.58 (s, 3H), 1.49-1.35 (m, 9H).

Procedure 5: tert-butyl (Z)-(4-(5-((1,3-bis(2-azidoethyl)-2-oxo-2,3-dihydro-1H-benzo[d]imidazol-5-yl)carbamoyl)-3-(3-(N,N-dimethylsulfamoyl)phenyl)-2-methyl-1H-indol-1-yl)-3-fluorobut-2-en-1-yl)carbamate (6)

To a stirring suspension of compound (5) (120 mg, 0.16 mmol) and triethylamine (0.11 mL, 0.78 mmol) in acetone (4.0 mL) under $N_2$ at 0° C. was added methanesulfonyl chloride (0.05 mL, 0.63 mmol) dropwise at 0° C. The resulting mixture was warmed to rt and stirring was continued for 2 h. The reaction mixture was then concentrated to dryness in vacuo and the residue was taken up in DMF (2.0 mL). To this was then added sodium azide (102 mg, 1.57 mmol). The resulting suspension was then heated at 90° C. for 1 h. The reaction mixture was partitioned between ethyl acetate (20 mL) and water (10 mL). The organic layer was washed with further water (2×10 mL) and sat. aq. NaCl, and dried over $Na_2SO_4$. The solvent removed under vacuum to afford compound (6) (126 mg, 99%) as a yellow foam. LCMS: for $C_{38}H_{43}FN_{12}O_6S$ calculated 814.3, found 815.3 $[M+H]^+$. $^1$H NMR (300 MHz, Methanol-$d_4$) δ ppm: 8.24 (d, J=1.7 Hz, 1H), 7.93-7.83 (m, 3H), 7.81-7.71 (m, 3H), 7.61 (d, J=8.7 Hz, 1H), 7.37 (dd, J=8.5, 1.9 Hz, 1H), 7.24 (d, J=8.6 Hz, 1H), 5.08 (d, J=11.5 Hz, 2H), 4.91 (dt, J=32.9, 6.9 Hz, 1H), 4.12 (dt, J=8.0, 3.1 Hz, 4H), 3.79-3.63 (m, 6H), 2.77 (s, 6H), 2.57 (s, 3H), 1.42 (s, 9H).

Procedure 6: tert-butyl ((Z)-4-(3-(3-(N,N-dimethylsulfamoyl)phenyl)-2-methyl-5-((2-oxo-1,3-bis(2-(4-(2-(5-((3aS,4S,6aR)-2-oxohexahydro-1H-thieno[3,4-d]imidazol-4-yl)pentanamido)ethyl)-1H-1,2,3-triazol-1-yl)ethyl)-2,3-dihydro-1H-benzo[d]imidazol-5-yl)carbamoyl)-1H-indol-1-yl)-3-fluorobut-2-en-1-yl)carbamate (7)

Compound (7) was prepared according to the protocol outlined in Example 3, procedure 4 using compound (6) and Int-C. The crude material (137 mg) was progressed to the next step.

Procedure 7: N,N'-((((5-(1-((Z)-4-amino-2-fluorobut-2-en-1-yl)-3-(3-(N,N-dimethylsulfamoyl)phenyl)-2-methyl-1H-indole-5-carboxamido)-2-oxo-1H-benzo[d]imidazole-1,3(2H)-diyl)bis(ethane-2,1-diyl))bis(1H-1,2,3-triazole-1,4-diyl))bis(ethane-2,1-diyl))bis(5-((3aS,4S,6aR)-2-oxohexahydro-1H-thieno[3,4-d]imidazol-4-yl)pentanamide) hydrochloride (Compound 1-4)

Title compound (1-4) was prepared from compound (6) using the protocol outlined in Example 1, procedure 2 (89.0 mg, 71%) as an orange solid. LCMS: for $C_{61}H_{77}FN_{18}O_8S_3$ calculated 1305.6, found 1306.6 $[M+H]^+$. $^1$H NMR (300 MHz, Methanol-$d_4$) δ ppm: 8.60 (s, 2H), 8.24 (s, 1H), 7.98-7.75 (m, 6H), 7.68 (d, J=8.3 Hz, 1H), 7.23 (d, J=7.3 Hz, 1H), 7.02 (d, J=7.8 Hz, 1H), 5.23 (d, J=10.4 Hz, 2H), 5.08 (dt, J=31.3, 6.9 Hz, 1H), 4.64 (s, 2H), 4.45 (s, 6H), 3.66 (t, J=6.5 Hz, 2H), 3.57-3.41 (m, 4H), 3.34-3.17 (m, 4H), 3.02

(td, J=28.6, 26.8, 12.5 Hz, 4H), 2.79 (s, 8H), 2.62 (s, 3H), 2.20 (d, J=20.3 Hz, 4H), 1.88-1.28 (m, 16H).

Example 5

Preparation of 5-(1-((Z)-4-amino-2-fluorobut-2-en-1-yl)-3-(3-(N,N-dimethylsulfamoyl)phenyl)-2-methyl-1H-indole-5-carboxamido)-$N^1$,$N^3$-bis(5-(5-((3aS,4S,6aR)-2-oxohexahydro-1H-thieno[3,4-d]imidazol-4-yl)pentanamido)pentyl)isophthalamide hydrochloride (Compound 1-5)

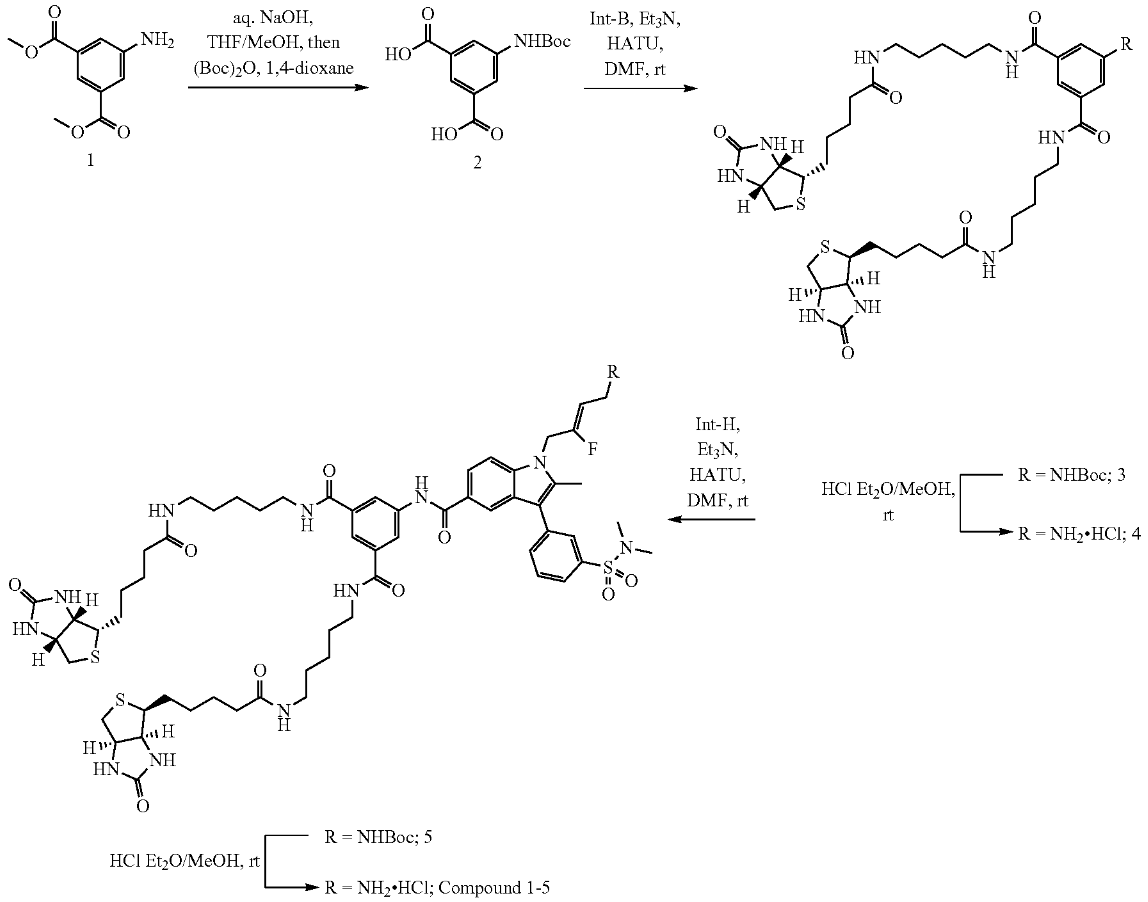

Procedure 1: 5-((tert-butoxycarbonyl)amino)isophthalic acid (2)

To a stirring solution of compound (1) (2.00 g, 8.43 mmol) in THF/MeOH (1:1, 20.0 mL) at rt was added aqueous sodium hydroxide (2.0 M; 9.27 mL, 18.5 mmol). The resulting mixture was stirred at rt overnight. Then organic solvent was removed in vacuo, and the resulting residue was diluted with water (10 mL). After cooling to 5° C., a solution of di-tert-butyl dicarbonate (2.02 g, 9.27 mmol) in 1,4-dioxane (20.0 mL) was added dropwise. The reaction mixture was warmed to rt and stirring was continued overnight. The organic solvent was removed in vacuo, and the aqueous mixture was acidified to pH=4 by addition of 2.0 M aqueous HCl. The resulting precipitated solid was collected by filtration and dried in an oven at 60° C. overnight to afford compound (2) (2.50 g, 100%) as a white solid. $^1$H NMR (300 MHz, DMSO-$d_6$) δ ppm: 9.77 (s, 2H), 8.29 (d, J=1.6 Hz, 2H), 8.08 (t, J=1.5 Hz, 1H), 1.50 (s, 9H).

Procedure 2: tert-butyl (3,5-bis((5-(5-((3aS,4S,6aR)-2-oxohexahydro-1H-thieno[3,4-d]imidazol-4-yl)pentanamido)pentyl)carbamoyl)phenyl)carbamate (3)

Compound (3) was prepared according to the protocol outlined in Example 1, procedure 1 using compound (2) and Int-B (100 mg, 62%) as a colorless gum. LCMS: for $C_{43}H_{67}N_9O_8S_2$ calculated 901.5, found 902.5 [M+H]$^+$. $^1$H NMR (300 MHz, Methanol-$d_4$) δ ppm: 8.03-7.96 (m, 3H), 7.87 (q, J=1.6 Hz, 1H), 4.56-4.47 (m, 2H), 4.34-4.27 (m, 2H), 3.37 (d, J=1.4 Hz, 4H), 3.28-3.12 (m, 6H), 2.93 (ddd, J=12.8, 5.0, 1.3 Hz, 2H), 2.71 (d, J=12.6 Hz, 2H), 2.20 (t, J=7.2 Hz, 4H). 1.77-1.50 (in. 25H). 1.50-1.28 (in. 8H).

Procedure 3: 5-amino-N[1],N[3]-bis(5-(5-((3aS,4S,6aR)-2-oxohexahydro-1H-thieno[3,4-d]imidazol-4-yl)pentanamido)pentyl)isophthalamide hydrochloride (4)

Compound (4) was prepared from compound (3) using the protocol described in Example 1, procedure 2 (90.0 mg, 97%) as a white foam. LCMS: for $C_{38}H_{59}N_9O_6S_2$ calculated 801.4, found 802.5 $[M+H]^+$.

Procedure 4: tert-butyl (Z)-(4-(5-((3,5-bis((5-(5-(2-oxohexahydro-1H-thieno[3,4-d]imidazol-4-yl)pentanamido)pentyl)carbamoyl)phenyl)carbamoyl)-3-(3-(N,N-dimethylsulfamoyl)phenyl)-2-methyl-1H-indol-1-yl)-3-fluorobut-2-en-1-yl)carbamate (5)

Compound (5) was prepared from compound (4) adopting the protocol described in Example 1, procedure 1 (using Int-H as the coupling partner) (30.0 mg, 25%) as a white solid. LCMS: for $C_{65}H_{89}FN_{12}O_{11}S_3$ calculated 1328.6, found 1329.9 $[M+H]^+$. $^1$H NMR (300 MHz, Methanol-$d_4$) δ ppm: 8.28 (d, J=1.6 Hz, 3H), 8.02-7.94 (m, 2H), 7.93-7.87 (m, 3H), 7.81-7.78 (m, 2H), 7.64 (d, J=8.6 Hz, 1H), 5.09 (d, J=11.8 Hz, 2H), 4.95 (dt, J=34.1, 7.2 Hz, 1H), 4.51-4.42 (m, 2H), 4.26 (dd, J=7.8, 4.5 Hz, 2H), 3.74 (d, J=6.8 Hz, 2H), 3.43 (t, J=6.8 Hz, 4H), 3.28-3.09 (m, 6H), 2.89 (dd, J=12.8, 4.9 Hz, 2H), 2.79 (s, 6H), 2.68 (d, J=12.7 Hz, 2H), 2.58 (s, 3H), 2.24-2.13 (m, 4H), 1.76-1.22 (m, 33H).

Procedure 5: 5-(1-((Z)-4-amino-2-fluorobut-2-en-1-yl)-3-(3-(N,N-dimethylsulfamoyl)phenyl)-2-methyl-1H-indole-5-carboxamido)-N[1],N[3]-bis(5-(5-((3aS,4S,6aR)-2-oxohexahydro-1H-thieno[3,4-d]imidazol-4-yl)pentanamido)pentyl)isophthalamide hydrochloride (Compound 1-5)

Title compound (1-5) was prepared from compound (5) using the protocol described in Example 1, procedure 2 (27.0 mg, 95%) as an off white solid. LCMS: for $C_{60}H_{81}FN_{12}O_9S_3$ calculated 1228.5, found 1231.1 $[M+H]^+$. 1H NMR (300 MHz, Methanol-$d_4$) δ ppm: 8.30 (d, J=1.7 Hz, 1H), 8.28 (d, J=1.6 Hz, 2H), 8.01 (t, J=1.6 Hz, 1H), 7.97-7.87 (m, 3H), 7.86-7.79 (m, 2H), 7.67 (d, J=8.7 Hz, 1H), 5.23 (d, J=9.3 Hz, 2H), 4.94 (dt, J=33.7, 7.7 Hz, 1H), 4.48 (dd, J=7.9, 4.7 Hz, 2H), 4.28 (dd, J=7.9, 4.4 Hz, 2H), 3.66 (d, J=7.4 Hz, 2H), 3.44 (t, J=6.8 Hz, 4H), 3.27-3.12 (m, 6H), 2.91 (dd, J=12.8, 4.9 Hz, 2H), 2.80 (s, 6H), 2.69 (d, J=12.7 Hz, 2H), 2.61 (s, 3H), 2.18 (t, J=7.3 Hz, 4H), 1.82-1.26 (m, 24H).

Example 6

Preparation of 5-(4-(1-((Z)-4-amino-2-fluorobut-2-en-1-yl)-3-(3-(N,N-dimethylsulfamoyl)phenyl)-2-methyl-1H-indol-5-yl)-1H-1,2,3-triazol-1-yl)-N[1],N[3]-bis(5-(5-((3aS,4S,6aR)-2-oxohexahydro-1H-thieno[3,4-d]imidazol-4-yl)pentanamido)pentyl)isophthalamide hydrochloride (Compound 1-6)

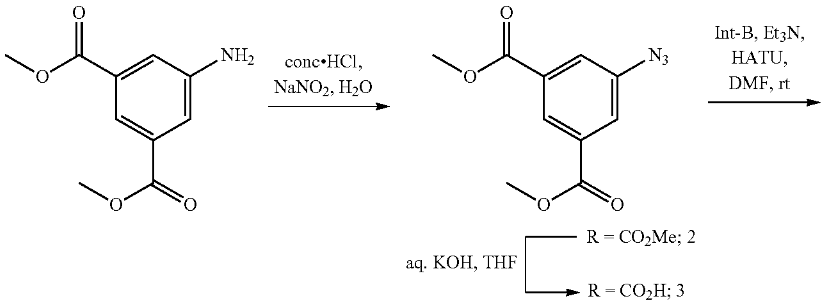

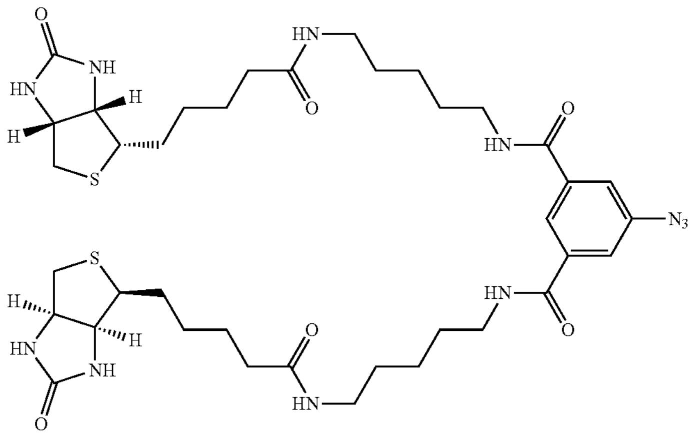

4

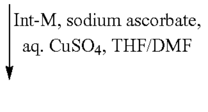

-continued

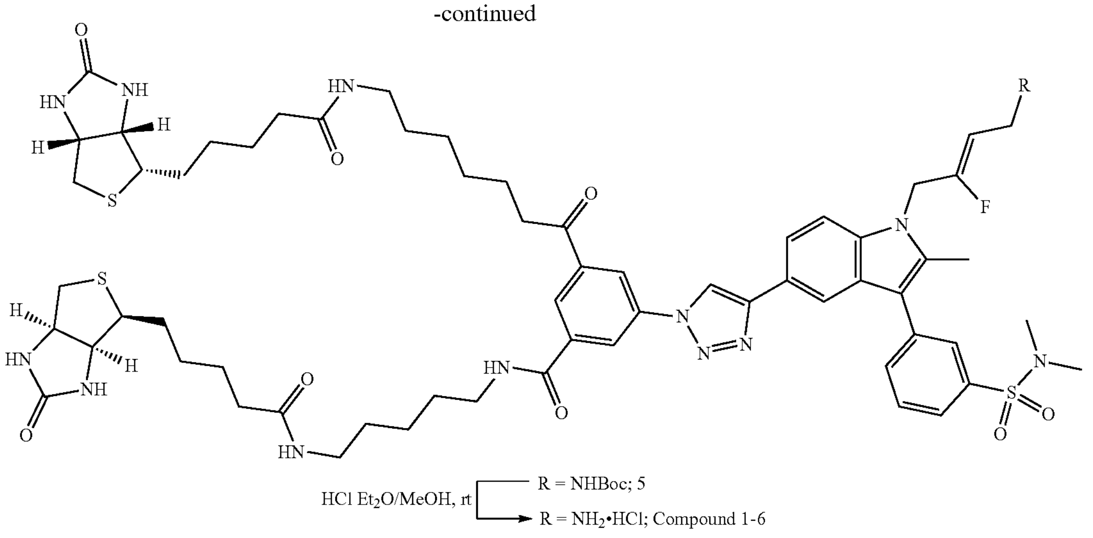

Procedure 1: dimethyl 5-azido isophthalate (2)

To a stirring solution of compound (1) (2.00 g, 8.43 mmol) in water (14.0 mL) at 0° C. was added aqueous HCl (2.0 M; 21.1 mL, 42.2 mmol) followed by a solution of sodium nitrite (1.16 g, 16.9 mmol) in water (6.0 mL). The resulting mixture was stirred at 0° C. for 15 min. To this mixture was added a solution of sodium azide (1.10 g, 16.9 mmol) in water (10 mL) dropwise. After addition was complete, stirring was continued at 0° C. for a further 30 min. The resulting solid precipitate was filtered and washed with water (2×5 mL) and then air dried to afford compound (2) (2.20 g, 99%) was as a white solid. $^1$H NMR (300 MHz, DMSO-$d_6$) δ ppm: 8.24 (t, J=1.5 Hz, 1H), 7.82 (d, J=1.5 Hz, 2H), 3.91 (s, 6H).

Procedure 2: 5-azido isophthalic acid (3)

To a stirring solution of compound (2) (1.10 g, 4.18 mmol) in MeOH/THF (1:1; 20.0 mL) at rt was added an aqueous sodium hydroxide (2.0 M; 10.5 mL, 21.0 mmol). The resulting mixture was stirred at rt overnight. The organic solvent was removed in vacuo and the aqueous mixture was acidified to pH=4 by addition of 2 M aqueous HCl. The resulting precipitated solid was filtered and washed with water (2×5 mL) and air dried to afford compound (3) (800 mg, 92%) as an off-white solid. $^1$H NMR (300 MHz, DMSO-$d_6$) δ 8.24 (t, J=1.5 Hz, 1H), 7.77 (d, J=1.4 Hz, 2H).

Procedure 3: 5-azido-$N^1$,$N^3$-bis(5-(5-((3aS,4S,6aR)-2-oxohexahydro-1H-thieno[3,4-d]imidazol-4-yl)pentanamido)pentyl)isophthalamide (4)

Compound (4) was prepared from compound (3) following the protocol described in Example 1, procedure 1 using Int-B as the coupling partner (295 mg, 36%) as a colorless gum. LCMS: for $C_{38}H_{57}N_{11}O_6S_2$ calculated 827.4, found 828.4 [M+H]$^+$.

Procedure 4: tert-butyl ((Z)-4-(5-(1-(3,5-bis((5-(5-((3aS,4S,6aR)-2-oxohexahydro-1H-thieno[3,4-d]imidazol-4-yl)pentanamido)pentyl)carbamoyl)phenyl)-1H-1,2,3-triazol-4-yl)-3-(3-(N,N-dimethylsulfamoyl)phenyl)-2-methyl-1H-indol-1-yl)-3-fluorobut-2-en-1-yl)carbamate (5)

Compound (5) was prepared from compound (4) following the protocol described in Example 3, procedure 4 (using Int-M as the coupling partner) (225 mg, 46%) as a white solid. $^1$H NMR (300 MHz, DMSO-$d_6$) δ ppm: 9.39 (s, 1H), 8.80 (s, 1H), 8.52 (d, J=1.4 Hz, 1H), 8.39 (s, 1H), 8.19 (s, 1H), 7.94-7.70 (m, 6H), 6.44 (s, 2H), 6.37 (s, 2H), 5.15 (d, J=13.5 Hz, 2H), 5.01 (dt, J=32.9, 7.1 Hz, 1H), 4.34-4.25 (m, 2H), 3.60 (s, 2H), 3.38-3.26 (m, 6H), 3.12-3.00 (m, 4H), 2.80 (dd, J=12.4, 5.0 Hz, 2H), 2.68 (s, 6H), 2.55 (d, J=18.3 Hz, 2H), 2.51 (s, 3H), 2.04 (t, J=7.3 Hz, 4H), 1.68-1.18 (m, 33H).

Procedure 5: 5-(4-(1-((Z)-4-amino-2-fluorobut-2-en-1-yl)-3-(3-(N,N-dimethylsulfamoyl)phenyl)-2-methyl-1H-indol-5-yl)-1H-1,2,3-triazol-1-yl)-$N^1$,$N^3$-bis(5-(5-((3aS,4S,6aR)-2-oxohexahydro-1H-thieno[3,4-d]imidazol-4-yl)pentanamido)pentyl) isophthalamide hydrochloride (Compound 1-6)

Title compound 1-6 was prepared from compound (5) following the protocol detailed in Example 1, procedure 2 (208 mg, 99%) as an off-white solid. LCMS: for $C_{61}H_{81}FN_{14}O_8S_3$ calculated 1252.6, found 1254.4 [M+H]$^+$. $^1$H NMR (300 MHz, Methanol-$d_4$) δ ppm: 9.02 (s, 1H), 8.55 (d, J=1.5 Hz, 2H), 8.41 (t, J=1.5 Hz, 1H), 8.19 (s, 1H), 7.99-7.73 (m, 5H), 7.63 (d, J=8.6 Hz, 1H), 5.19 (d, J=8.5 Hz, 2H), 4.88 (dt, J=35.3, 7.6 Hz, 1H), 4.46 (dd, J=8.0, 4.7 Hz, 2H), 4.26 (dd, J=7.9, 4.4 Hz, 2H), 3.66 (d, J=7.5 Hz, 2H), 3.48 (t, J=6.8 Hz, 4H), 3.23 (t, J=6.7 Hz, 4H), 3.19-3.10 (m, 2H), 2.90 (dd, J=12.8, 4.9 Hz, 2H), 2.82 (s, 6H), 2.68 (d, J=12.7 Hz, 2H), 2.59 (s, 3H), 2.18 (t, J=7.3 Hz, 4H), 1.82-1.25 (m, 24H).

Example 7

Preparation of 4-(((Z)-4-amino-2-fluorobut-2-en-1-yl)sulfonyl)-N-((1-(13-oxo-17-((3aS,4S,6aR)-2-oxo-hexahydro-1H-thieno[3,4-d]imidazol-4-yl)-3,6,9-trioxa-12-azaheptadecyl)-1H-1,2,3-triazol-4-yl) methyl)benzamide hydrochloride (Compound 1-7)

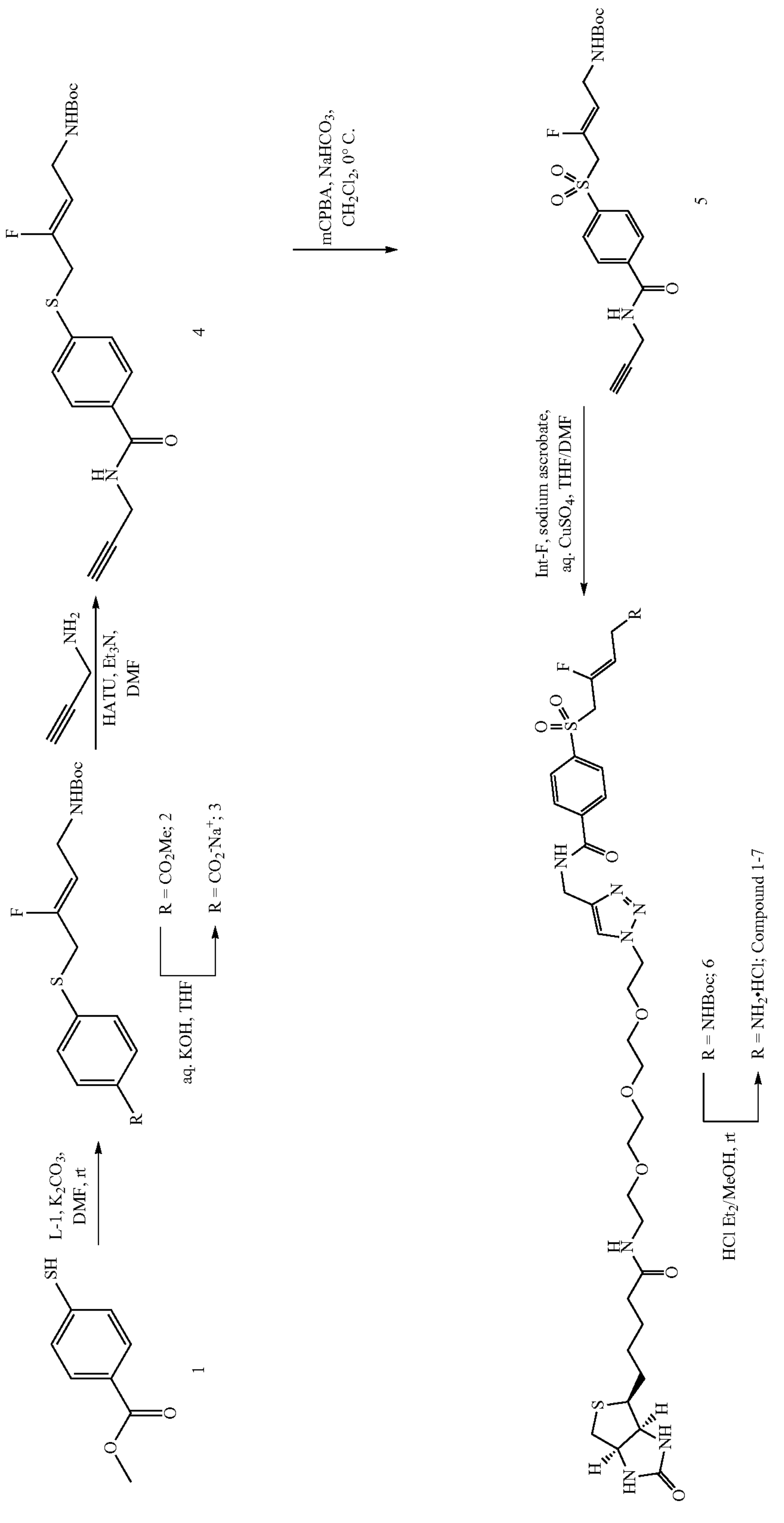
L-1, $K_2CO_3$,
DMF, rt
1
aq. KOH, THF
R = $CO_2Me$; 2
R = $CO_2^-Na^+$; 3
HATU, $Et_3N$,
DMF
4
mCPBA, $NaHCO_3$,
$CH_2Cl_2$, 0° C.
5
Int-F, sodium ascrobate,
aq. $CuSO_4$, THF/DMF
HCl $Et_2$/MeOH, rt
R = NHBoc; 6
R = $NH_2$•HCl; Compound 1-7

Procedure 1: methyl (Z)-4-((4-((tert-butoxycarbonyl)amino)-2-fluorobut-2-en-1-yl)thio)benzoate (2)

To a stirring suspension of compound (1) (500 mg, 2.97 mmol) and potassium carbonate (616 mg, 4.46 mmol) in DMF (10.0 mL) at rt under Ar was added L-1 (797 mg, 2.97 mmol). The resulting mixture was left to stir at rt overnight. The reaction mixture was diluted with water (50 mL) at which time a solid precipitated. The solid was isolated by filtration, and air-dried to afford compound (2) (1.05 g, 99%). $^1$H NMR (300 MHz, $CDCl_3$) δ ppm: 8.00-7.93 (m, 2H), 7.42-7.35 (m, 2H), 4.94 (dt, J=35.0, 7.1 Hz, 1H), 3.93 (s, 3H), 3.79 (t, J=6.7 Hz, 2H), 3.71-3.62 (m, 2H), 1.44 (s, 9H).

Procedure 2: sodium (Z)-4-((4-((tert-butoxycarbonyl)amino)-2-fluorobut-2-en-1-yl)thio)benzoate (3)

To a stirring suspension of compound (2) (0.50 g, 1.41 mmol) in THF (2.0 mL) at rt was added aqueous potassium hydroxide (1.8 M; 5.00 mL, 9.00 mmol). The resulting mixture was stirred at rt for 1 h. Tlc analysis after this showed very little conversion. An additional amount of aqueous KOH (1.8 M; 5.00 mL, 9.00 mmol) was added, and the reaction mixture was heated at 60° C. for 3 h. The reaction was diluted with water (20 mL), and then extracted with ethyl acetate (2×20 mL) (the sodium salt of the desired product was found to be very soluble in ethyl acetate). The combined extracts were dried over $Na_2SO_4$, and concentrated in vacuo to afford compound (3) (450 mg, 88%) as a glassy colorless solid. $^1$H NMR (300 MHz, DMSO-$d_6$) δ ppm: 7.82-7.76 (m, 2H), 7.30-7.22 (m, 2H), 7.01 (t, J=5.8 Hz, 1H), 4.91 (dt, J=36.8, 6.8 Hz, 1H), 3.81 (d, J=18.4 Hz, 2H), 3.54 (t, J=6.4 Hz, 2H), 1.36 (s, 9H).

Procedure 3: tert-butyl (Z)-(3-fluoro-4-((4-(prop-2-yn-1-ylcarbamoyl)phenyl)thio)but-2-en-1-yl)carbamate (4)

Compound (4) was prepared from compound (3) following the protocol described in Example 1, procedure 1 (using propargylamine as the coupling partner) (230 mg, 54%) as a white solid. $^1$H NMR (300 MHz, $CDCl_3$) δ ppm: 7.76-7.69 (m, 2H), 7.39 (d, J=8.1 Hz, 2H), 4.88 (dt, J=35.8, 7.4 Hz, 1H), 4.25 (dd, J=5.3, 2.5 Hz, 2H), 3.84-3.70 (m, 2H), 3.62 (d, J=16.2 Hz, 2H), 2.29 (t, J=2.5 Hz, 1H), 1.44 (s, 9H).

Procedure 4: tert-butyl (Z)-(3-fluoro-4-((4-(prop-2-yn-1-ylcarbamoyl)phenyl)sulfonyl)but-2-en-1-yl) carbamate (5)

To a stirring solution of compound (4) (390 mg, 1.03 mmol) in $CH_2Cl_2$ (5 mL) at 0° C. was added sequentially water (5 mL), sodium hydrogen carbonate (433 mg, 5.15 mmol) and 3-chloroperbenzoic acid (mCPBA) (577 mg, 2.58 mmol). The resulting mixture was left to stir at 0° C. for 2 h. The reaction mixture was partitioned between sat. aq. $NaHCO_3$ and $CH_2CO_2$. The aqueous layer was extracted with further $CH_2Cl_2$. The combined organics were dried over $Na_2SO_4$ and then concentrated in vacuo to give a white solid. The crude solid was dissolved in hot methanol (10 mL), and then left overnight in the fridge. The crystallized product was isolated by filtration, washed with cold methanol, and then dried under high vacuum to afford compound (5) (230 mg, 54%) as a white solid. $^1$H NMR (300 MHz, $CDCl_3$) δ ppm: 8.05-7.95 (m, 4H), 4.91 (dt, J=34.9, 7.4 Hz, 1H), 4.30 (dd, J=5.2, 2.5 Hz, 2H), 3.95 (d, J=18.4 Hz, 2H), 3.78 (s, 2H), 2.34 (t, J=2.6 Hz, 1H), 1.46 (s, 9H).

Procedure 5: tert-butyl ((Z)-3-fluoro-4-((4-(((1-(13-oxo-17-((3aS,4S,6aR)-2-oxohexahydro-1H-thieno[3,4-d]imidazol-4-yl)-3,6,9-trioxa-12-azaheptadecyl)-1H-1,2,3-triazol-4-yl)methyl)carbamoyl)phenyl) sulfonyl)but-2-en-1-yl)carbamate (6)

Compound (6) was prepared from compound (5) according to the protocol outlined in Example 3, procedure 4 (using Int-F as the coupling partner) (150 mg, 80%) as a white solid. $^1$H NMR (300 MHz, $CDCl_3$) δ ppm: 9.36 (s, 1H), 8.15 (d, J=8.2 Hz, 2H), 8.09 (s, 1H), 7.96 (d, J=8.2 Hz, 2H), 4.96 (dt, J=36.1, 7.2 Hz, 1H), 4.77 (qd, J=15.2, 5.5 Hz, 2H), 4.63-4.51 (m, 3H), 4.39 (dd, J=7.8, 4.5 Hz, 1H), 4.03-3.89 (m, 4H), 3.76 (s, 2H), 3.70-3.53 (m, 10H), 3.43 (s, 2H), 3.16 (d, J=5.2 Hz, 1H), 3.00-2.87 (m, 1H), 2.87-2.72 (m, 1H), 2.08 (d, J=7.8 Hz, 2H), 1.78-1.33 (m, 15H).

Procedure 6: 4-(((Z)-4-amino-2-fluorobut-2-en-1-yl) sulfonyl)-N-((1-(13-oxo-17-((3aS,4S,6aR)-2-oxohexahydro-1H-thieno[3,4-d]imidazol-4-yl)-3,6,9-trioxa-12-azaheptadecyl)-1H-1,2,3-triazol-4-yl) methyl)benzamide hydrochloride (Compound 1-7)

Title compound 1-7 was prepared from compound (6) using the protocol detailed in Example 1, procedure 2 (98.0 mg, 71%) as a white solid. LCMS: for $C_{32}H_{47}FN_8O_8S_2$ calculated 754.3, found 755.3 $[M+H]^+$. $^1$H NMR (300 MHz, Methanol-$d_4$) δ ppm: 8.26 (s, 1H), 8.18-8.05 (m, 4H), 5.26 (t, J=7.4 Hz, 1H), 5.15 (t, J=7.4 Hz, 1H), 4.75 (s, 2H), 4.69 (t, J=5.0 Hz, 2H), 4.57 (dd, J=8.0, 4.7 Hz, 1H), 4.50-4.34 (m, 3H), 3.95 (dd, J=5.5, 4.4 Hz, 2H), 3.70-3.49 (m, 12H), 3.25 (dt, J=9.9, 5.4 Hz, 1H), 2.97 (dd, J=12.9, 4.9 Hz, 1H), 2.75 (d, J=12.8 Hz, 1H), 2.23 (t, J=7.3 Hz, 2H), 1.83-1.35 (m, 6H).

Example 8

Preparation of 2-(((Z)-4-amino-2-fluorobut-2-en-1-yl)sulfonyl)-N-(5-(5-((3aS,4S,6aR)-2-oxohexahydro-1H-thieno[3,4-d]imidazol-4-yl)pentanamido)pentyl) benzamide hydrochloride (Compound 1-8)

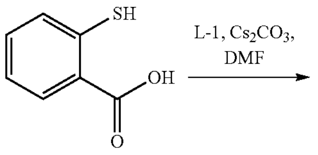

1

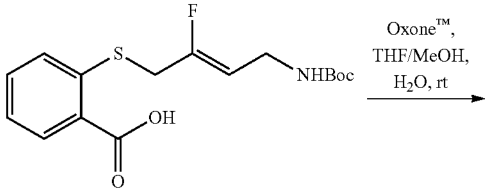

2

-continued

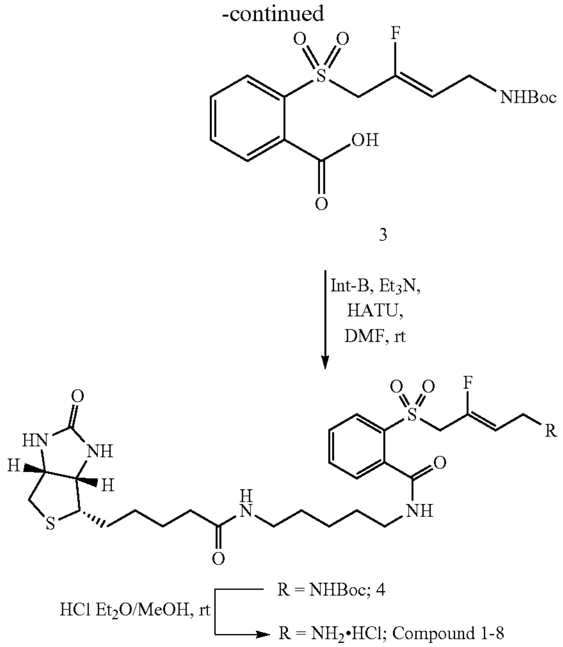

Procedure 1: (Z)-2-((4-((tert-butoxycarbonyl)amino)-2-fluorobut-2-en-1-yl)thio)benzoic acid (2)

To a stirring solution of compound (1) (1.00 g, 6.49 mmol) and L-1 (1.74 g, 6.49 mmol) in DMF (7.0 mL) at rt was added cesium carbonate (6.34 g, 19.5 mmol) in 3 portions. The resulting mixture was stirred at rt for 1 h. The reaction mixture was diluted with water (70 mL) and acidified to pH=5 by addition of aqueous 2 M HCl. The product was extracted with ethyl acetate (3×50 mL) and the combined organics were washed with sat. aq. $NH_4Cl$ (50 mL) and then sat. aq. NaCl (50 mL). After drying over $Na_2SO_4$ the solvent was removed in vacuo to afford compound (2) (2.20 g, 99%) as an off-white solid. $^1$H NMR (300 MHz, $CDCl_3$) δ ppm: 8.12 (dd, J=7.8, 1.6 Hz, 1H), 7.52 (ddd, J=8.9, 7.3, 1.6 Hz, 1H), 7.38 (d, J=8.0 Hz, 1H), 7.28 (d, J=8.7 Hz, 1H), 5.03 (dt, J=35.1, 7.1 Hz, 1H), 4.62 (br. s, 1H), 3.81 (t, J=6.6 Hz, 2H), 3.68 (d, J=14.2 Hz, 2H), 1.46 (s, 9H).

Procedure 2: (Z)-2-((4-((tert-butoxycarbonyl)amino)-2-fluorobut-2-en-1-yl)sulfonyl)benzoic acid (3)

To a stirring solution of compound (2) (1.10 g, 3.22 mmol) in MeOH/THF (1:1; 10 mL) at rt was added a solution of Oxone® monopersulfate (3.96 g, 12.9 mmol) in water (10.0 mL) slowly. The resulting mixture was stirred at this temperature for 8 h. The reaction mixture was diluted with ethyl acetate (30 mL) and stirred at rt for 5 min. The solvent was carefully decanted, and a further portion of ethyl acetate (30 mL) was added to the residue. Stirring was continued for a further 5 min before decanting the sovent. The combined supernatant was washed with sat. aq. sodium metabisulfite (2×30 mL) and sat. aq. NaCl. After drying over $Na_2SO_4$, the solvent was removed in vacuo to afford compound (3) (880 mg, 73%) as an off-white foam. $^1$H NMR (300 MHz, $CDCl_3$) δ ppm: 8.13 (d, J=7.4 Hz, 1H), 7.88 (dd, J=7.4, 1.7 Hz, 1H), 7.81-7.63 (m, 2H), 6.28 (br. s, 1H), 5.08 (dt, J=34.2, 7.1 Hz, 1H), 4.51 (d, J=19.5 Hz, 2H), 3.81 (t, J=6.0 Hz, 2H), 1.48 (s, 9H).

Procedure 3: 2-(((Z)-4-amino-2-fluorobut-2-en-1-yl)sulfonyl)-N-(5-(5-((3aS,4S,6aR)-2-oxohexahydro-1H-thieno[3,4-d]imidazol-4-yl)pentanamido)pentyl)benzamide hydrochloride (Compound 1-8)

Title compound 1-8 was prepared from compound (3) following the protocols outlined in Example 1, procedures 1 (using Int-B as the coupling partner) and 2 (87.0 mg, 96%) as a yellow solid. LCMS: for $C_{26}H_{38}FN_5O_5S_2$ calculated 583.2, found 584.3 $[M+H]^+$. $^1$H NMR (300 MHz, Methanol-$d_4$) δ 8.07 (dd, J=7.8, 1.3 Hz, 1H), 7.83 (td, J=7.5, 1.3 Hz, 1H), 7.72 (td, J=7.7, 1.4 Hz, 1H), 7.62 (dd, J=7.5, 1.4 Hz, 1H), 5.20 (dt, J=32.7, 7.4 Hz, 1H), 4.69 (d, J=19.5 Hz, 2H), 4.56 (dd, J=8.0, 4.7 Hz, 1H), 4.37 (dd, J=7.9, 4.4 Hz, 1H), 3.63 (d, J=7.4 Hz, 2H), 3.39 (t, J=6.8 Hz, 2H), 3.30-3.18 (m, 3H), 2.97 (dd, J=12.8, 4.9 Hz, 1H), 2.75 (d, J=12.8 Hz, 1H), 2.23 (t, J=7.4 Hz, 2H), 1.84-1.37 (m, 12H).

Example 9

Preparation of 3-(((Z)-4-amino-2-fluorobut-2-en-1-yl)sulfonyl)-N-(5-(5-((3aS,4S,6aR)-2-oxohexahydro-1H-thieno[3,4-d]imidazol-4-yl)pentanamido)pentyl)benzamide hydrochloride (Compound 1-9)

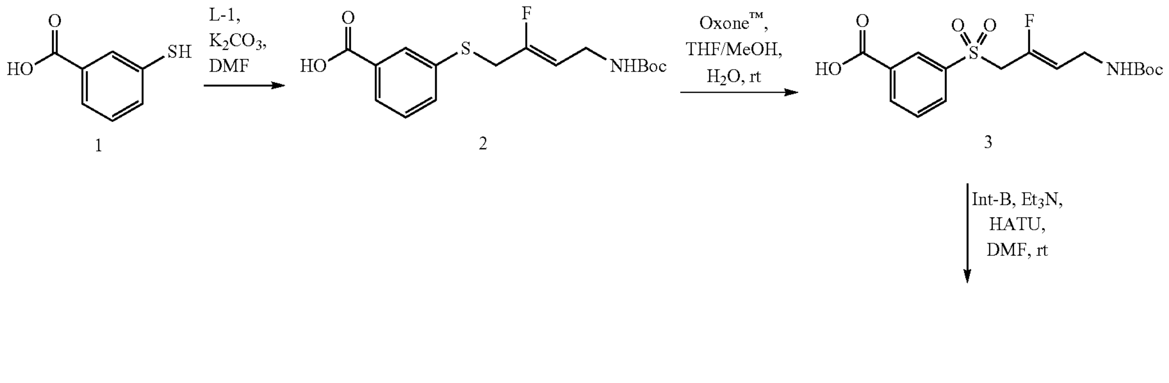

-continued

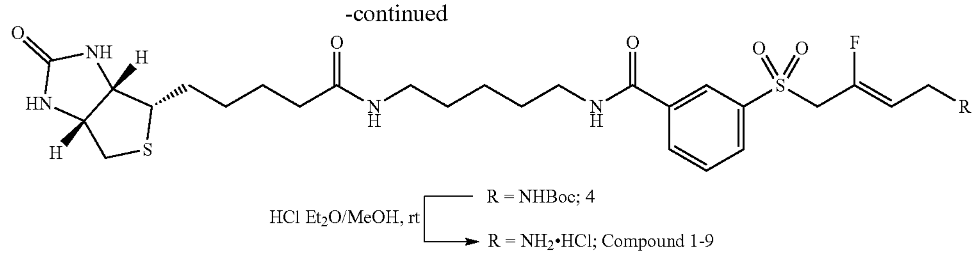

Procedure 1: (Z)-3-((4-((tert-butoxycarbonyl)amino)-2-fluorobut-2-en-1-yl)thio)benzoic acid (2)

To a stirring solution of compound (1) (500 mg, 3.24 mmol) and L-1 (869 mg, 3.24 mmol) in DMF (3.0 mL) at rt was added potassium carbonate (672 mg, 4.86 mmol). The resulting mixture was stirred at rt for 1 h. The reaction mixture was diluted was water (30 mL) and stirring was continued for 15 min. The precipitated solid was isolated by filtration and dried under high vacuum to afford compound (2) (1.10 g, 99%) as a white solid. $^1$H NMR (300 MHz, $CDCl_3$) δ ppm: 8.14 (t, J=1.8 Hz, 1H), 8.00 (d, J=7.8 Hz, 1H), 7.68-7.63 (m, 1H), 7.45 (t, J=7.7 Hz, 1H), 4.86-4.71 (m, 1H), 3.78 (t, J=6.7 Hz, 2H), 3.60 (d, J=17.2 Hz, 2H), 1.44 (s, 9H).

Procedures 2, 3 and 4: 3-(((Z)-4-amino-2-fluorobut-2-en-1-yl)sulfonyl)-N-(5-(5-((3aS,4S,6aR)-2-oxo-hexahydro-1H-thieno[3,4-d]imidazol-4-yl)pentanamido)pentyl)benzamide hydrochloride (Compound 1-9)

Title compound 1-9 was prepared from compound (2) according to the protocols described Example 8, procedure 2 followed by Example 1, procedure 1 (using Int-B as the coupling partner) and finally, Example 1, procedure 2 (34.0 mg, 100%) as a tan colored solid. LCMS: for $C_{26}H_{38}FN_5O_5S_2$ calculated 583.2, found 584.3 $[M+H]^+$. $^1$H NMR (300 MHz, DMSO-$d_6$) δ ppm: 8.89 (t, J=5.5 Hz, 1H), 8.40 (t, J=1.7 Hz, 1H), 8.24 (dt, J=8.0, 1.3 Hz, 1H), 8.19-8.01 (m, 4H), 7.86-7.72 (m, 2H), 5.14 (dt, J=34.7, 7.2 Hz, 1H), 4.71 (d, J=19.7 Hz, 2H), 4.31 (dd, J=7.7, 4.8 Hz, 1H), 4.13 (dd, J=7.8, 4.4 Hz, 1H), 3.52-3.40 (m, 2H), 3.28 (q, J=6.7 Hz, 2H), 3.06 (dq, J=19.3, 6.3 Hz, 3H), 2.82 (dd, J=12.5, 5.0 Hz, 1H), 2.58 (d, J=12.4 Hz, 1H), 2.05 (t, J=7.3 Hz, 2H), 1.69-1.19 (m, 12H).

Example 10

Preparation of 3-(((Z)-4-amino-2-fluorobut-2-en-1-yl)sulfonyl)-N-(3,5-bis(4-(5-((3aS,4S,6aR)-2-oxo-hexahydro-1H-thieno[3,4-d]imidazol-4-yl)pentanoyl)piperazine-1-carbonyl)phenyl)benzamide hydrochloride (Compound 1-10)

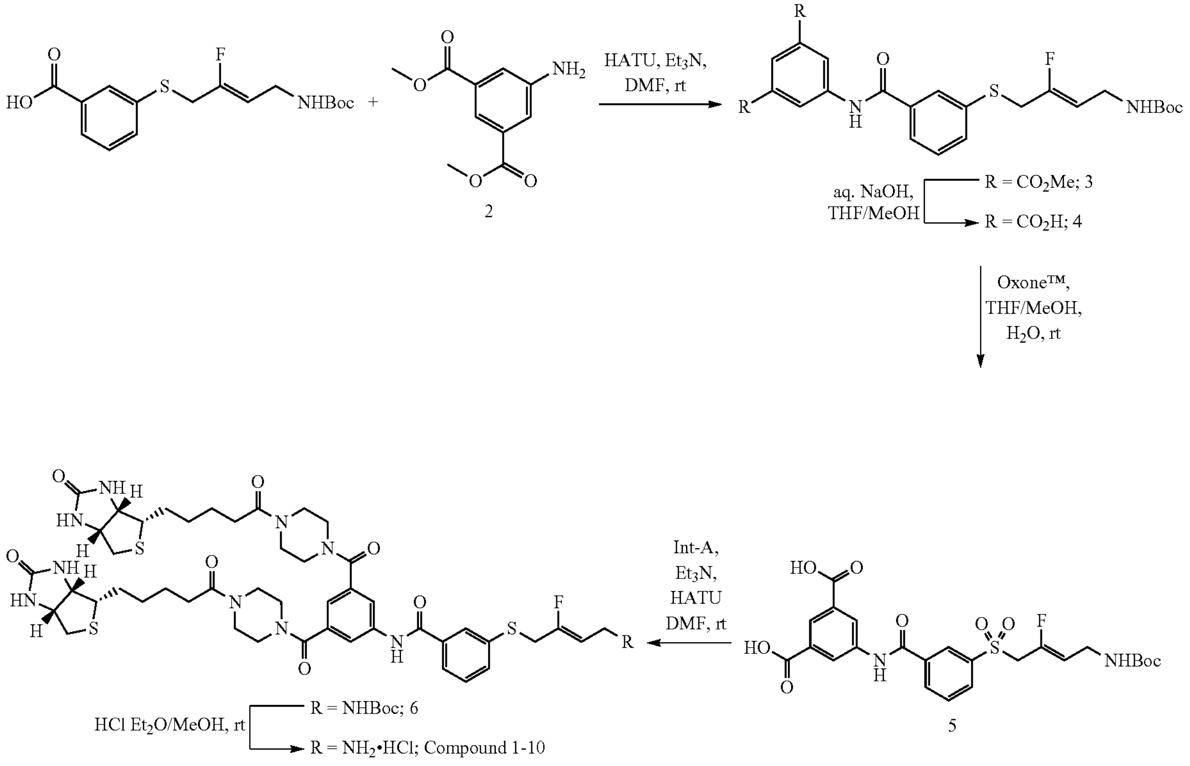

Procedure 1: dimethyl (Z)-5-(3-((4-((tert-butoxycarbonyl)amino)-2-fluorobut-2-en-1-yl)thio)benzamido) isophthalate (3)

To a stirring solution of compound (1) (the synthesis is described in Example 9, procedure 1) (800 mg, 2.34 mmol), compound (2) (588 mg, 2.81 mmol) and triethylamine (1.14 mL, 8.20 mmol) in DMF (8.0 mL) at rt under $N_2$ was added HATU (1.07 g, 2.81 mmol). The resulting yellow mixture was stirred at rt overnight. The reaction mixture was diluted with water (80 mL), and after stirring for 10 min, a sticky gum formed. The liquid was decanted, a further portion of water (80 mL) added to the gum, and stirring continued for a further 10 min. The liquid was once again decanted and the crude material purified over silica gel (40 g), eluting with 20-40% ethyl acetate in hexanes to afford compound (3) (915 mg, 59%) as a white foam. $^1$H NMR (300 MHz, $CDCl_3$) δ ppm: 8.59 (d, J=1.6 Hz, 2H), 8.46 (t, J=1.5 Hz, 1H), 7.93 (t, J=1.8 Hz, 1H), 7.78 (d, J=7.7 Hz, 1H), 7.58 (dt, J=8.0, 1.4 Hz, 1H), 7.42 (t, J=7.8 Hz, 1H), 4.66 (dt, J=35.0, 7.0 Hz, 1H), 3.95 (s, 6H), 3.74 (d, J=5.9 Hz, 2H), 3.57 (d, J=16.8 Hz, 2H), 1.38 (s, 9H).

Procedure 2: (Z)-5-(3-((4-((tert-butoxycarbonyl) amino)-2-fluorobut-2-en-1-yl)thio)benzamido)isophthalic acid (4)

To a stirring solution of compound (3) (915 mg, 1.37 mmol) in MeOH/THF (1:1; 10 mL) at rt was added aqueous sodium hydroxide (2 M; 5.0 mL, 10.0 mmol). The resulting mixture was stirred at rt overnight. The solvent was removed in vacuo, and the residue was taken up in water (20 mL). After washing with ethyl acetate (20 mL), the aqueous layer was acidified to pH=4 by addition of aqueous 2.0 M HCl. The resulting solid was isolated by filtration, and air dried to afford compound (4) (640 mg, 92%) as a white solid. $^1$H NMR (300 MHz, DMSO-$d_6$) δ ppm: 10.58 (s, 2H), 8.64 (d, J=1.5 Hz, 2H), 8.23 (t, J=1.6 Hz, 1H), 8.01 (t, J=1.8 Hz, 1H), 7.86 (dt, J=7.7, 1.4 Hz, 1H), 7.64 (dt, J=7.9, 1.3 Hz, 1H), 7.51 (t, J=7.8 Hz, 1H), 6.98 (t, J=5.8 Hz, 1H), 4.94 (dt, J=36.8, 6.8 Hz, 1H), 3.94 (d, J=18.6 Hz, 2H), 3.54 (t, J=6.4 Hz, 2H), 1.34 (s, 9H).

Procedure 3: (Z)-5-(3-((4-((tert-butoxycarbonyl) amino)-2-fluorobut-2-en-1-yl)sulfonyl)benzamido) isophthalic acid (5)

Compound (5) was prepared from compound (4) following to the protocol outlined in Example 8, procedure 2 (310 mg, 86%) as a white solid. $^1$H NMR (300 MHz, DMSO-$d_6$) δ ppm: 13.34 (s, 2H), 10.88 (s, 1H), 8.52 (t, J=1.8 Hz, 1H), 8.39 (dt, J=8.1, 1.3 Hz, 1H), 8.25 (t, J=1.6 Hz, 1H), 8.12 (dt, J=7.9, 1.3 Hz, 1H), 7.85 (t, J=7.8 Hz, 1H), 7.02 (t, J=5.8 Hz, 1H), 4.92 (dt, J=36.3, 6.7 Hz, 1H), 4.57 (d, J=19.5 Hz, 2H), 3.55 (t, J=6.4 Hz, 2H), 1.35 (s, 9H).

Procedures 4 and 5: 3-(((Z)-4-amino-2-fluorobut-2-en-1-yl)sulfonyl)-N-(3,5-bis(4-(5-((3aS,4S,6aR)-2-oxohexahydro-1H-thieno[3,4-d]imidazol-4-yl)pentanoyl)piperazine-1-carbonyl)phenyl)benzamide hydrochloride (Compound 1-10)

Title compound 1-10 was prepared from compound (5) using the protocols outlined in Example 1, procedure 1 followed by Example 1, procedure 2 (28.0 mg, 99%) as an off-white solid. LCMS: for $C_{47}H_{61}FN_{10}O_9S_3$ calculated 1024.4, found 1025.4 $[M+H]^+$. $^1$H NMR (300 MHz, Methanol-$d_4$) δ ppm: 8.56 (s, 1H), 8.37 (d, J=7.8 Hz, 1H), 8.21 (d, J=7.7 Hz, 1H), 8.04 (d, J=1.3 Hz, 2H), 7.87 (t, J=7.9 Hz, 1H), 7.36 (s, 1H), 5.23 (dt, J=32.9, 7.4 Hz, 1H), 4.63 (dd, J=8.0, 4.7 Hz, 2H), 4.54-4.37 (m, 4H), 3.99-3.51 (m, 18H), 3.40-3.25 (m, 2H), 3.00 (dd, J=13.2, 4.7 Hz, 2H), 2.78 (d, J=12.9 Hz, 2H), 2.50 (s, 4H), 1.93-1.39 (m, 12H).

Example 11

Preparation of (3aS,4S,6aR)-4-(5-(4-(3-(3-(((Z)-4-amino-2-fluorobut-2-en-1-yl)sulfonyl)phenoxy)propyl)-1H-1,2,3-triazol-1-yl)pentyl)tetrahydro-1H-thieno[3,4-d]imidazol-2(3H)-one hydrochloride (Compound 1-11)

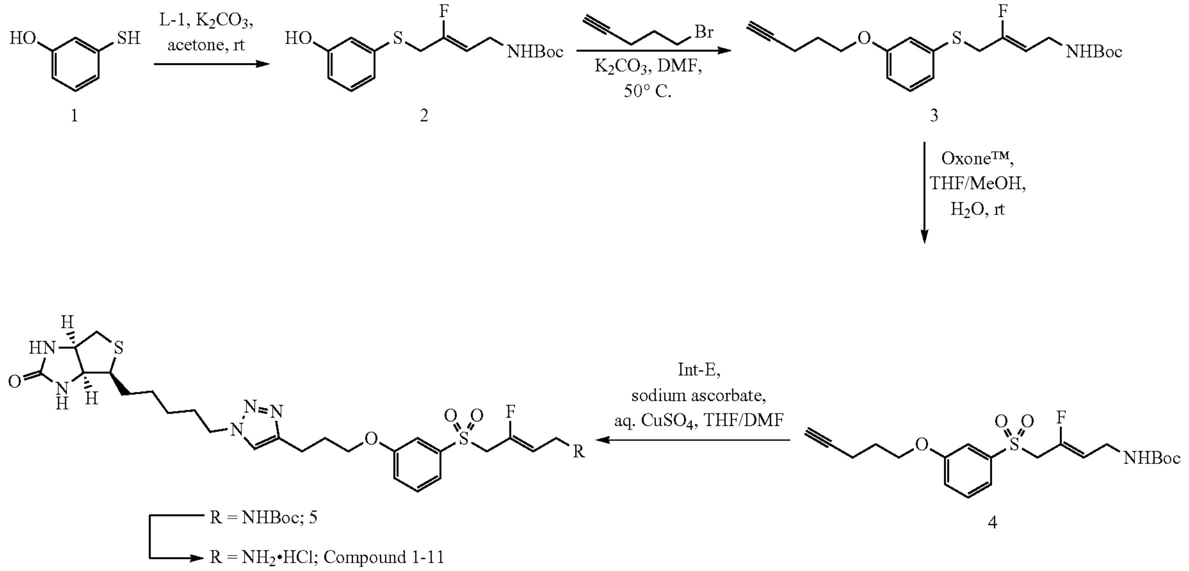

Procedure 1: tert-butyl (Z)-(3-fluoro-4-((3-hydroxyphenyl)thio)but-2-en-1-yl)carbamate (2)

To a stirring suspension of compound (1) (1.00 g, 7.93 mmol) and potassium carbonate (1.10 g, 7.93 mmol) in acetone (25 mL) was added L-1 (2.03 g, 7.20 mmol). The resulting mixture was stirred at rt for 1.5 h. The reaction mixture was filtered and the solvent was removed in vacuo. The residue was dissolved in ethyl acetate and then washed with sat. aq. NaCl. The organics were dried over $Na_2SO_4$ and concentrated under vacuum to afford compound (2) (2.40 g, 97%). $^1H$ NMR (300 MHz, $CDCl_3$) δ ppm: 7.18 (t, J=7.9 Hz, 1H), 7.08-7.00 (m, 1H), 6.97 (d, J=7.7 Hz, 1H), 6.83-6.76 (m, 1H), 4.78 (dt, J=34.5, 7.6 Hz, 1H), 3.80 (s, 2H), 3.47 (d, J=17.5 Hz, 2H), 1.48 (s, 9H).

Procedure 2: tert-butyl (Z)-(3-fluoro-4-((3-(pent-4-yn-1-yloxy)phenyl)thio)but-2-en-1-yl)carbamate (3)

To a stirring suspension of compound (2) (1.00 g, 3.19 mmol) and potassium carbonate (882 mg, 6.38 mmol) in DMF (25 mL) was added 5-bromopent-1-yne (516 mg, 3.51 mmol). The resulting mixture was heated to 50° C. and stirring was continued for 8 h. The reaction mixture was partitioned between sat. aq. sodium carbonate and ethyl acetate. The organic layer was washed with further sat. aq. sodium carbonate and then sat. aq. NaCl. The organics were dried over $Na_2SO_4$, and concentrated in vacuo. The crude material was purified over silica gel, eluting with 5-80% ethyl acetate in hexane to afford compound (3) (0.79 g, 65%) as a light yellow oil. $^1H$ NMR (300 MHz, $CDCl_3$) δ ppm: 7.23 (ddd, J=8.2, 7.6, 0.5 Hz, 1H), 7.01-6.94 (m, 2H), 6.81 (ddd, J=8.3, 2.5, 1.0 Hz, 1H), 4.82 (dt, J=34.9, 7.1 Hz, 1H), 4.51 (br. s, 1H), 4.08 (t, J=6.1 Hz, 2H), 3.77 (t, J=6.7 Hz, 2H), 3.57 (d, J=12 Hz, 2H), 2.43 (td, J=7.0, 2.6 Hz, 2H), 2.09-1.95 (m, 3H), 1.45 (s, 9H).

Procedures 3, 4 and 5: (3aS,4S,6aR)-4-(5-(4-(3-(3-(((Z)-4-amino-2-fluorobut-2-en-1-yl)sulfonyl)phenoxy)propyl)-1H-1,2,3-triazol-1-yl)pentyl)tetrahydro-1H-thieno[3,4-d]imidazol-2(3H)-one hydrochloride (Compound 1-11)

Title compound 1-11 was prepared from compound (3) using, sequentially, the protocols outlined in Example 8, procedure 2; Example 3, procedure 4 (using Int-E as the coupling partner) and finally, Example 1, procedure 2 (110 mg, 100%) as a white solid. LCMS: for $C_{25}H_{35}FN_6O_4S_2$ calculated 566.2, found 567.2 $[M+H]^+$. $^1H$ NMR (300 MHz, DMSO-$d_6$) δ ppm: 8.13 (s, 3H), 7.95 (s, 1H), 7.59 (t, J=7.9 Hz, 1H), 7.49 (ddd, J=7.7, 1.8, 1.1 Hz, 1H), 7.42 (dd, J=2.5, 1.6 Hz, 1H), 7.34 (ddd, J=8.2, 2.6, 1.1 Hz, 1H), 5.17 (dt, J=34.6, 7.2 Hz, 1H), 4.64 (d, J=19.7 Hz, 2H), 4.36-4.25 (m, 3H), 4.20-4.09 (m, 3H), 3.53-3.40 (m, 2H), 3.14-3.04 (m, 1H), 2.88-2.76 (m, 3H), 2.58 (d, J=12.5 Hz, 1H), 2.09 (p, J=6.7 Hz, 2H), 1.87-1.72 (m, 2H), 1.67-1.20 (m, 8H).

Example 12

Preparation of (3aS,3a'S,4S,4'S,6aR,6a'R)-4,4'-(((((5-(1-(3-(((Z)-4-amino-2-fluorobut-2-en-1-yl)sulfonyl)benzil)-1H-1,2,3-triazol-4-yl)-1,3-phenylene)bis(oxy))bis(propane-3,1-diyl))bis(1H-1,2,3-triazole-4,1-diyl))bis(pentane-5,1-diyl))bis(tetrahydro-1H-thieno[3,4-d]imidazol-2(3H)-one) hydrochloride (Compound 1-12)

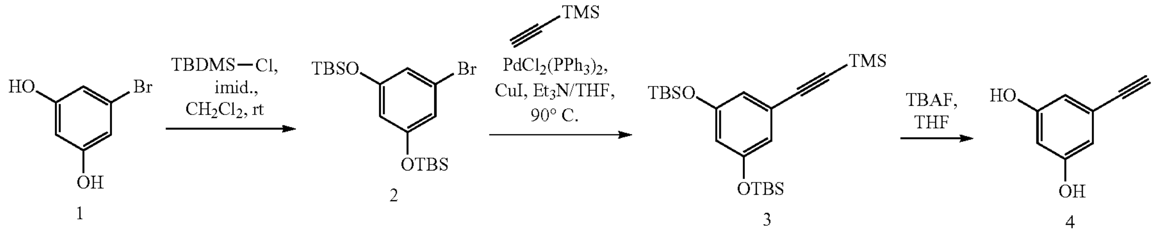

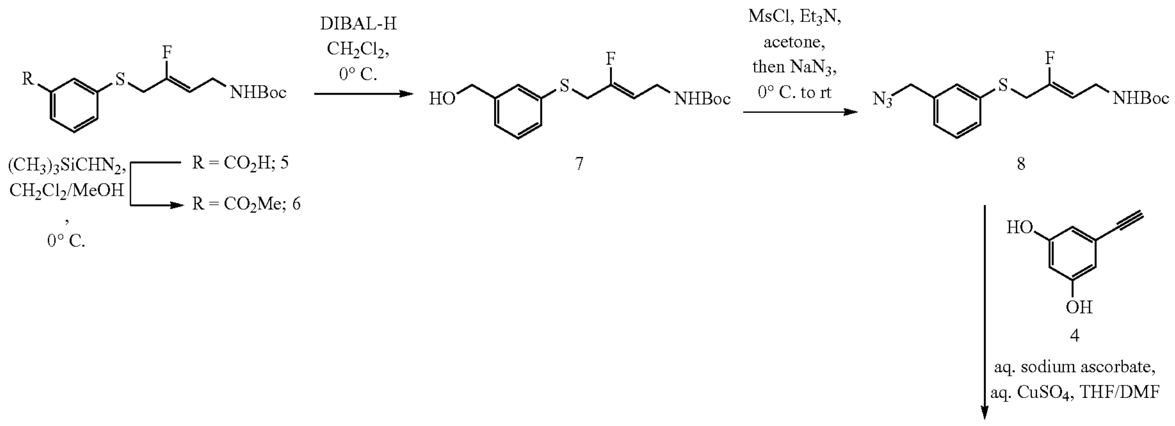

-continued

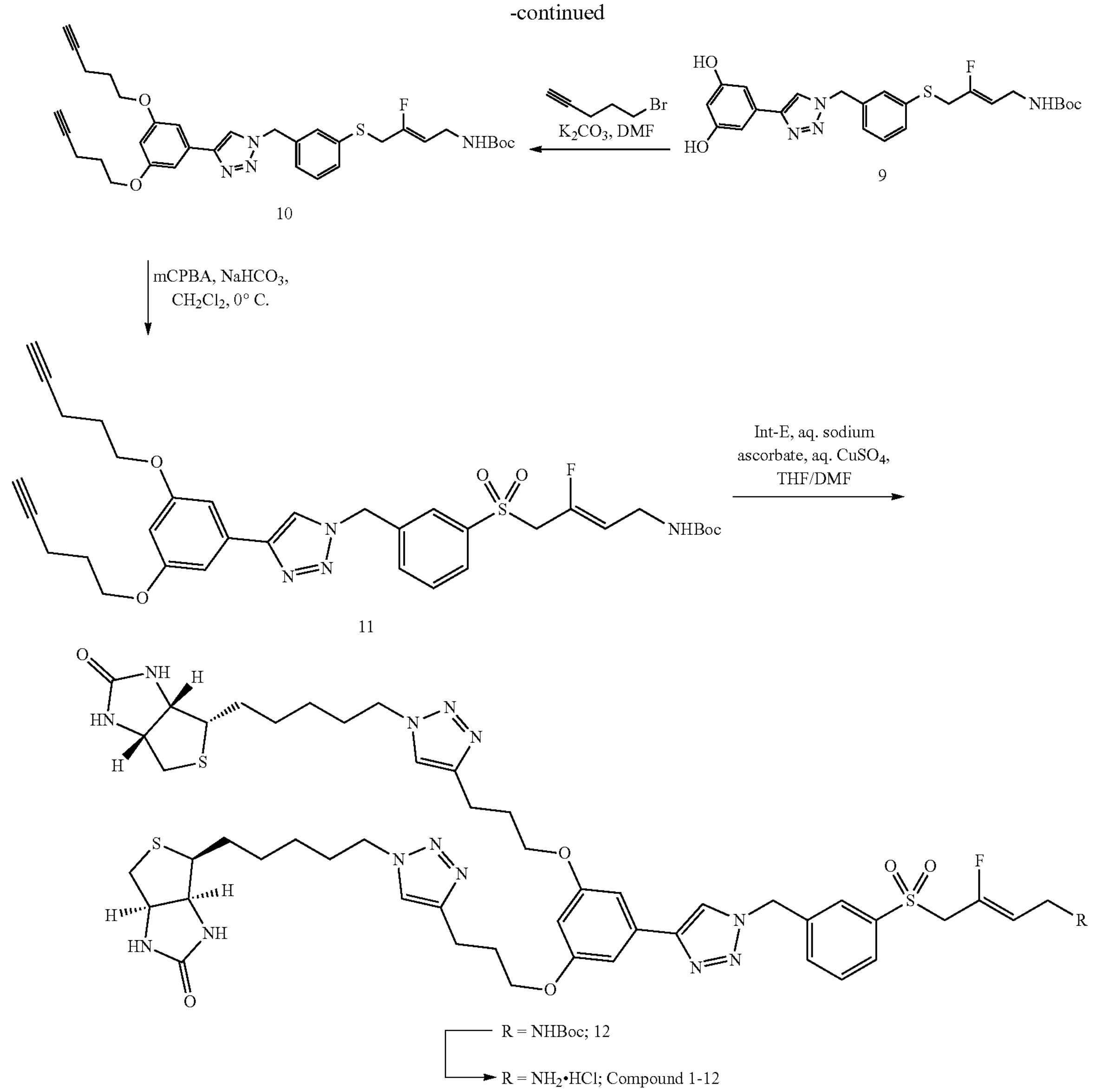

Procedure 1: ((5-bromo-1,3-phenylene)bis(oxy))bis (tert-butyldimethylsilane) (2)

To a stirring solution of compound (1) (1.00 g, 5.29 mmol) and imidazole (1.08 g, 15.9 mmol) in $CH_2Cl_2$ (25 mL) at rt under Ar was added tert-butyldimethylsilyl chloride (TBDMS-Cl) (2.39 g, 15.9 mmol) in one lot. The resulting mixture was stirred at this temperature overnight. The reaction mixture was filtered to remove precipitated imidazole hydrochloride, and the filtrate was concentrated in vacuo to give a pale yellow oil. The crude material was purified over silica gel, eluting with hexane to afford compound (2) (1.75 g, 79%) as a colorless oil. $^1H$ NMR (300 MHz, $CDCl_3$) δ ppm: 6.65 (d, J=2.2 Hz, 2H), 6.27 (t, J=2.1 Hz, 1H), 0.99 (s, 18H), 0.22 (s, 12H).

Procedure 2: ((5-((trimethylsilyl)ethynyl)-1,3-phenylene)bis(oxy))bis(tert-butyldimethylsilane) (3)

A stirring solution of compound (2) (835 mg, 2.00 mmol) and (trimethylsilyl)acetylene (TMS-acetylene) (589 mg, 6.00 mmol) in THF/$Et_3N$ (1:1; 5 mL) in a sealable reaction vessel at rt was degassed by passing a stream of Ar gas through it for 15 min. To this was added copper (I) iodide (38.1 mg, 0.20 mmol) and dichlorobis(triphenylphosphine) palladium (II) (140 mg, 0.20 mmol), and the reaction vessel was sealed. The resulting mixture was heated at 90° C. for 7 h. The reaction mixture was diluted with ethyl acetate (50 mL) and then filtered through Celite™. The filtrate was washed with water (40 mL), sat. aq. NaCl (40 mL), then dried over $Na_2SO_4$, and concentrated in vacuo. The crude material was purified over silica gel, eluting with hexane followed by 50% ethyl acetate in hexane to afford compound (3) (955 mg, 100%) as a colorless oil. $^1H$ NMR (300 MHz, $CDCl_3$) δ ppm: 6.60 (d, J=2.3 Hz, 2H), 6.34 (t, J=2.2 Hz, 1H), 1.00 (s, 18H), 0.27 (s, 9H), 0.22 (s, 12H).

Procedure 3: 5-ethynylbenzene-1,3-diol (4)

To a stirring solution of compound (3) (700 mg, 1.60 mmol) in THF (5.5 mL) at rt was added TBAF (1.0 M in THF; 5.63 mL, 5.63 mmol) dropwise. The resulting mixture was stirred at rt for 30 min. The reaction mixture was diluted with water (50 mL) followed by aq. HCl (2.0 M; 7.0 mL). Stirring was continued for a further 5 min. The product was extracted with ethyl acetate (20 mL) and $CH_2Cl_2$ (3×20 mL) and the combined organic layers were dried over $Na_2SO_4$ and concentrated in vacuo. The crude material was purified over silica gel (12 g), eluting with 0-10% ethyl acetate in hexanes to afford compound (4) (340 mg, 52%) as a brown oil. $^1$H NMR (300 MHz, Methanol-$d_4$) δ ppm: 6.39 (d, J=2.2 Hz, 2H), 6.29 (t, J=2.3 Hz, 1H), 3.33 (s, 1H).

Procedure 4: methyl (Z)-3-((4-((tert-butoxycarbonyl)amino)-2-fluorobut-2-en-1-yl)thio)benzoate (6)

To a stirring solution of compound (5) (the synthesis is described in Example 9, procedure 1) (1.10 g, 3.22 mmol) in $CH_2Cl_2$/MeOH (5:1; 6.0 mL) at 0° C. was added diazomethyl(trimethyl)silane (1.03 mL, 6.44 mmol) dropwise. The resulting mixture was stirred for 30 min at this temperature. At this time, tlc indicated the presence of 30-40% unreacted starting material. Additional diazomethyl(trimethyl)silane (1.03 mL, 6.44 mmol) was added and stirring was continued for a further 30 min at 0° C. The reaction was quenched by the addition of acetic acid (1.0 mL). The reaction mixture was then concentrated in vacuo. To the residue was added water (20 mL) and the resulting, precipitated solid was filtered, washed with water (2.0 mL), and then dried under high vacuum to afford compound (6) (1.20 g, 100%) as a white solid. This material was progressed to the next step without further purification. $^1$H NMR (300 MHz, $CDCl_3$) δ ppm: 8.10-8.06 (m, 1H), 7.94 (ddd, J=7.8, 1.6, 1.2 Hz, 1H), 7.60 (ddd, J=7.8, 2.0, 1.2 Hz, 1H), 7.41 (td, J=7.8, 0.5 Hz, 1H), 4.77 (dt, J=34.8, 7.1 Hz, 1H), 4.59 (br. s, 1H), 3.95 (s, 3H), 3.77 (t, J=6.5 Hz, 2H), 3.64-3.51 (m, 2H), 1.44 (s, 9H).

Procedure 5: tert-butyl (Z)-(3-fluoro-4-((3-(hydroxymethyl)phenyl)thio)but-2-en-1-yl)carbamate (7)

To a stirring solution of compound (6) (1.20 g, 3.38 mmol) in $CH_2Cl_2$ (20.0 mL) at 0° C. was added diisobutylaluminium hydride (1.0 M in $CH_2Cl_2$; 11.8 mL, 11.8 mmol) dropwise. The resulting mixture was stirred at this temperature for 30 min. The reaction mixture was quenched by addition of aqueous NaOH (2.0 M; 25 mL) and then diluted further with water (20 mL). The product was extracted with $CH_2Cl_2$ (3×40 mL). The combined organic layers were dried over $Na_2SO_4$ and then concentrated in vacuo to afford compound (7) (1.00 g, 90%) as a white solid. This material was progressed to the next step without further purification. $^1$H NMR (300 MHz, $CDCl_3$) δ ppm: 7.48 (td, J=1.7, 0.8 Hz, 1H), 7.40-7.23 (m, 3H), 4.70 (d, J=6.0 Hz, 2H), 4.64 (dt, J=35.1, 7.6 Hz, 1H), 3.74 (s, 2H), 3.51 (d, J=17.6 Hz, 2H), 2.39 (br. s, 1H), 1.44 (s, 9H).

Procedure 6: tert-butyl (Z)-(4-((3-(azidomethyl)phenyl)thio)-3-fluorobut-2-en-1-yl)carbamate (8)

To a stirring solution of compound (7) (1.00 g, 3.05 mmol) and triethylamine (0.64 mL, 4.58 mmol) in acetone (20.0 mL) at 0° C. was added methanesulfonyl chloride (0.28 mL, 3.67 mmol) drop-wise. The mixture was stirred at this temperature for 1 h. The reaction mixture was then filtered to remove precipitated triethylamine hydrochloride. The filtrate was used immediately in the next step. To the stirring filtrate at 0° C. was added sodium azide (596 mg, 9.16 mmol). The resulting suspension was stirred at 0° C. for 5 min and then warmed to rt. Stirring was continued at this temperature overnight. The reaction mixture was concentrated in vacuo, and the resulting residue was partitioned between water (50 mL) and ethyl acetate (20 ml). The aqueous layer was extracted with further ethyl acetate (2×20 mL), and the combined organics were washed with water (20 ml), dried over $Na_2SO_4$ and then concentrated in vacuo to afford compound (8) (1.10 g, 87%) as a yellow solid. $^1$H NMR (300 MHz, $CDCl_3$) δ ppm: 7.42-7.31 (m, 3H), 7.22 (dt, J=7.1, 1.7 Hz, 1H), 4.79 (dt, J=34.0, 6.7 Hz, 1H), 4.51 (s, 1H), 4.36 (s, 2H), 3.77 (t, J=6.7 Hz, 2H), 3.57 (dt, J=17.0, 0.8 Hz, 2H), 1.45 (d, J=2.4 Hz, 9H).

Procedure 7: tert-butyl (Z)-(4-((3-((4-(3,5-dihydroxyphenyl)-1H-1,2,3-triazol-1-yl)methyl)phenyl)thio)-3-fluorobut-2-en-1-yl)carbamate (9)

To a stirring solution of compound (4) (177 mg, 1.32 mmol) and compound (8) (465 mg, 1.32 mmol) in THF (4.0 mL) and DMF (1.0 mL) at rt was added aqueous sodium ascorbate (1.0 M; 2.00 mL, 2.00 mmol) followed by aqueous copper sulfate pentahydrate (1.0 M; 2.00 mL, 2.00 mmol). The resulting mixture was left to stir overnight. The reaction mixture was diluted with water (50 mL) at which time a solid precipitate formed. The solid was collected by filtration, and then dried under high vacuum to afford compound (9) (640 mg, 100%) as a black solid. This material was progressed to the next step and purification was performed subsequently.

Procedure 8: tert-butyl (Z)-(4-((3-((4-(3,5-bis(pent-4-yn-1-yloxy)phenyl)-1H-1,2,3-triazol-1-yl)methyl)phenyl)thio)-3-fluorobut-2-en-1-yl)carbamate (10)

To a stirring solution of compound (9) (640 mg, 1.31 mmol) in DMF (2.0 mL) at rt was added sequentially potassium carbonate (636 mg, 4.60 mmol) and 5-bromopent-1-yne (483 mg, 3.29 mmol). The resulting suspension was heated at 50° C. for 2 h and then at 80° C. for a further 1 h. After cooling to rt, the reaction mixture was partitioned between water (50 mL) and ethyl acetate (20 mL). The aqueous layer was extracted with further ethyl acetate (20 mL), and the combined organics were washed with sat aq. $NH_4Cl$ (2×20 mL), brine (20 mL), dried over $Na_2SO_4$ and then concentrated in vacuo. The crude material was purified over silica gel (24 g), eluting with 20%-50% ethyl acetate in hexanes to afford compound (10) (410 mg, 50%) as a yellow oil. $^1$H NMR (300 MHz, $CDCl_3$) δ ppm: 7.72 (s, 1H), 7.40-7.27 (m, 3H), 7.17 (dt, J=7.3, 1.7 Hz, 1H), 7.00 (d, J=2.2 Hz, 2H), 6.46 (t, J=2.3 Hz, 1H), 5.55 (s, 2H), 4.88-4.65 (m, 2H), 4.11 (td, J=6.6, 6.1, 2.3 Hz, 4H), 3.74 (t, J=6.7 Hz, 2H), 3.54 (d, J=16.9 Hz, 2H), 2.41 (td, J=7.0, 2.6 Hz, 4H), 2.04-1.94 (m, 6H), 1.43 (s, 9H).

Procedure 9: tert-butyl (Z)-(4-((3-((4-(3,5-bis(pent-4-yn-1-yloxy)phenyl)-1H-1,2,3-triazol-1-yl)methyl)phenyl)sulfonyl)-3-fluorobut-2-en-1-yl)carbamate (11)

To a stirring solution of compound (10) (205 mg, 0.33 mmol) in $CH_2Cl_2$ (2.0 mL) was added sat. aq. $NaHCO_3$ (2.0 mL). After cooling the reaction mixture to 0° C., mCPBA (186 mg, 0.83 mmol) was added in one portion. The resulting mixture was stirred at 0° C. for 15 min and then rt for 1 h. Tlc after this time indicated complete consumption of starting material. The reaction was quenched by addition of saturated sodium bisulfite solution (4.0 mL), and the product was extracted with $CH_2Cl_2$ (3×20 mL). The combined organics were washed with sat. aq. $NaHCO_3$, water and brine, then dried over $Na_2SO_4$ and concentrated in vacuo to afford a yellow foam. The crude material was purified over silica gel to afford compound (11) (140 mg, 65%). $^1$H NMR (300 MHz, $CDCl_3$) S ppm: 8.06-7.88 (m, 2H), 7.83 (s, 1H), 7.72-7.51 (m, 2H), 7.00 (d, J=2.3 Hz, 2H), 6.47 (t, J=2.3 Hz, 1H), 5.69 (s, 2H), 4.95 (dt, J=34.6, 6.7 Hz, 2H), 4.19-4.06 (m, 4H), 3.91 (dd, J=18.4, 5.3 Hz, 2H), 3.76 (t, J=6.6 Hz, 2H), 2.41 (td, J=7.0, 2.6 Hz, 2H), 2.21-2.16 (m, 4H), 2.05-1.93 (m, 4H), 1.44 (d, J=1.3 Hz, 9H).

Procedure 10: tert-butyl ((Z)-4-((3-((4-(3,5-bis(3-(1-(5-((3aS,4S,6aR)-2-oxohexahydro-1H-thieno[3,4-d]imidazol-4-yl)pentyl)-1H-1,2,3-triazol-4-yl)propoxy)phenyl)-1H-1,2,3-triazol-1-yl)methyl)phenyl)sulfonyl)-3-fluorobut-2-en-1-yl)carbamate (12)

To a stirred solution of Int-E (132 mg, 0.52 mmol) and compound (11) (140 mg, 0.22 mmol) in THF/DMF (4:1; 5.0 mL) at rt was added aqueous sodium ascorbate (1.0 M; 0.65 mL, 0.65 mmol) followed by aqueous copper sulfate pentahydrate (1.0 M; 0.65 mL, 0.65 mmol). The resulting mixture was left to stir at rt overnight. The reaction mixture was diluted with water (50 mL) at which time a solid precipitated. The solid was collected by filtration. The crude material was purified over silica gel (12 g), eluting with 5%-13% methanol in $CH_2Cl_2$ to afford compound (12) (170 mg, 68%) as a white foam. LCMS: for $C_{54}H_{73}FN_{14}O_8S_3$ calculated 1160.5, found 1161.5 [M+H]$^+$.

Procedure 11: (3aS,3a'S,4S,4'S,6aR,6a'R)-4,4'-(((((5-(1-(3-(((Z)-4-amino-2-fluorobut-2-en-1-yl)sulfonyl)benzyl)-1H-1,2,3-triazol-4-yl)-1,3-phenylene)bis(oxy))bis(propane-3,1-diyl))bis(1H-1,2,3-triazole-4,1-diyl))bis(pentane-5,1-diyl))bis(tetrahydro-1H-thieno[3,4-d]imidazol-2(3H)-one) hydrochloride (Compound 1-12)

To a stirring solution of compound (12) (170 mg, 0.15 mmol) in MeOH (1.0 mL) at rt was added ethereal HCl (2.0 M; 1.0 mL, 2.0 mmol). The resulting mixture was stirred at rt for 1.5 h. The reaction mixture was concentrated in vacuo and the resulting gum was triturated with ethyl acetate to afford a solid. The solid and ethyl acetate were transferred, en masse into a vial, and the solid was spun down in a centrifuge (4000 rpm for 5 min). The ethyl acetate was decanted, and the solid "cake" was washed by further addition of ethyl acetate followed by brief sonication. After spinning down once again on the centrifuge, the supernatant was decanted and the solid "cake" was dried under high vacuum. The solid was then dissolved in water and, after lyophilization, the title compound (1-12) (107 mg, 67%) was obtained as a yellow solid. LCMS: for $C_{49}H_{65}FN_{14}O_6S_3$ calculated 1060.4, found 1061.5 [M+H]$^+$. $^1$H NMR (300 MHz, Methanol-$d_4$) δ ppm: 8.55 (s, 1H), 8.40 (s, 2H), 7.96-8.04 (m, 2H), 7.83-7.71 (m, 2H), 6.98 (s, 2H), 6.43 (s, 1H), 5.84 (s, 2H), 5.20 (dt, J=33.0, 7.1 Hz, 1H), 4.56 (s, 4H), 4.40 (d, J=19.1 Hz, 2H), 4.14 (s, 4H), 3.66 (d, J=6.9 Hz, 2H), 3.23-3.03 (m, 6H), 2.93 (d, J=12.8 Hz, 2H), 2.72 (d, J=12.6 Hz, 2H), 2.26 (br. s, 4H), 1.99 (br. s, 4H), 1.75-1.31 (m, 16H).

Example 13

Preparation of (3aS,3a'S,4S,4'S,6aR,6a'R)-4,4'-(((((3-(((Z)-4-amino-2-fluorobut-2-en-1-yl)sulfonyl)phenyl)azanediyl)bis(propane-3,1-diyl))bis(1H-1,2,3-triazole-4,1-diyl))bis(pentane-5,1-diyl))bis(tetrahydro-1H-thieno[3,4-d]imidazol-2(3H)-one) hydrochloride (Compound 1-13)

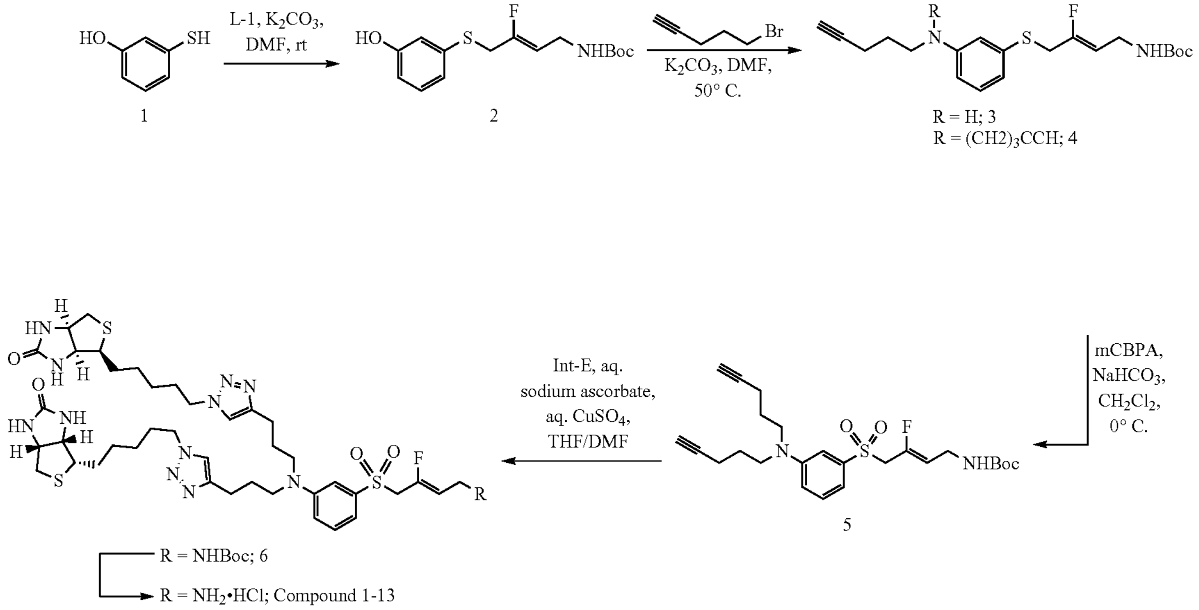

1
2
R = H; 3
R = (CH2)3CCH; 4
5
R = NHBoc; 6
R = $NH_2$•HCl; Compound 1-13

Procedure 1: tert-butyl (Z)-(4-((3-aminophenyl) thio)-3-fluorobut-2-en-1-yl)carbamate (2)

To a stirring solution of 3-aminobenzenethiol (2.05 g, 16.4 mmol) in DMF (16 mL) at rt was added potassium carbonate (2.47 g, 17.9 mmol) followed by L-1 (4.00 g, 14.9 mmol). The resulting mixture was left to stir at rt, overnight. Water (100 mL) was added and the product was extracted with ethyl acetate (40 mL). The organic layer was then washed with sat. aq. $NaHCO_3$ (40 mL), aqueous NaOH (2.0 M; 40 mL), water (40 mL) and sat. aq. NaCl (40 mL). After drying over $Na_2SO_4$, the organic solvent was removed in vacuo to afford compound (2) (4.66 g, 90%) as a viscous oil. This material was progressed to the next step without further purification. $^1H$ NMR (300 MHz, $CDCl_3$) δ ppm: 7.11 (t, J=7.8 Hz, 1H), 6.80 (ddd, J=7.7, 1.7, 0.9 Hz, 1H), 6.75 (t, J=2.0 Hz, 1H), 6.59 (ddd, J=8.0, 2.3, 0.9 Hz, 1H), 4.91-4.68 (m, 1H), 4.55 (br. s, 1H), 3.88-3.65 (m, 4H), 3.53 (dt, J=17.0, 0.8 Hz, 2H), 1.46 (s, 9H).

Procedure 2: tert-butyl (Z)-(4-((3-(di(pent-4-yn-1-yl)amino)phenyl)thio)-3-fluorobut-2-en-1-yl)carbamate (4)

To a stirred suspension of compound (2) (800 mg, 2.56 mmol) and potassium carbonate (778 mg, 5.63 mmol) in DMF (8.0 mL) was added 5-bromopent-1-yne (941 mg, 6.40 mmol). The resulting mixture was heated to reflux, and stirring was continued for 6 h. The reaction mixture was partitioned between ethyl acetate (50 mL) and water (20 mL). Organic layer was washed with water (2×10 mL), brine (10 mL), dried over $Na_2SO_4$ and then concentrated in vacuo. The crude material was purified over silica gel, eluting with 0-40% ethyl acetate in hexane to give, firstly, compound (4) followed by compound (3). LCMS (compound (3)): for $C_{20}H_{27}FN_2O_2S$ calculated 378.2, found 379.4 $[M+H]^+$; LCMS (compound (4)): for $C_{25}H_{33}FN_2O_2S$ calculated 444.2, found 445.4 $[M+1]^+$.

Procedures 3, 4 and 5: (3aS,3a'S,4S,4'S,6aR,6a'R)-4,4'-(((((3-(((Z)-4-amino-2-fluorobut-2-en-1-yl) sulfonyl)phenyl)azanediyl)bis(propane-3,1-diyl))bis (1H-1,2,3-triazole-4,1-diyl))bis(pentane-5,1-diyl))bis (tetrahydro-1H-thieno[3,4-d]imidazol-2(3H)-one) hydrochloride (Compound 1-13)

Title compound 1-13 was prepared from compound (4) following, sequentially, protocols described in Example 7, procedure 4; Example 3, procedure 4 (using Int-E as the coupling partner) and finally Example 1, procedure 2 (17.0 mg, 100%) as an orange solid. LCMS: for $C_{40}H_{59}FN_{12}O_4S_3$ calculated 886.4, found 887.4 $[M+H]^+$.

Example 14

Preparation of (3aS,4S,6aR)-4-(4-(4-(3-((3-(((Z)-4-amino-2-fluorobut-2-en-1-yl)sulfonyl)phenyl)amino) propyl)-1H-1,2,3-triazol-1-yl)butyl)tetrahydro-1H-thieno[3,4-d]imidazol-2(3H)-one hydrochloride (Compound 1-14)

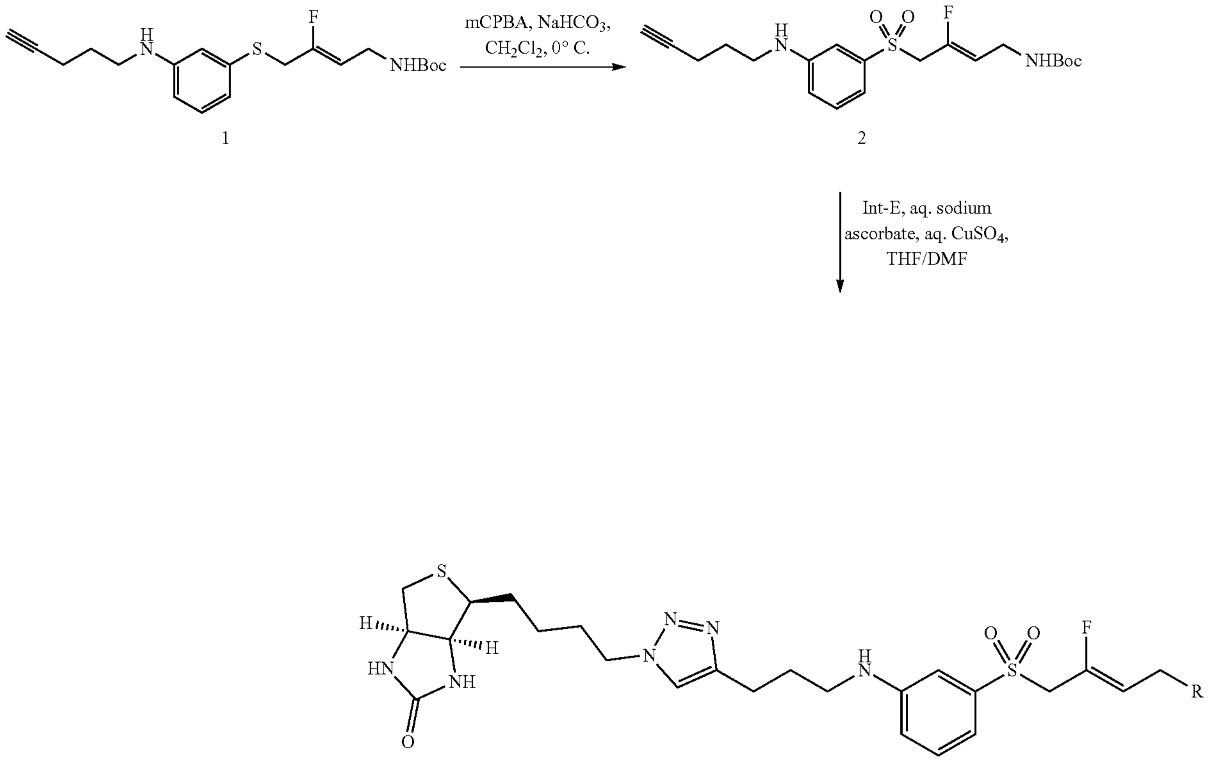

R = NHBoc; 3

R = $NH_2$•HCl; Compound 1-14

Title compound 1-14 was prepared from compound (1) (synthesized in Example 13, procedure 2) following, sequentially, protocols described in Example 7, procedure 4, Example 3, procedure 4 (using Int-E as the coupling partner) and Example 1, procedure 2 (6.0 mg, 92%) as a white solid. LCMS: for $C_{25}H_{36}FN_7O_3S_2$ calculated 565.2, found 566.3 $[M+H]^+$.

Example 15

Preparation of N-((1-(4-(((1-((Z)-4-amino-2-fluorobut-2-en-1-yl)-1H-1,2,3-triazol-4-yl)(4-(N,N-dimethylsulfamoyl)phenyl)methoxy)methyl)phenyl)-1H-1,2,3-triazol-4-yl)methyl)-5-((3aS,4S,6aR)-2-oxohexahydro-1H-thieno[3,4-d]imidazol-4-yl)pentanamide hydrochloride (Compound 1-15)

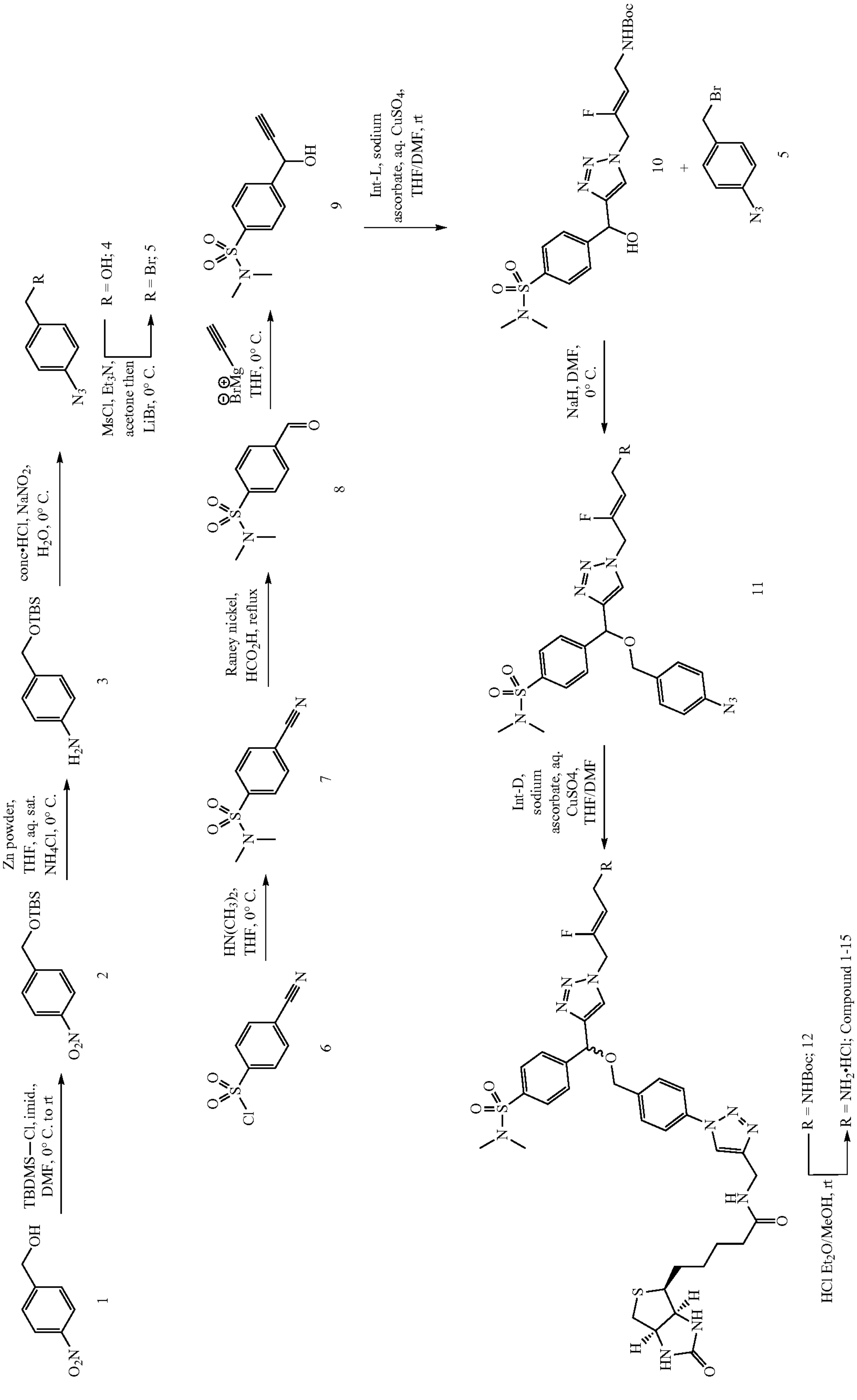
1 2 3 4 5 6 7 8 9 10 + 5 11

Procedure 1: tert-butyldimethyl((4-nitrobenzyl)oxy)silane (2)

To a stirring solution of compound (1) (1.00 g, 6.53 mmol) and imidazole (889 mg, 13.1 mmol) in DMF (6.5 mL) at 0° C. was added tert-butyldimethylsilyl chloride (TBS-Cl) (1.18 g, 7.84 mmol) in one portion. The resulting mixture was stirred at 0° C. for 5 min and then warmed up to rt where stirring was continued for a further 1 h. Water (65 mL) was added and the product was extracted with ethyl acetate (3×30 mL). The combined organics were washed with sat. aq. $NH_4Cl$ (20 mL) and sat. aq. NaCl (20 mL). After drying over $Na_2SO_4$, the organic solvent was removed in vacuo to afford compound (2) (1.75 g, 100%) as a yellow oil. This material was progressed to the next step without further purification. $^1H$ NMR (300 MHz, $CDCl_3$) δ ppm: 8.25-8.17 (m, 2H), 7.53-7.47 (m, 2H), 4.85 (d, J=1.0 Hz, 2H), 0.98 (s, 9H), 0.14 (s, 6H).

Procedures 2 and 3: (4-azidophenyl)methanol (4)

Compound (4) was prepared from compound (2) following, sequentially, the protocols described in Example 3, procedure 2 and Example 6, procedure 1 (500 mg, 100%). $^1H$ NMR (300 MHz, $CDCl_3$) δ ppm: 7.40-7.33 (m, 2H), 7.07-7.00 (m, 2H), 4.68 (s, 2H).

Procedure 4: 1-azido-4-(bromomethyl)benzene (5)

To a stirring solution of compound (4) (500 mg, 3.35 mmol) and triethylamine (0.70 mL, 5.03 mmol) in acetone (10.0 mL) at 0° C. was added methanesulfonyl chloride (0.31 mL, 4.02 mmol). The resulting mixture was stirred at 0° C. for 30 min. The reaction mixture was then filtered to remove precipitated trimethylamine hydrochloride. The filtrate was cooled to 0° C. and to this was added lithium bromide (1.46 g, 16.8 mmol) in one portion. The resulting suspension was stirred at 0° C. for 5 min and then warmed to rt where stirring was continued for 1.5 h. The reaction mixture was filtered and the filtrate was concentrated in vacuo. The residue was diluted with water (20 mL) and the product was then extracted with $CH_2Cl_2$ (3×20 mL). The combined organics were dried over $Na_2SO_4$ and then concentrated in vacuo. The crude material was purified over silica gel (20 g), eluting with 20% ethyl acetate in hexane to afford compound (5) (540 mg, 76%) as a yellow oil. $^1H$ NMR (300 MHz, $CDCl_3$) δ ppm: 7.43-7.36 (m, 2H), 7.06-6.98 (m, 2H), 4.50 (s, 2H).

Procedure 6: 4-cyano-N,N-dimethylbenzenesulfonamide (7)

To a stirring solution of dimethylamine (9.42 mL, 74.4 mmol) in THF (20 mL) at 0° C. was added a solution of compound (6) (3.00 g, 14.9 mmol) in THF (4.0 mL) over 5 min. The resulting mixture was warmed to rt and stirring was continued for 30 min. The reaction mixture was then concentrated under cacuum. The residue was diluted with water (40 mL), and the product was extracted with $CH_2Cl_2$ (3×20 mL). The combined organics were dried over $Na_2SO_4$ and then concentrated in vacuo to afford compound (7) (3.01 g, 95%) as a white solid. This material was progressed to the next step without further purification. 1H NMR (300 MHz, $CDCl_3$) δ ppm: 7.97-7.83 (m, 4H), 2.78 (s, 6H).

Procedure 7: 4-formyl-N,N-dimethylbenzenesulfonamide (8)

To a solution of compound (7) (3.10 g, 14.7 mmol) in formic acid (38.0 mL, 14.7 mmol) was added Raney nickel (2.84 g, 14.7 mmol). The resulting mixture was heated to reflux, and stirring was continued for 1 h. The reaction mixture was diluted with ethyl acetate (20 mL) and then filtered through Celite™. The filtrate was concentrated, and the resulting residue was redissolved in ethyl acetate (50 mL). The organics were washed with brine, dried over $Na_2SO_4$, and then concentrated in vacuo to afford compound (8) (3.10 g, 99%) as a white solid. This material was progressed to the next step without further purification. $^1H$ NMR (300 MHz, $CDCl_3$) δ ppm: 10.13 (s, 1H), 8.10-8.05 (m, 2H), 7.99-7.94 (m, 2H), 2.77 (s, 6H).

Procedure 8: 4-(1-hydroxyprop-2-yn-1-yl)-N,N-dimethylbenzenesulfonamide (9)

To a stirring solution of compound (8) (3.00 g, 7.03 mmol) in THF (20 mL), at 0° C. was added ethynylmagnesium bromide (2.0 M in THF; 21.1 mL, 10.6 mmol) dropwsie. The resulting mixture was left to stir at 0° C. for 30 min. To the reaction mixture was added, cautiously, sat. aq. $NH_4Cl$ (2.0 mL). After diluting with further sat. aq. $NH_4Cl$ (40 mL), the product was extracted with ethyl acetate (3×50 mL). The combined organics were dried over $Na_2SO_4$ and then concentrated in vacuo. The crude material was purified over silica gel (60 g), eluting with 40% ethyl acetate in hexane to afford compound (9) (1.45 g, 86%) as a pale yellow oil. $^1H$ NMR (300 MHz, $CDCl_3$) δ ppm: 7.82 (d, J=8.6 Hz, 2H), 7.79-7.73 (m, 2H), 4.14 (q, J=7.1 Hz, 1H), 2.74 (s, 6H), 1.28 (t, J=7.2 Hz, 1H).

Procedure 9: tert-butyl (Z)-(3-fluoro-4-(4-(hydroxy(4-((methyl-12-azanyl)sulfonyl)phenyl)methyl)-1H-1,2,3-triazol-1-yl)but-2-en-1-yl)carbamate (10)

Compound (10) was prepared by coupling compound (9) and Int-L following the protocol detailed in Example 3, procedure 4 (1.50 g, 76%) as an off-white solid. $^1H$ NMR (300 MHz, $CDCl_3$) δ ppm: 7.75-7.69 (m, 2H), 7.67-7.61 (m, 2H), 6.09 (d, J=4.2 Hz, 1H), 5.14 (dt, J=34.6, 6.8 Hz, 1H), 5.04-4.92 (m, 2H), 4.87 (t, J=6.1 Hz, 1H), 4.29 (d, J=4.3 Hz, 1H), 3.85-3.74 (m, 2H), 2.69 (s, 6H), 1.42 (s, 9H).

Procedure 10: tert-butyl (Z)-(4-(4-(((4-azidobenzyl)oxy)(4-(N,N-dimethylsulfamoyl)phenyl)methyl)-1H-1,2,3-triazol-1-yl)-3-fluorobut-2-en-1-yl)carbamate (11)

To a stirring solution of compound (10) (250 mg, 0.53 mmol) in DMF (2.0 mL) at 0° C. under $N_2$ was added sodium hydride (60 w % in paraffin oil; 42.6 mg, 1.06 mmol). The resulting solution was left to stir at this temperature for 15 min after which time a solution of compound (5) (synthesis described in Example 15, procedures 1-4) (113 mg, 0.53 mmol) in DMF (0.5 mL) was added dropwise. After complete addition, stirring was continued for a further 30 min at 0° C. The reaction mixture was partitioned between sat. aq. NaCl (20 mL) and ethyl acetate (20 mL) and the aqueous layer was extracted with further ethyl acetate (20 mL). The combined organics were dried over $Na_2SO_4$ and concentrated in vacuo. The crude material was purified over silica gel (20 g), eluting with 50% ethyl acetate in hexanes followed by 75% ethyl acetate in hexane to afford compound (11) (134 mg, 42%) as a pale yellow oil. $^1H$ NMR (300 MHz, $CDCl_3$) δ ppm: 7.81-7.75 (m, 2H), 7.67-7.60 (m, 2H), 7.53 (s, 1H), 7.38-7.31 (m, 2H), 7.06-6.99 (m, 2H), 5.78 (s, 1H), 5.19 (dt, J=34.8, 6.8 Hz, 1H), 5.01 (dd, J=16.8, 2.9 Hz, 2H), 4.58 (s, 2H), 4.13 (q, J=7.1 Hz, 1H), 3.90-3.77 (m, 2H), 2.73 (s, 6H), 1.44 (s, 9H).

Procedures 11 and 12: N-((1-(4-(((1-((Z)-4-amino-2-fluorobut-2-en-1-yl)-1H-1,2,3-triazol-4-yl)(4-(N,N-dimethylsulfamoyl)phenyl)methoxy)methyl)phenyl)-1H-1,2,3-triazol-4-yl)methyl)-5-((3aS,4S,6aR)-2-oxohexahydro-1H-thieno[3,4-d]imidazol-4-yl)pentanamide hydrochloride (Compound 1-15)

Title compound 1-15 was prepared from compound (11) following, sequentially, the protocols described in Example 3, procedure 4 (using Int-D as the coupling partner), and Example 1, procedure 2 (55.0 mg, 76%) as a pale yellow solid. LCMS: for $C_{35}H_{44}FN_{11}O_5S_2$ calculated 781.3, found 782.4 $[M+H]^+$. $^1H$ NMR (300 MHz, Methanol-$d_4$) δ ppm: 8.68 (s, 1H), 8.25 (s, 1H), 7.82 (m, 6H), 7.63 (d, J=8.0 Hz, 2H), 5.95 (s, 1H), 5.46 (dt, J=35.2, 7.8 Hz, 1H), 5.37 (d, J=16.6 Hz, 2H), 4.79-4.65 (m, 3H), 4.60 (s, 2H), 4.50 (dd, J=8.1, 4.1 Hz, 1H), 3.69 (d, J=7.2 Hz, 2H), 3.33-3.26 (m, 1H), 2.98 (dd, J=13.1, 4.5 Hz, 1H), 2.77 (d, J=13.0 Hz, 1H), 2.69 (s, 6H), 2.35 (t, J=7.1 Hz, 2H), 1.84-1.37 (m, 6H).

Example 16

Preparation of N-((1-(4-(((1-((Z)-4-amino-2-fluorobut-2-en-1-yl)-1H-1,2,3-triazol-4-yl)(4-(N,N-dimethylsulfamoyl)phenyl)methoxy)methyl)phenyl)-1H-1,2,3-triazol-4-yl)methyl)-1-(5-((3aS,4S,6aR)-2-oxohexahydro-1H-thieno[3,4-d]imidazol-4-yl)pentanamido)-3,6,9,12-tetraoxapentadecan-15-amide hydrochloride (Compound 1-16)

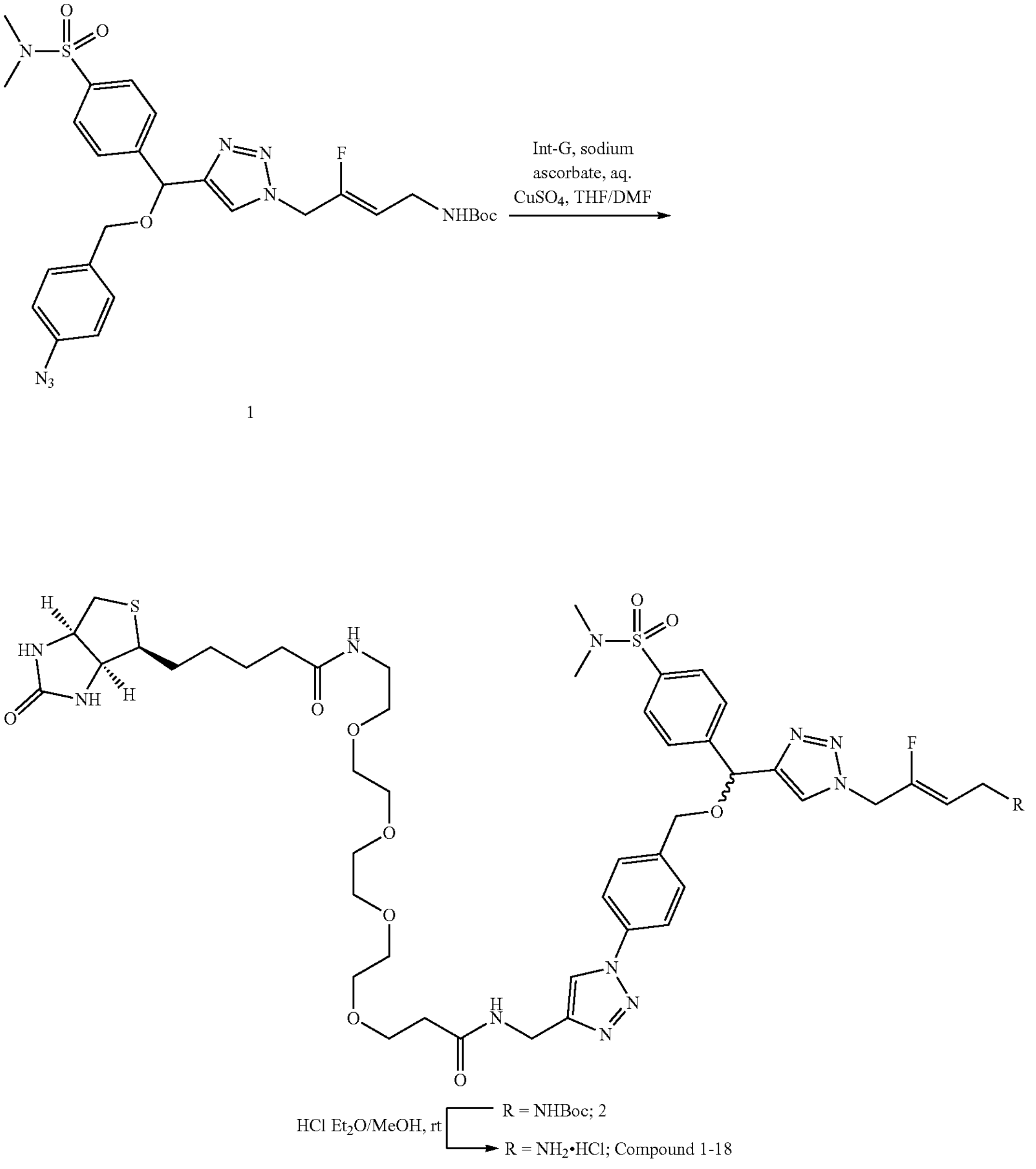

Title compound 1-16 was prepared from compound (1) (the synthesis of compound (1) is detailed in Example 15, procedures 1-9) according to the protocol described in Example 3, procedure 4 (using Int-G as the coupling partner) followed by Example 1, procedure 2 (20.0 mg, 85%) as a yellow, glassy solid. LCMS: for $C_{46}H_{65}FN_{12}O_{10}S_2$ calculated 1028.4, found 1029.4 $[M+H]^+$. $^1H$ NMR (300 MHz, DMSO-$d_6$) δ ppm: 8.59 (s, 1H), 8.46 (t, J=5.5 Hz, 1H), 8.20 (br. s, 3H), 8.16 (s, 1H), 7.90-7.82 (m, 2H), 7.81-7.71 (m, 4H), 7.61-7.53 (m, 2H), 5.94 (s, 1H), 5.46-5.28 (m, 3H), 4.62 (d, J=1.6 Hz, 2H), 4.42-4.35 (m, 2H), 4.30 (dd, J=7.8, 4.8 Hz, 1H), 4.12 (dd, J=7.8, 4.4 Hz, 1H), 3.63 (t, J=6.5 Hz, 2H), 3.48 (d, J=2.5 Hz, 16H), 3.42-3.34 (m, 2H), 3.22-3.13 (m, 2H), 3.09 (dt, J=8.6, 5.7 Hz, 1H), 2.81 (dd, J=12.4, 5.0 Hz, 1H), 2.61 (s, 6H), 2.39 (t, J=6.5 Hz, 2H), 2.06 (t, J=7.3 Hz, 2H), 1.83-1.18 (m, 6H).

Example 17

Method to Determine the Ability of Compounds of the Invention to Inhibit LOX and LOXL1-4 from Different Sources Lysyl oxidase (LOX) is an extracellular copper dependent enzyme which oxidizes peptidyl lysine and hydroxylysine residues in collagen and lysine residues in elastin to produce peptidyl alpha-aminoadipic-delta-semialdehydes. This catalytic reaction can be irreversibly inhibited by β-aminopropionitrile (BAPN) that binds to the active site of LOX (Tang S. S., Trackman P. C. and Kagan H. M., Reaction of aortic lysyl oxidase with beta-aminoproprionitrile. *J Biol Chem* 1983; 258: 4331-4338). There are five LOX family members; these are LOX, LOXL1, LOXL2, LOXL3 and LOXL4. LOX and LOXL family members can be acquired as recombinant active proteins from commercial sources, or extracted from animal tissues like bovine aorta, tendons, pig skin; or prepared from cell cultures. The inhibitory effects of the compounds of the present invention were tested against the given LOX-LOXL preparation using a high-throughput coupled colorimetric method (Holt A. and Palcic M., A peroxidase-coupled continuous absorbance plate-reader assay for flavin monoamine oxidases, copper-containing amine oxidases and related enzymes. *Nat. Protoc.* 2006; 1: 2498-2505). The assay was developed using either 384 or 96 well format. Briefly, in a standard 384 well plate assay 25 μL of a dilution of any of the isoenzymes and orthologues in 1.2 M urea, 50 mM sodium borate buffer (pH 8.2) were added into each well in the presence of 1 μM mofegiline and 0.5 mM pargyline (to inhibit SSAO and MAO-B and MAO-A, respectively). Test compounds were dissolved in DMSO and tested in a Concentration Response Curve (CRC) with 11 data points, typically in the micromolar or nanomolar range after incubation with the enzyme for 30 min at 37° C. 25 μL of a reaction mixture containing twice the $K_M$ concentration of putrescine (Sigma Aldrich, e.g. 20 mM for LOX, or 10 mM for LOXL2 and LOXL3), 120 μM Amplex Red (Sigma Aldrich) and 1.5 U/mL horseradish peroxidase (Sigma Aldrich) prepared in 1.2 M urea, 50 mM sodium borate buffer (pH 8.2) were then added to the corresponding wells. The above volumes were doubled in the case of 96 well plates. The fluorescence (RFU) was read every 2.5 m n for 30 m u at a range of temperatures from 37° C. to 45° C., excitation 565 nm and emission 590 nm (Optima; BMG labtech). The slope of the kinetics for each well was calculated using MARS data analysis software (BMG labtech) and this value was used to deduce the $IC_{50}$ value (Dotmatics). The ability of the inventive compounds to inhibit the amine oxidase activity LOX and other family members is shown in Table 1.

TABLE 1

LOX and LOXL1-4 inhibitory activities of examples of compounds of the invention

| Compound | Bovine LOX Activity $IC_{50}$ (nanomolar) | Human LOXL1 Activity $IC_{50}$ (nanomolar) | Human LOXL2 Activity $IC_{50}$ (nanomolar) | Human LOXL3 Activity $IC_{50}$ (nanomolar) | Human LOXL4 Activity $IC_{50}$ (nanomolar) |
|---|---|---|---|---|---|
| 1-1 | >300 | | <300 | | |
| 1-2 | >300 | | <300 | | |
| 1-3 | >300 | | <300 | | |
| 1-4 | >300 | | <300 | | |
| 1-5 | >300 | | <300 | | |
| 1-6 | >300 | | <300 | | |
| 1-7 | >300 | | >300 | | |
| 1-8 | >300 | | >300 | | |
| 1-9 | >300 | | >300 | | |
| 1-10 | >300 | | >300 | | |
| 1-11 | >300 | | <300 | | |
| 1-12 | >300 | >300 | <300 | >300 | <300 |
| 1-13 | >300 | | >300 | | |
| 1-14 | >300 | | >300 | | |
| 1-15 | <300 | | <300 | <300 | |
| 1-16 | >300 | | <300 | | |

Example 18

Use of a Bead/Antibody Complex to Capture, Isolate and Detect LOXL2 Enzyme from Biological Samples In the immunoassay, capture beads (paramagnetic, coated with anti-LOXL2 antibody (AF2639); 25 μL at 1.6×107 beads/mL) were combined in a cuvette with a biological sample (e.g. human blood serum or plasma, 25 μL, diluted 4-fold in assay buffer 0.5% Casein, 0.25% Tween-20 in 1×PBS; 75 μL), suspected of containing LOXL2 protein, and detector antibody (biotinylated anti-LOXL2 antibody—Fitzgerald 70R-12876) during the incubation (35 minutes, with intermittent shaking, at room temperature). Target molecules (LOXL2) present in the sample were captured by the antibody coated beads and bound with the biotinylated antibody detector simultaneously. After incubation, beads were pelleted by magnet, excess sample/buffer and reagents were aspirated off, and beads were resuspended in wash buffer, to remove unbound proteins and excess reagents. Following a wash, a conjugate of streptavidin-p-galactosidase (SβG; 100 μL at 300 pM) was mixed with the beads and incubated (5 minutes with intermittent shaking at room temperature). SβG bound to the biotinylated detector antibodies and resulted in enzyme-labelling of captured LOXL2. Following a final wash, the beads were resuspended in a resorufin-p-D-galactopyranoside (RGP) substrate solution and transferred to a Simoa Disc (containing a microarray to separate beads into individual microwells). After settling into the microarray via gravity, beads were then sealed in microwells with oil. If LOXL2 was captured and labelled on the bead, β-galactosidase hydrolysed the RGP substrate in the microwell into a fluorescent product that provided the signal for measurement. A single-labelled target molecule results in sufficient fluorescent signal in 30 seconds to be detected and counted by the Simoa optical system. At low target concentration, the percentage of bead-containing wells in the array that have a positive signal is proportional to the amount of target present in the sample. At higher target concentration, when most of the bead-containing wells have one or more labelled target molecules, the total fluorescence signal is proportional to the amount of target present in the sample. The concentration of target in unknown samples was interpolated from the calibration curve. FIG. 1A depicts the inventors' use of a bead/antibody complex to capture, isolate and detect LOXL2 enzyme from biological samples.

Example 19

Figure 1B:
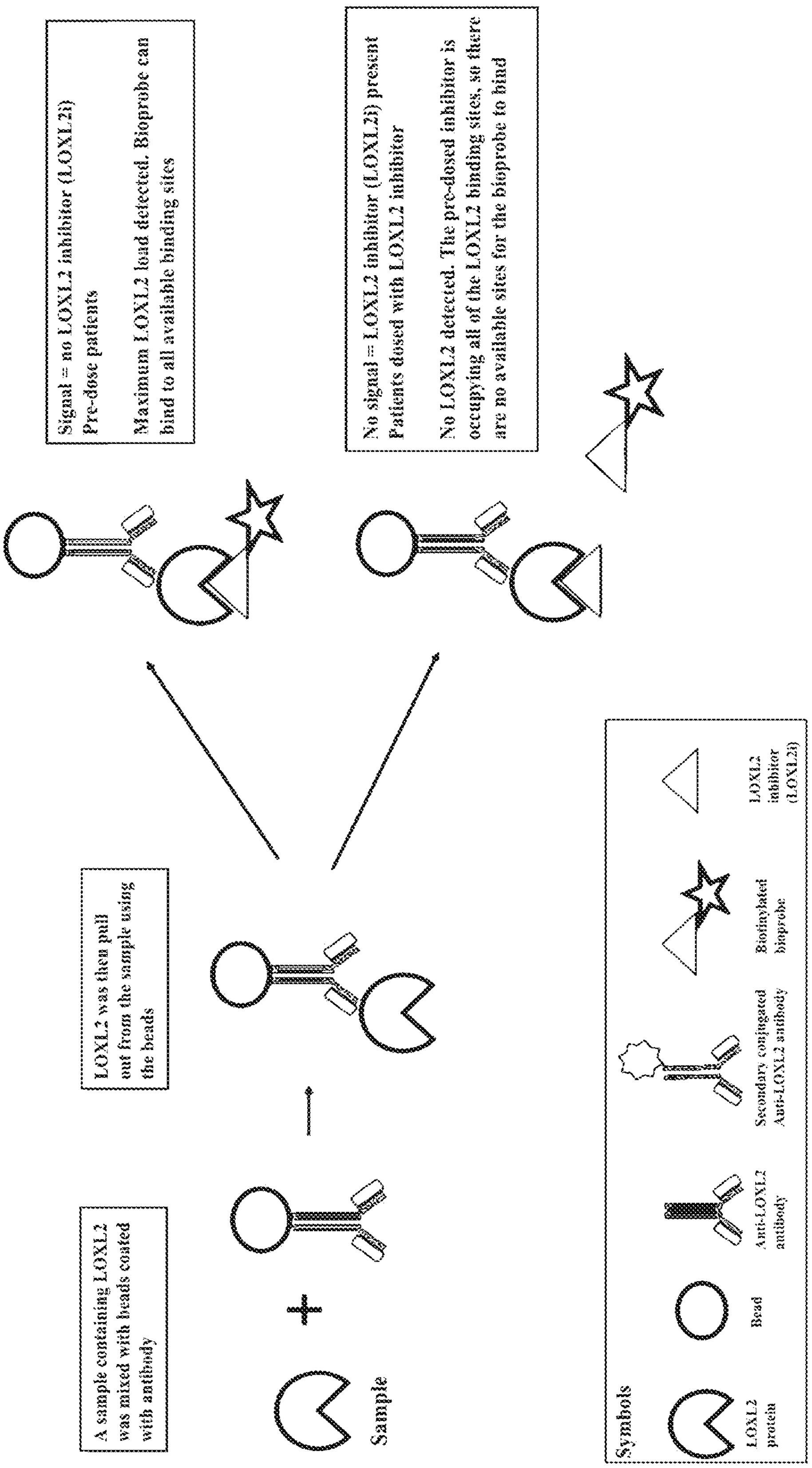
FIG. 1B illustrates schematically the general strategy for the use of a bead/antibody complex/bioprobe to capture, isolate and detect LOXL2 enzyme from biological samples. Also shown schematically in FIG. 1B is the predosing of subjects with a LOXL2 inhibitor. If a LOXL2 inhibitor is added and subsequently binds to the enzymatically active site of LOXL2, there will be no active sites for the bioprobe to bind to, resulting in no signal to be detected.

Use of a Bead/Antibody Complex to Capture, Isolate and Detect Enzymatically Active LOXL2 Enzyme In the immunoassay, capture beads (paramagnetic, coated with anti-LOXL2 capture antibody (AF2639); 100 uL at 4×106 beads/mL) were combined in a cuvette with a biological sample (e.g. human blood serum or plasma, 25 μL, diluted 4-fold in assay buffer 0.5% Casein, 0.25% Tween-20 in 1×PBS; 75 μL), suspected of containing LOXL2 protein, and detector bioprobe (biotinylated anti-LOXL2 bioprobe compounds 1-1 or 1-12, 25 μL at 7.2 μM; these bioprobes bind to the enzymatically active site of the LOXL2 protein) during the incubation (54 minutes, with intermittent shaking, at room temperature). Target molecules (LOXL2) present in the sample were captured by the antibody coated beads and bound with the biotinylated detector bioprobe simultaneously. After incubation, beads were pelleted by magnet, excess sample/buffer and reagents were aspirated off, and beads were resuspended in wash buffer, to remove unbound proteins and excess reagents. Following a wash, a conjugate of streptavidin-p-galactosidase (SβG; 100 μL at 350 pM) was mixed with the beads and incubated (5 minutes with intermittent shaking at room temperature). SβG bound to the biotinylated detector bioprobe and resulted in enzyme-labelling of captured LOXL2. Following a final wash, the beads were resuspended in a resorufin-β-D-galactopyranoside (RGP) substrate solution and transferred to a Simoa Disc (containing a microarray to separate beads into individual microwells). After settling into the microarray via gravity, beads were then sealed in microwells with oil. If LOXL2 was captured and labelled on the bead, β-galactosidase hydrolysed the RGP substrate in the microwell into a fluorescent product that provided the signal for measurement. A single-labelled target molecule results in sufficient fluorescent signal in 30 seconds to be detected and counted by the Simoa optical system. A positive signal by the detection system confirms the presence of the bioprobe. This indicates that LOXL2 is enzymatically available thus the enzyme is active. A negative signal by the detection system confirms the absence of the bioprobe. This indicates that LOXL2 is enzymatically unavailable thus the enzyme is inactive. FIG. 1B depicts the inventors' use of a bead/antibody/bioprobe complex to capture, isolate and detect LOXL2 from biological samples. FIG. 1B further depicts application of the invention for determination/quantification of any residual enzymatically active LOXL2 in samples from patients pre-dosed with a LOXL2 inhibitor (LOXL2i). Binding of the LOXL2 inhibitor to the enzymatically active site of LOXL2 will preclude binding of the bioprobe, thus resulting in an absence of detection signal.

The method described in Example 18, with a capture antibody and second, detection antibody was utilized to determine the total LOXL2 concentration in a sample, both the enzymatically active and enzymatically inactive LOXL2 concentration. The method described in Example 19, with a capture antibody and bioprobe was utilized to determine the concentration of enzymatically active LOXL2 in a sample.

Example 20

Bead/Antibody/Antibody Assay Development—Capture and Detection Antibody Selection To select the best antibody/antibody combination to detect LOXL2, the capture antibody was conjugated to beads or bound on high protein binding plates (such as microlon 600, high binding, flat bottom, Greiner 655061 using coating buffer containing 71.5 mM $NaHCO_3$ and 28.5 mM $Na_2CO_3$) and incubated overnight at 4° C. After washing (with a mild detergent, such as 0.05% Tween 20/TBS) to remove excess and unbound antibody, the beads or plates were then incubated with blocking solution (1-5% BSA/TBS) to block any free binding spots, for a suitable time (1 hour) at room temperature. The blocking solution was then removed and recombinant human LOXL2 was added and incubated for a suitable time (3 hours) at 4° C. After washing (with a mild detergent) to remove excess/unbound protein the detection antibody (which is conjugated with biotin) was incubated for a suitable time (2 hours) at 4° C. After washing (with a mild detergent), streptavidin conjugated to horseradish peroxidase was added and incubated for 3 hours at room temperature. After an additional washing step (with a mild detergent) the detection substrate, TMB (3,3',5,5'-tetramethylbenzidine was added. After 1 hour, 2.0 M aqueous $H_2SO_4$ was added and the signal immediately measured with maximum absorbance at 450 nm.

The signal is proportional to the amount of captured LOXL2. Numerous antibodies were tested for the capture and detection steps, as considerable variation in the specific lysyl oxidase signal was observed between various combinations of capture and detection antibodies. The optimal combination allows a substantial assay dynamic range by providing the strongest signal to noise ratio over a large lysyl oxidase concentration range.

Figure 2:
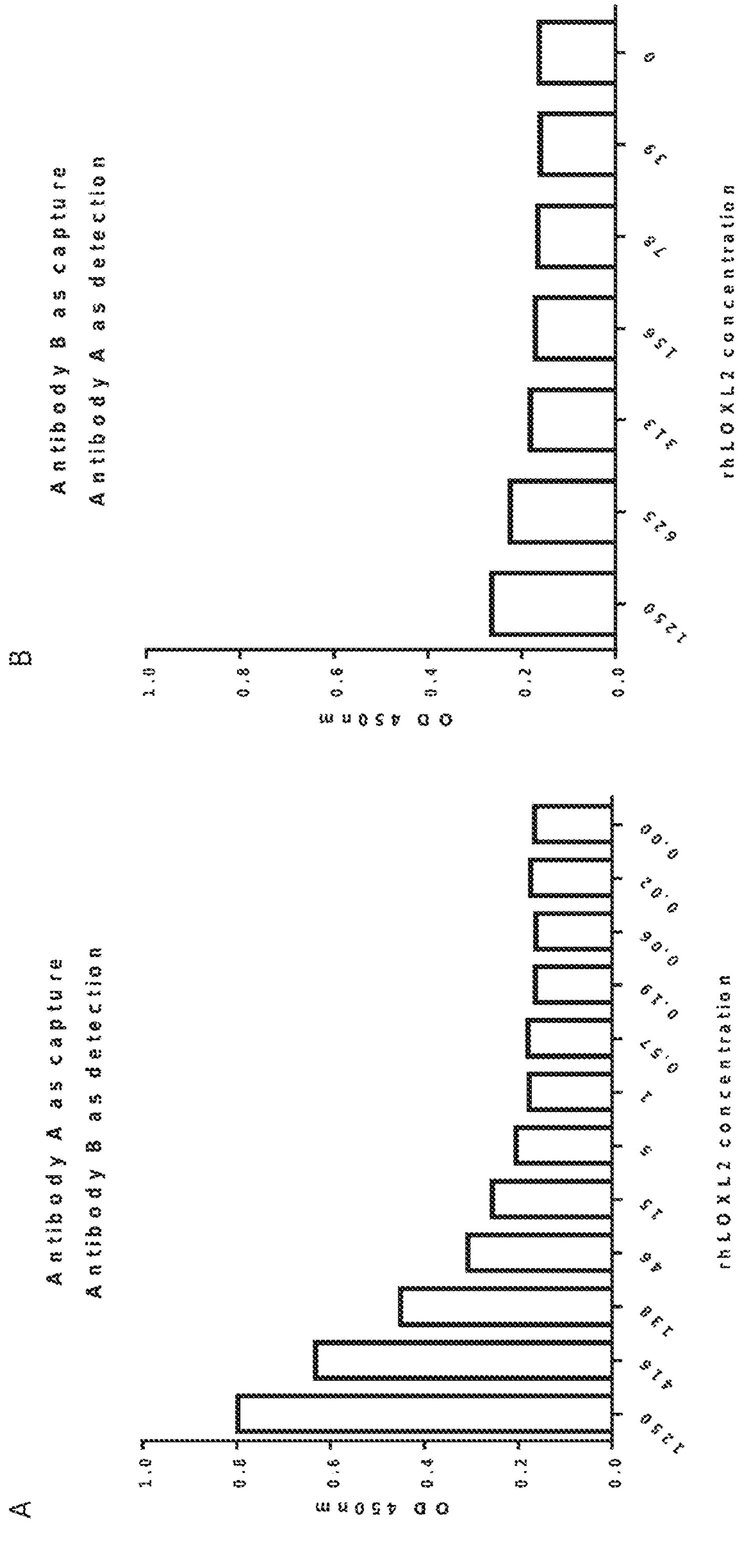
FIGS. 2A and 2B depict the absorbance values (optical density 450 nm) from the antibody/antibody assay, using two antibodies. Specifically.

FIG. 2 depicts the absorbance values (optical density 450 nm) from the antibody/antibody assay, using two antibodies. FIG. 2A) 3.12 μg/mL of Antibody A (AF2639) is used as the capture; rhLOXL2 was used as the antigen and 5 μg/mL Antibody B (Fitzgerald 70R-12876) was used as the detection. Concentration of rhLOXL2 ranges from 0-1250 ng/mL. FIG. 2B) 1.56 μg/mL of Antibody B was used as the capture, rhLOXL2 was used as the antigen and 5 μg/mL antibody A was used as the detection. Concentration of rhLOXL2 ranges from 0-1250 ng/mL. The combination of antibody A as a capture with antibody B as the detection gave a strong signal with a wide dynamic range (FIG. 2A) while the reverse combination (FIG. 2B) yielded a poor signal.

Example 21

Selection of Capturing Antibody for Bioprobe Assay to Determine Amount of Uninhibited LOXL2

Antibody A (AF2639) was conjugated to beads, bound to high protein binding plates (microlon 600, high binding, flat bottom, Greiner 655061 using coating buffer containing 71.5 mM $NaHCO_3$ and 28.5 mM $Na_2CO_3$) overnight at 4° C. After washing with a mild detergent (0.05% Tween 20) to remove excess and unbound antibody, the beads or plates were then incubated with blocking solution (1-5% BSA/TBS) to block any free binding spots, for 1 hour at room temperature. The blocking solution was then removed and rhLOXL2 was added and incubated for 3 hours at 4° C. After washing (with a mild detergent) to remove excess/unbound protein, bioprobe Compound 1-1 (which is conjugated with biotin) was incubated for 2 hours at 37° C. at a concentration between $IC_{50}$ to $IC_{100}$ of the rhLOXL2 (as measured in a standard biochemical assay eg Amplex Red/Resorufin). After a washing step (with a mild detergent) streptavidin conjugated to horseradish peroxidase or an appropriate label was added and incubation was continued for 1 hour at room temperature. After an additional washing step (with mild TBS/tween detergent), a detection substrate (resorufin or TMB) was added followed by the fluorescence read at Excitation: 565 nm/Emmission: 590 nm or maximum absorbance at 450 nm. A suitable capture antibody will allow for bioprobe binding whilst providing a large signal.

Figure 3:
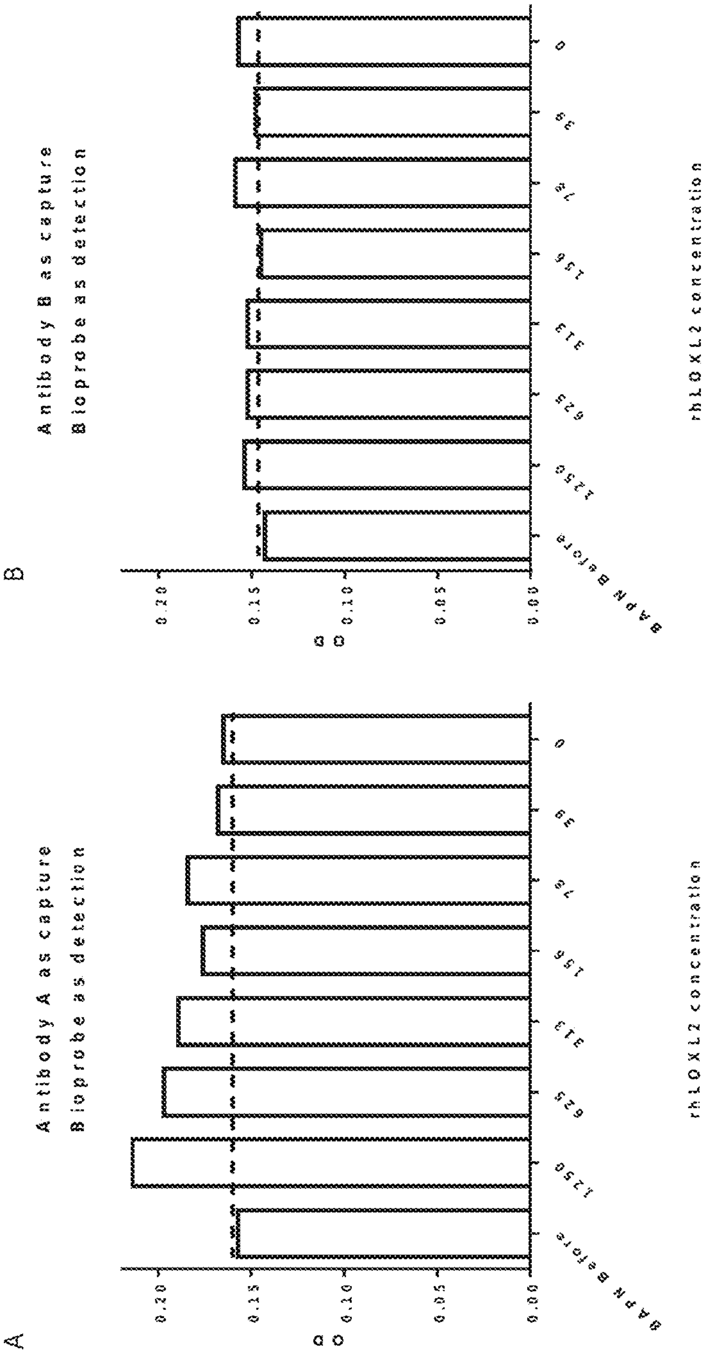
FIG. 3 depicts the absorbance values (optical density 450 nm) from the antibody/chemical probe assay, using one antibody and a bioprobe with one biotin moiety (Compound 1-1).

When antibody A (AF2639) was used as the capture antibody, the bioprobe shows a specific rhLOXL2 signal (the signal is ablated by the use of the pan-LOX inhibitor BAPN) (FIG. 3A). While the use of Antibody B (Fitzgerald 70R-12876)—as the capture antibody—prevents the detection of rhLOXL2 by the bioprobe (Compound 1-1) (FIG. 3B). FIG. 3 depicts the absorbance values (optical density 450 nm) from the antibody/bioprobe assay, using one antibody and Compound 1-1 (FIG. 3A) AF2639 was used as the capture antibody, rhLOXL2 was used as the antigen and 80 nM of Compound 1-1 was used as the detection. FIG. 3B) Fitzgerald 70R-12876 was used as the capture antibody, rhLOXL2 is used as the antigen and 80 nM of Compound 1-1 is used as the detection.

Figure 4:
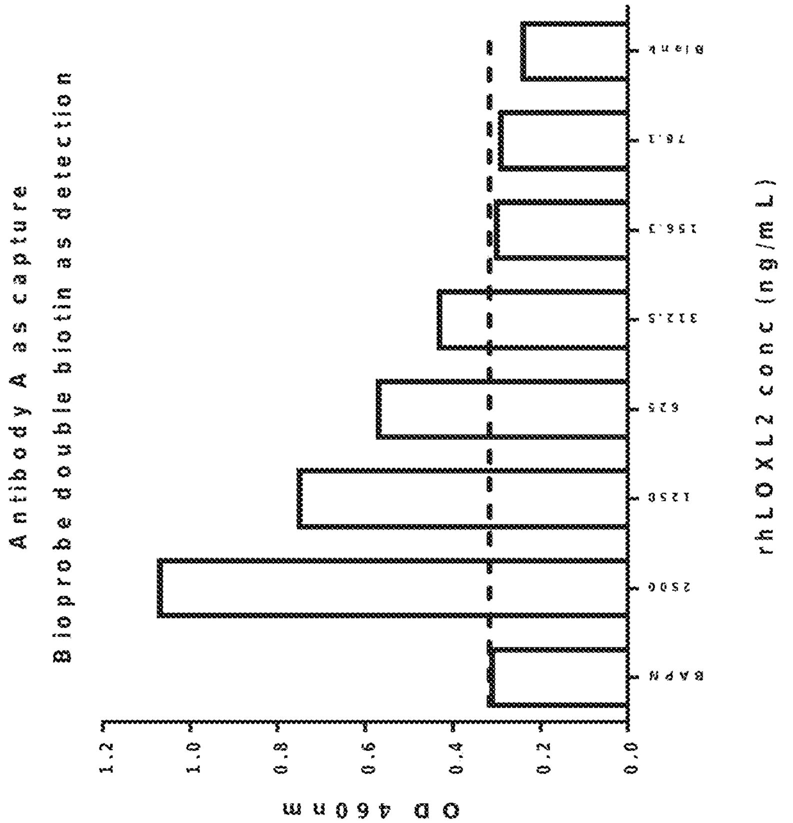
FIG. 4 depicts the absorbance values (optical density 460 nm) from the antibody/bioprobe assay, using one antibody and a bioprobe with two biotin moieties (Compound 1-12). Antibody A (AF2639) was used as the capture, rhLOXL2 was used as the antigen and 78 nM of the bioprobe Compound 1-12 was used as the detection.

When the bioprobe contains two biotin moieties, the signal is more robust than a single biotin counterpart. FIG. 4 depicts the absorbance values (optical density 460 nm) from the antibody/bioprobe assay, using one antibody and a bioprobe possessing two biotin moieties. AF2639 was used as the capture, rhLOXL2 was used as the antigen and 78 nM of Compound 1-12 was used for detection.

Example 22

Selection of Detection Antibody that does not Interfere with Bioprobe Binding

Figure 5:
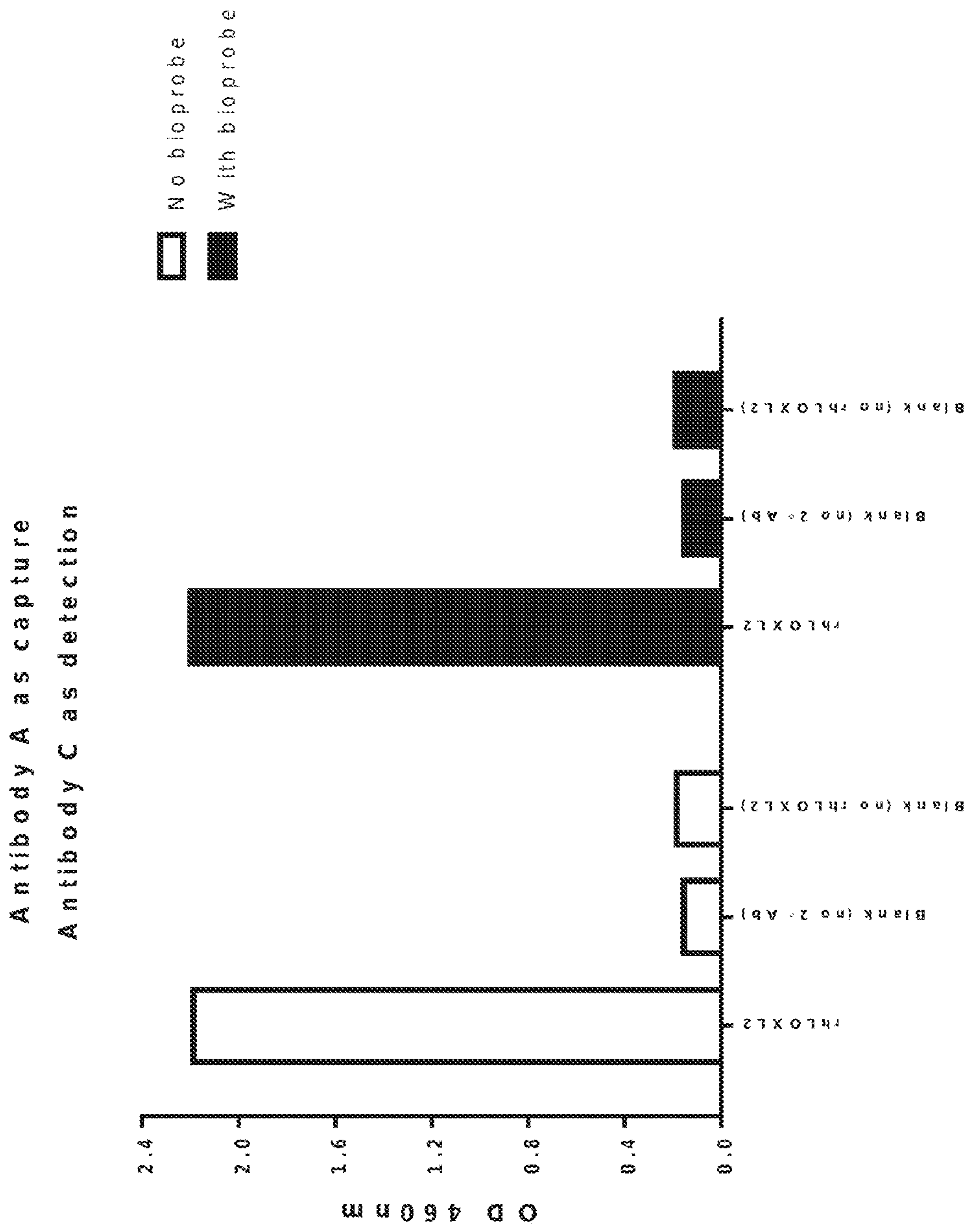
FIG. 5 depicts the absorbance values (optical density 460 nm) from the antibody/antibody assay, using two antibodies. Antibody A (AF2639) was used as the capture antibody, 1250 ng/mL rhLOXL2 was used as the antigen and antibody C (C-AB179810) was used as the detection antibody. 400 nM of bioprobe Compound 1-1 was pre-incubated with rhLOXL2 before ELISA commenced.

A further aim was directed at determining whether the presence of bioprobe (Compound 1-1), pre-incubated and bound to the active site of rhLOXL2, would affect antibody binding and detection by sandwich ELISA. The results, depicted in FIG. 5, revealed no difference in rhLOXL2 detection levels in the presence or absence of bioprobe, Compound 1-1. This confirmed that the bioprobe bound to rhLOXL2 does not prevent binding by either a capture antibody or second, detection antibody in the sandwich ELISA. FIG. 5 depicts the absorbance values (optical density 460 nm) from the antibody/antibody assay, using two antibodies. Antibody A (AF2639) was used as the capture antibody, 1250 ng/mL rhLOXL2 was used as the antigen and antibody C (C-AB179810) was used as the detection antibody. 400 nM of Compound 1-1 was pre-incubated with rhLOXL2 before commencement of the ELISA assay.

Example 23

LOXL2 Concentration Assay

The LOXL2 Concentration Assay uses a Simoa HD-1 analyzer (Quanterix Corporation) and Single Molecule Array (Simoa) technology to run a 2-step digital immunoassay, to measure the quantity of total LOXL2 in human serum. The Simoa technology is described in the following reference: Rissin D M, Kan C W, Campbell T G, et al. Single-molecule enzyme-linked immunosorbent assay detects serum proteins at subfemtomolar concentrations. Nat Biotech 2010; 28:595-99.

Prior to being loaded on the analyzer, samples (25 μL) were diluted 4-fold in Assay Buffer (0.5% Casein, 0.25% Tween-20 in 1×PBS).

In the LOXL2 Protein Concentration 2-step immunoassay, target-antibody (AF2639)-coated paramagnetic beads (500k per mL) were combined with diluted sample and biotinylated detector antibody (Fitzgerald 70R-12876; 0.4 μg/mL) in the same incubation cuvette for 35 minutes. Target molecules present in the sample were captured by the antibody coated beads and bind with the biotinylated antibody detector simultaneously. Following a wash, a conjugate of streptavidin-p-galactosidase (SβG) at 150 pM was mixed with the beads and incubated for 5 minutes. SβG binds to the biotinylated detector antibodies, resulting in enzyme labeling of captured target. Following a final wash, the beads were resuspended in a resorufin β-D-galactopyranoside (RGP) substrate solution and transferred to the Simoa Disc. Individual beads are then sealed within microwells in the array. If the target has been captured and labeled on the bead, p-galactosidase hydrolyzes the RGP substrate in the microwell into a fluorescent product that provides the signal for measurement.

A single-labeled target molecule results in sufficient fluorescent signal in 30 seconds to be detected and counted by the Simoa optical system. At low target concentration, the percentage of bead-containing wells in the array that have a positive signal is proportional to the amount of target present in the sample. At higher target concentration, when most of the bead-containing wells have one or more labeled target molecules, the total fluorescence signal is proportional to the amount of target present in the sample. The concentration of target in unknown samples is interpolated from the calibration curve.

Figure 6:
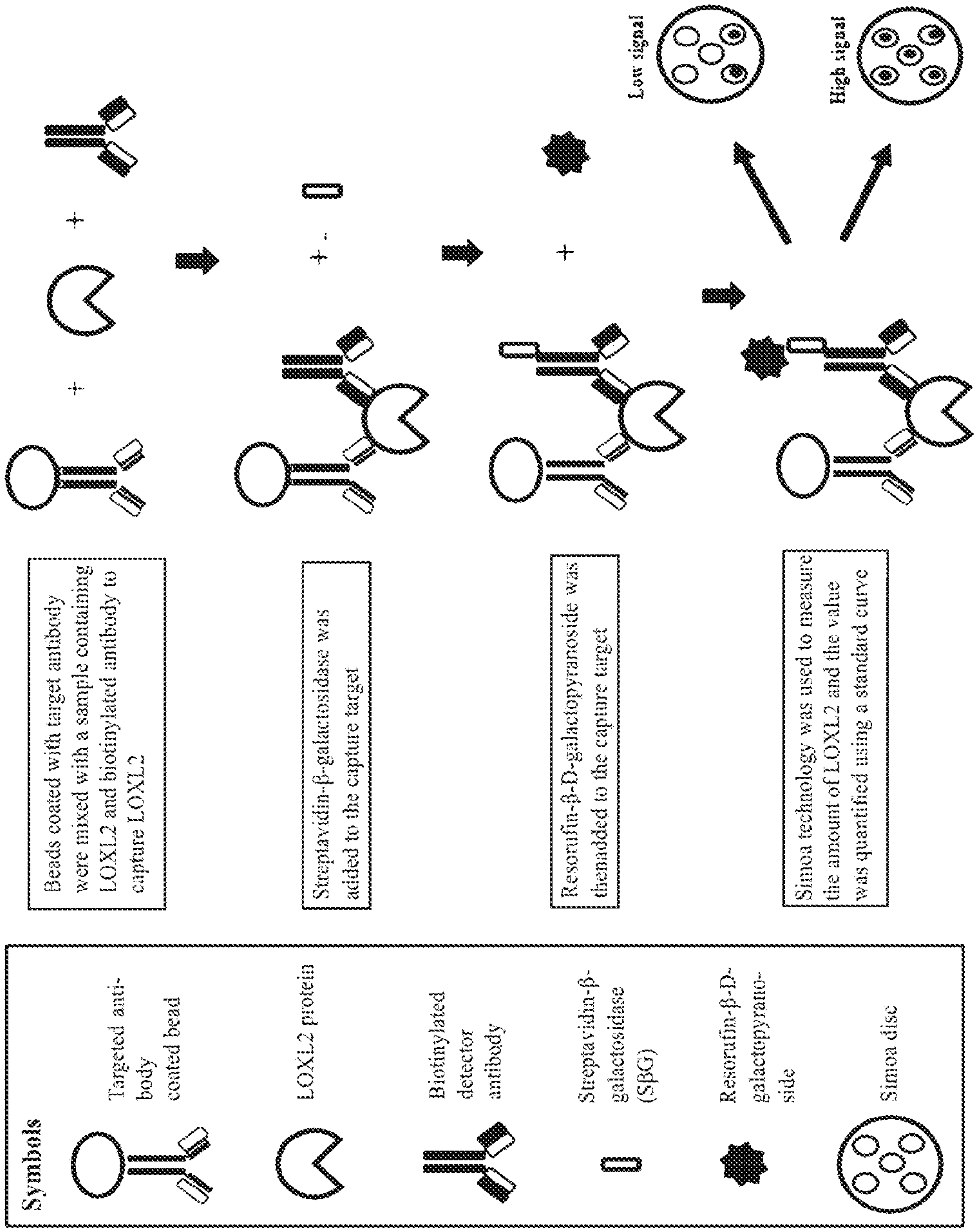
FIG. 6 is a schematic representation of the LOXL2 protein concentration assay utilising the Simoa technology—LOXL2 protein concentration 2-step immunoassay.

The LOXL2 protein concentration assay utilising the Simoa technology is represented schematically in FIG. 6.

Example 24

LOXL2 Bioprobe Activity Assay

The LOXL2 Bioprobe Assay used a Simoa HD-1 analyzer and Simoa technology to run a 2-step digital immunoassay, to measure the activity of unbound LOXL2 in human serum.

This assay used the same anti-LOXL2 capture antibody as for the Protein Concentration Assay. The bioprobe (Compound 1-12) was diluted down to 130 μM in deionized $H_2O$ prior to being diluted in Detector Buffer. Before being loaded onto the analyzer, samples (25 μL) were diluted 4-fold in Assay Buffer (0.5% Casein, 2% Polyethylene Glycol 20k, 0.5% Seracon, 0.5% Tween-20 in 1×PBS). To determine the background signal, diluted samples were pre-incubated for 30 min with a LOX inhibitor beta-aminoproprionitrile (BAPN).

In the LOXL2 Bioprobe Activity 2-step immunoassay, target-antibody-coated paramagnetic beads (500k per mL) were combined with diluted sample and biotinylated detector-bioprobe (1.2 μM) in the same incubation cuvette for 54 minutes. Target molecules present in the sample were captured by the antibody coated beads and bonded to the biotinylated bioprobe (Compound 1-12) simultaneously. Following a wash, a conjugate of streptavidin-β-galactosidase (SβG) at 150 pM was mixed with the beads and incubated for 5 minutes. SβG was then bound to the biotin moiety of the bioprobe, resulting in enzyme labeling of captured target. Following a final wash, the beads were resuspended in a resorufin β-D-galactopyranoside (RGP) substrate solution and transferred to the Simoa Disc. Individual beads were then sealed within microwells in the array. Target that had been captured and labeled on the bead, in turn, effected hydrolysis of the RGP substrate in the microwell into a fluorescent product, providing the signal for measurement.

A single-labeled target molecule results in sufficient fluorescent signal in 30 seconds to be detected and counted by the Simoa optical system. At low target concentration, the percentage of bead-containing wells in the array that have a positive signal is proportional to the amount of target present in the sample. At higher target concentration, when most of the bead-containing wells have one or more labeled target molecules, the total fluorescence signal is proportional to the amount of target present in the sample. The concentration of target in unknown samples is interpolated from the calibration curve.

Figure 7:
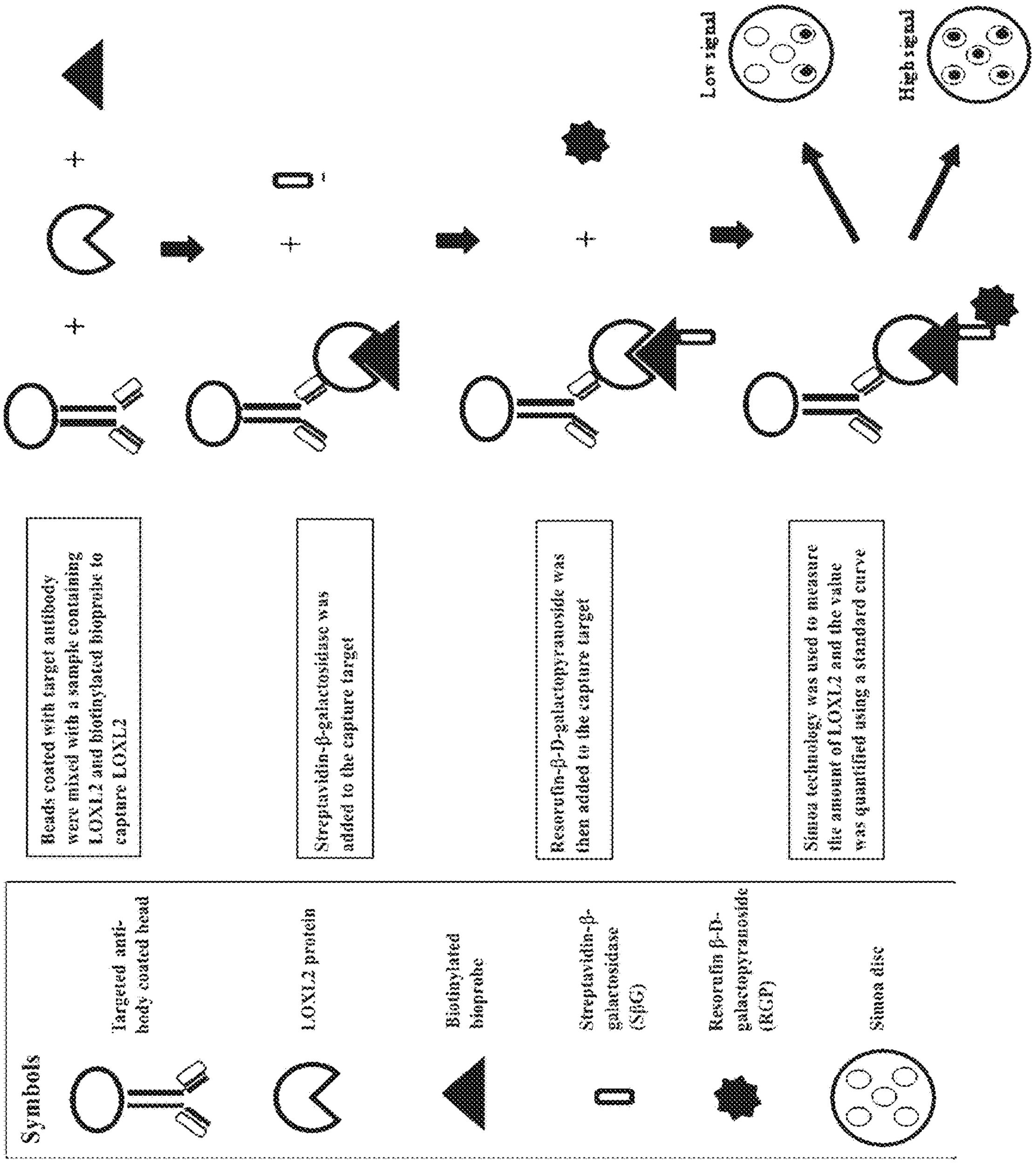
FIG. 7 is a schematic representation of the LOXL2 bioprobe activity assay utilising the Simoa technology.

The LOXL2 bioprobe activity assay utilising the Simoa technology is represented schematically in FIG. 7.

Example 25

ELISA Assay Validation—Human Samples

LOXL2 protein concentration assay was performed as outlined above in Example 23. Samples contained hrLOXL2 at the indicated concentrations. The assay is performed in the two-step mode and the raw signal is reported. As shown in Tables 2 and 3, the ratio of the signal in the presence of enzyme (S) over the signal in the absence of enzyme (noise, N) is calculated and shows a concentration dependent relationship.

Table 2 shows the determination of the dynamic range of the LOXL2 detection using the antibody (AF2639)/antibody (Fitzgerald 70R-12876) assay.

TABLE 2

| rec hLOXL2 pg/mL | S/N |
|---|---|
| 0 | |
| 5 | 2.8 |
| 50 | 18.6 |
| 500 | 160.3 |
| 5000 | 1121.7 |

Table 3 demonstrates the determination of the dynamic range of the LOXL2 detection using the antibody (AF2639)/bioprobe (Compound 1-12) assay.

TABLE 3

| rec hLOXL2 (pg/mL) | S/N |
|---|---|
| 0 | |
| 4.88 | 1.14 |
| 19.5 | 1.57 |
| 78.1 | 3.01 |
| 313 | 9.36 |
| 1250 | 30.5 |
| 5000 | 103 |
| 20000 | 325 |

The lower limit of detection ranges from 3-20 μg/mL within each assay.

Example 26

Determination of $IC_{50}$ of a LOXL2 Inhibitor in Human Blood Serum or Plasma

Figure 8:
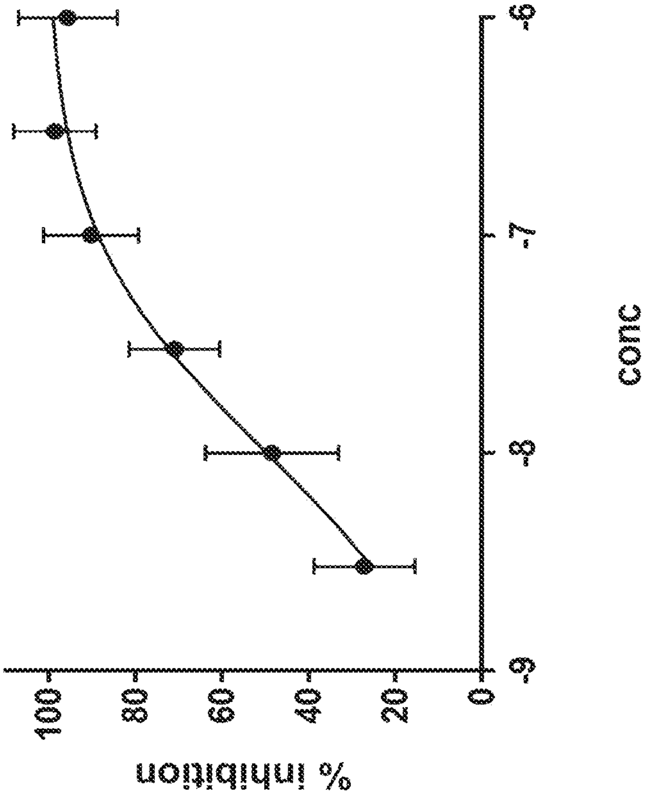
FIG. 8 shows determination of the $IC_{50}$ of a LOXL2 inhibitor upon incubation with human plasma.

A LOXL2 bioprobe activity assay was performed in a two step mode as outlined above for the bioprobe activity assay. Samples were human native LOXL2 from human serum or plasma. FIG. 8 shows the determination of $IC_{50}$ of a LOXL2 inhibitor upon incubation with human serum using the bioprobe activity assay. In brief, a concentrated solution of LOXL2 inhibitor (Compound 112; patent WO 2017/136870) was spiked into human serum to achieve the indicated final concentrations. These samples were incubated for 20-40 min between 20-37° C. The bioprobe activity assay is then performed as described above.

Example 27

Method of Determining Sustained Inhibition of LOXL2 by Bioprobe Compounds of the Invention Jump dilution experiment: The assay was developed using a 96 well format and the starting enzyme concentration was sufficient in order to provide a signal-to-noise (S/N)>5 after 100 fold dilution. The enzyme was incubated for 40 minutes at 37° C. in presence of 10× or (where needed to ascertain inhibitor concentration exceeding enzyme concentration) 30× $IC_{50}$ concentrations of the test inhibitor. After the incubation, the mixture was diluted 50× in assay buffer, followed by a further 2× dilution in Amplex Red (AR)-horseradish peroxidase (HRP)-putrescine reaction mixture prior to the fluorescent measurement. Results were expressed as % recovery of the signal after a specified time by comparison with non-inhibited controls.

Figure 9:
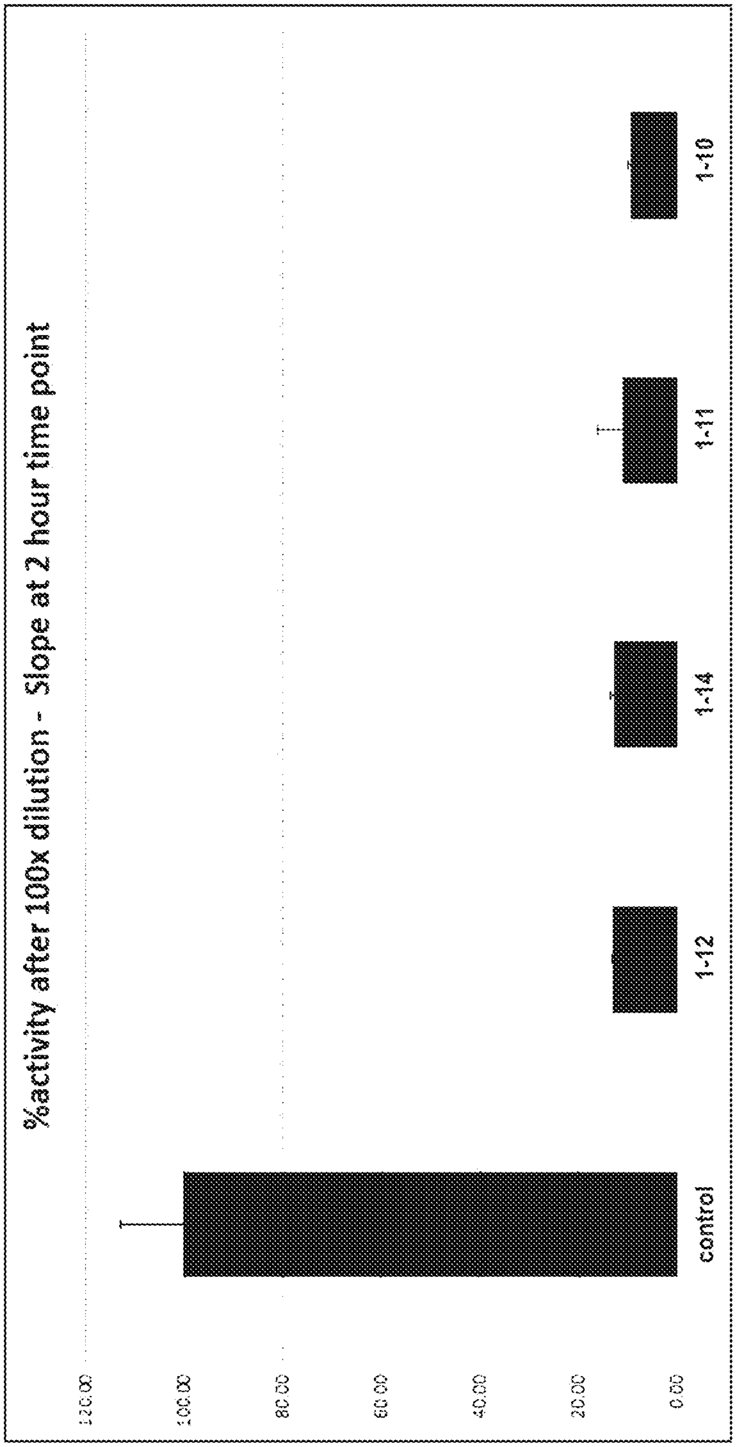
FIG. 9 depicts sustained inhibition of LOXL2 enzymatic activity by compounds described in the current invention as determined using a jump dilution assay.

Bioprobe compounds described herein exert sustained and significant inhibition of LOXL2. Results are shown graphically in FIG. 9—enzyme was preincubated with compounds of the current invention (10×$IC_{50}$). Enzyme/inhibitor complex was then diluted 100× and remaining activity assessed by AR/HRP assay up to 2 hours following dilution.

Example 28

Screening for LOX Capture and Detection Antibodies for the LOX Protein Concentration and Bioprobe Assay.

To measure protein expression, samples were subjected to western blotting. The primary antibodies employed were rabbit anti-LOX antibody: Sigma, L4794 and Abcam ab219369. Secondary antibody utilised was a HRP-conjugated goat anti rabbit antibody (Invitrogen, 31462). Signals were visualised with super-signal West-Pico Chemiluminescent Substrate (Thermo Fisher Scientific, PI-34087) and optimal signal was recorded with ChemiDoc (Biorad).

Numerous LOX antibodies were screened, via western blots, against human recombinant protein of LOX family members (LOX, LOXL1, LOXL2, LOXL3 and LOXL4) and LOX from different species (human, bovine and mouse). If the antibodies passed this initial screen, they were then tested for specificity to LOX against conditioned media and/or cell lysates that were generated from normal human lung fibroblasts (NHLF) that were treated with LOX-siRNA or control siRNA.

Figure 10A:
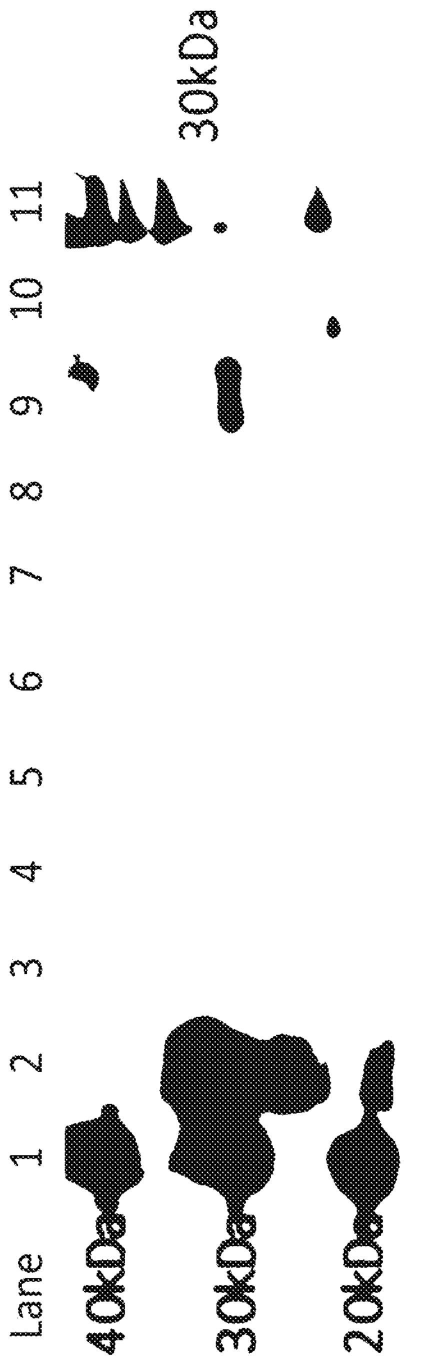
FIG. 10A-10C depict the western blots used for testing the LOX capture antibody (L4794, Antibody D) (FIGS. 10A-B) and the LOX detection antibody (ab219369) (FIG. 10C). Specifically.
Figure 10B:
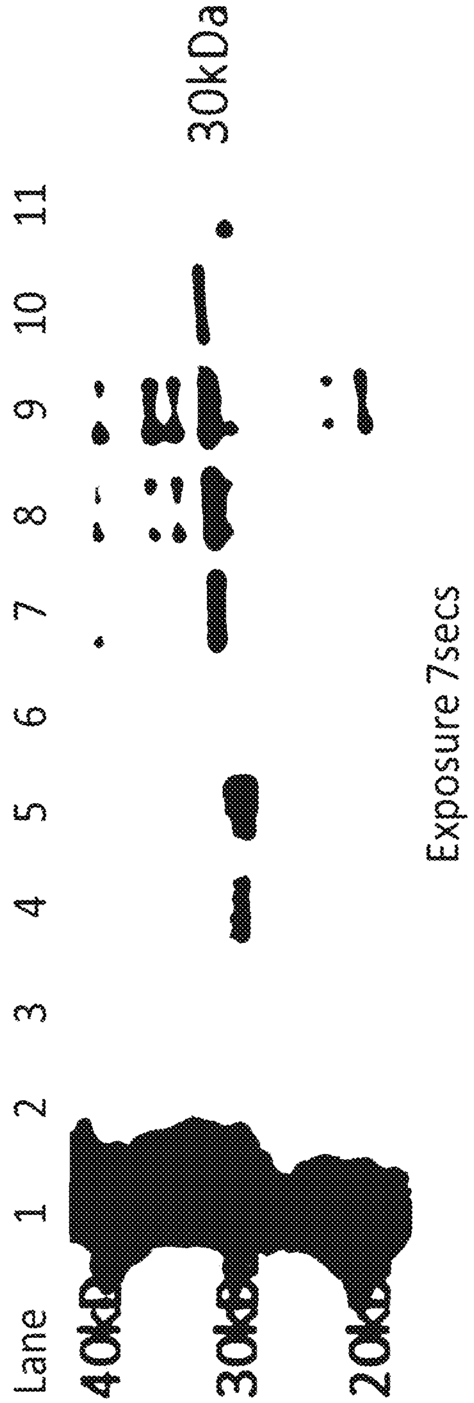
Figure 10C:
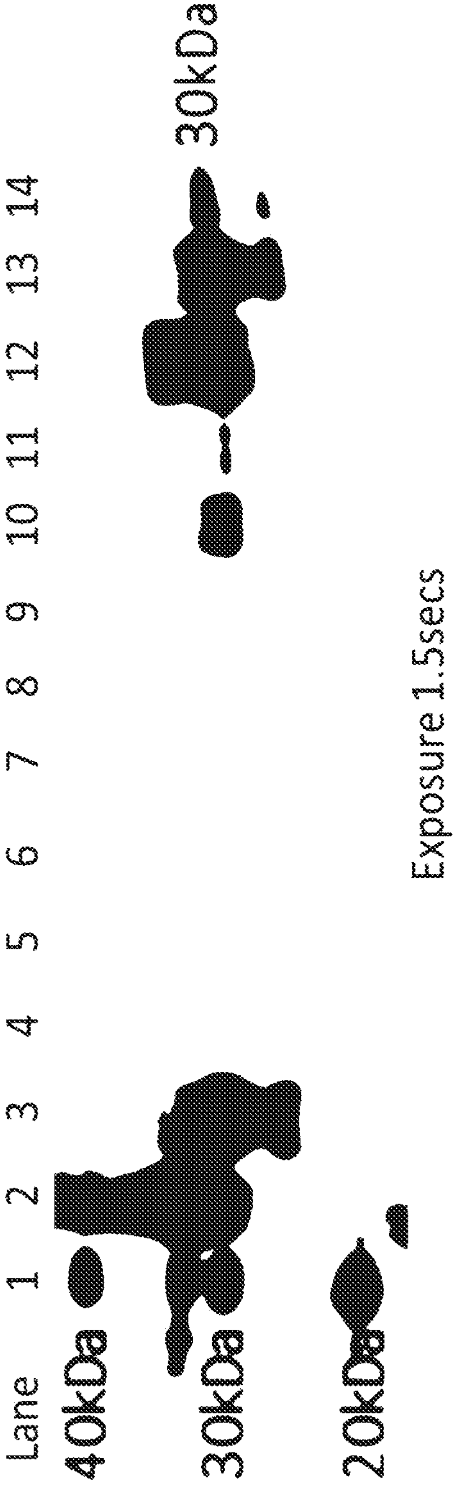

Through this screening process, Antibody C (Sigma, L4794) was selected as the LOX capture antibody and Antibody D (abeam, ab219369) as the LOX detection antibody. FIG. 10A depicts Antibody C detecting human recombinant LOX and no other LOXL family members. FIG. 10B shows that if siRNA for human LOX knocks down the expression of LOX in NHLF cells then Antibody C can also no longer detect the LOX, demonstrating that the band detected by antibody C is LOX. It should also be noted that Antibody C does not detect the active form of Mouse LOX. FIG. 10C demonstrates that Antibody D detects human recombinant LOX, LOXL1 and LOXL4. Furthermore, FIG. 10C also shows Antibody D is specific to mature LOX by showing the LOX SiRNA knockdown. As Antibody D detects multiple lysyl oxidase family members it is not suitable as a capture antibody, but can be utilised as a detection antibody.

Example 29

LOX Concentration Assay

The LOX Concentration Assay uses a Simoa HD-1 analyzer (Quanterix Corporation) and Single Molecule Array (Simoa) technology to run a 2-step digital immunoassay, to measure the quantity of total LOX in human serum. The Simoa technology is described in the following reference: Rissin D M, Kan C W, Campbell T G, et al. Single-molecule enzyme-linked immunosorbent assay detects serum proteins at subfemtomolar concentrations. Nat Biotech 2010; 28:595-99.

Prior to being loaded on the analyzer samples are diluted at least 5-fold in Assay Buffer (1% BSA, 0.25% Rabbit Serum, 2% PEG (20k MW), 0.55% Tween-20, 1×PBS; used to dilute samples, controls, and detector reagent)

In the LOX Protein Concentration 2-step immunoassay, target-antibody (L4794)-coated paramagnetic beads (500k per mL) were combined with diluted sample and biotinylated detector antibody (ab219369) in the same incubation cuvette for 35 minutes. Target molecules present in the sample were captured by the antibody coated beads and bound to the biotinylated antibody detector simultaneously. Following a wash, a conjugate of streptavidin-β-galactosidase (SβG) at 150 pM was mixed with the beads and incubated for 5 minutes. SβG binds to the biotinylated detector antibodies, resulting in enzyme labeling of captured target. Following a final wash, the beads were resuspended in a resorufin β-D-galactopyranoside (RGP) substrate solution and transferred to the Simoa Disc. Individual beads were then sealed within microwells in the array. Target that had been captured and labeled on the bead, in turn, effected hydrolysis of the RGP substrate in the microwell into a fluorescent product, providing the signal for measurement.

A single-labeled target molecule results in sufficient fluorescent signal in 30 seconds to be detected and counted by the Simoa optical system. At low target concentration, the percentage of bead-containing wells in the array that have a positive signal is proportional to the amount of target present in the sample. At higher target concentration, when most of the bead-containing wells have one or more labeled target molecules, the total fluorescence signal is proportional to the amount of target present in the sample. The concentration of target in unknown samples is interpolated from the calibration curve.

The LOX protein concentration assay utilising the Simoa technology is analagous to that represented schematically in FIG. 6.

Table 4 shows the determination of the dynamic range of the human recombinant LOX protein concentration detection using the capture antibody (L4794)/detection antibody (ab219369). The estimated limit of detection is 0.006 ng/mL. Signal to noise (S/N) is the ratio of the signal in the presence of the enzyme (S) over the noise (N) (buffer without rhLOX protein added). A signal above 1 is considered a LOX specific signal. The human recombinant LOX was serially diluted (1 in 4 series) with the starting concentration at 25 ng/ml.

TABLE 4

| rhLOX ng/mL | S/N |
|---|---|
| 0 | |
| 0.0244 | 1.83 |
| 0.0977 | 3.63 |
| 0.391 | 12.4 |
| 1.56 | 33.2 |
| 6.25 | 108 |
| 25.0 | 338 |

Table 5 shows detection of native LOX (human fibroblast conditioned media) spiked into human serum using the LOX protein concentration assay. LOX protein is detectable in human serum.

TABLE 5

| Sample: amount of conditioned media spiked into sample | Concentration (ng/ml) |
|---|---|
| Sample 1: human serum | 3.02 |
| Sample 2: human serum | 5.33 |
| Sample 1 + conditioned media (10× diluted) | 658 |
| Sample 2 + conditioned media (10× diluted) | 736 |
| Sample 1 + conditioned media (100× diluted) | 37.8 |
| Sample 2 + conditioned media (100× diluted) | 48.2 |

Example 30

LOX Bioprobe Activity Assay

The LOX Bioprobe Assay used a Simoa HD-1 analyzer and Simoa technology to run a 2-step digital immunoassay, to measure the activity of unbound LOX in human serum.

This assay used the same anti-LOX capture antibody as for the Protein Concentration Assay. The bioprobe (Compound 1-12) was diluted down to 130 μM in deionized $H_2O$ prior to being diluted in Detector Buffer. Before being loaded onto the analyzer, samples were diluted at least 6 fold in Assay Buffer (1% BSA, 0.25% Rabbit Serum, 2% PEG (20k MW), 0.55% Tween-20, 1×PBS; used to dilute samples, controls, and detector reagent). To determine the background signal, diluted samples were pre-incubated for 30 min with LOX inhibitor beta-aminoproprionitrile (BAPN).

In the LOX Bioprobe Activity 2-step immunoassay, target-antibody-coated paramagnetic beads (500k per mL) were combined with diluted sample and biotinylated detector-bioprobe (1.2 M) in the same incubation cuvette for 54 minutes. Target molecules present in the sample were captured by the antibody coated beads and bound to the biotinylated bioprobe (Compound 1-12) simultaneously. Following a wash, a conjugate of streptavidin-β-galactosidase (SβG) at 150 pM was mixed with the beads and incubated for 5 minutes. SβG binds to the biotin moiety of the bioprobe, resulting in enzyme labeling of captured target. Following a final wash, the beads were resuspended in a resorufin β-D-galactopyranoside (RGP) substrate solution and transferred to the Simoa Disc. Individual beads were then sealed within microwells in the array. Target that had been captured and labeled on the bead, in turn, effected hydrolysis of the RGP substrate in the microwell into a fluorescent product, providing the signal for measurement.

A single-labeled target molecule results in sufficient fluorescent signal in 30 seconds to be detected and counted by the Simoa optical system. At low target concentration, the percentage of bead-containing wells in the array that have a positive signal is proportional to the amount of target present in the sample. At higher target concentration, when most of the bead-containing wells have one or more labeled target molecules, the total fluorescence signal is proportional to the amount of target present in the sample. The concentration of target in unknown samples is interpolated from the calibration curve.

The LOX bioprobe activity assay utilising the Simoa technology is analagous to that represented schematically in FIG. 7.

Table 6 shows the LOX bioprobe assay detects LOX activity in human serum spiked with Human fibroblast conditioned media (CM, ×100 diluted). S/N is the ratio of the signal in the presence of the enzyme (S) over the noise (N) (Signal remaining after the enzyme is inhibited). A signal above 1 is considered LOX specific activity. Note that BAPN (a panLOX inhibitor) significantly reduces the signal demonstrating the signal is LOX specific and related to the active site. It is also evident that the human serum has LOX specific activity.

TABLE 6

| Sample 1 | Average signal | S/N |
|---|---|---|
| Sample 1: Serum only | 0.0134 | 1.43 |
| Sample 1: Serum + CM | 0.0272 | 2.92 |
| Sample 2: Serum + CM + BAPN | 0.0093 | |

TABLE 6-continued

| Sample 1 | Average signal | S/N |
|---|---|---|
| Sample 1: Serum only | 0.0126 | 1.63 |
| Sample 2: Serum + CM | 0.0353 | 4.56 |
| Sample 2: Serum + CM + BAPN | 0.0077 | |

Table 7 shows the LOX bioprobe assay can detect LOX activity in human serum. S/N is the ratio of the signal in the presence of the enzyme (S) over the noise (N) (Signal remaining after the enzyme is inhibited). A signal above 1 is considered LOX specific activity.

TABLE 7

| Sample (Human serum) | S/N |
|---|---|
| Sample 1 | 3.48 |
| Sample 2 | 5.80 |
| Sample 3 | 4.30 |
| Sample 4 | 5.59 |

The invention claimed is:

1. A bioprobe of formula W-L-Z, wherein W represents an affinity tag; L represents a linker; and Z represents a moiety that binds to a protein selected from the group consisting of LOX, LOXL1, LOXL2, LOXL3 and LOXL4 protein, wherein Z is a moiety of Formula Ib:

Formula Ib

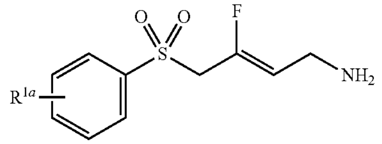

wherein:

$R^{1a}$ is selected from the group consisting of hydrogen, $C_{1-6}$alkyl, —O—$C_{1-6}$alkyl and —C(O)$NR^2R^3$ or represents an attachment point for L; and $R^2$ and $R^3$ are independently selected from the group consisting of hydrogen and $C_{1-6}$alkyl.

2. A method for determining a measure of the concentration of a protein selected from a lysyl oxidase (LOX) protein and a lysyl oxidase-like (LOXL) protein in a sample containing or suspected of containing the protein, comprising:

(a) obtaining a sample containing or suspected of containing the protein from a subject;

(b) contacting the sample with:

(i) a capture antibody specific for the protein under conditions sufficient to form a protein/capture antibody complex; and (ii) the bioprobe of claim 1; and (c) performing an immunoassay to measure the total concentration of the protein in the sample, wherein the immunoassay is a digital ELISA.

3. The method of claim 2, wherein the bioprobe is selected from the group consisting of:
Compound 1-7
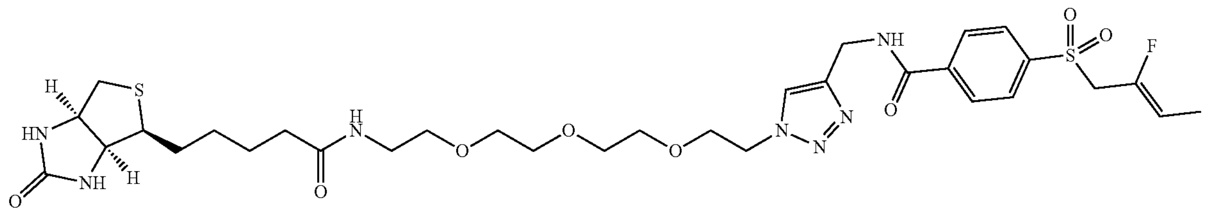
Compound 1-8
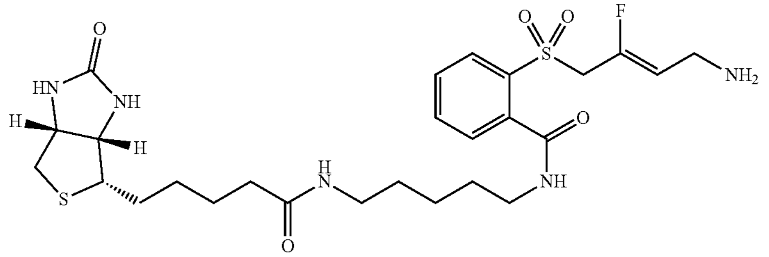
Compound 1-9
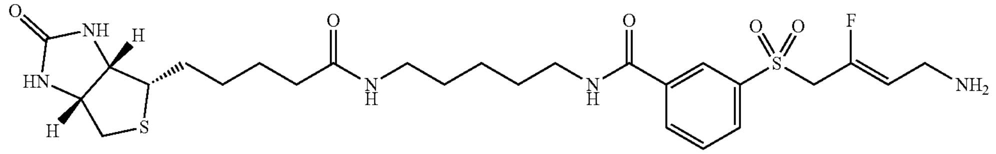
Compound 1-10
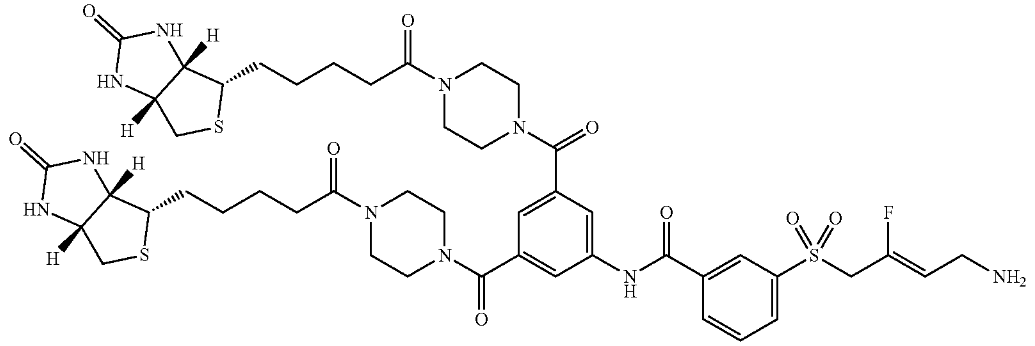
Compound 1-11
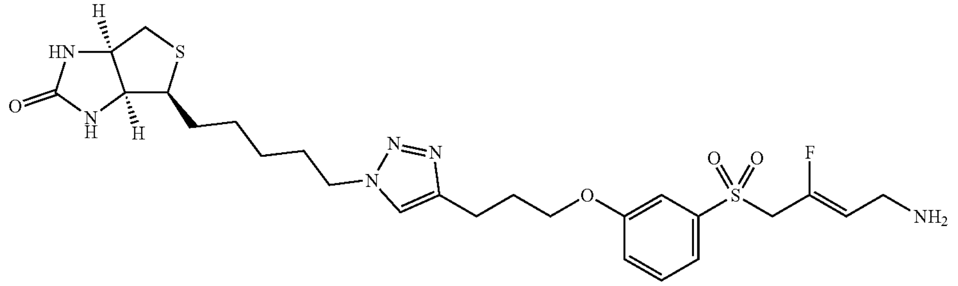

-continued

Compound 1-12

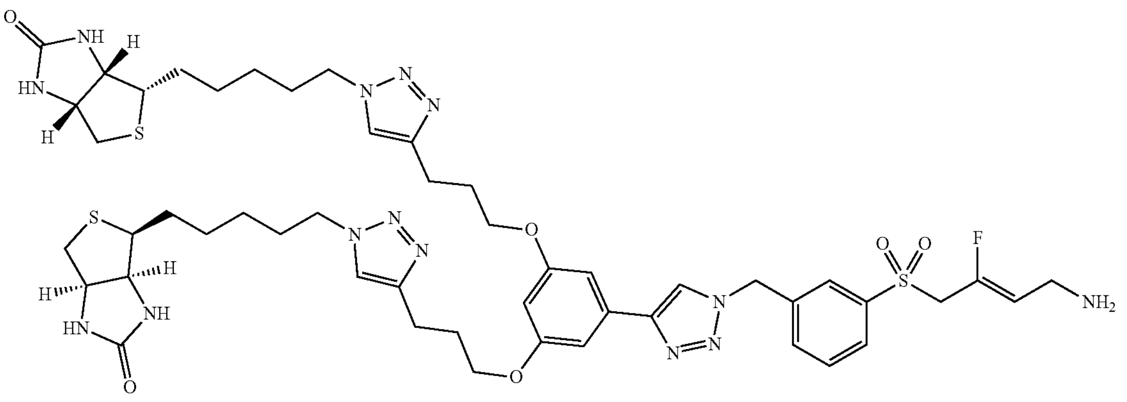

Compound 1-13

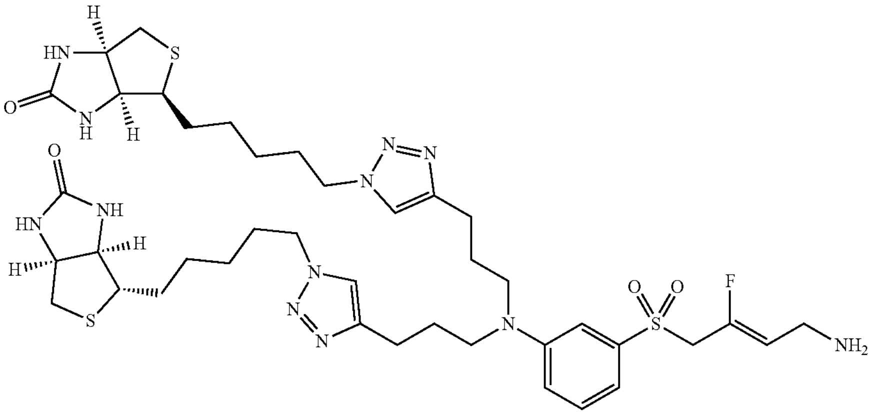

Compound 1-14

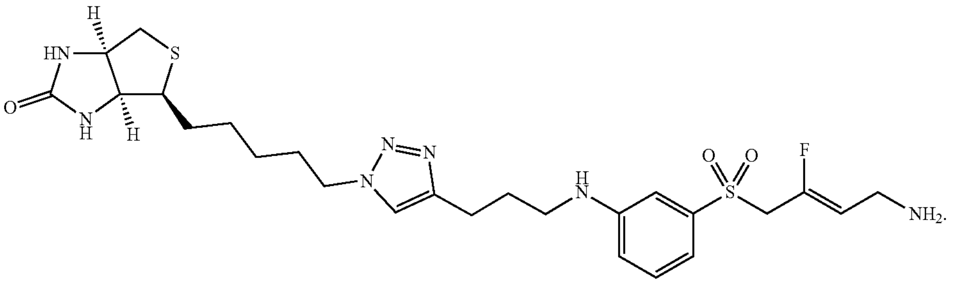

4. A method for determining the extent of enzyme inhibition of a protein selected from a lysyl oxidase (LOX) protein and a lysyl oxidase-like (LOXL) protein by a LOX or LOXL inhibitor, the method comprising:

(a) obtaining a sample containing or suspected of containing the protein from a subject;

(b) contacting the sample with a first amount of the LOX or LOXL inhibitor;

(c) contacting the sample with:

(i) a capture antibody specific for the protein under conditions sufficient to form a protein/capture antibody complex; and (ii) a bioprobe of claim 1; and (d) performing an immunoassay to measure the concentration of the protein with an enzymatic pocket occupied by the bioprobe, wherein the immunoassay is a digital ELISA.

5. The method according to claim 4, further comprising determining the measure of the concentration of the protein in the sample from step (a) according to a method comprising:

contacting the sample with:

(i) a capture antibody specific for the protein under conditions sufficient to form a protein/capture antibody complex; and (ii) the bioprobe of claim 1; and performing an immunoassay to measure the total concentration of the protein in the sample, wherein the immunoassay is a digital ELISA.

6. The method according to claim 4, further comprising determining the measure of the concentration of the protein in the sample from step (a) or (b) by:

(e) contacting the sample with a capture antibody specific for the protein under conditions sufficient to form a protein/capture antibody complex; and (f) adding a detection antibody specific for the protein to the sample, then performing a second immunoassay to measure the total concentration of the protein in the sample, wherein the second immunoassay is a digital ELISA.

7. The method according to claim 4, wherein the binding of the LOX or LOXL inhibitor to the enzymatic pocket of the protein does not interfere with the immunoassay to measure the concentration of the protein; or wherein the binding of the capture antibody to the protein does not interfere with the binding of the bioprobe to the enzymatic pocket of the protein; or wherein the binding of the capture antibody to the protein does not interfere with the binding of the LOX or LOXL inhibitor to the enzymatic pocket of the protein.

8. The method according to claim 4, wherein the LOX or LOXL inhibitor is administered to a subject, the method comprising replacing step (a) and (b) with steps:

(a1) administering a first amount of the LOX or LOXL inhibitor to the subject; and (b1) obtaining a sample containing or suspected of containing the protein from the subject after a predetermined period of time.

9. The method according to claim 8, wherein the method further comprises measuring the concentration of the protein in a sample obtained from the subject prior to administration of the LOX or LOXL inhibitor.

10. The method according to claim 2, further comprising:

(d) comparing the measured total concentration of the protein in the sample to a standard level; and (e) identifying patients likely to benefit from treatment with a LOX or LOXL inhibitor.

11. The method according to claim 2, further comprising:

(d) comparing the measured total concentration of the protein in the sample to a standard level, wherein a difference in the concentration of the protein present in the sample compared to the standard level is indicative of the subject having a condition associated with the protein; and wherein the condition associated with the protein is selected from the group consisting of a liver disorder, a kidney disorder, a lung disorder, fibrosis, cancer and angiogenesis.

12. The method according to claim 2, wherein the sample is a bodily fluid or a tissue sample.

13. The method according to claim 12, wherein the bodily fluid is blood or a blood component.

14. The method according to claim 2, wherein the volume of the sample is less than 1 mL.

15. The method according to claim 2, wherein the protein concentration is measured at a picomolar concentration.

16. The method according to claim 2, wherein the LOXL protein is a LOXL2 protein.

17. The method according to claim 2, wherein the capture antibody is AF2639 and the detection antibody is Fitzgerald 70R-12876.

18. The method according to claim 2, wherein the protein is LOX.

19. The method according to claim 2, wherein the capture antibody is L4794 and the detection antibody is ab219369.

20. The method according to claim 2, wherein the affinity tag is biotin.

21. A kit for determining a measure of the concentration of a protein selected from a lysyl oxidase (LOX) protein and a lysyl oxidase-like (LOXL) protein in a sample, the kit comprising a capture antibody specific for the protein, and the bioprobe of claim 1.

22. A kit for determining the extent of enzyme inhibition of a protein selected from a lysyl oxidase (LOX) protein and a lysyl oxidase-like (LOXL) protein by a LOX or LOXL inhibitor, the kit comprising:

a capture antibody specific for the protein, the bioprobe of claim 1, and a detection antibody specific for the protein.

* * * * *